United States Patent
Greene et al.

(10) Patent No.: US 12,428,455 B2
(45) Date of Patent: Sep. 30, 2025

(54) DOMINANT NEGATIVE CEBPB AND CEBPD PROTEINS AND METHODS OF USE FOR DECREASING VIABILITY OF NEOPLASTIC CELLS

(71) Applicants: The Trustees of Columbia University in the City of New York, New York, NY (US); The Regents of the University of California, Oakland, CA (US)

(72) Inventors: Lloyd A. Greene, Larchmont, NY (US); Xiaotian Sun, Fort Lee, NJ (US); James M. Angelastro, David, CA (US)

(73) Assignees: The Trustees of Columbia University in the City of New York, New York, NY (US); The Regents of the University of California, Oakland, CA (US)

( * ) Notice: Subject to any disclaimer, the term of this patent is extended or adjusted under 35 U.S.C. 154(b) by 966 days.

(21) Appl. No.: 17/170,151

(22) Filed: Feb. 8, 2021

(65) Prior Publication Data
US 2021/0163551 A1     Jun. 3, 2021

Related U.S. Application Data

(63) Continuation-in-part of application No. PCT/US2019/045518, filed on Aug. 7, 2019.
(60) Provisional application No. 62/716,123, filed on Aug. 8, 2018.

(51) Int. Cl.
| | |
|---|---|
| *C07K 14/47* | (2006.01) |
| *A61K 31/337* | (2006.01) |
| *A61K 31/4706* | (2006.01) |
| *A61K 31/704* | (2006.01) |
| *A61K 38/17* | (2006.01) |
| *A61P 35/00* | (2006.01) |

(52) U.S. Cl.
CPC ............ *C07K 14/47* (2013.01); *A61K 31/337* (2013.01); *A61K 31/4706* (2013.01); *A61K 31/704* (2013.01); *A61K 38/1709* (2013.01); *A61P 35/00* (2018.01); *C07K 2319/10* (2013.01)

(58) Field of Classification Search
CPC .. C07K 14/47; C07K 2319/10; A61K 31/337; A61K 31/4706; A61K 31/704; A61K 38/1709; A61K 38/00; A61P 35/00; A61P 25/00; C12N 15/113; C12N 2310/14
See application file for complete search history.

(56) References Cited

U.S. PATENT DOCUMENTS

| | | |
|---|---|---|
| 6,348,185 B1 | 2/2002 | Piwnica-Worms |
| 2003/0027314 A1* | 2/2003 | Vinson .................. C12N 15/11 435/325 |

OTHER PUBLICATIONS

GenPept database [CCAAT/enhancer-binding protein delta, [*Homo sapiens*], GenBanck: AAB27293.1, PRI Aug. 25, 1993, <https://www.ncbi.nlm.nih.gov/protein/AAB27293.1>, downloaded Jan. 12, 2024]. (Year: 1993).*
Aguilar-Morante et al., "Decreased CCAAT/Enhancer Binding Protein β Expression Inhibits the Growth of Glioblastoma Cells," *Neuroscience* 176:110-119, 2011.
Alves et al., "Membrane interaction and perturbation mechanisms induced by two cationic cell penetrating peptides with distinct charge distribution," *Biochimica et Biophysica Acta* 1780(7-8):948-959, 2008.
Balamurugan et al. "The tumour suppressor C/EBPδ inhibits FBXW7 expression and promotes mammary tumour metastasis," *The EMBO Journal* 29(24):4106-4117, 2010.
Balamurugan et al., "The Many Faces of C/EBPδ and their Relevance for Inflammation and Cancer," *Int. J. Biol. Sci.* 9:917-933, 2013.
Banerjee et al., "Loss of C/EBPδ enhances IR-induced cell death by promoting oxidative stress and mitochondrial dysfunction," *Free Radic Biol Med.* 99:296-307, Oct. 2016 (HHS Public Access Author Manuscript, available in PMC Nov. 6, 2017). (26 pages).
Bellet-Amalric et al., "Interaction of the third helix of Antennapedia homeodomain and a phospholipid monolayer, studied by ellipsometry and PM-IRRAS at the air-water interface," *Biochimica et Biophysica Acta* 1467:131-143, 2000.
Bera et al., "Structural Elucidation of Cell-Penetrating Penetratin Peptide in Model Membranes at Atomic Level: Probing Hydrophobic Interactions in the Blood-Brain-Barrier," *Biochemistry* 55(35):4982-4996, Sep. 6, 2016 (HHS Public Access Author Manuscript, available in PMC Sep. 6, 2017). (31 pages).
Bolton et al., "Cellular uptake and spread of the cell-permeable peptide penetratin in adult rat brain," *European Journal of Neuroscience* 12:2847-2855, 2000.
Brodsky, "Translocation of Proteins across the Endoplasmic Reticulum Membrane," *International Review of Cytology* 178:277-328, 1998.
Bundy et al., "CCAAT/enhancer binding protein beta (C/EBPβ)-2 transforms normal mammary epithelial cells and induces epithelial to mesenchymal transition in culture," *Oncogene* 22:869-883, 2003.
Califano et al., "The recurrent architecture of tumour initiation, progression and drug sensitivity," *Nat Rev Cancer* 17(2):116-130, 2017 (HHS Public Access Author Manuscript, available in PMC Aug. 3, 2017). (35 pages).
Cao et al., "CCAAT enhancer binding protein β has a crucial role in regulating breast cancer cell growth via activating the TGF-β-Smad3 signaling pathway," *Experimental and Therapeutic Medicine* 14:1554-1560, 2017.

(Continued)

*Primary Examiner* — Sudhakar Katakam
(74) *Attorney, Agent, or Firm* — Amster, Rothstein & Ebenstein LLP

(57) ABSTRACT

Dominant negative forms of CEBPB and CEBPD, and cell-penetrating forms thereof are described. Methods for using the dominant negative forms of CEBPB and CEBPD proteins, and cell-penetrating forms thereof, for decreasing viability of neoplastic cells and treating cancer in a subject are also described.

11 Claims, 73 Drawing Sheets
Specification includes a Sequence Listing.

(56) References Cited

OTHER PUBLICATIONS

Cao et al., "Regulated expression of three C/EBP isoforms during adipose conversion of 3T3-L1 cells," *Genes & Development 5*:1538-1552, 1991.

Carro et al., "The transcriptional network for mesenchymal transformation of brain tumours," *Nature 463*:318-325, Jan. 21, 2010. (10 pages).

Derossi et al., "Trojan peptides: the penetratin system for intracellular delivery," *Trends in Cell Biology 8*:84-87, Feb. 1998.

Dunican et al., "Designing Cell-Permeant Phosphopeptides to Modulate Intracellular Signaling Pathways," *Biopolymers 60*:45-60, 2001.

Duprez, "A New Role for C/EBPβ in Acute Promyelocytic Leukemia," *Cell Cycle 3*(4):389-390, Apr. 2004.

Elmquist et al., "VE-Cadherin-Derived Cell-Penetrating Peptide, pVEC, with Carrier Functions," *Experimental Cell Research 269*:237-244, 2001.

Fischer et al., "Structure-activity relationship of truncated and substituted analogues of the intracellular delivery vector Penetratin," *J. Peptide Res. 55*:163-172, 2000.

Futaki et al., "Arginine-Rich Peptides: An Abundant Source of Membrane-Permeable Peptides Having Potential as Carriers for Intracellular Protein Delivery," *The Journal of Biological Chemistry 276*(8):5836-5840, Feb. 23, 2001.

Gardiner et al., "C/EBPβ-1 promotes transformation and chemoresistance in Ewing sarcoma cells," *Oncotarget 8*(16):26013-26026, 2017.

Gombart et al., "Mutations in the gene encoding the transcription factor CCAAT/enhancer binding protein α in myelodysplastic syndromes and acute myeloid leukemias," *Blood 99*(4):1332-1340, Feb. 15, 2002.

Grimm et al., "The Role of C/EBPβ in Mammary Gland Development and Breast Cancer," *Journal of Mammary Gland Biology and Neoplasia 8*(2):191-204, Apr. 2003.

Hällbrink et al., "Cargo delivery kinetics of cell-penetrating peptides," *Biochimica et Biophysica Acta 1515*:101-109, 2001.

Huang et al., "The C/EBPβ-LINC01133 axis promotes cell proliferation in pancreatic ductal adenocarcinoma through upregulation of CCNG1," *Cancer Letters 421*:63-72, 2018.

International Search Report, mailed Jan. 15, 2020, for International Patent Application No. PCT/US2019/045518. (6 pages).

Ji et al., "C/EBPβ Promotion of MMP3-Dependent Tumor Cell Invasion and Association with Metastasis in Colorectal Cancer," *Genetic Testing and Molecular Biomarkers 22*(1):5-10, 2018.

Kilk et al., "Cellular Internalization of a Cargo Complex with a Novel Peptide Derived from the Third Helix of the Islet-1 Homeodomain. Comparison with the Penetratin Peptide," *Bioconjugate Chem. 12*(6):911-916, 2001.

Kim et al., "C/EBPβ Regulates Metastatic Gene Expression and Confers TNF-α Resistance to Prostate Cancer Cells," *The Prostate 69*:1435-1447, 2009.

Kumar et al., "Transvascular delivery of small interfering RNA to the central nervous system," *Nature 448*:39-43, Jul. 5, 2007. (7 pages).

Letoha et al., "Membrane translocation of penetratin and its derivatives in different cell lines," *Journal of Molecular Recognition 16*:272-279, 2003.

Li et al., "CCAAT enhancer binding protein β promotes tumor growth and inhibits apoptosis in prostate cancer by methylating estrogen receptor β," *Neoplasma 65*(1):34-41, 2018.

Li et al., "Differential Control of the CCAAT/Enhancer-binding Protein β (C/EBPβ) Products Liver-enriched Transcriptional Activating Protein (LAP) and Liver-enriched Transcriptional Inhibitory Protein (LIP) and the Regulation of Gene Expression during the Response to Endoplasmic Reticulum Stress," *The Journal of Biological Chemistry 283*(33):22443-22456, Aug. 15, 2008.

Lindgren et al., "Cell-penetrting peptides," *TiPS 21*:99-103, Mar. 2000.

Liu et al., "C/EBPβ enhances platinum resistance of ovarian cancer cells by reprogramming H3K79 methylation," *Nature Communications 9*:1739, 2018. (13 pages).

Magzoub et al., "Interaction and structure induction of cell-penetrating peptides in the presence of phospholipid vesicles," *Biochimica et Biophysica Acta 1512*:77-89, 2001.

Marigo et al., "Tumor-Induced Tolerance and Immune Suppression Depend on the C/EBPβ Transcription Factor," *Immunity 32*:790-802, Jun. 25, 2010.

Morris et al., "A new peptide vector for efficient delivery of oligonucleotides into mammalian cells," *Nucleic Acids Research 25*(14):2730-2736, 1997.

Okuma et al., "Regulation of mouse chondrocyte differentiation by CCAAT/enhancer-binding—proteins," *Biomedical Research 36*(1):21-29, 2015. (18 pages).

Pal et al., "C/EBPβ regulates transcription factors critical for proliferation and survival of multiple myeloma cells," *Blood 114*(18):3890-3898, Oct. 29, 2009.

Pooga et al., "Cell penetration by transportan," *The FASEB Journal 12*:67-77, Jan. 1998.

Reinke et al., "Networks of bZIP protein-protein interactions diversified over a billion years of evolution," *Science 340*(6133):730-734, May 10, 2013 (NIH Public Access Author Manuscript, available in PMC Jul. 30, 2014). (9 pages).

Scheller et al., "Structural Requirements for Cellular Uptake of -Helical Amphipathic Peptides," *Journal of Peptide Science 5*:185-194, 1999.

Shuman et al., "Cell Cycle-Dependent Phosphorylation of C/EBPβ Mediates Oncogenic Cooperativity between C/EBPβ and H-Ras$^{V12}$," *Molecular and Cellular Biology 24*(17):7380-7391, Sep. 2004.

Suzuki et al., "Possible Existence of Common Internalization Mechanisms among Arginine-rich Peptides," *The Journal of Biological Chemistry 277*(4):2437-2443, Jan. 25, 2002.

Szpirer et al., "Chromosomal Localization in Man and Rat of the Genes Encoding the Liver-Enriched Transcription Factors C/EBP, DBP, and HNF1/LFB-1 (CEBP, DBP, and Transcription Factor 1, TCF1, Respectively) and of the Hepatocyte Growth Factor/Scatter Factor Gene (HGF)," *Genomics 13*:293-300, 1992.

Thorén et al., "The Antennapedia peptide penetratin translocates across lipid bilayers—the first direct observation," *FEBS Letters 482*:265-268, 2000.

Tregnago et al., "CREB engages C/EBPδ to initiate leukemogenesis," *Leukemia 30*:1887-1896, 2016.

Troy et al., "Downregulation of Cu/Zn Superoxide Dismutase Leads to Cell Death via the Nitric Oxide-Peroxynitrite Pathway," *The Journal of Neuroscience 16*(1):253-261, 1996.

Troy et al., "Nedd2 Is Required for Apoptosis after Trophic Factor Withdrawal, But Not Superoxide Dismutase (SOD1) Downregulation, in Sympathetic Neurons and PC12 Cells," *The Journal of Neuroscience 17*(6):1911-1918, Mar. 15, 1997.

Troy et al., "The contrasting roles of ICE family proteases and interleukin-1β in apoptosis induced by trophic factor withdrawal and by copper/zinc superoxide dismutase down-regulation," *Proc. Natl. Acad. Sci. USA 93*:5635-5640, May 1996.

Vivès et al., "A Truncated HIV-1 Tat Protein Basic Domain Rapidly Translocates through the Plasma Membrane and Accumulates in the Cell Nucleus," *The Journal of Biological Chemistry 272*(25):16010-16017, Jun. 20, 1997.

Wang et al., "CEBPD amplification and overexpression in urothelial carcinoma: a driver of tumor metastasis indicating adverse prognosis," *Oncotarget 6*(31):31069-31084, 2015.

Wang et al., "Inhibition of the EGFR/STAT3/CEBPD Axis Reverses Cisplatin Cross-resistance with Paclitaxel in the Urothelial Carcinoma of the Urinary Bladder," *Clin Cancer Res 23*(2):503-513, Jan. 15, 2017.

Williams et al., "A family of C/EBP-related proteins capable of forming covalently linked leucine zipper dimers in vitro," *Genes & Development 5*: 1553-1567, 1991.

Williams et al., "CRP2 (C/EBPβ) contains a bipartite regulatory domain that controls transcriptional activation, DNA binding and cell specificity," *The EMBO Journal 14*(13):3170-3183, 1995.

Wu et al., "CCAAT/Enhancer-binding Protein & Mediates Tumor Necrosis Factor α-induced Aurora Kinase C Transcription and

(56) References Cited

OTHER PUBLICATIONS

Promotes Genomic Instability," *The Journal of Biological Chemistry 286*(33):28662-28670, Aug. 19, 2011.

Yin et al., "Transglutaminase 2 Inhibition Reverses Mesenchymal Transdifferentiation of Glioma Stem Cells by Regulating C/EBPβ Signaling," *Cancer Res 77*(18):4973-4984, Sep. 15, 2017.

Zhao et al., "Chemical engineering of cell penetrating antibodies," *Journal of Immunological Methods 254*:137-145, 2001.

Zhu et al., "CCAAT/enhancer binding protein-β is a mediator of keratinocyte survival and skin tumorigenesis involving oncogenic Ras signaling," *PNAS 99*(1):207-212, Jan. 8, 2002.

\* cited by examiner y axis is cell viability % y axis is cell viability % y axis is cell viability %

CP-DN-CEBPB

CP-DN-CEBPD

Control

CP-DN-CEBPB

CP-DN-CEBPD

Control

Y axis is Soft Agar Relative Colony Forming Activity

Y axis is Soft Agar Relative Colony Forming Activity

Y axis is Culture Dish Relative Colony Forming Activity

Y axis is Culture Dish Relative Colony Forming Activity y axis is Relative IL6 mRNA Levels y axis is Relative IL8 mRNA Levels y axis is Relative ASNS mRNA Levels

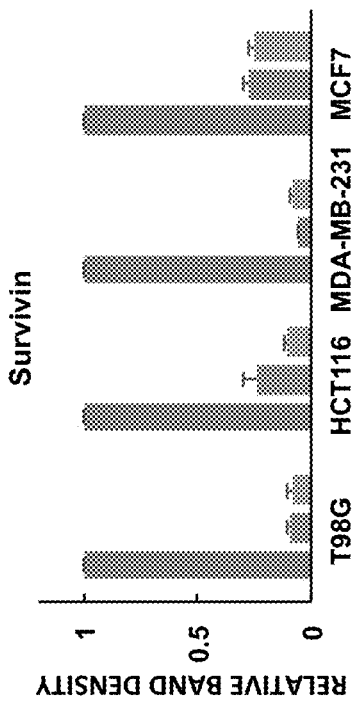
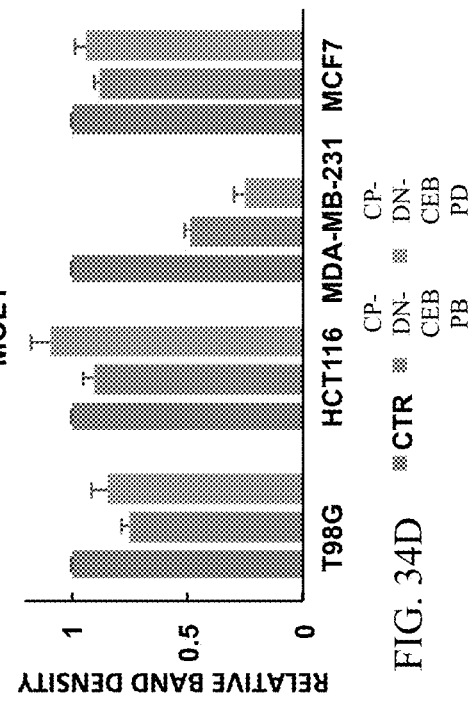
FIG. 34A
FIG. 34B
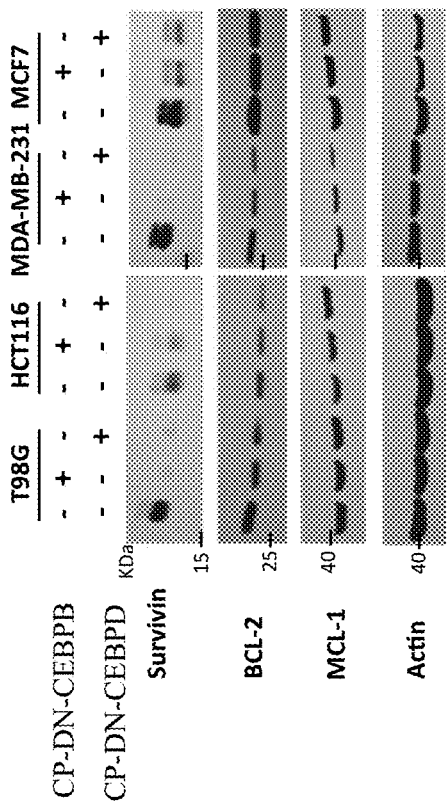
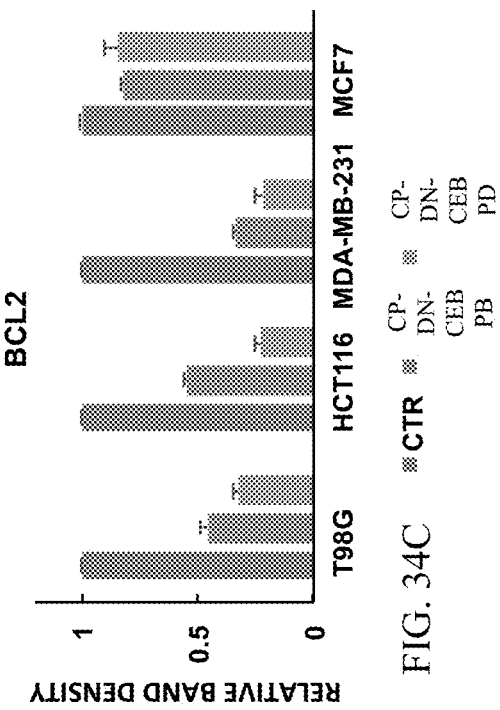
FIG. 34C
FIG. 34D y axis is Relative BMF mRNA levels

VEHICLE  CP-DN-CEBPD

DOMINANT NEGATIVE CEBPB AND CEBPD PROTEINS AND METHODS OF USE FOR DECREASING VIABILITY OF NEOPLASTIC CELLS

CROSS REFERENCE TO RELATED APPLICATION

This application is a continuation-in-part of PCT/US2019/045518 filed Aug. 7, 2019, which claims the benefit of priority of U.S. Provisional patent Application No. 62/716,123 filed Aug. 8, 2018, and, both of which are hereby incorporated by reference in their entireties.

STATEMENT OF GOVERNMENT INTEREST

This invention was made with government support under NS083795 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Aug. 29, 2019, is named 070050_6238_SL.txt and is 29,874 bytes in size.

TECHNICAL FIELD

The present disclosure relates to proteins and methods for decreasing viability of neoplastic cells, including tumor cells. In particular, the present disclosure relates to dominant negative (DN) forms of CCAAT/enhancer-binding protein beta (CEBPB) and CCAAT/enhancer-binding protein delta (CEBPD) proteins and methods of use thereof for decreasing viability of neoplastic cells and treating cancer in a subject.

BACKGROUND

Approximately one million people are diagnosed with cancer each year, and many millions of people in the United States of all ages are currently living with some form of cancer. Despite intensive research, discovery of new therapeutic targets and development of new drugs for treating cancer remains challenging.

SUMMARY

According to a first aspect, a dominant-negative CEBPB protein is described. The dominant-negative CEBPB protein consists essentially of a CEBPB leucine zipper domain having an amino acid sequence

```
                                        (SEQ ID NO: 1)
LETQHKVLELTAENERLQKKVEQLSRELSTLRNLFKQL.
```

According to a second aspect, a dominant negative CEBPD protein is described. The dominant negative CEBPD protein consists essentially of a CEBPD leucine zipper domain having an amino acid sequence

```
                                        (SEQ ID NO: 2)
KLVELSAENEKLHQRVEQLTRDLAGLRQFFK.
```

According to a third aspect, a composition is described. The composition includes a dominant negative CEBPB protein or a dominant negative CEBPD protein, or a combination thereof, and a pharmaceutically acceptable excipient.

According to a fourth aspect, a method of decreasing activity or viability of a neoplastic cell is described. The method includes contacting the neoplastic cell with a dominant negative CEBPB protein or a dominant negative CEBPD protein, or a combination thereof, for a time and under conditions sufficient to cause a decrease in activity or viability of the neoplastic cell.

According to a fifth aspect, a method of treating cancer in a subject is described. The method includes administering to the subject an effective amount of a dominant negative CEBPB protein or a dominant negative CEBPD protein, or a combination thereof.

According to a sixth aspect, a polynucleotide is described. The polynucleotide includes a sequence encoding a dominant negative CEBPB protein or a dominant negative CEBPD protein.

In any of the disclosed implementations, the dominant negative CEBPB protein, dominant negative CEBPD protein, compositions, methods and polynucleotides may further include the following details, which may be combined with one another in any combinations unless clearly mutually exclusive:

(i) the dominant negative CEBPB protein may not include a functional DNA binding domain;
(ii) the functional DNA binding domain may have an amino acid sequence

```
                                        (SEQ ID NO: 3)
KKTVDKHSDEYKIRRERNNIAVRKSRDKAKMRN;
```

(iii) the CEBPB leucine zipper domain may have an N-terminal end, wherein an extended leucine zipper domain is linked to the N-terminal end, the extended leucine zipper domain having an amino acid sequence selected from

```
                                        (SEQ ID NO: 4)
LEQRAEELARENEELEKEAEELEQENAE, (SEQ ID NO: 5)
LARENEELEKEAEELEQENAE, (SEQ ID NO: 6)
LEKEAEELEQENAE,
and (SEQ ID NO: 7)
LEQENAE;
```

(iv) the dominant negative CEBPB protein may have a cell penetrating peptide linked directly or indirectly to the CEBPB leucine zipper domain;
(v) the cell penetrating peptide linked directly or indirectly to the CEBPB leucine zipper domain may be penetratin 1;
(vi) the dominant negative CEBPD protein may not include a functional DNA binding domain;
(vii) the functional DNA binding domain may have an amino acid sequence

```
                                        (SEQ ID NO: 51)
DRGSPEYRQRRERNNIAVRKSRDKAKRRNQEMQQK;
```

(viii) the CEBPD leucine zipper domain may have an N-terminal end, wherein an extended leucine zipper domain is linked to the N-terminal end, the extended leucine zipper domain having an amino acid sequence selected from

LEQRAEELARENEELEKEAEELEQENAE, (SEQ ID NO: 4)

LARENEELEKEAEELEQENAE, (SEQ ID NO: 5)

LEKEAEELEQENAE, (SEQ ID NO: 6)
and

LEQENAE; (SEQ ID NO: 7)

(ix) the dominant negative CEBPD protein may have a cell penetrating peptide linked directly or indirectly to the CEBPD leucine zipper domain; and (x) the cell penetrating peptide linked directly or indirectly to the CEBPD leucine zipper domain may be penetratin 1.

For a more complete understanding of the present disclosure and the associated features and advantages, reference is now made to the following description, taken in conjunction with the accompanying drawings, which are not to scale, and in which.

Figure 3:
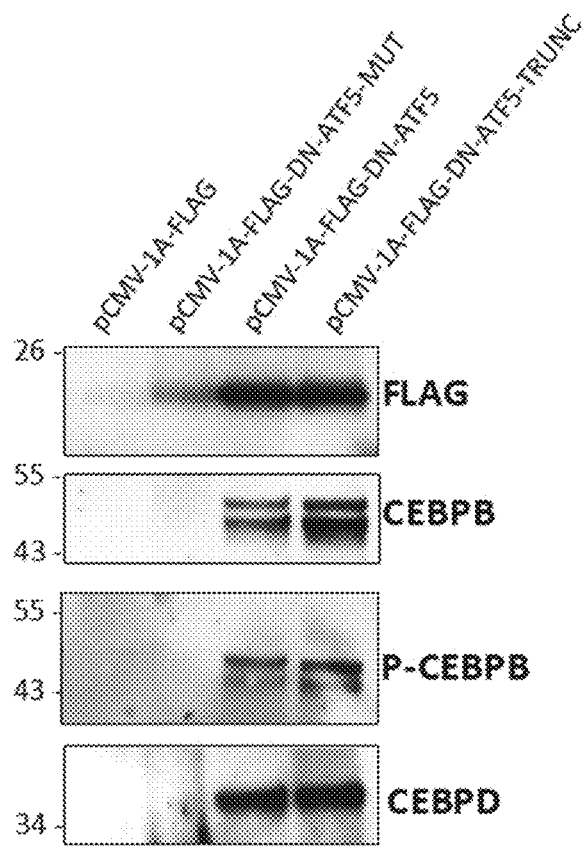

FIG. 3 is a set of exemplary images of Western immunoblots of lysates of cells transfected with plasmids expressing a FLAG-tagged intact ATF5 leucine zipper (pCMV-1A-3×FLAG-DN-ATF5-TRUNC), or a FLAG-tagged intact ATF5 leucine zipper plus a mutated ATF5 DNA binding domain containing an extended leucine zipper (pCMV-1A-FLAG-DN-ATF5), or a version of pCMV-1A-FLAG-DN-ATF5 also mutated in the leucine zipper to replace the relevant leucine residues with glycine residues (pCMV-1A-FLAG-DN-ATF5-MUT), or a control plasmid lacking an ATF5 construct (pCMV-1A-FLAG). The immunoblots were probed with antibodies to detect FLAG, CEBPB, p-CEBPB, or CEBPD.

Figure 4B:
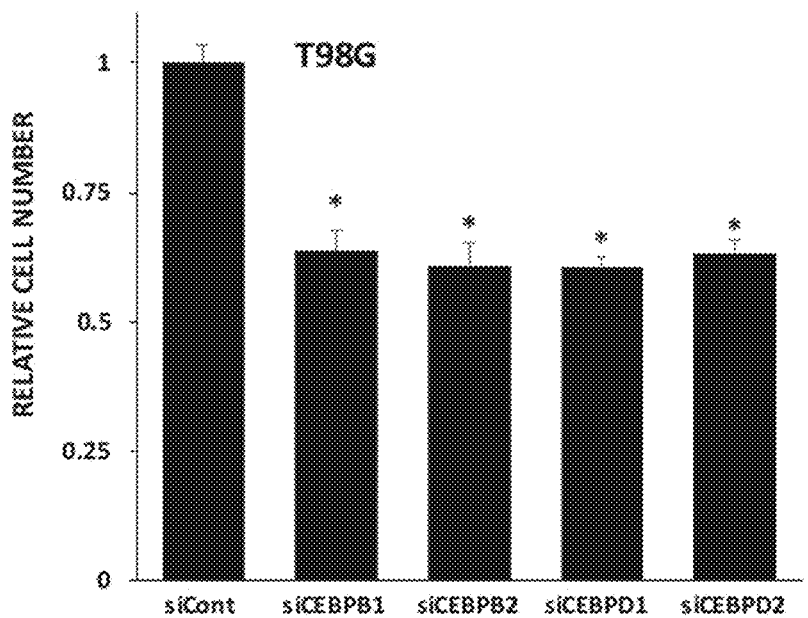
Figure 4A:
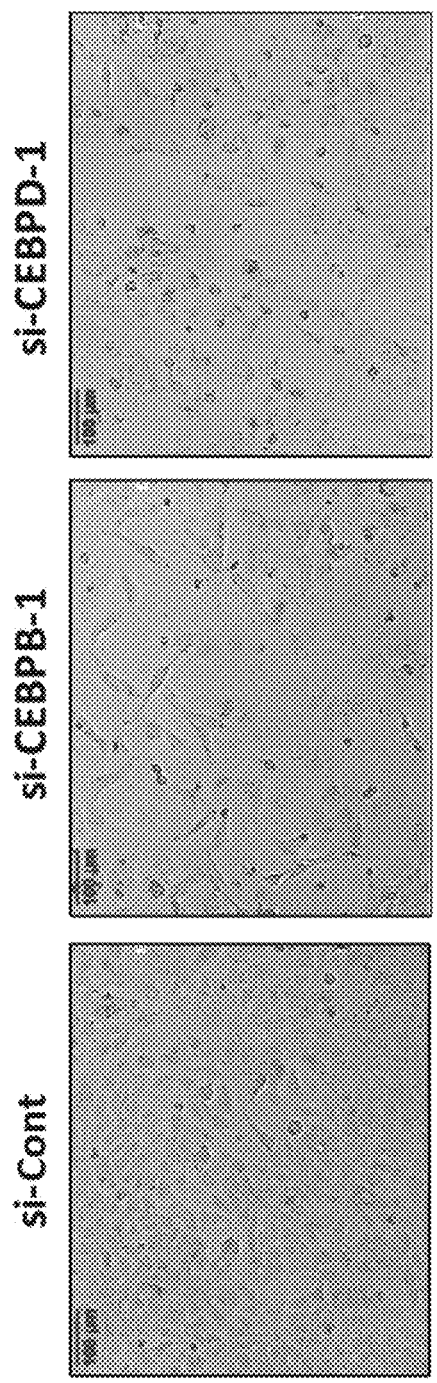

FIG. 4A is set of exemplary micrograph images of cultured T98G cells transfected with siRNAs targeting CEBPB (si-CEBPB-1), CEBPD (si-CEBPD-1), or a non-targeting siRNA control (si-CTR). Scale bar=100 μm.

FIG. 4B is a graph reporting exemplary quantification of the relative number of T98 cells following transfection of the cells with siRNAs targeting CEBPB (siCEBPB-1 or siCEBPB-2), CEBPD (siCEBPD-1 or siCEBPD-2), or a non-targeting control (siCont).

Figure 4C:
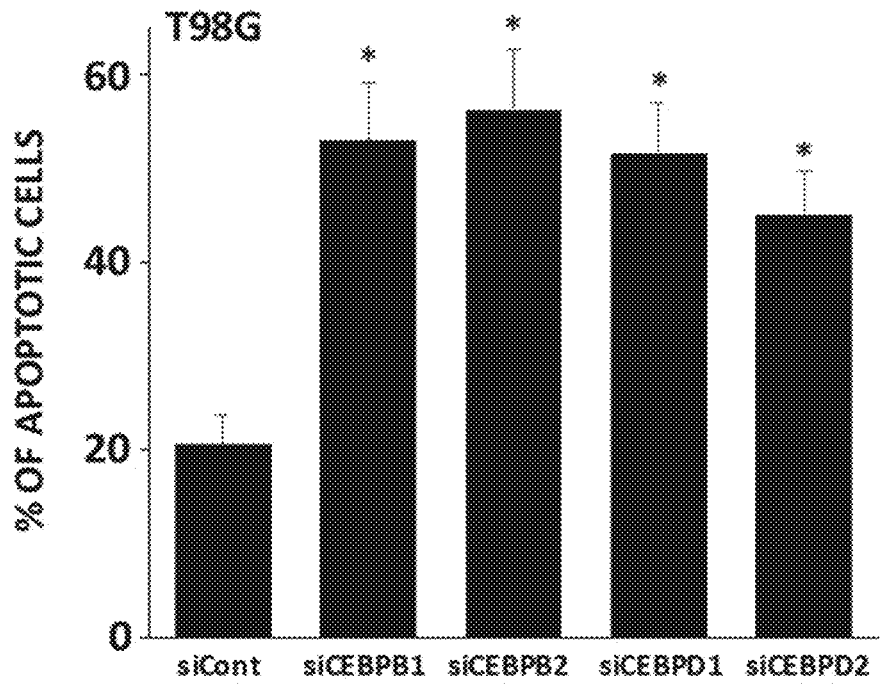

FIG. 4C is a graph reporting exemplary quantification of the percentage of apoptotic T98 cells following transfection of the cells with siRNAs targeting CEBPB (siCEBPB-1 or siCEBPB-2), CEBPD (siCEBPD-1 or siCEBPD-2), or a non-targeting control (siCont).

Figure 4D:
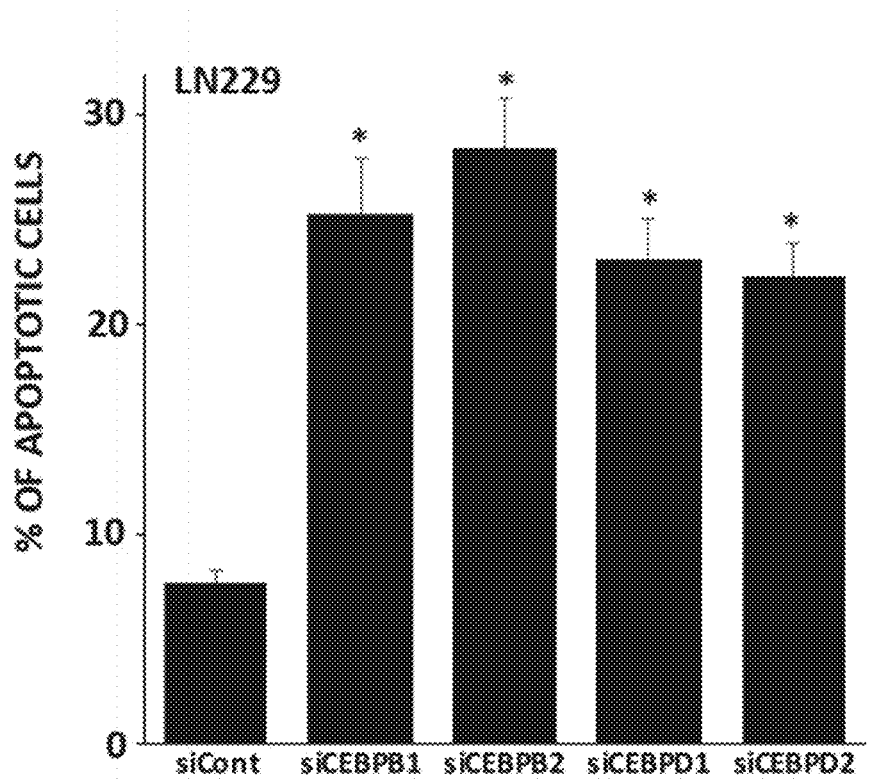

FIG. 4D is a graph reporting exemplary quantification of the percentage of apoptotic LN229 cells following transfection of the cells with siRNAs targeting CEBPB (siCEBPB-1 or siCEBPB-2), CEBPD (siCEBPD-1 or siCEBPD-2), or a non-targeting control (siCont).

Figure 4E:
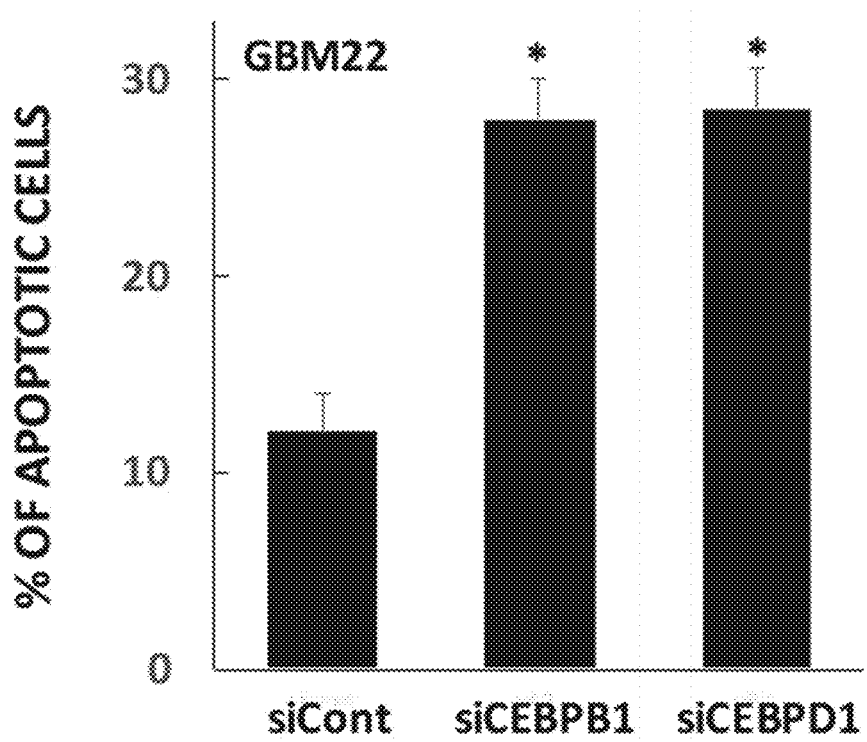

FIG. 4E is a graph reporting exemplary quantification of the percentage of apoptotic GBM22 cells following transfection of the cells with siRNAs targeting CEBPB (siCEBPB-1), CEBPD (siCEBPD-1), or a non-targeting control (siCont).

Figure 4F:
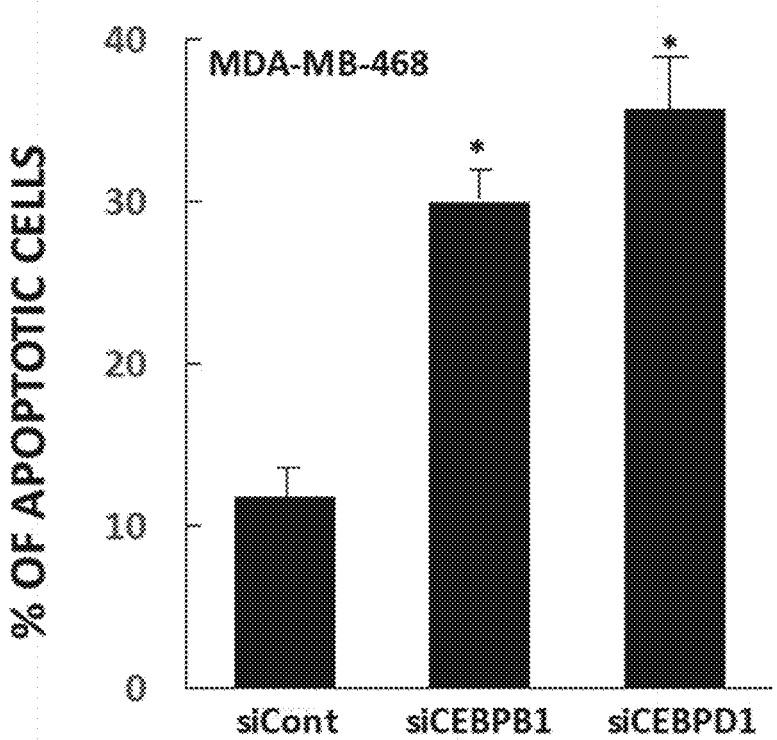

FIG. 4F is a graph reporting exemplary quantification of the percentage of apoptotic MDA-MB-468 cells following transfection of the cells with siRNAs targeting CEBPB (siCEBPB-1), CEBPD (siCEBPD-1), or a non-targeting control (siCont).

Figure 4G:
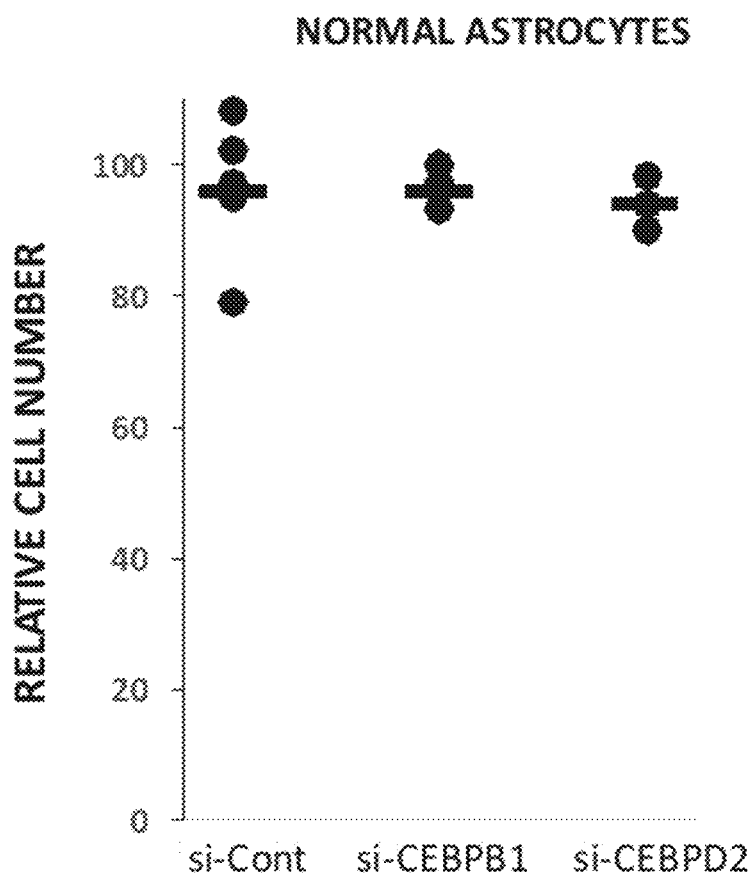

FIG. 4G is a graph reporting exemplary quantification of the relative number of normal astrocytes following transfection of the cells with siRNAs targeting CEBPB (si-CEBPB1), CEBPD (si-CEBPD1), or a non-targeting control (si-Cont).

Figure 4H:
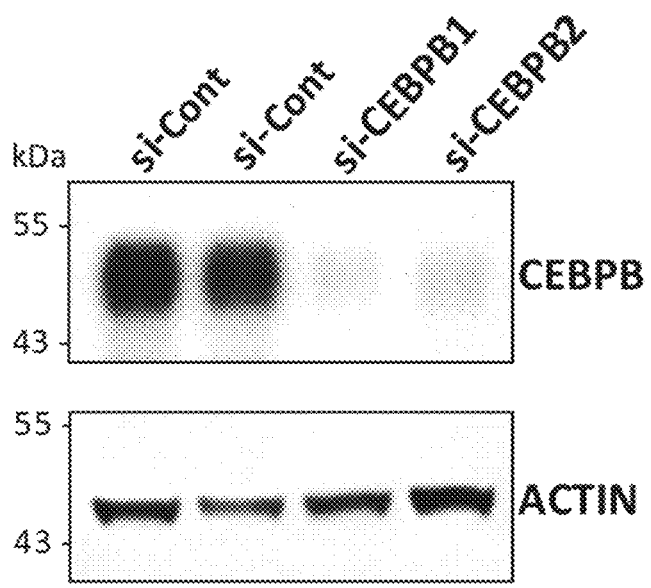

FIG. 4H is a set of exemplary images of Western immunoblots of lysates of cells transfected with siRNAs targeting CEBPB (si-CEBPB1 or si-CEBPB2) or a non-targeting control (si-CTR). The immunoblots were probed with antibodies to detect CEBPB, or actin as a loading control.

Figure 4I:
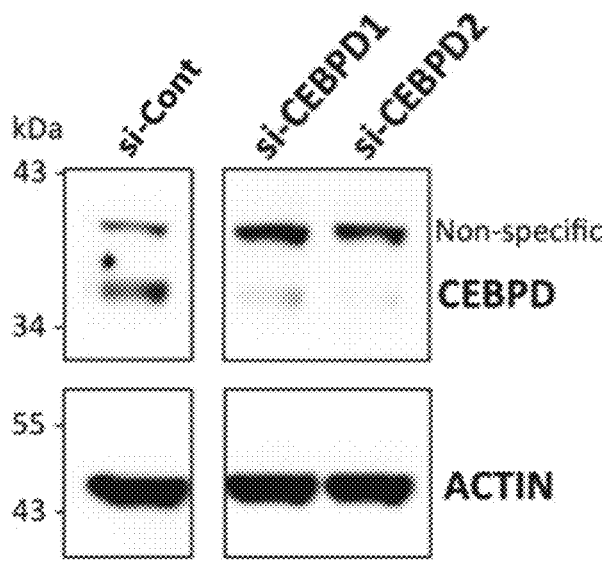

FIG. 4I is a set of exemplary images of Western immunoblots of lysates of cells transfected with siRNAs targeting CEBPD (siCEBPD-1 or siCEBPD-2), or a non-targeting control (si-CTR). The immunoblots were probed with antibodies to detect CEBPD, or actin as a loading control.

Figure 5:
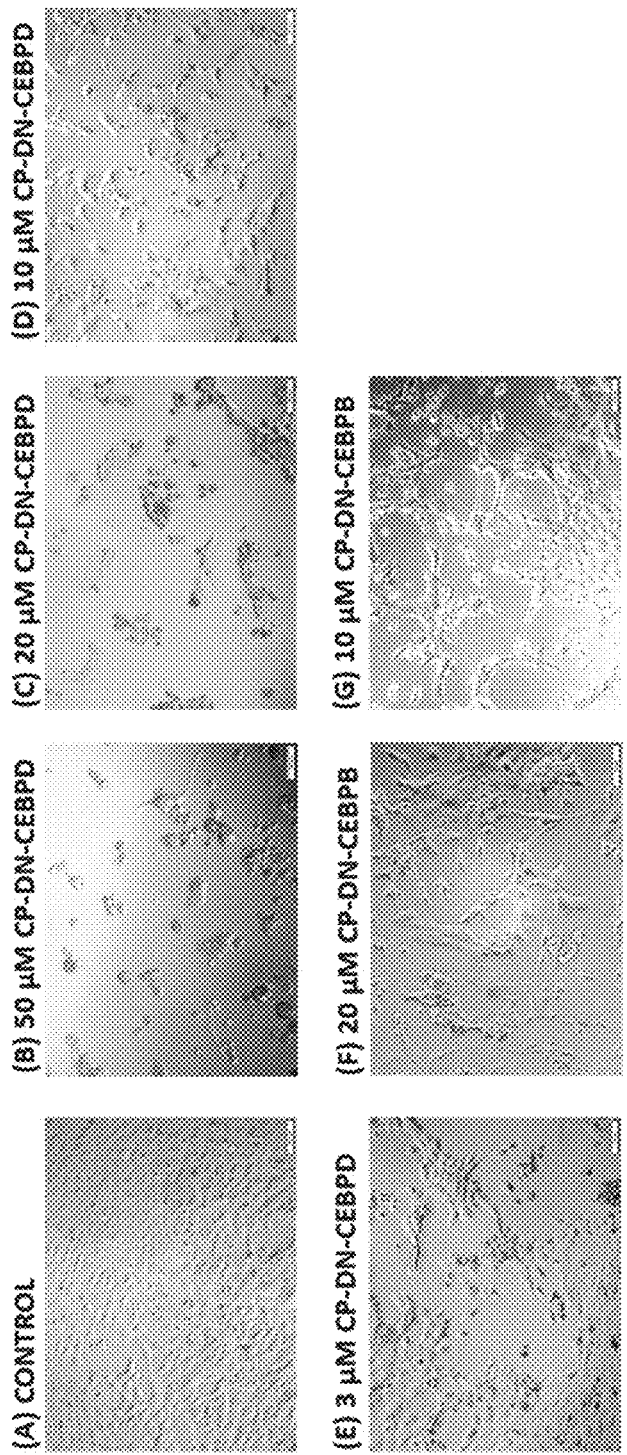

FIG. 5 is a set of exemplary micrograph images of cultured T98G cells, either untreated (Control), or treated with a cell penetrating dominant negative CEBPB (CP-DN-CEBPB) at 10 μM or 20 μM doses, or cell penetrating dominant negative CEBPD (CP-DN-CEBPD) at 3 μM, 10 μM, 20 μM or 50 μM doses.

Figure 6A:
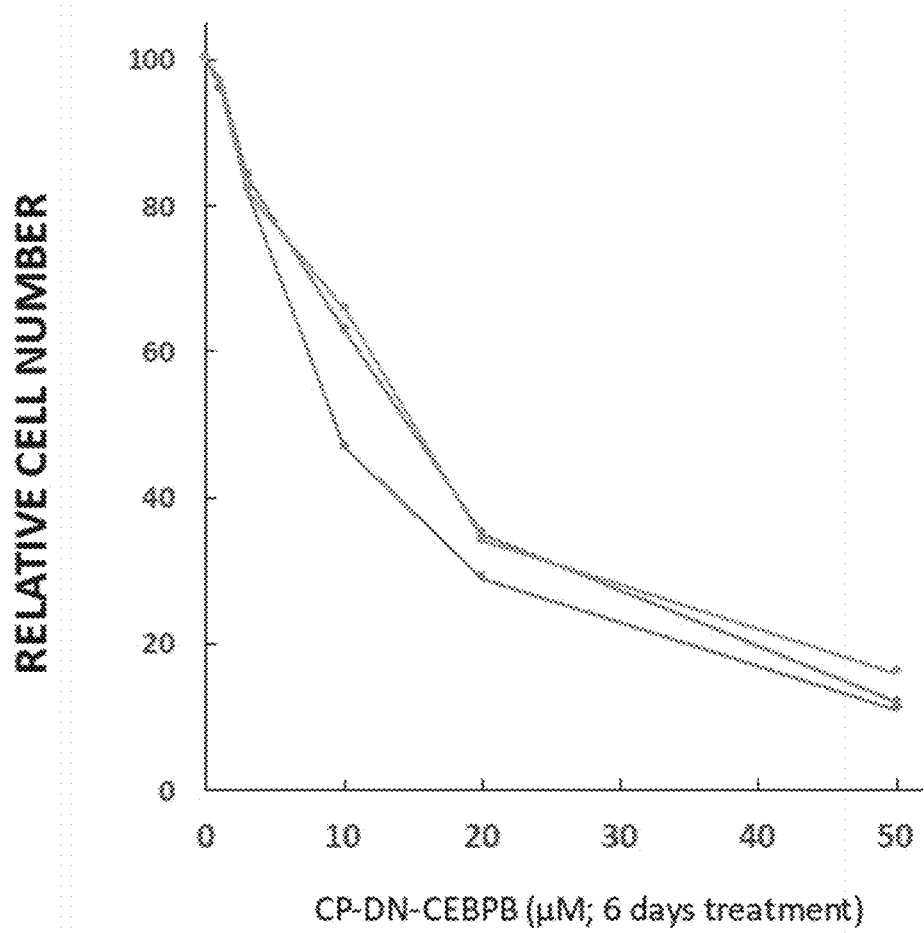

FIG. 6A is a graph reporting exemplary quantification of relative number of T98G cells following 6 days treatment with a cell penetrating dominant negative CEBPB (CP-DN-CEBPB) at doses of 0 μM to 50 μM. Exemplary data are shown from three independent experiments in triplicate.

Figure 6B:
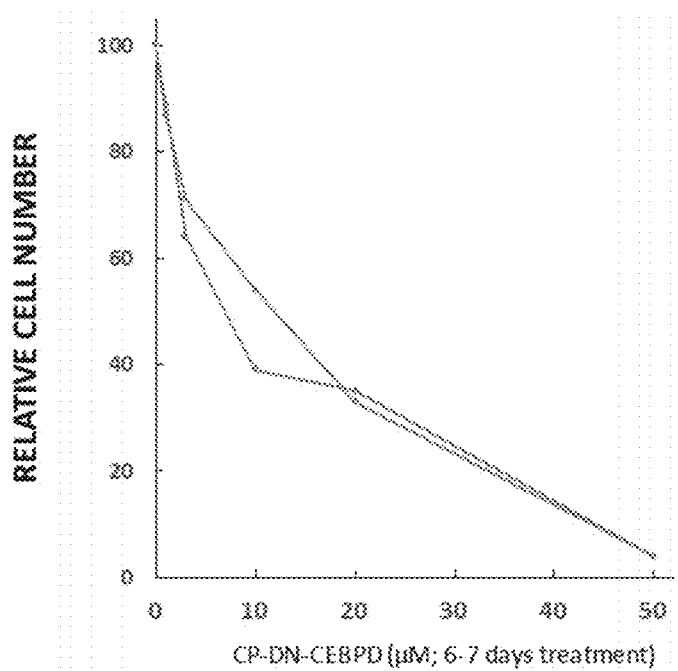

FIG. 6B is a graph reporting exemplary quantification of relative number of T98G cells following 6-7 days treatment with a cell penetrating dominant negative CEBPD (CP-DN-CEBPD) at doses of 0 μM to 50 μM. Exemplary data are shown from two independent experiments in triplicate.

Figure 7A:
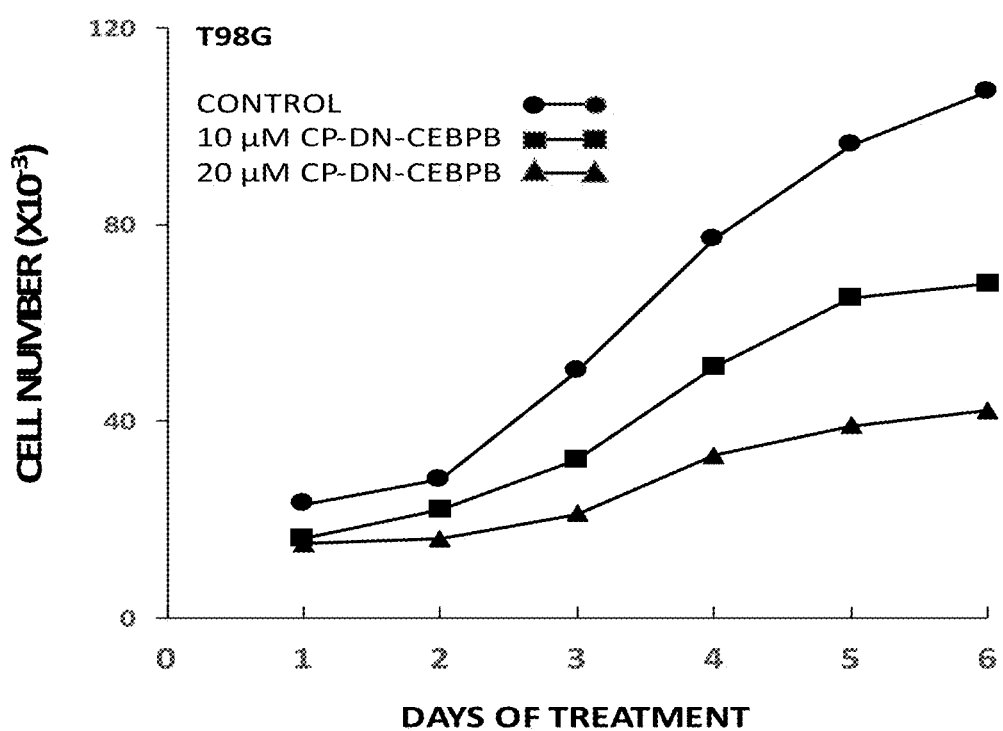

FIG. 7A is a graph reporting exemplary quantification of the number of T98G cells, either untreated (control), or after 1-6 days of treatment with a cell penetrating dominant negative CEBPB (CP-DN-CEBPB) at 10 μM or 20 μM doses.

Figure 7B:
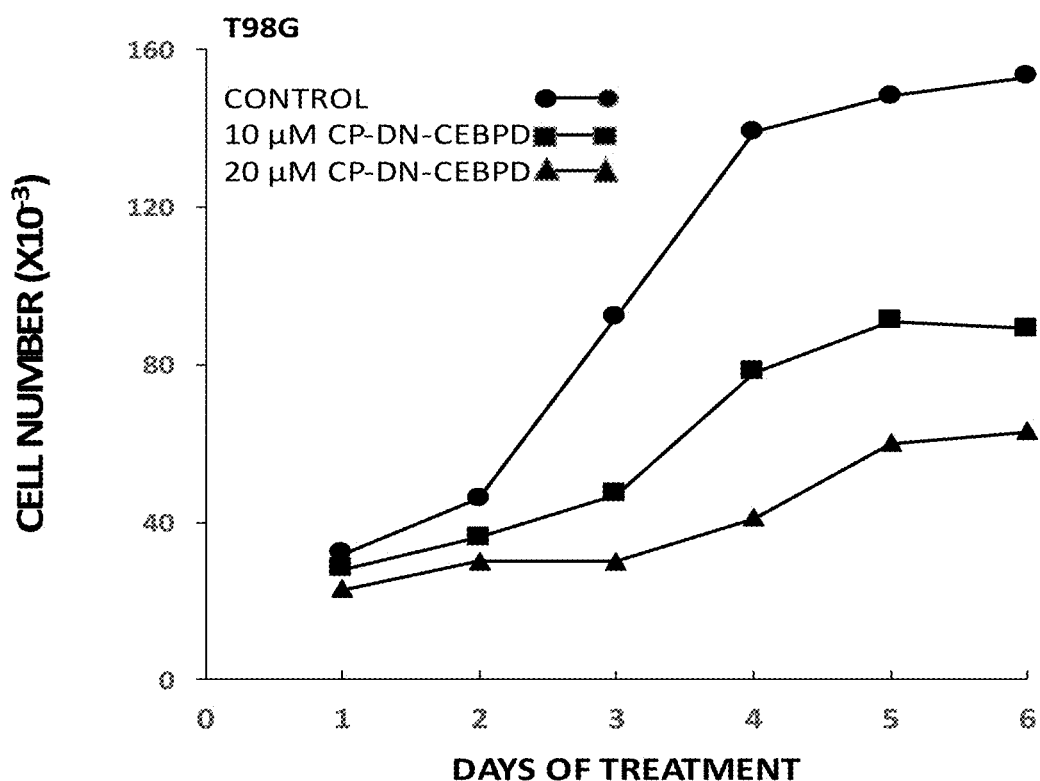

FIG. 7B is a graph reporting exemplary quantification of the number of T98G cells, either untreated (control), or after 1-6 days of treatment with a cell penetrating dominant negative CEBPD (CP-DN-CEBPD) at 10 μM or 20 μM doses.

Figure 8A:
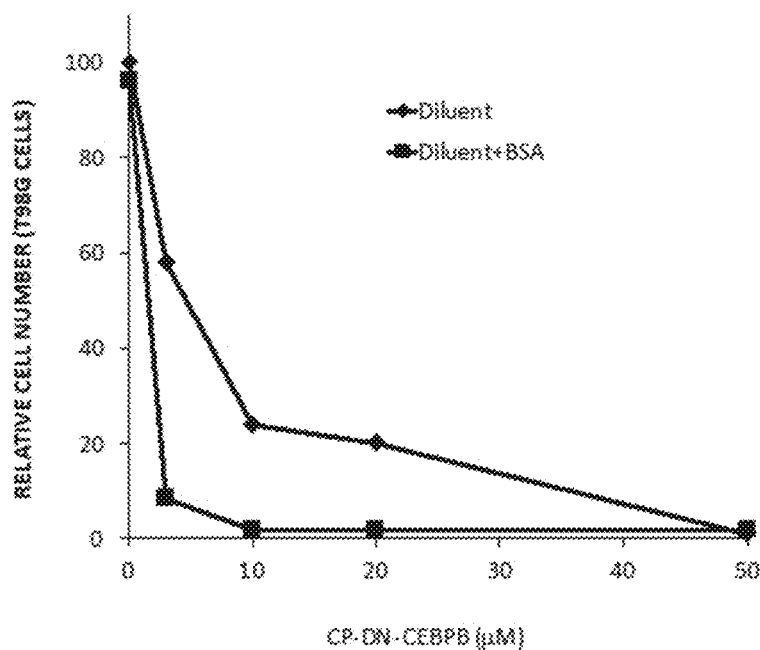

FIG. 8A is a graph reporting exemplary quantification of relative number of T98G cells following 6 days treatment with a cell penetrating dominant negative CEBPB (CP-DN-CEBPB) at doses of 0 μM to 50 μM, formulated with or without bovine serum albumin (BSA). Exemplary data are shown from four replicates.

Figure 8B:
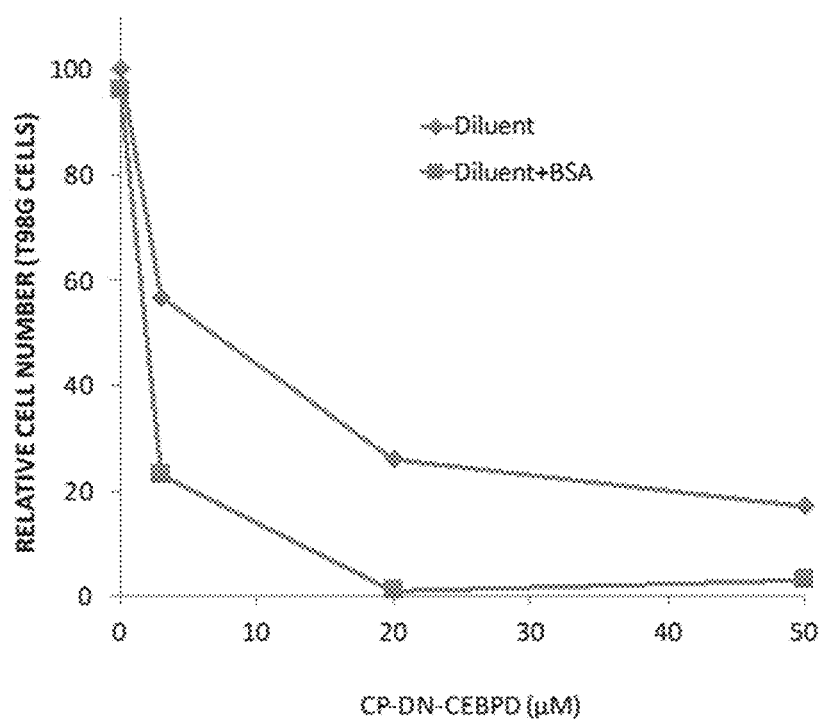

FIG. 8B is a graph reporting exemplary quantification of relative number of T98G cells following 6 days treatment with a cell penetrating dominant negative CEBPD (CP-DN-CEBPD) at doses of 0 μM to 50 μM, formulated with or without bovine serum albumin (BSA). Exemplary data are shown from four replicates.

Figure 9A:
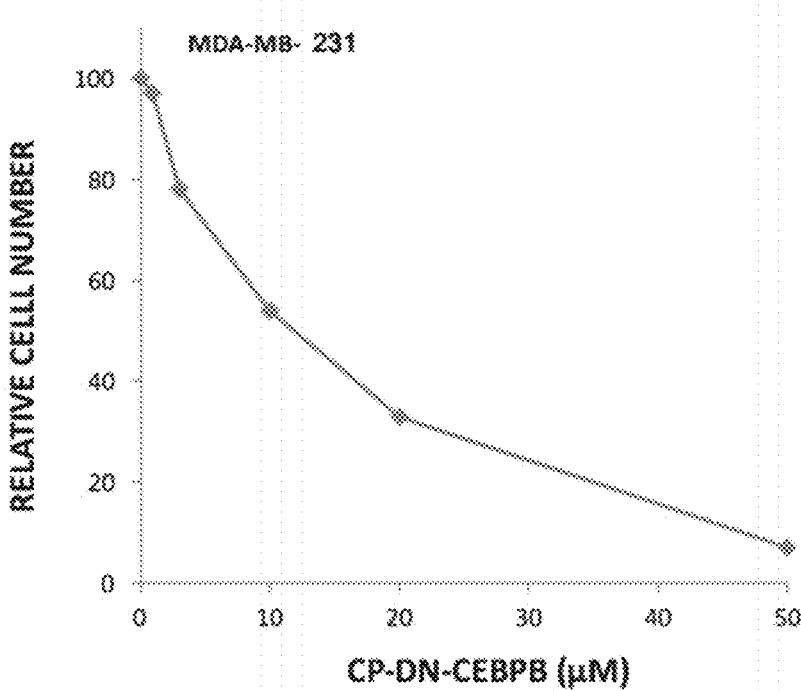

FIG. 9A is a graph reporting exemplary quantification of relative numbers of MDA-MB-231 breast cancer cells following 6 days treatment with a cell penetrating dominant negative CEBPB (CP-DN-CEBPB) at doses of 0 µM to 50 µM.

Figure 9B:
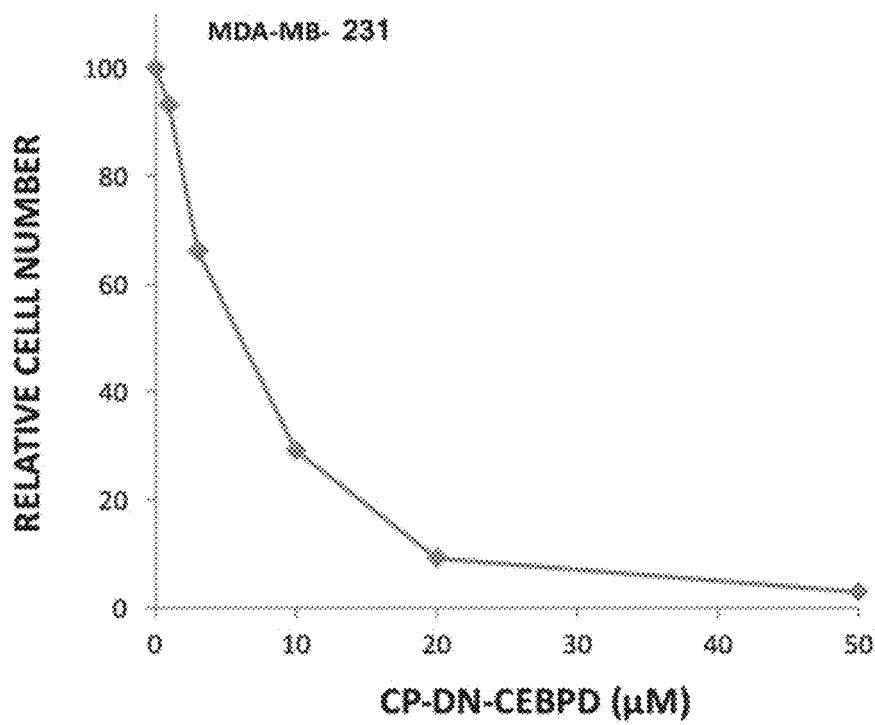

FIG. 9B is a graph reporting exemplary quantification of relative numbers of MDA-MB-231 breast cancer cells following 6 days treatment with a cell penetrating dominant negative CEBPD (CP-DN-CEBPD) at doses of 0 µM to 50 µM.

Figure 9C:
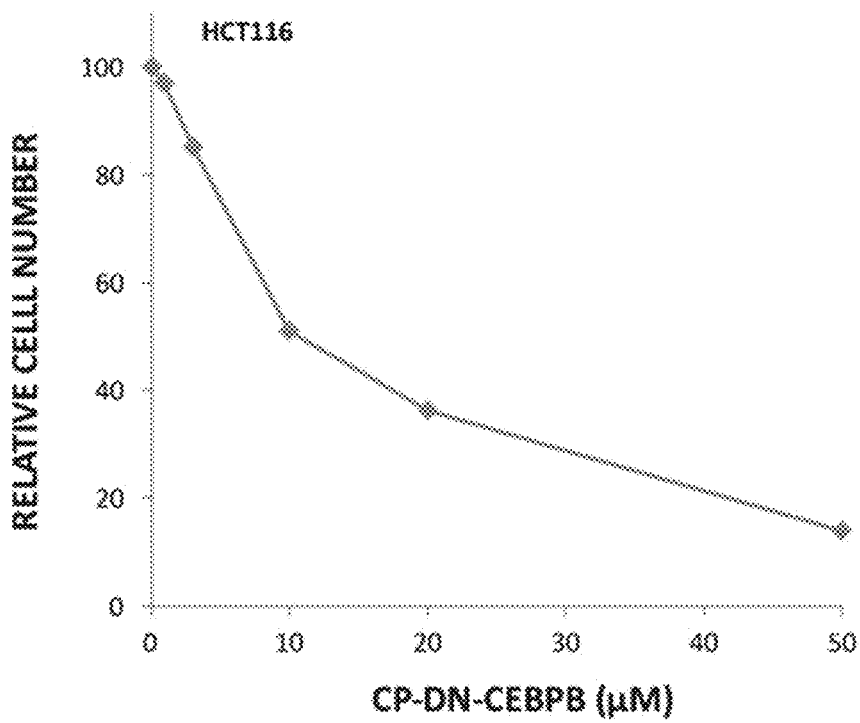

FIG. 9C is a graph reporting exemplary quantification of relative numbers of HCT116 colon cancer cells following 6 days treatment with a cell penetrating dominant negative CEBPB (CP-DN-CEBPB) at doses of 0 µM to 50 µM.

Figure 9D:
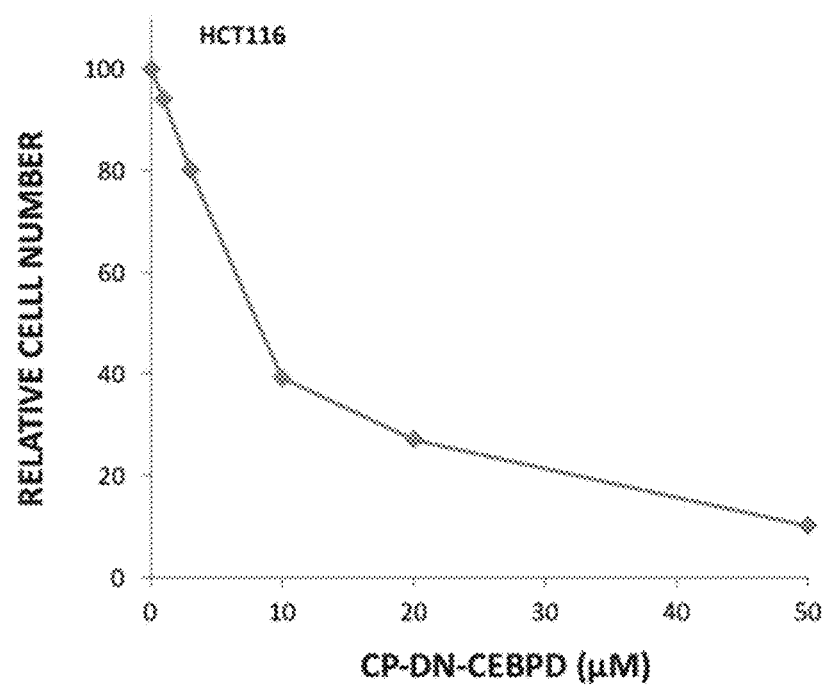

FIG. 9D is a graph reporting exemplary quantification of relative numbers of HCT116 colon cancer cells following 6 days treatment with a cell penetrating dominant negative CEBPD (CP-DN-CEBPD) at doses of 0 µM to 50 µM.

Figure 9E:
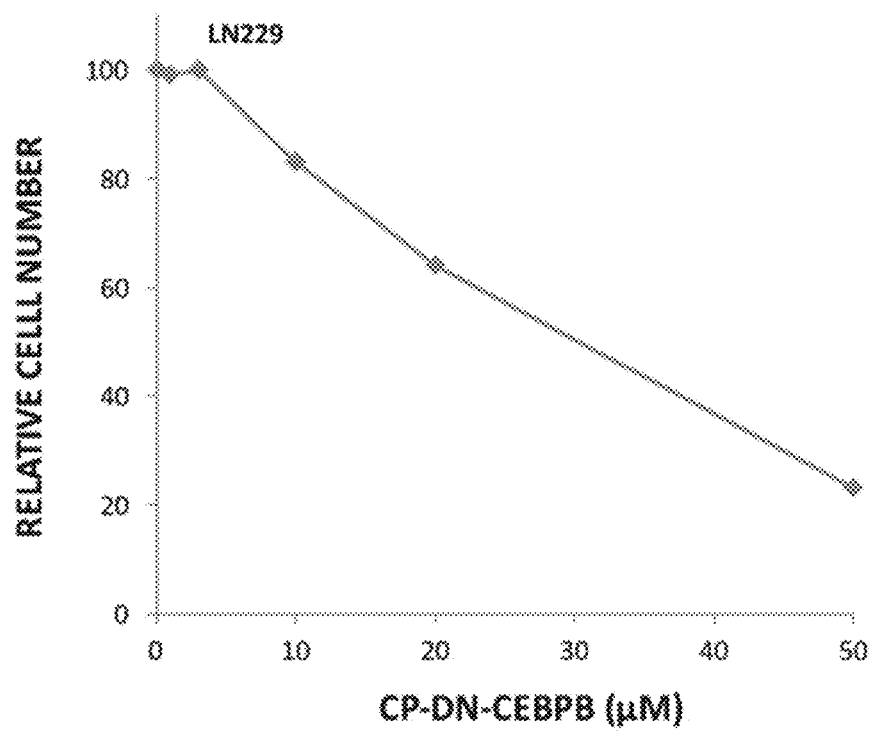

FIG. 9E is a graph reporting exemplary quantification of relative numbers of LN229 glioblastoma cells following 6 days treatment with a cell penetrating dominant negative CEBPB (CP-DN-CEBPB) at doses of 0 µM to 50 µM.

Figure 9F:
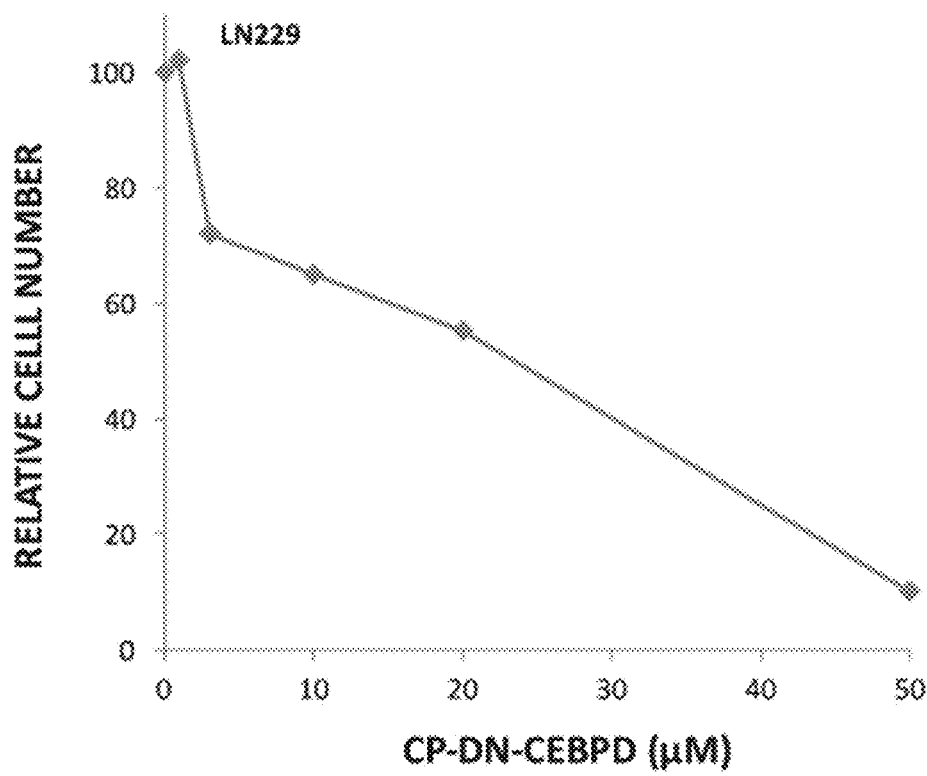

FIG. 9F is a graph reporting exemplary quantification of relative numbers of LN229 glioblastoma cells following 6 days treatment with a cell penetrating dominant negative CEBPD (CP-DN-CEBPD) at doses of 0 µM to 50 µM.

Figure 9G:
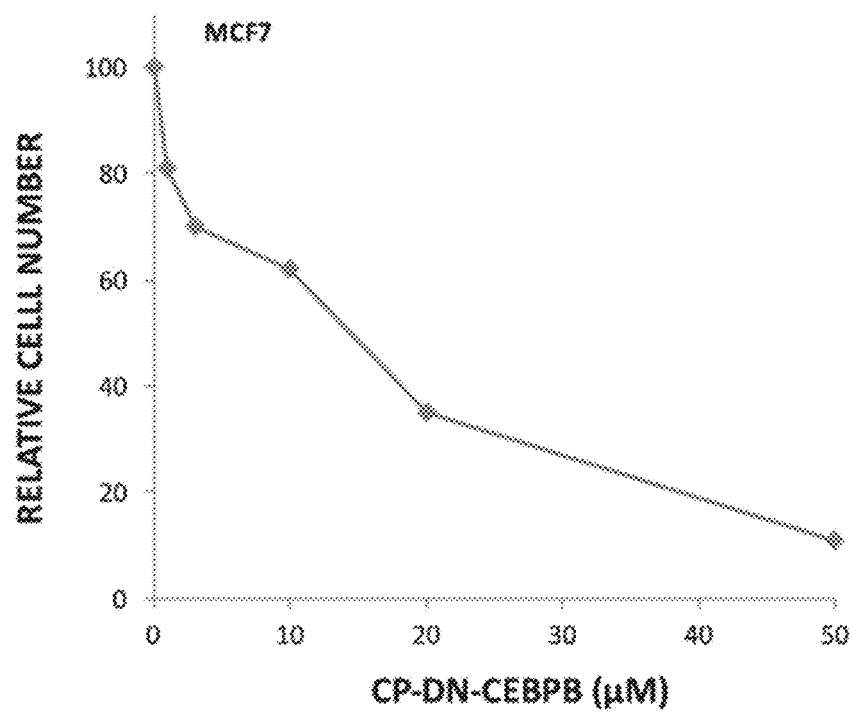

FIG. 9G is a graph reporting exemplary quantification of relative numbers of MCF7 breast cancer cells following 6 days treatment with a cell penetrating dominant negative CEBPB (CP-DN-CEBPB) at doses of 0 µM to 50 µM.

Figure 9H:
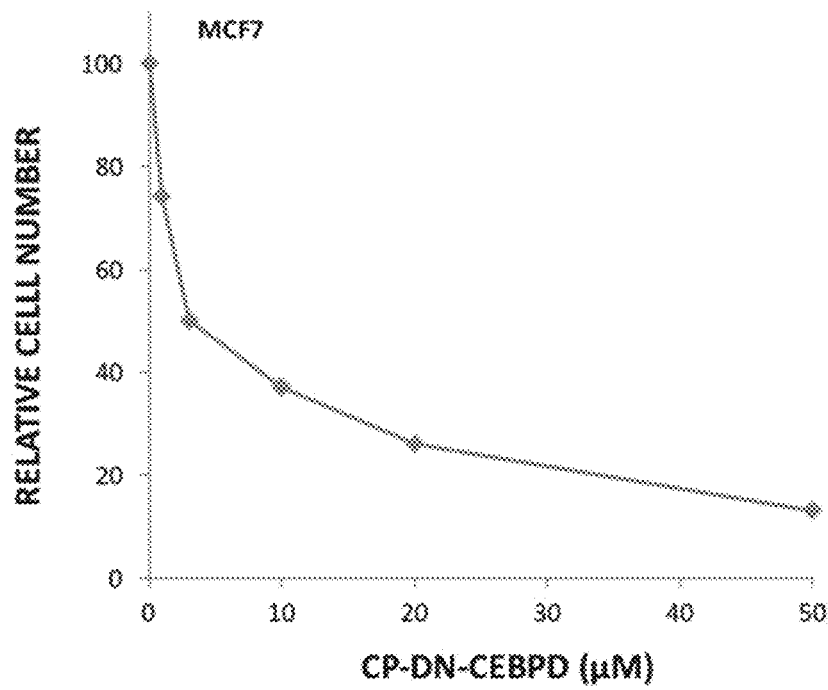

FIG. 9H is a graph reporting exemplary quantification of relative numbers of MCF7 breast cancer cells following 6 days treatment with a cell penetrating dominant negative CEBPD (CP-DN-CEBPD) at doses of 0 µM to 50 µM.

Figure 10A:
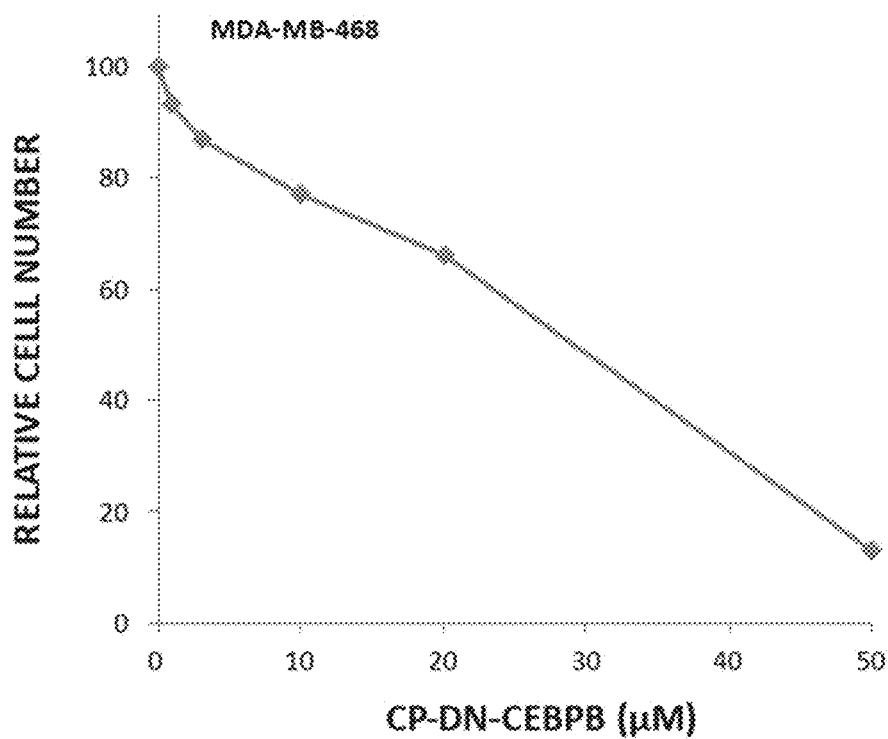

FIG. 10A is a graph reporting exemplary quantification of relative numbers of MDA-MB-468 breast cancer cells following 6 days treatment with a cell penetrating dominant negative CEBPB (CP-DN-CEBPB) at doses of 0 µM to 50 µM.

Figure 10B:
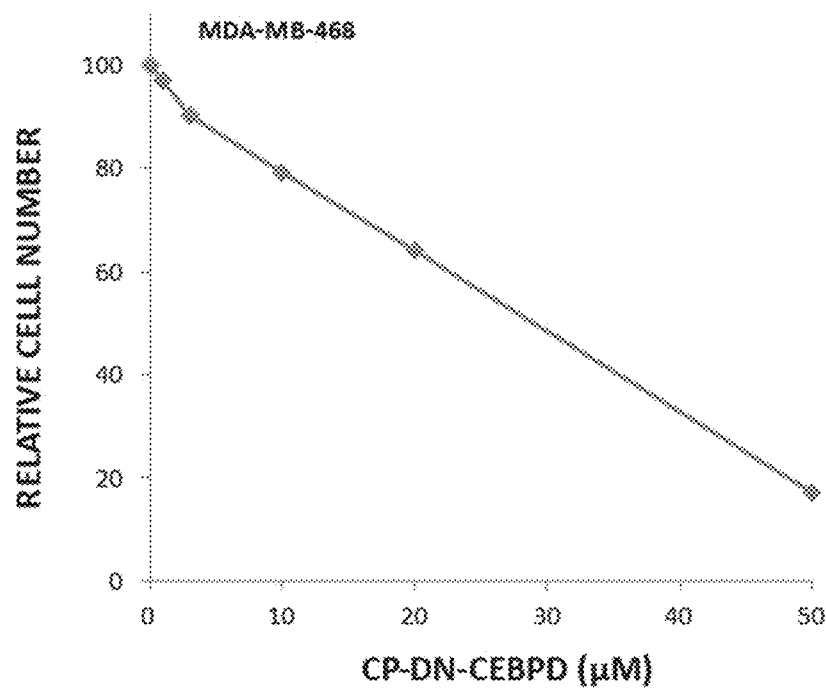

FIG. 10B is a graph reporting exemplary quantification of relative numbers of MDA-MB-468 breast cancer cells following 6 days treatment with a cell penetrating dominant negative CEBPD (CP-DN-CEBPD) at doses of 0 µM to 50 µM.

Figure 10C:
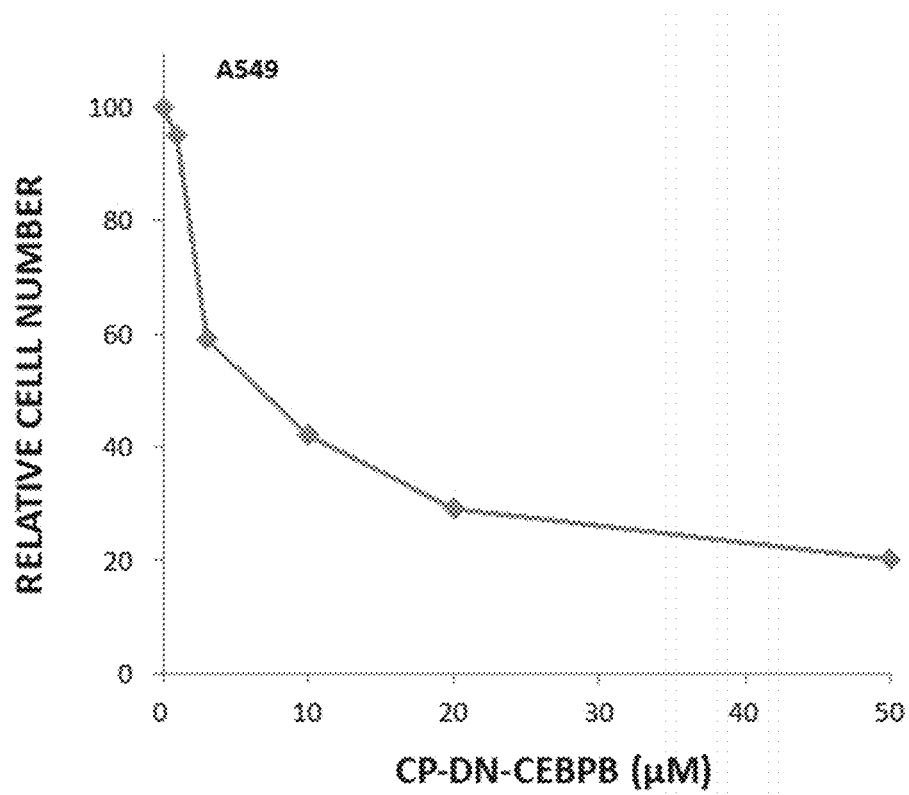

FIG. 10C is a graph reporting exemplary quantification of relative numbers of A549 lung cancer cells following 6 days treatment with a cell penetrating dominant negative CEBPB (CP-DN-CEBPB) at doses of 0 µM to 50 µM.

Figure 10D:
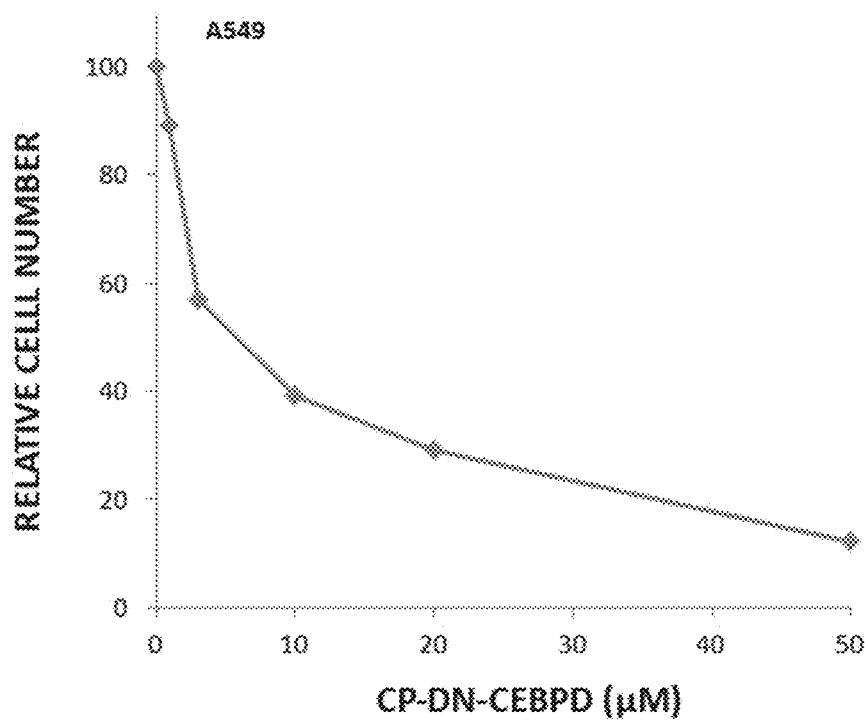

FIG. 10D is a graph reporting exemplary quantification of relative numbers of A549 lung cancer cells following 6 days treatment with a cell penetrating dominant negative CEBPD (CP-DN-CEBPD) at doses of 0 µM to 50 µM.

Figure 10E:
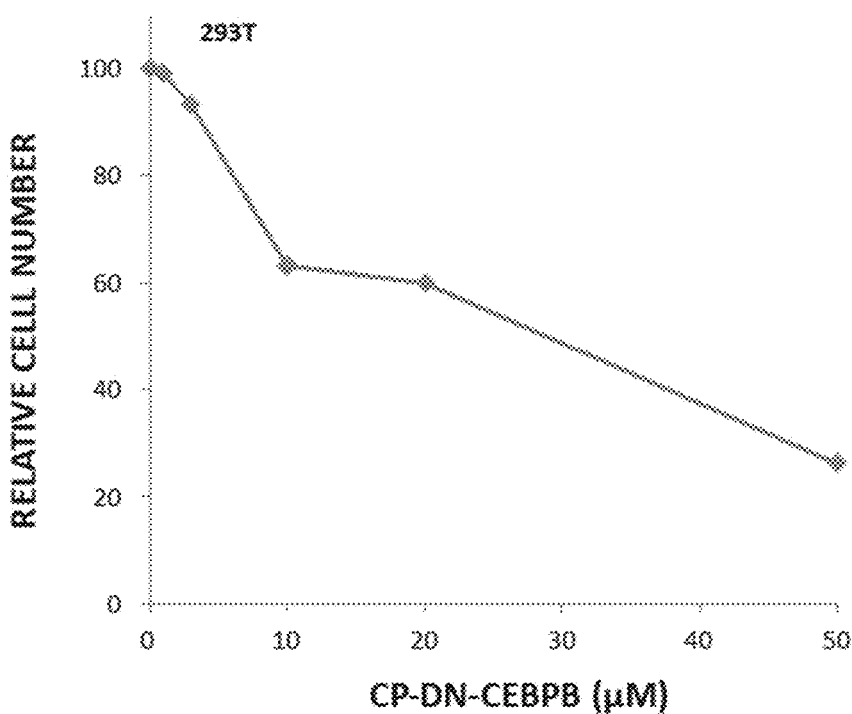

FIG. 10E is a graph reporting exemplary quantification of relative numbers of 293T transformed embryonic kidney cells following 6 days treatment with a cell penetrating dominant negative CEBPB (CP-DN-CEBPB) at doses of 0 µM to 50 µM.

Figure 10F:
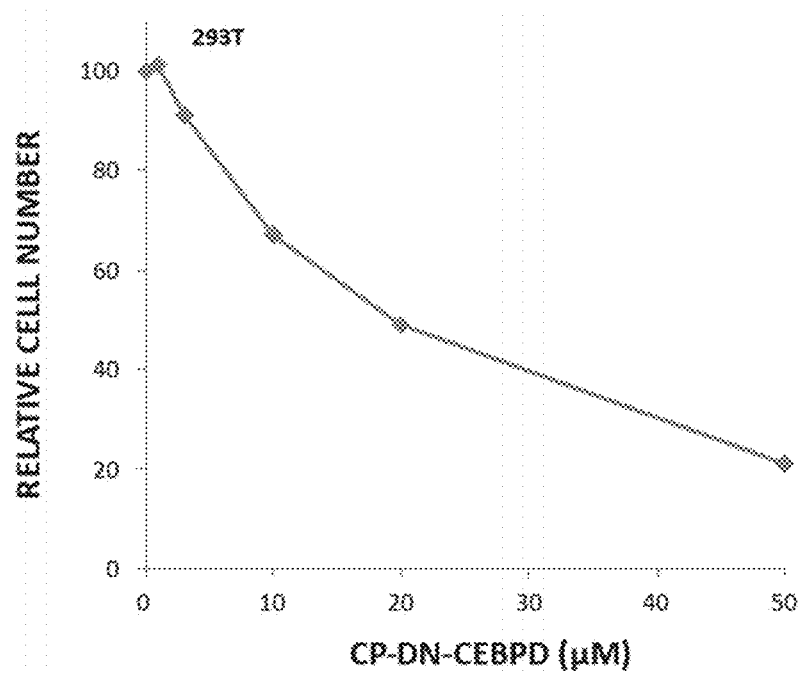

FIG. 10F is a graph reporting exemplary quantification of relative numbers of 293T transformed embryonic kidney cells following 6 days treatment with a cell penetrating dominant negative CEBPD (CP-DN-CEBPD) at doses of 0 µM to 50 µM.

Figure 11A:
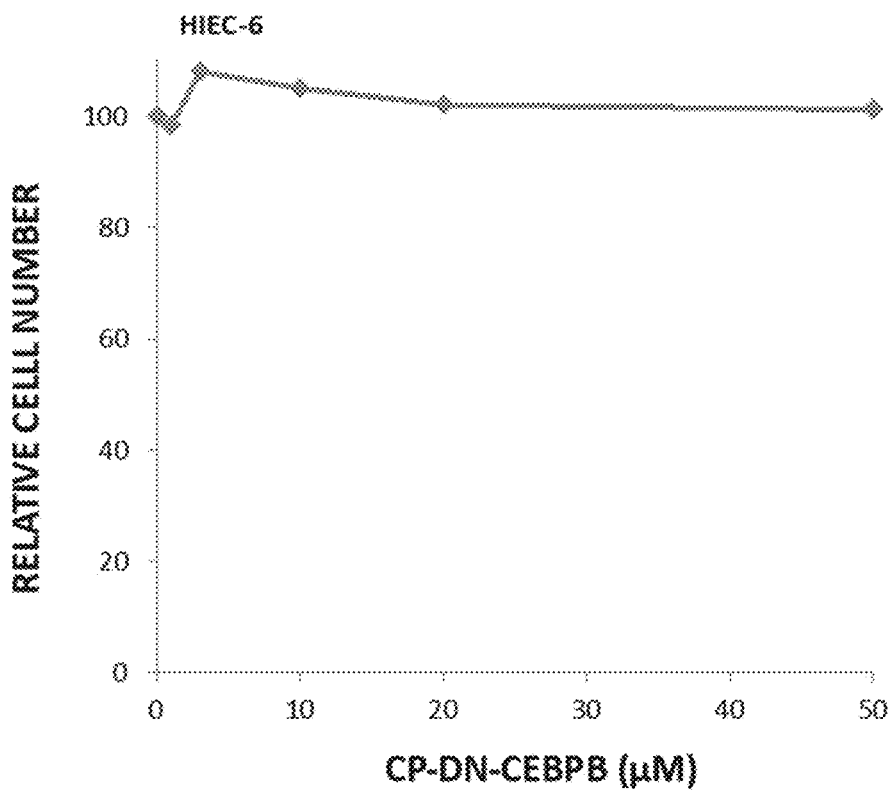

FIG. 11A is a graph reporting exemplary quantification of relative numbers of HIEC-6 non-cancer human intestinal epithelial cells following 6 days treatment with a cell penetrating dominant negative CEBPB (CP-DN-CEBPB) at doses of 0 µM to 50 µM.

Figure 11B:
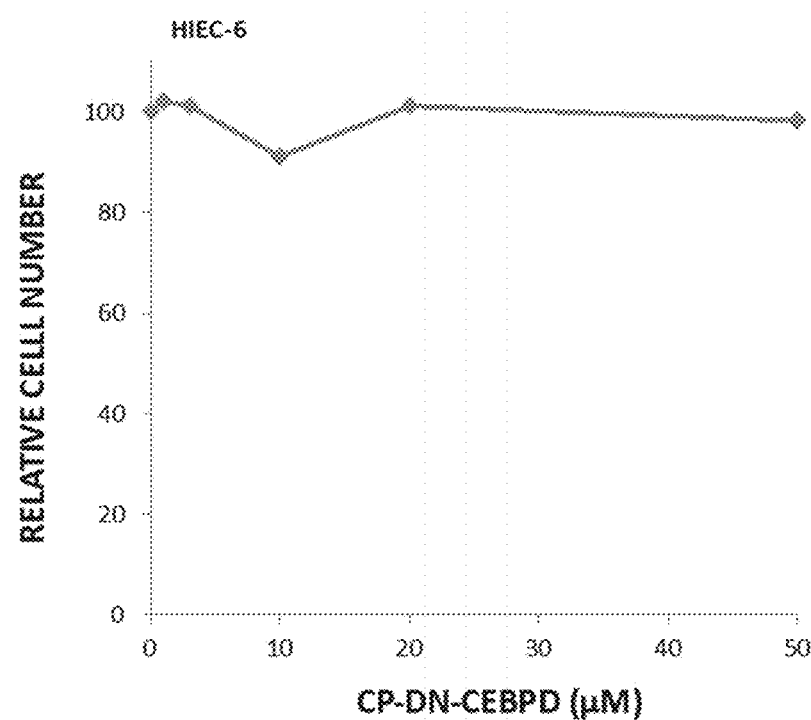

FIG. 11B is a graph reporting exemplary quantification of relative numbers of HIEC-6 non-cancer human intestinal epithelial cells following 6 days treatment with a cell penetrating dominant negative CEBPD (CP-DN-CEBPD) at doses of 0 µM to 50 µM.

Figure 11C:
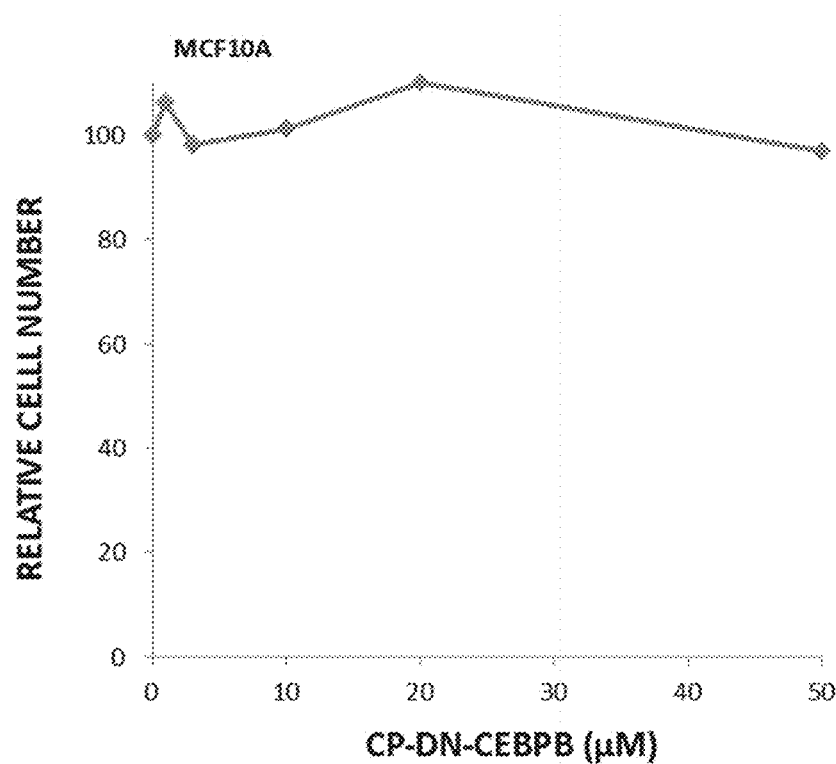

FIG. 11C is a graph reporting exemplary quantification of relative numbers of MCF10A non-cancer human breast epithelial cells following 6 days treatment with a cell penetrating dominant negative CEBPB (CP-DN-CEBPB) at doses of 0 µM to 50 µM.

Figure 11D:
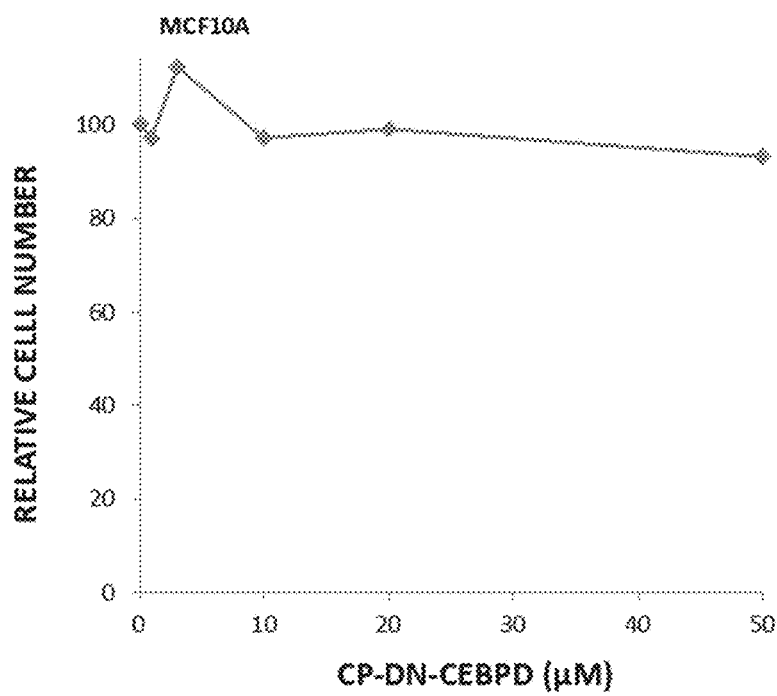

FIG. 11D is a graph reporting exemplary quantification of relative numbers of MCF10A non-cancer human breast epithelial cells following 6 days treatment with a cell penetrating dominant negative CEBPD (CP-DN-CEBPD) at doses of 0 µM to 50 µM.

Figure 12:
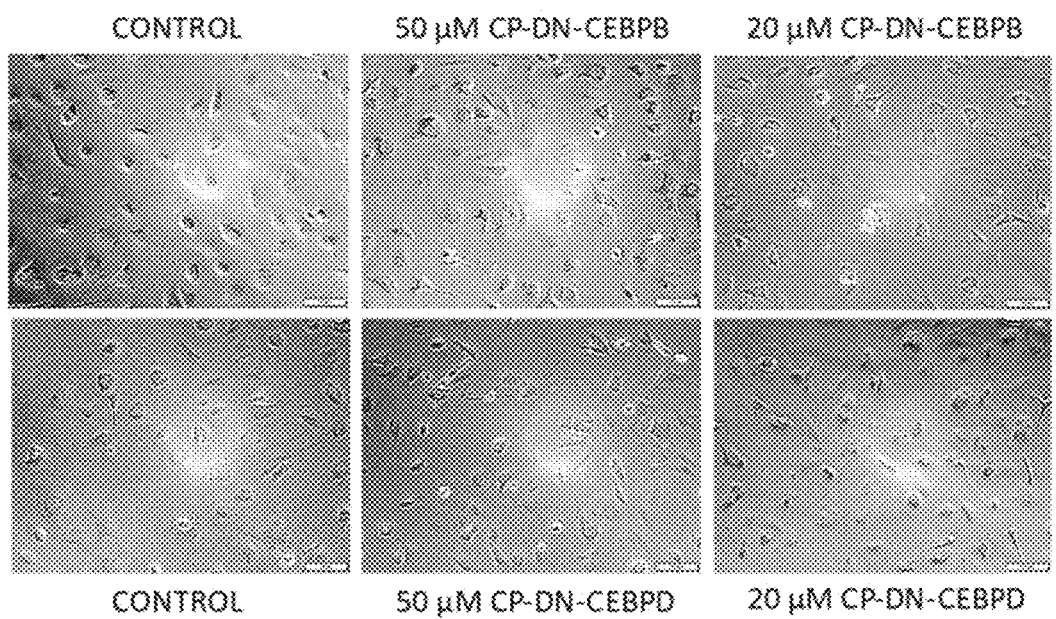

FIG. 12 is a set of exemplary micrograph images of cultured HIEC-6 cells, either untreated (Control), or treated with a cell penetrating dominant negative CEBPB (CP-DN-CEBPB) at 50 µM or 20 µM doses, or cell penetrating dominant negative CEBPD (CP-DN-CEBPD) at 50 µM, 20 µM doses.

Figure 13:
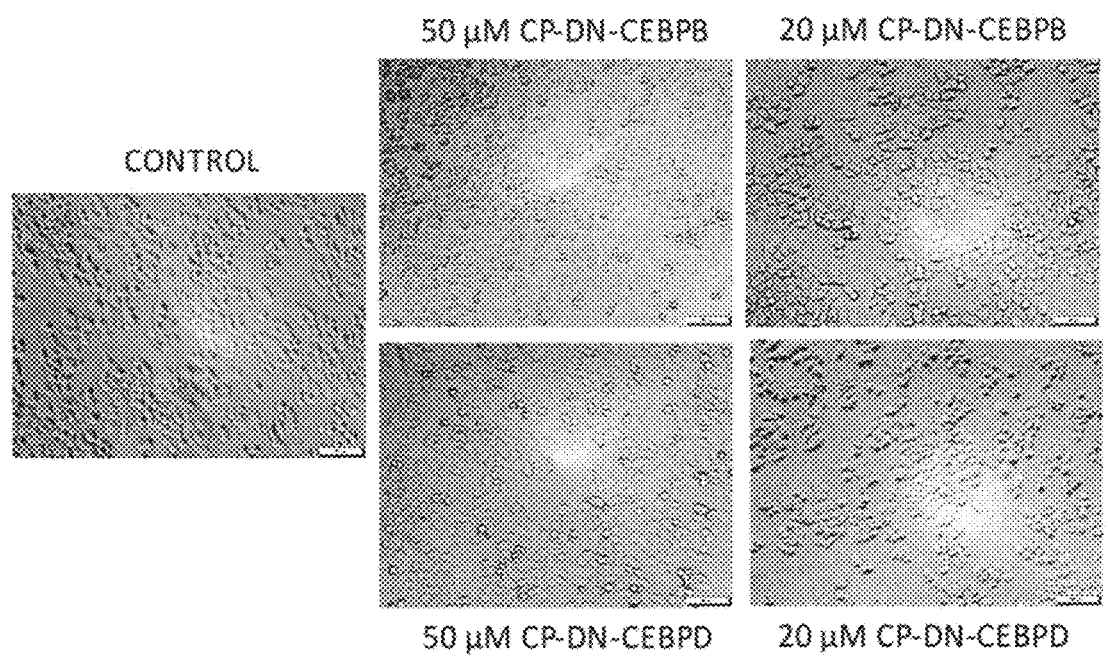

FIG. 13 is a set of exemplary micrograph images of cultured MCF10A cells, either untreated (Control), or treated with a cell penetrating dominant negative CEBPB (CP-DN-CEBPB) at 50 µM or 20 µM doses, or cell penetrating dominant negative CEBPD (CP-DN-CEBPD) at 50 µM or 20 µM doses.

Figure 14:
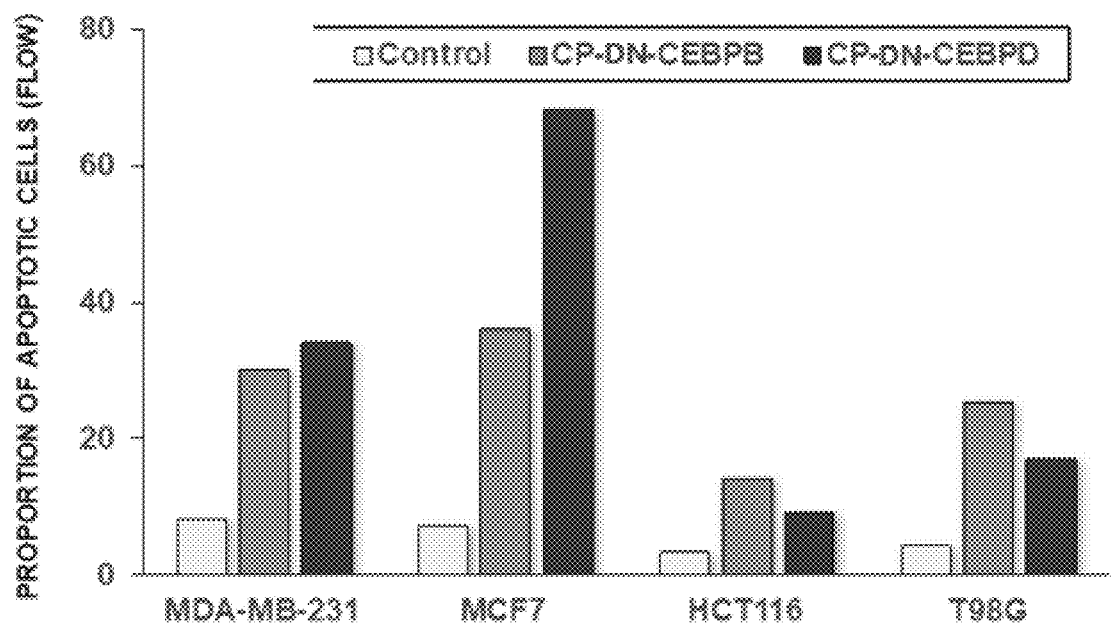

FIG. 14 is a graph reporting exemplary quantification of the proportion of apoptotic MDA-MB-231, MCF7, HCT116 and T98G cancer cell lines after 3 days treatment with 20 µM CP-DN-CEBPB and CP-DN-CEBPD, compared to untreated control cells.

Figure 15A:
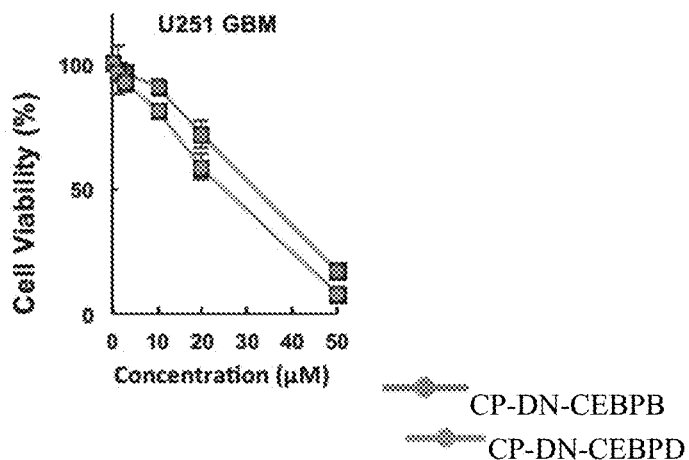

FIG. 15A is a graph reporting exemplary quantification of relative numbers of U251 gliblastoma multiforme cells following 6 days treatment with CP-DN-CEBPB or CP-DN-CEBPD at doses of 0 µM to 50 µM.

Figure 15B:
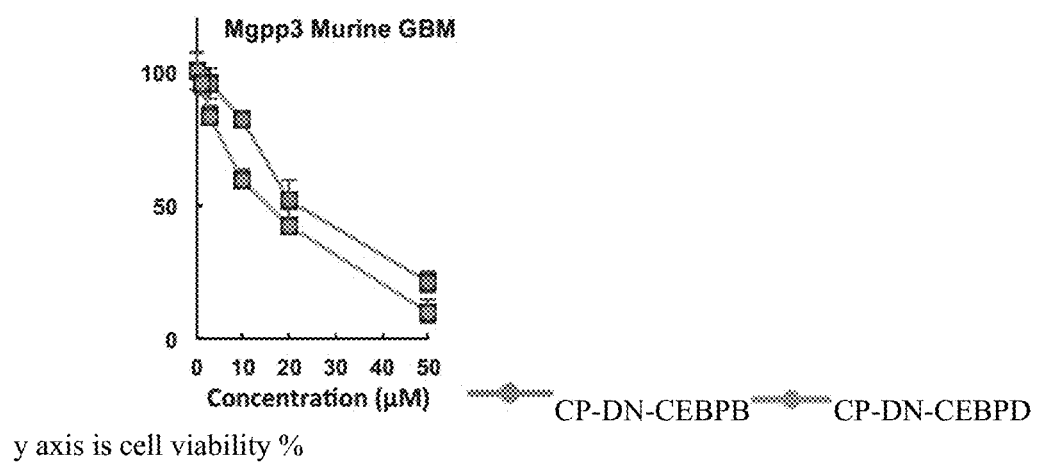

FIG. 15B is a graph reporting exemplary quantification of relative numbers of Mgpp3 murine proneural glioma cells following 6 days treatment with CP-DN-CEBPB or
CP-DN-CEBPD at doses of 0 µM to 50 µM.

Figure 15C:
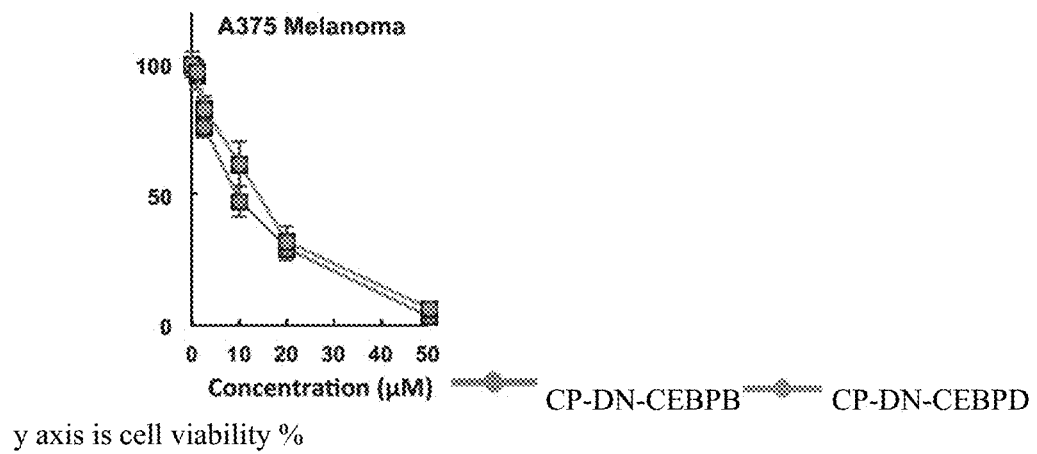

FIG. 15C is a graph reporting exemplary quantification of relative numbers of A375 melanoma cells following 6 days treatment with CP-DN-CEBPB or CP-DN-CEBPD at doses of 0 µM to 50 µM.

Figure 15D:
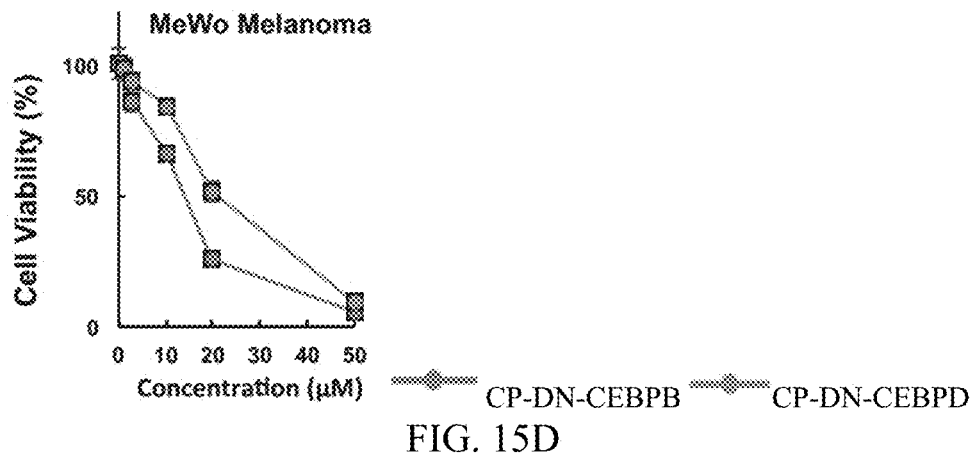

FIG. 15D is a graph reporting exemplary quantification of relative numbers of B16 murine melanoma cells following 6 days treatment with CP-DN-CEBPB or CP-DN-CEBPD at doses of 0 µM to 50 µM.

Figure 15E:
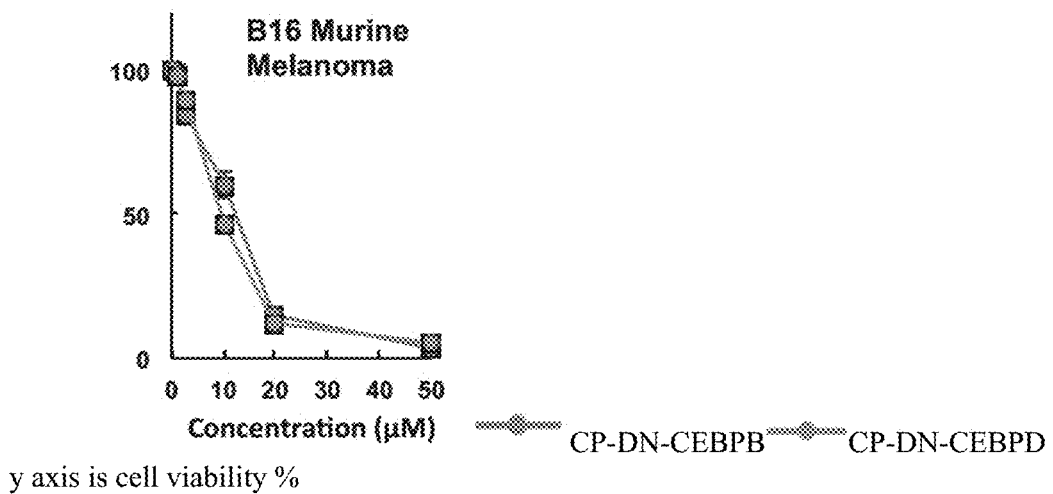

FIG. 15E is a graph reporting exemplary quantification of relative numbers of T98G murine melanoma cells following 6 days treatment with CP-DN-CEBPB or CP-DN-CEBPD at doses of 0 µM to 50 µM.

Figure 16A:
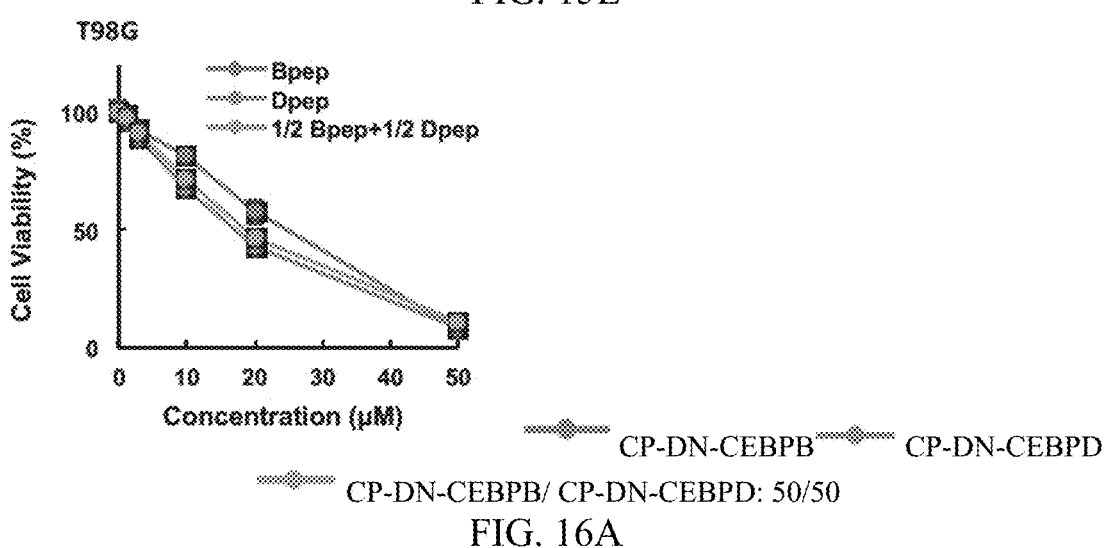

FIG. 16A is a graph reporting exemplary quantification of the relative numbers of T98G glioblastoma cells following 6 days treatment with CP-DN-CEBPB, CP-DN-CEBPD or a 50/50 (by concentration) mixture of CP-DN-CEBPB and CP-DN-CEBPD at doses of 0 µM to 50 µM.

Figure 16B:
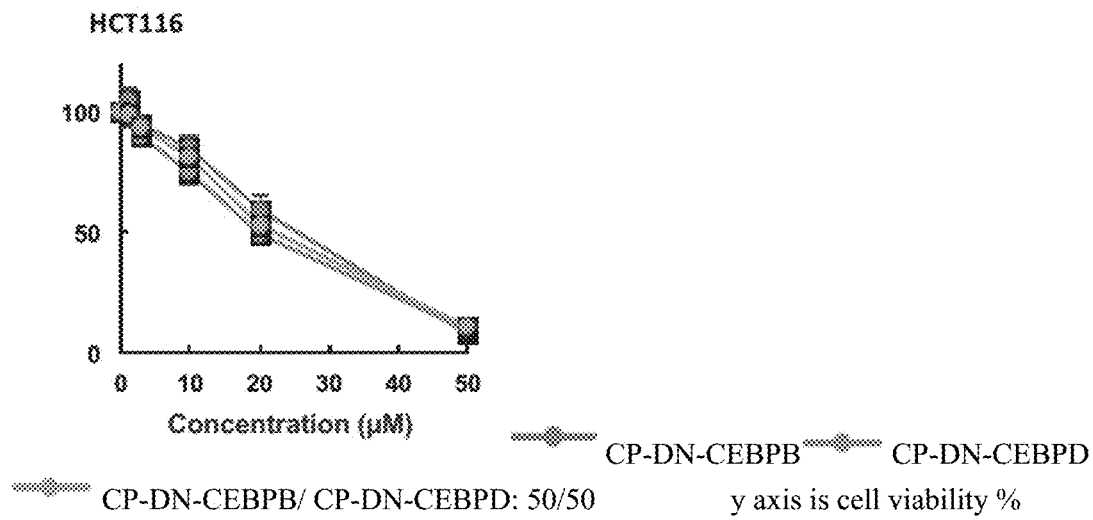

FIG. 16B is a graph reporting exemplary quantification of the relative numbers of HCT116 colon cancer cells following 6 days treatment with CP-DN-CEBPB, CP-DN-CEBPD or a 50/50 (by concentration) mixture of CP-DN-CEBPB and CP-DN-CEBPD at doses of 0 µM to 50 µM.

Figure 16C:
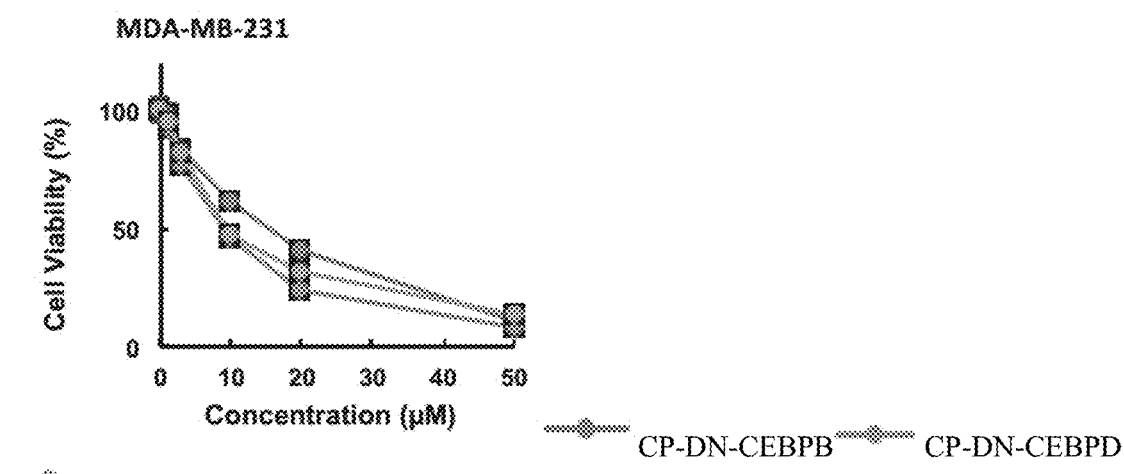

FIG. 16C is a graph reporting exemplary quantification of the relative numbers of MDA-MB-231 breast cancer cells following 6 days treatment with CP-DN-CEBPB, CP-DN-CEBPD or a 50/50 (by concentration) mixture of CP-DN-CEBPB and CP-DN-CEBPD at doses of 0 µM to 50 µM.

Figure 16D:
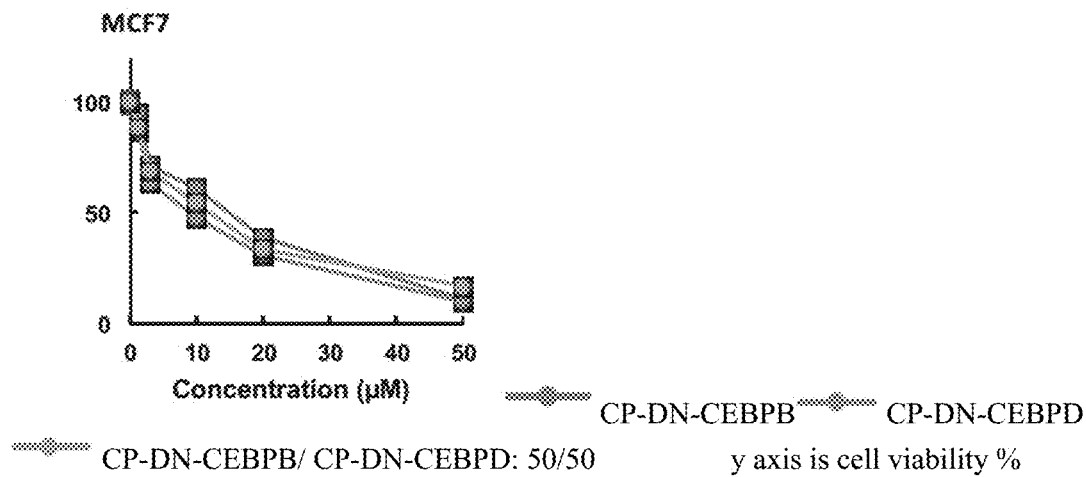

FIG. 16D is a graph reporting exemplary quantification of the relative numbers of MCF7 breast cancer cells following 6 days treatment with CP-DN-CEBPB, CP-DN-CEBPD or a 50/50 (by concentration) mixture of CP-DN-CEBPB and CP-DN-CEBPD at doses of 0 μM to 50 μM.

Figure 17A:
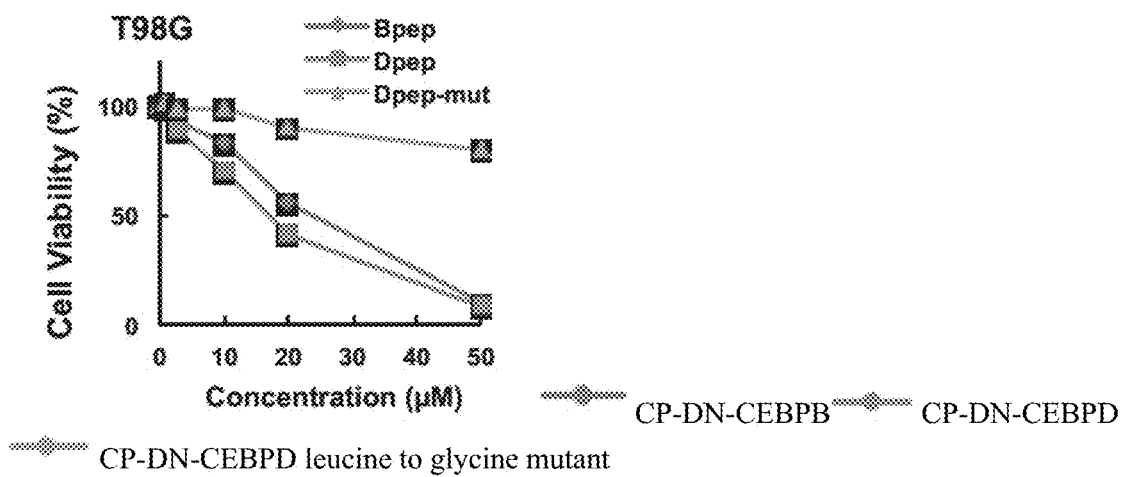

FIG. 17A is a graph reporting exemplary quantification of the relative numbers of TG98 glioblastoma cells following 6 days treatment with CP-DN-CEBPB, CP-DN-CEBPD or a CP-DN-CEBPB in which heptad repeat leucine residues in the leucine zipper were replaced with glycine.

Figure 17B:
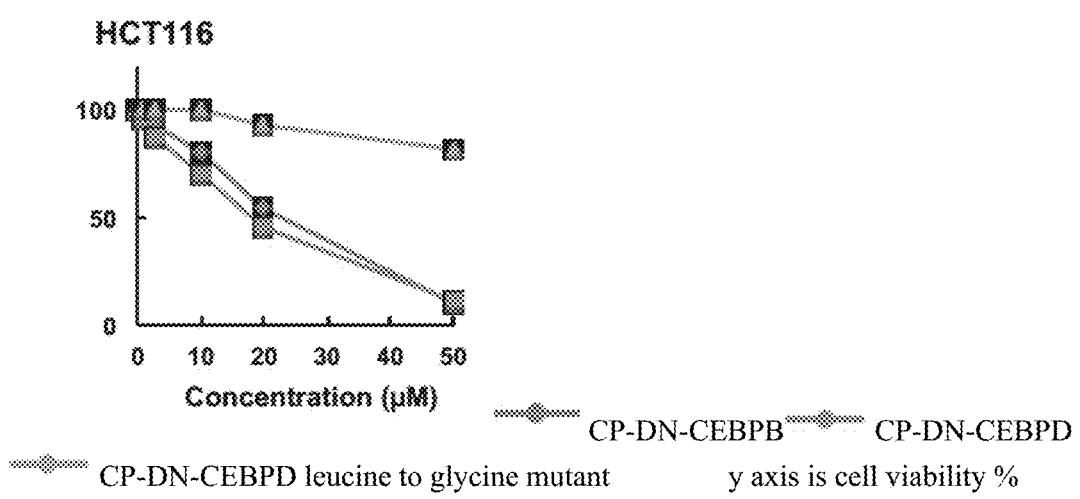

FIG. 17B is a graph reporting exemplary quantification of the relative numbers of HCT116 colon cancer cells following 6 days treatment with CP-DN-CEBPB, CP-DN-CEBPD or a CP-DN-CEBPB in which heptad repeat leucine residues in the leucine zipper were replaced with glycine.

Figure 17C:
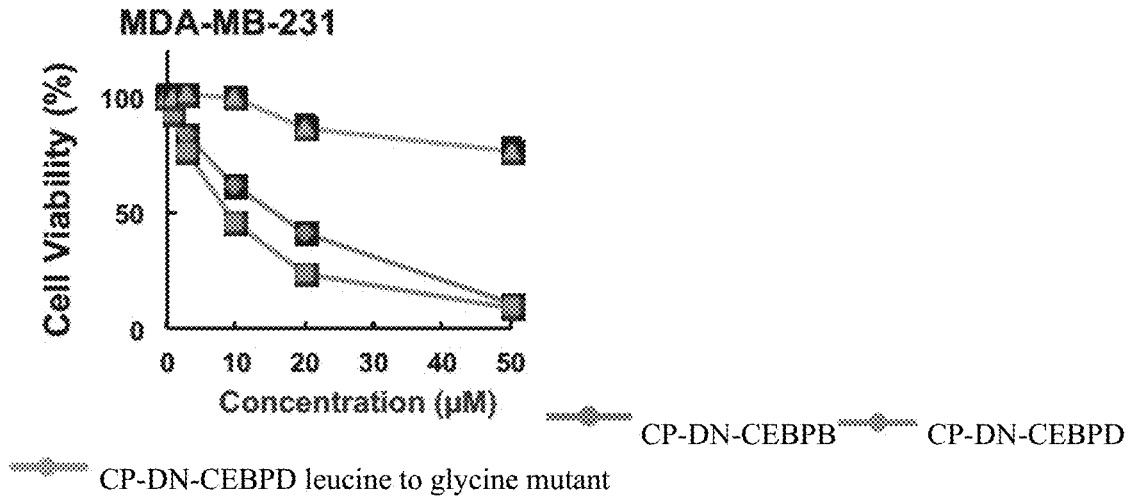

FIG. 17C is a graph reporting exemplary quantification of the relative numbers of MDA-MB-231 breast cancer cells following 6 days treatment with CP-DN-CEBPB, CP-DN-CEBPD or a CP-DN-CEBPB in which heptad repeat leucine residues in the leucine zipper were replaced with glycine.

Figure 17D:
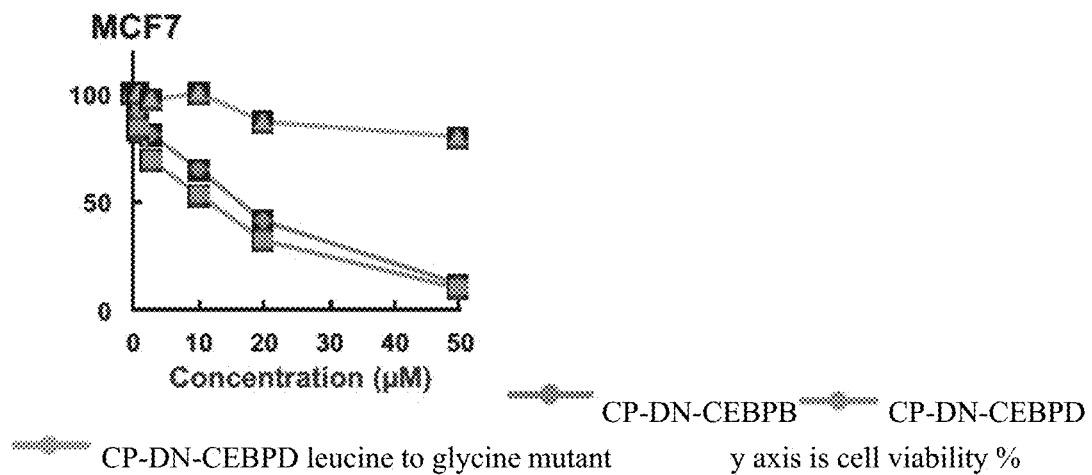

FIG. 17D is a graph reporting exemplary quantification of the relative numbers of MCF7 breast cancer cells following 6 days treatment with CP-DN-CEBPB, CP-DN-CEBPD or a CP-DN-CEBPB in which heptad repeat leucine residues in the leucine zipper were replaced with glycine.

Figure 18:
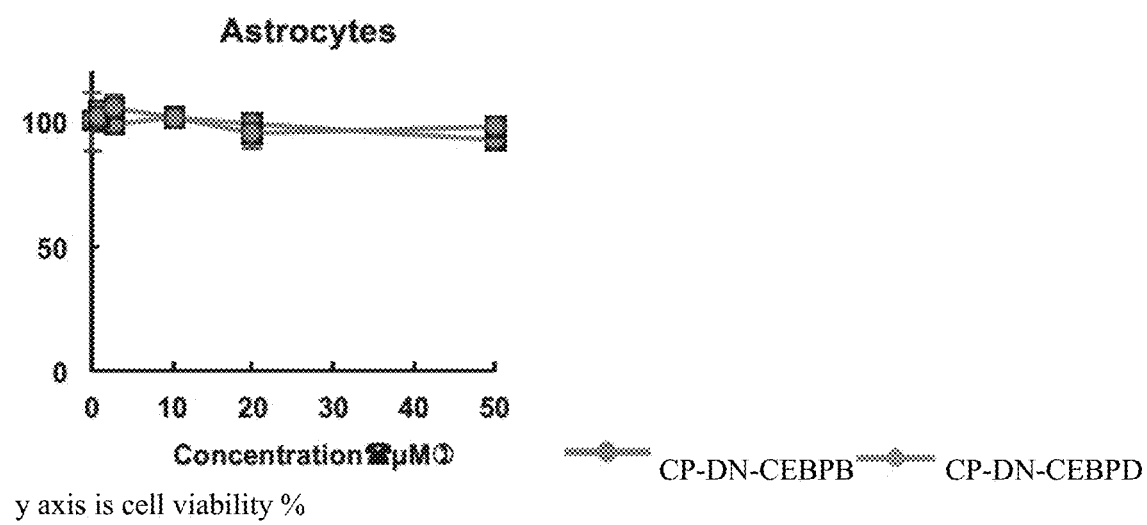

FIG. 18 is a graph reporting exemplary quantification of the relative numbers of cultured human astrocytes treated with CP-DN-CEBPB or CP-DN-CEBPD.

Figure 19:
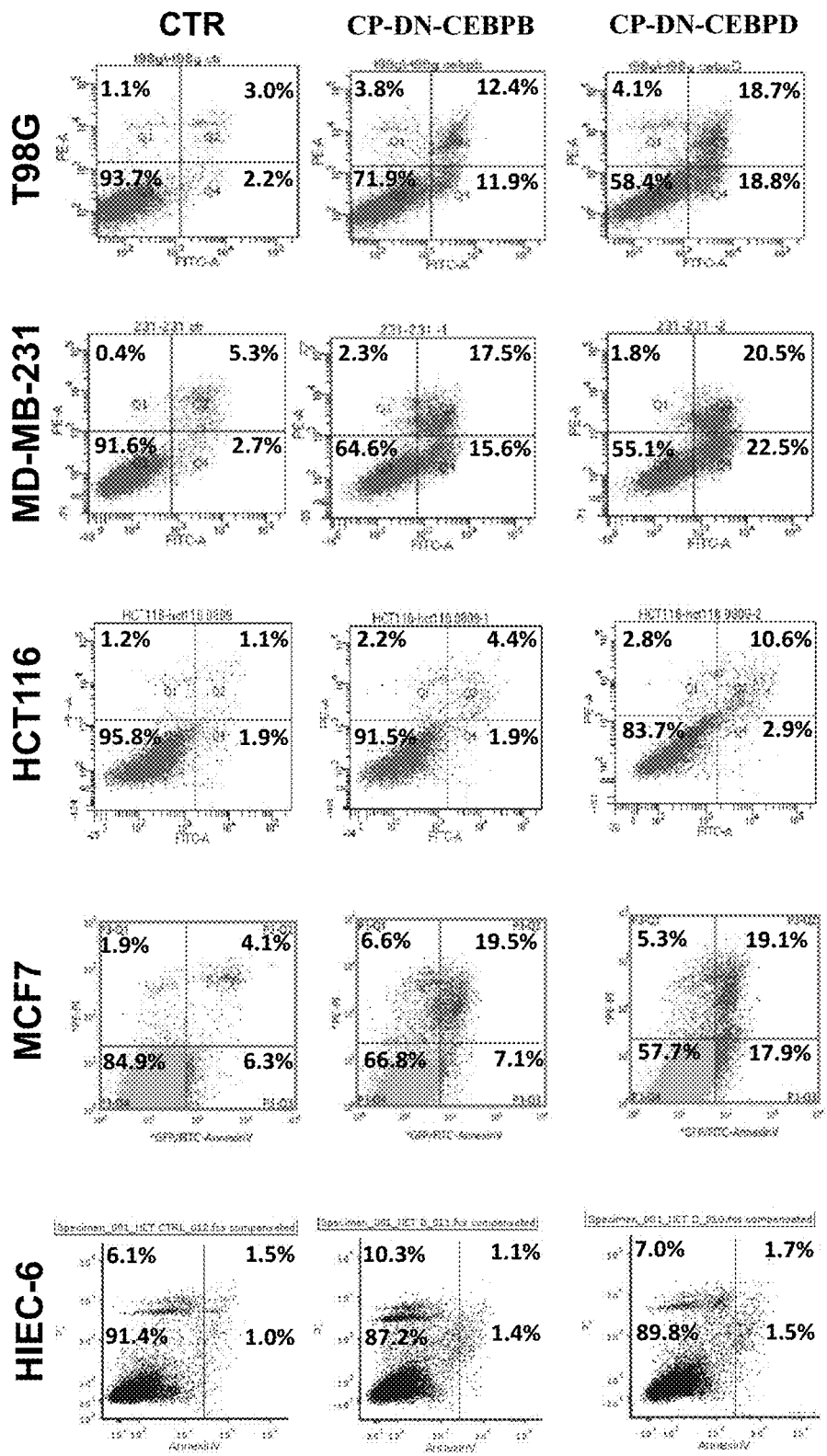

FIG. 19 is a set of exemplary flow cytometry plots showing levels of apoptosis for T98G, MDA-MB-231, HCT116, MCF7, or HIEC-6 cells following 3 days treatment with 20 μM CP-DN-CEBPB, CP-DN-CEBPD, or a control treatment. Values in each quadrant indicate % of apoptotic cells relative to total cells.

Figure 20A:
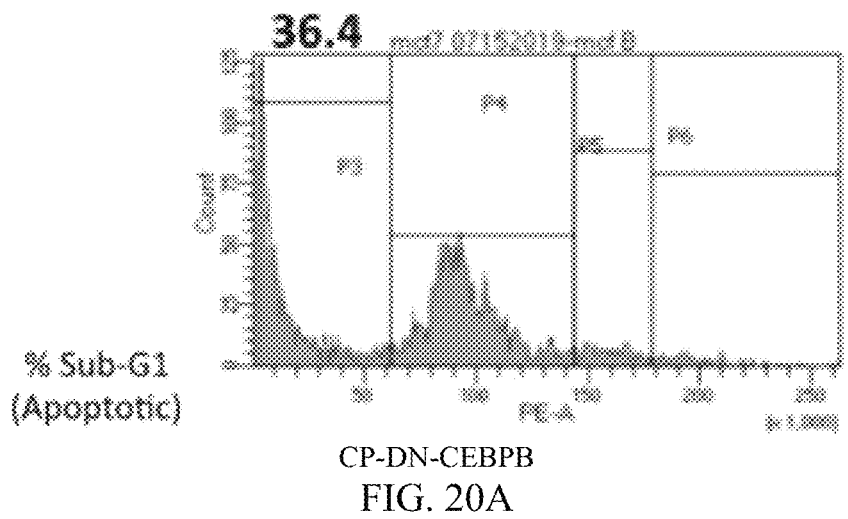

FIG. 20A is a graph reporting exemplary quantifications of subG1 DNA levels in MCF7 cells following 3 days treatment with 20 M CP-DN-CEBPB.

Figure 20B:
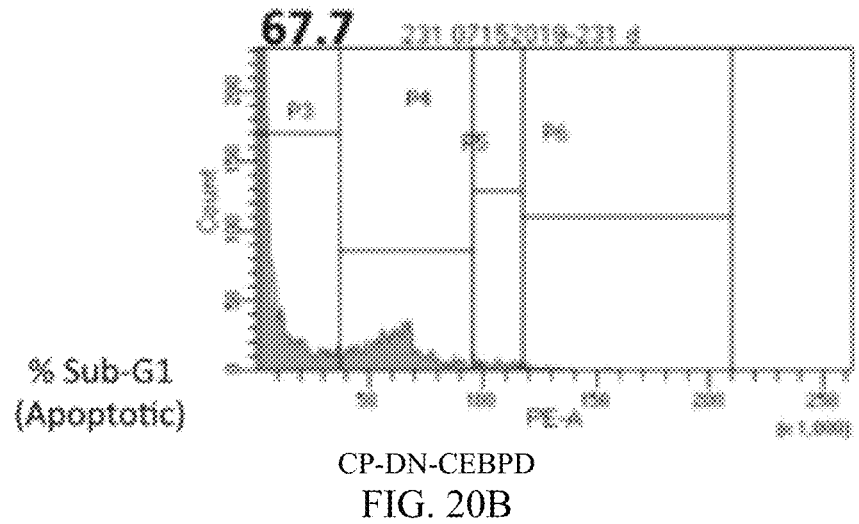

FIG. 20B is a graph reporting exemplary quantifications of subG1 DNA levels in MCF7 cells following 3 days treatment with 20 M CP-DN-CEBPD.

Figure 20C:
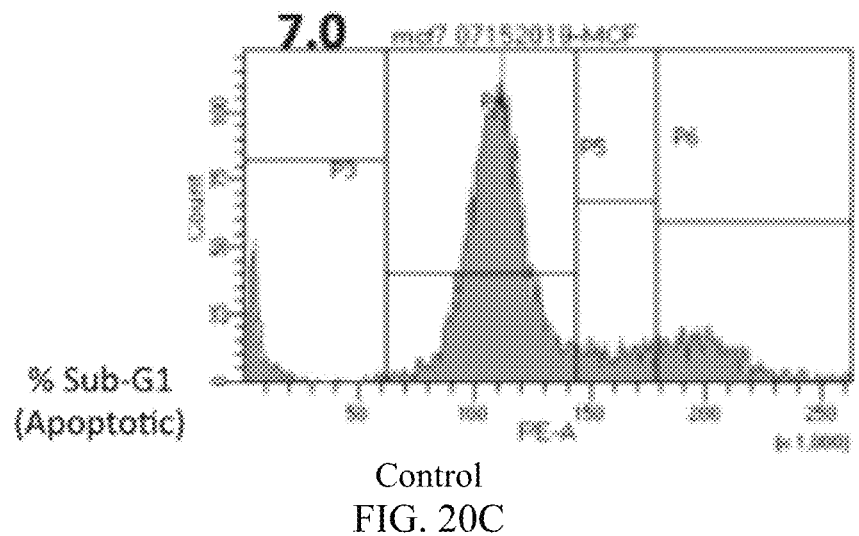

FIG. 20C is a graph reporting exemplary quantifications of subG1 DNA levels in MCF7 cells following 3 days treatment with a control for FIGS. 20A and 20B.

Figure 20D:
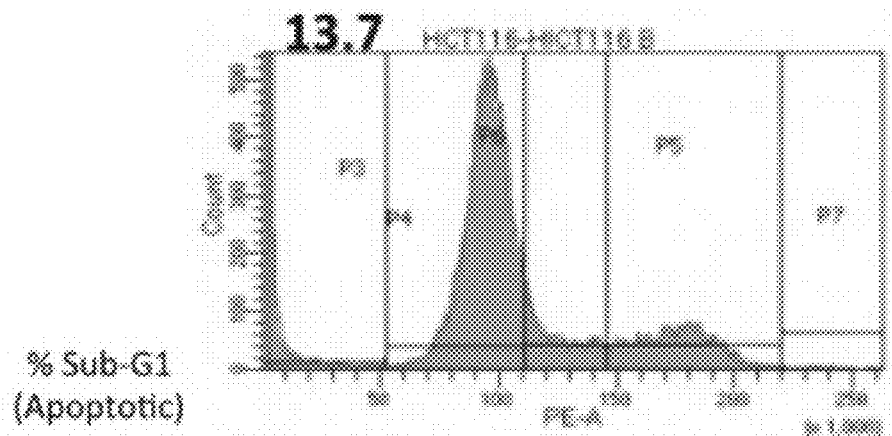

FIG. 20D is a graph reporting exemplary quantifications of subG1 DNA levels in HCT116 cells following 3 days treatment with 20 M CP-DN-CEBPB.

Figure 20E:
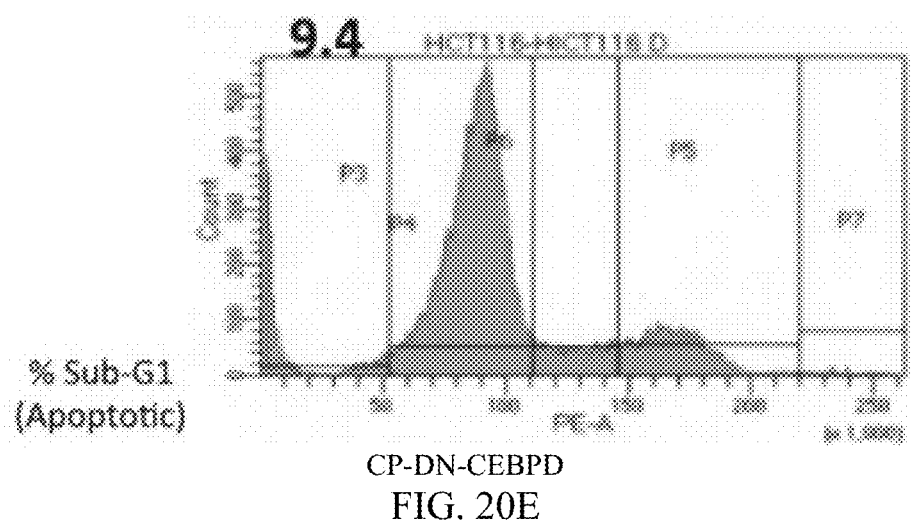

FIG. 20E is a graph reporting exemplary quantifications of subG1 DNA levels in HCT116 cells following 3 days treatment with 20 M CP-DN-CEBPD.

Figure 20F:
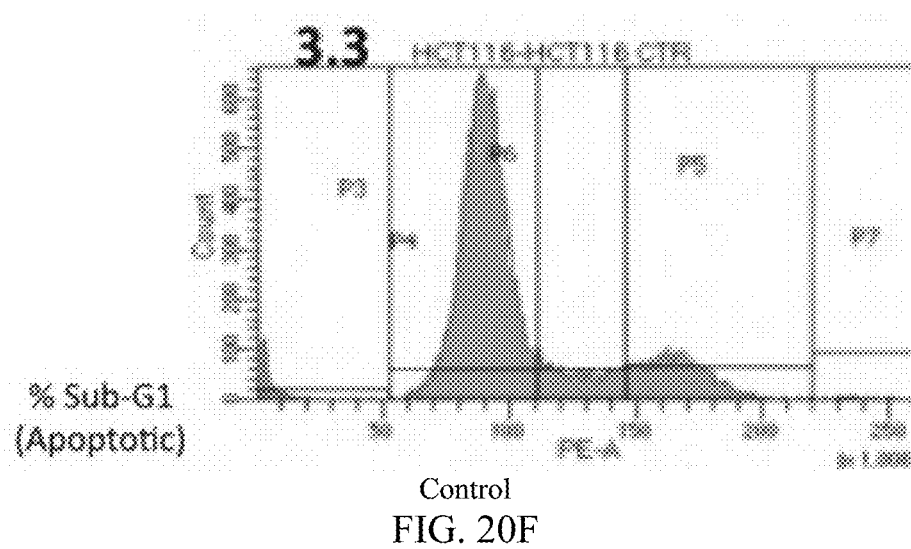

FIG. 20F is a graph reporting exemplary quantifications of subG1 DNA levels in HCT116 cells following 3 days treatment with a control for FIGS. 20D and 20E.

Figure 20G:
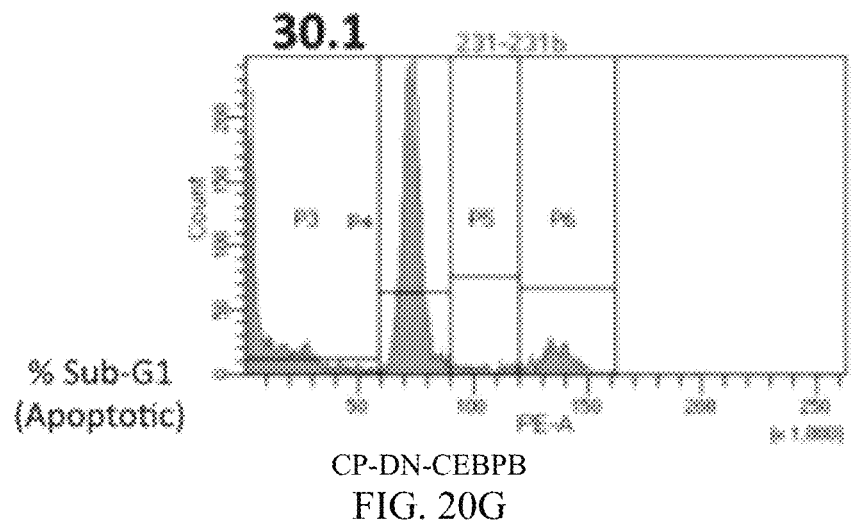

FIG. 20G is a graph reporting exemplary quantifications of subG1 DNA levels in MDA-MB-231 cells following 3 days treatment with 20 M CP-DN-CEBPB.

Figure 20H:
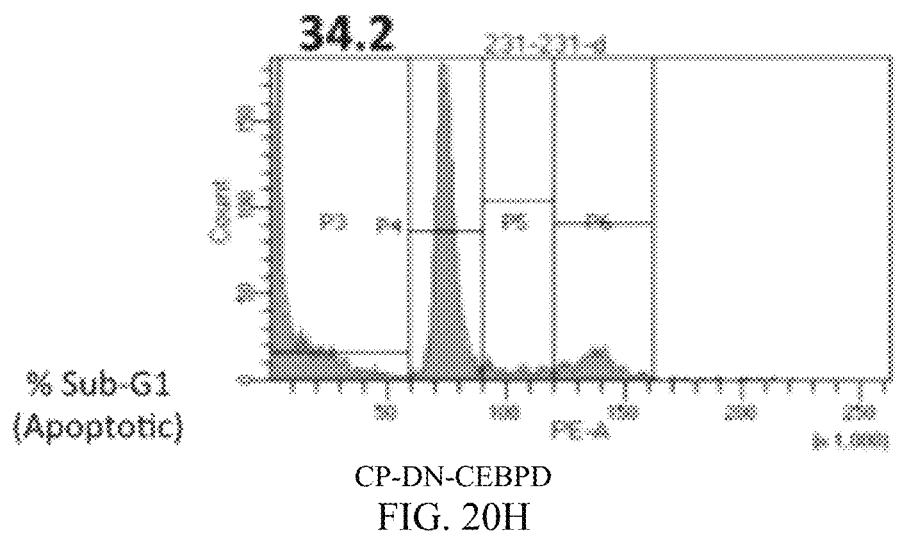

FIG. 20H is a graph reporting exemplary quantifications of subG1 DNA levels in MDA-MB-231 cells following 3 days treatment with 20 M CP-DN-CEBPD.

Figure 20I:
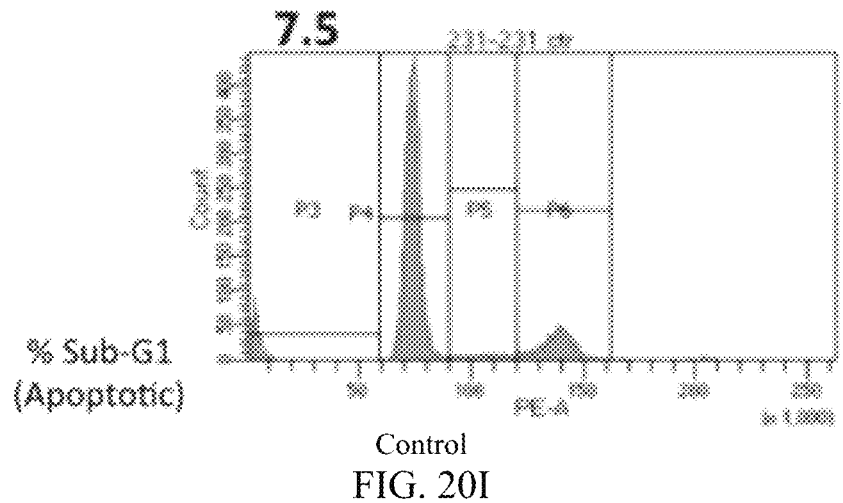

FIG. 20I is a graph reporting exemplary quantifications of subG1 DNA levels in MDA-MB-231 cells following 3 days treatment with a control for FIGS. 20G and 20H.

Figure 20J:
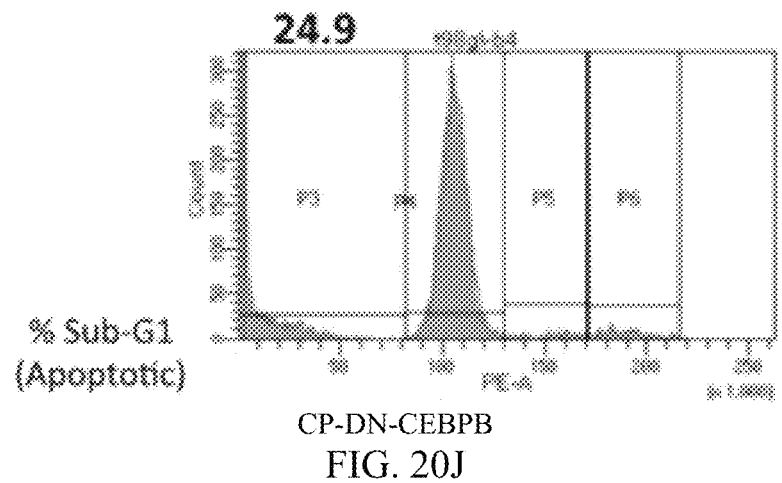

FIG. 20J is a graph reporting exemplary quantifications of subG1 DNA levels in T98G cells following 3 days treatment with 20 M CP-DN-CEBPB.

Figure 20K:
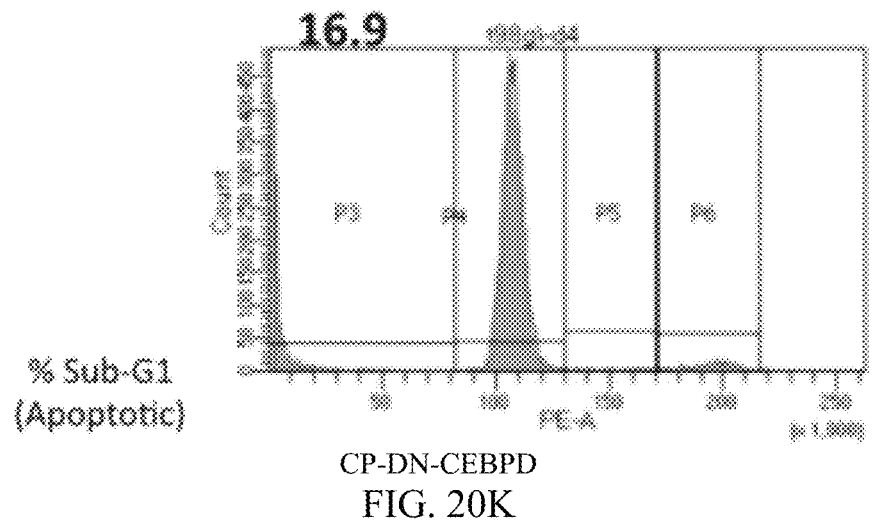

FIG. 20K is a graph reporting exemplary quantifications of subG1 DNA levels in T98G cells following 3 days treatment with 20 M CP-DN-CEBPD.

Figure 20L:
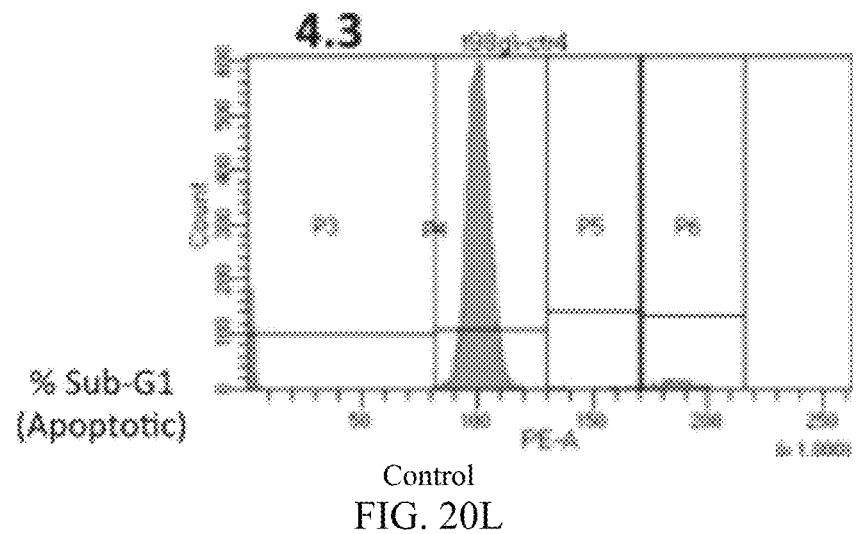

FIG. 20L is a graph reporting exemplary quantifications of subG1 DNA levels in T98G cells following 3 days treatment with a control for FIGS. 20J and 20K.

Figure 21A:
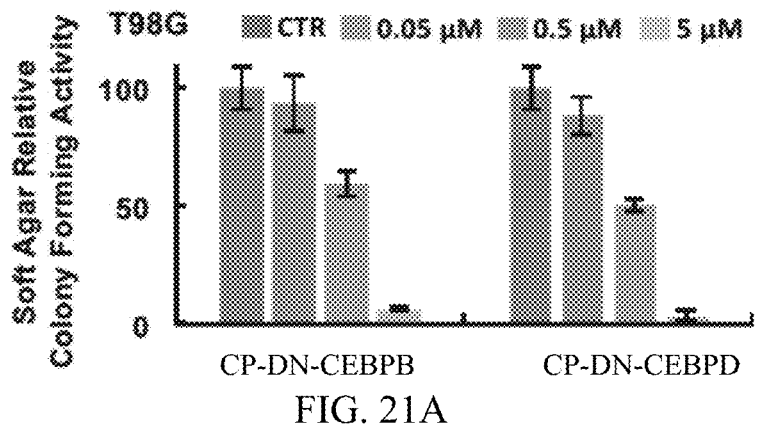

FIG. 21A is a graph reporting exemplary quantifications of relative colony forming activity of T98G cells at various concentrations of CP-DN-CEBPB, CP-DN-CEBPD, or a control treatment in soft agar.

Figure 21B:
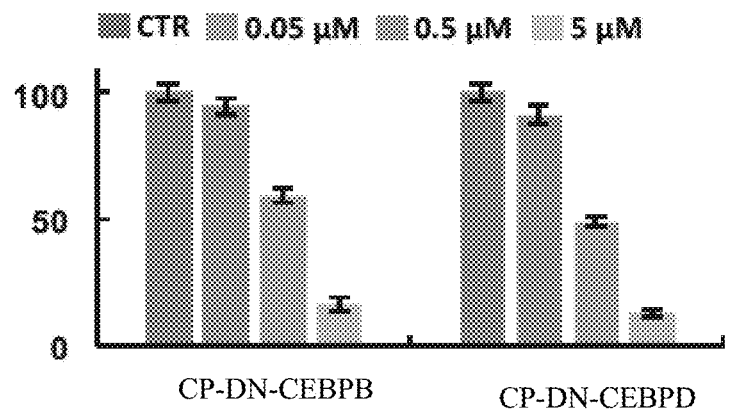

FIG. 21B is a graph reporting exemplary quantifications of relative colony forming activity of MDA-MB-231 cells at various concentrations of CP-DN-CEBPB, CP-DN-CEBPD, or a control treatment in soft agar.

Figure 21C:
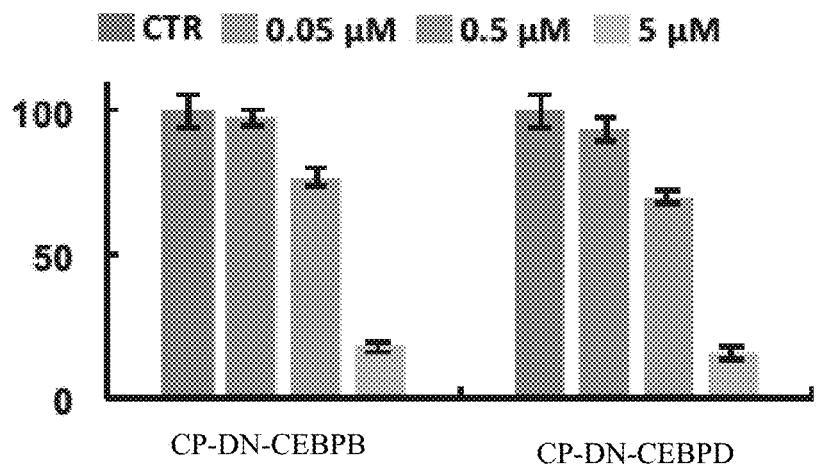

FIG. 21C is a graph reporting exemplary quantifications of relative colony forming activity of HCT116 cells at various concentrations of CP-DN-CEBPB, CP-DN-CEBPD, or a control treatment in soft agar.

Figure 21D:
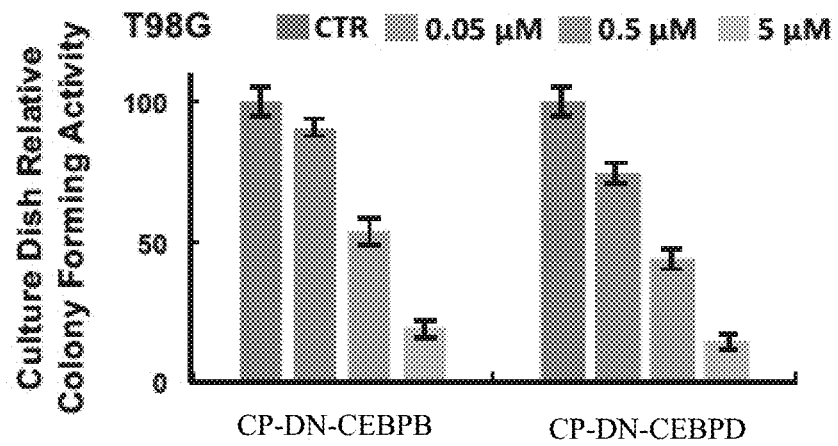

FIG. 21D is a graph reporting exemplary quantifications of relative colony forming activity of T98G cells at various concentrations of CP-DN-CEBPB, CP-DN-CEBPD, or a control treatment in a culture dish.

Figure 21E:
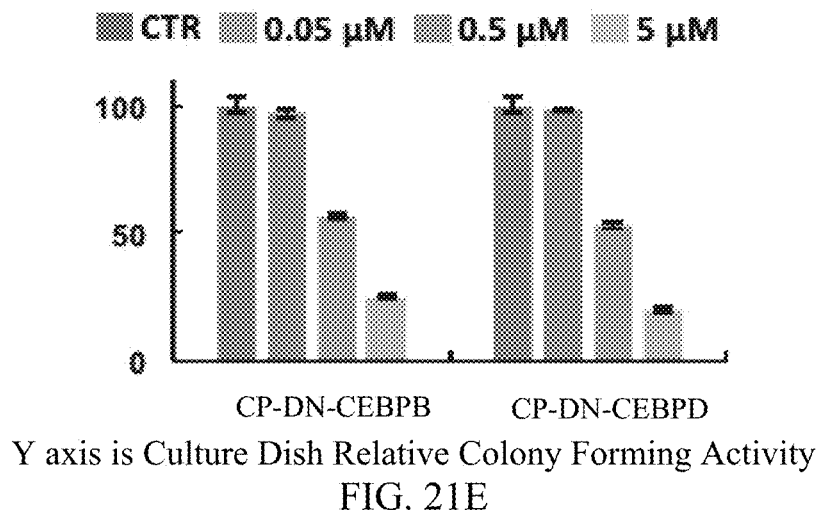

FIG. 21E is a graph reporting exemplary quantifications of relative colony forming activity of MDA-MB-231 cells at various concentrations of CP-DN-CEBPB, CP-DN-CEBPD, or a control treatment in a culture dish.

Figure 21F:
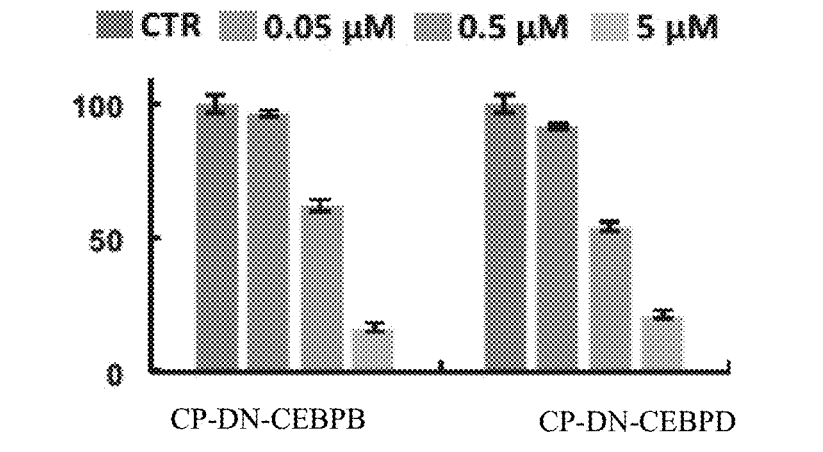

FIG. 21F is a graph reporting exemplary quantifications of relative colony forming activity of HCT116 cells at various concentrations of CP-DN-CEBPB, CP-DN-CEBPD, or a control treatment in a culture dish.

Figure 22A:
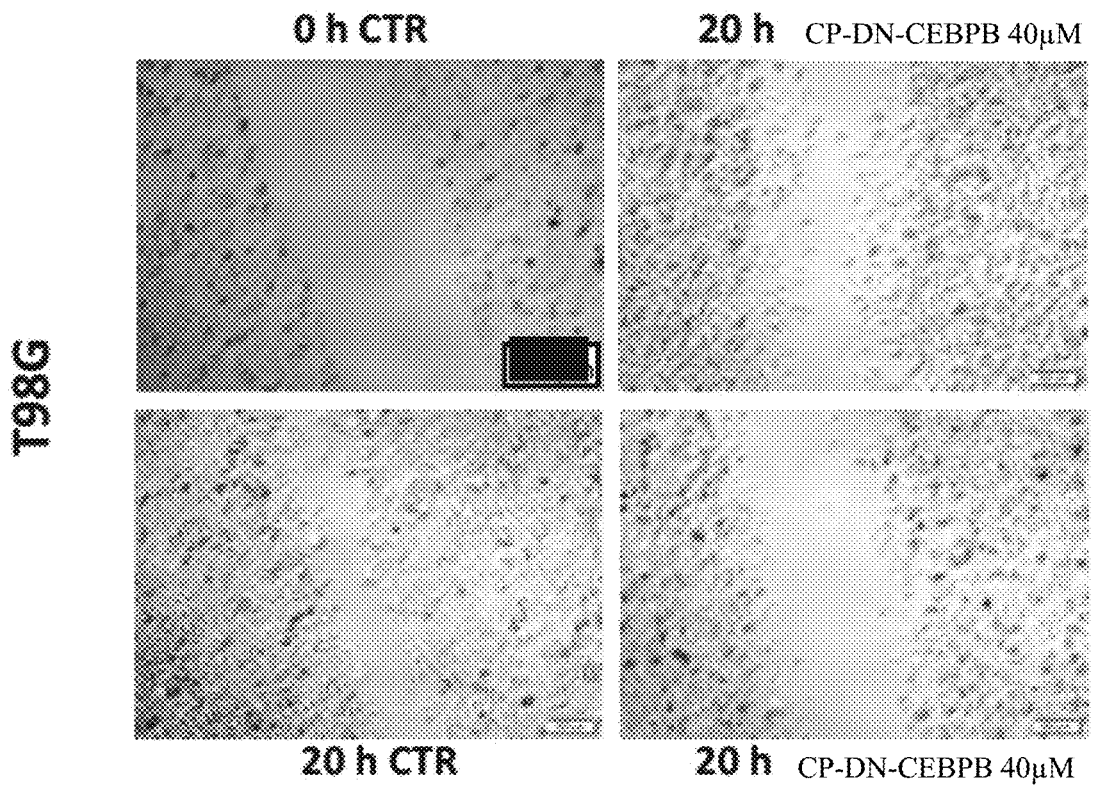

FIG. 22A is a set of exemplary representative photomicrographs showing exemplary T98G cell migration following 20 hours treatment at various concentrations of CP-DN-CEBPB, CP-DN-CEBPD, or control treatments.

Figure 22B:
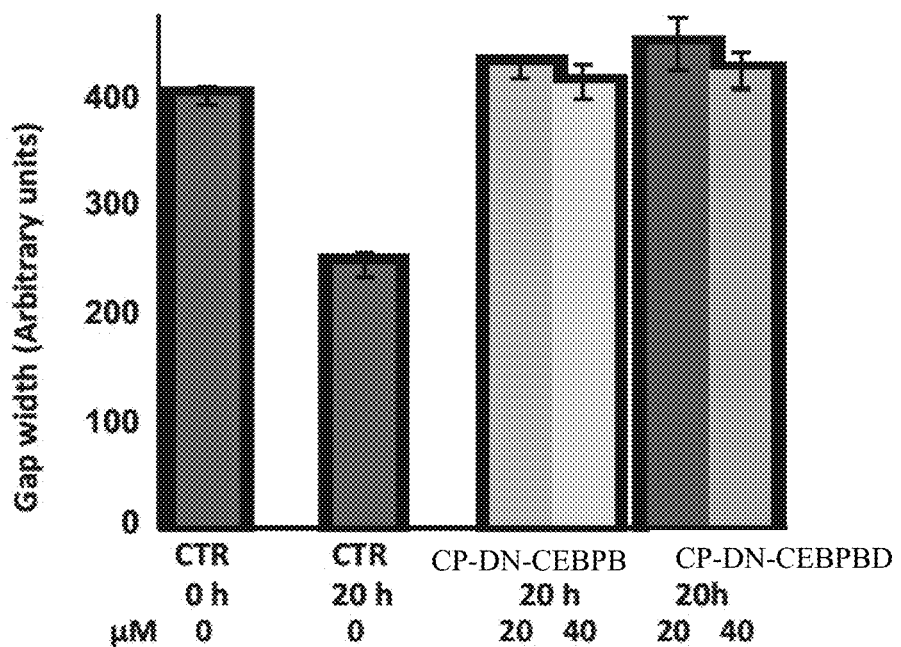

FIG. 22B is a graph reporting exemplary quantification of T98G cell migration following 20 hours treatment at various concentrations of CP-DN-CEBPB, CP-DN-CEBPD, or control treatments.

Figure 22C:
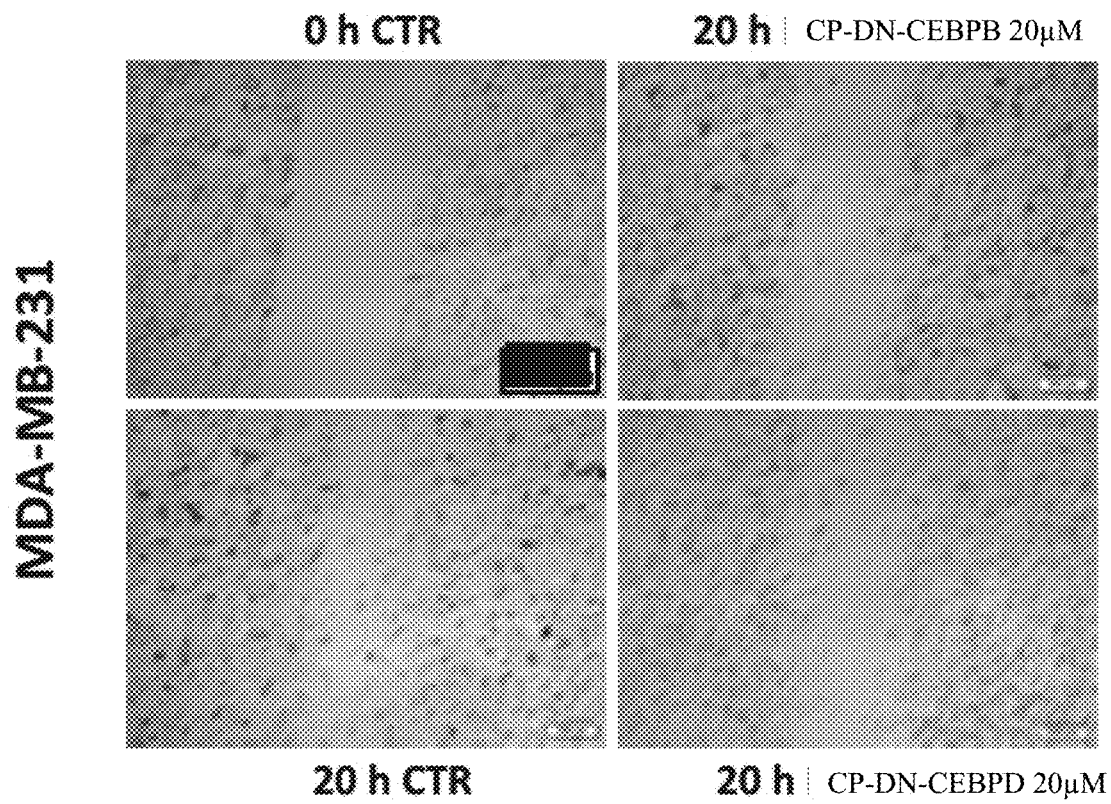

FIG. 22C is a set of exemplary representative photomicrographs showing exemplary MDA-MB-231 cell migration following 20 hours treatment at 20 μM concentrations of CP-DN-CEBPB, CP-DN-CEBPD, or control treatments.

Figure 22D:
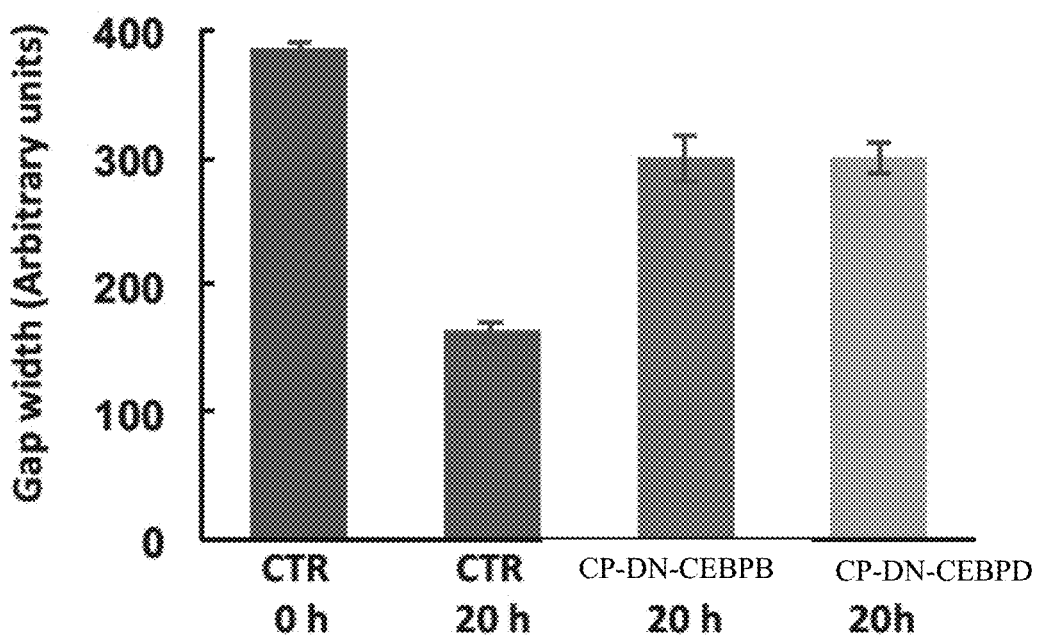

FIG. 22D is a graph reporting exemplary quantification of MDA-MB-231 cell migration following 20 hours treatment at 20 μM concentration of CP-DN-CEBPB, CP-DN-CEBPD, or control treatments.

Figure 23A:
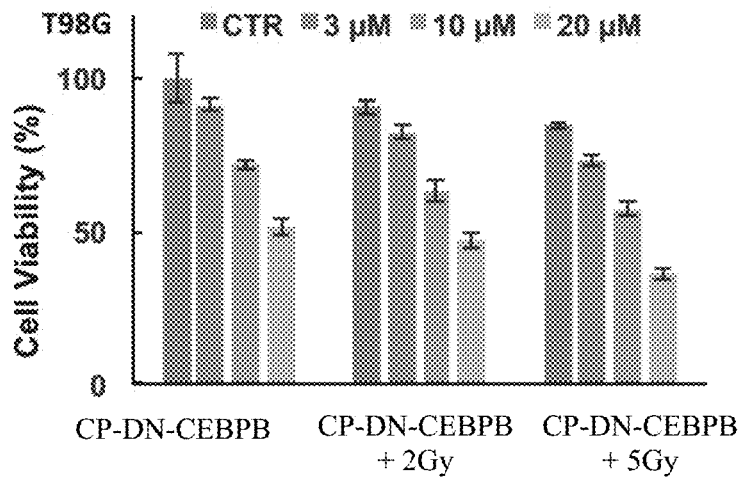

FIG. 23A is a graph reporting exemplary quantification of T98G cells following immediate treatment for 6 days with various concentrations of CP-DN-CEBPB after no irradiation or irradiation of the cells with 2 Gy or 5 Gy of gamma radiation.

Figure 23B:
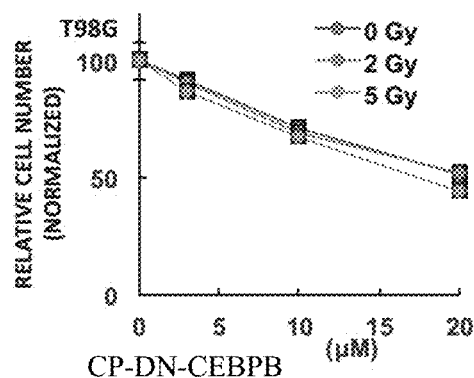

FIG. 23B is a graph reporting exemplary relative cell numbers of T98G cells following immediate treatment for 6 days with various concentrations of CP-DN-CEBPB after no irradiation or irradiation of the cells with 2 Gy or 5 Gy of gamma radiation, as compared to cells that received no CP-DN-CEBPB treatment.

Figure 23C:
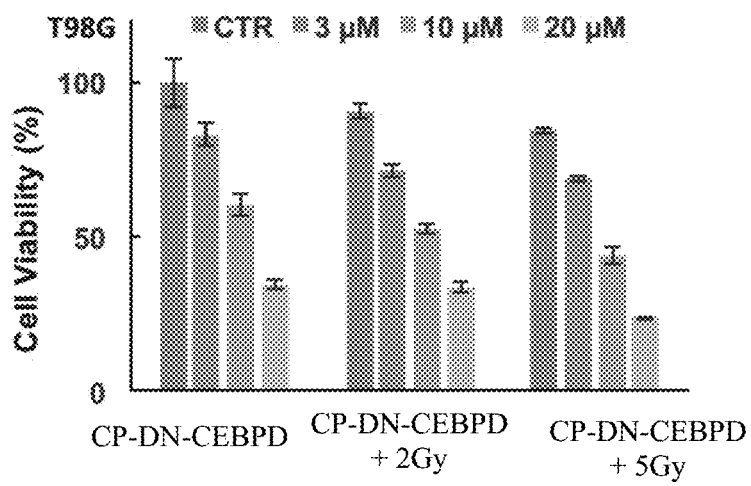

FIG. 23C is a graph reporting exemplary quantification of T98G cells following immediate treatment for 6 days with various concentrations of CP-DN-CEBPD after no irradiation or irradiation of the cells with 2 Gy or 5 Gy of gamma radiation.

Figure 23D:
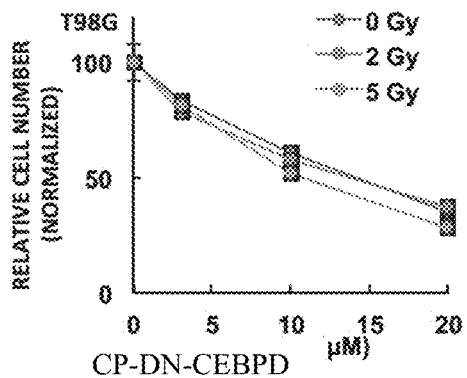

FIG. 23D is a graph reporting exemplary relative cell numbers of T98G cells following immediate treatment for 6 days with various concentrations of CP-DN-CEBPD after no irradiation or irradiation of the cells with 2 Gy or 5 Gy of gamma radiation, as compared to cells that received no CP-DN-CEBPD treatment.

Figure 23E:
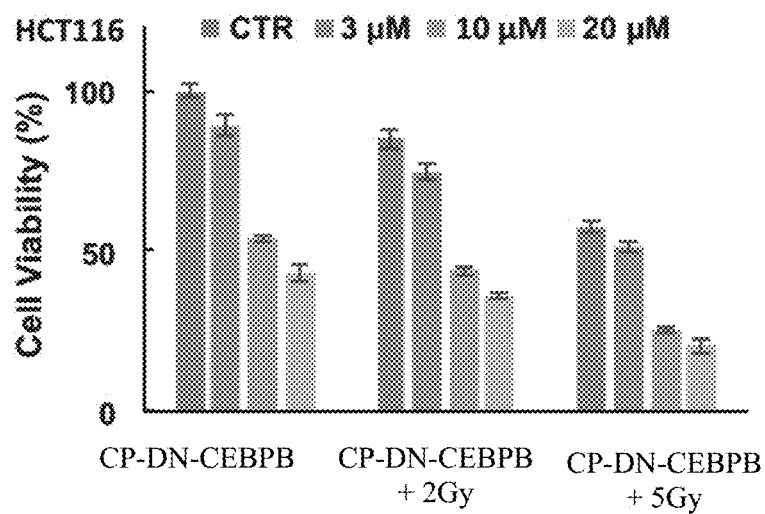

FIG. 23E is a graph reporting exemplary quantification of HCT116 cells following immediate treatment for 6 days with various concentrations of CP-DN-CEBPB after no irradiation or irradiation of the cells with 2 Gy or 5 Gy of gamma radiation.

Figure 23F:
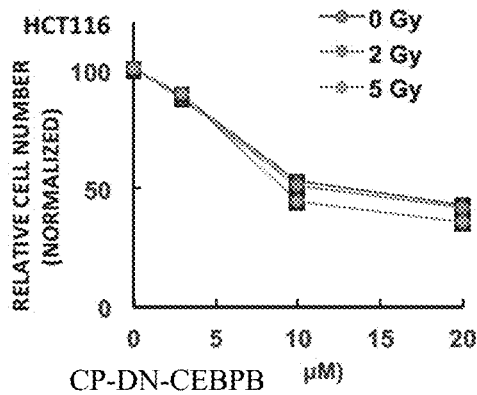

FIG. 23F is a graph reporting exemplary relative cell numbers of HCT116 cells following immediate treatment for 6 days with various concentrations of CP-DN-CEBPB after no irradiation or irradiation of the cells with 2 Gy or 5 Gy of gamma radiation, as compared to cells that received no CP-DN-CEBPB treatment.

Figure 23G:
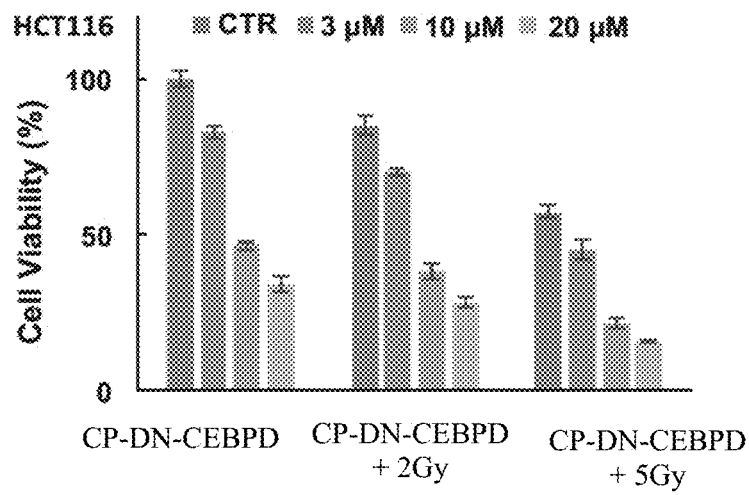

FIG. 23G is a graph reporting exemplary quantification of HCT116 cells following immediate treatment for 6 days with various concentrations of CP-DN-CEBPD after no irradiation or irradiation of the cells with 2 Gy or 5 Gy of gamma radiation.

Figure 23H:
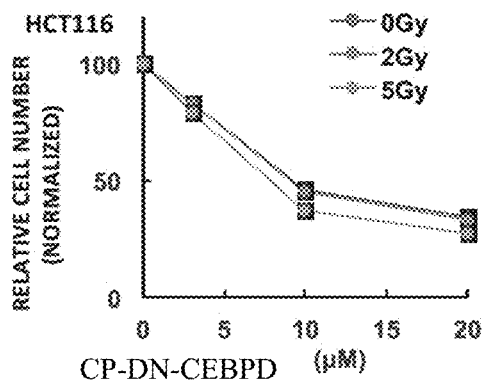

FIG. 23H is a graph reporting exemplary relative cell numbers of HCT116 cells following immediate treatment for 6 days with various concentrations of CP-DN-CEBPD after no irradiation or irradiation of the cells with 2 Gy or 5 Gy of gamma radiation, as compared to cells that received no CP-DN-CEBPD treatment.

Figure 24A:
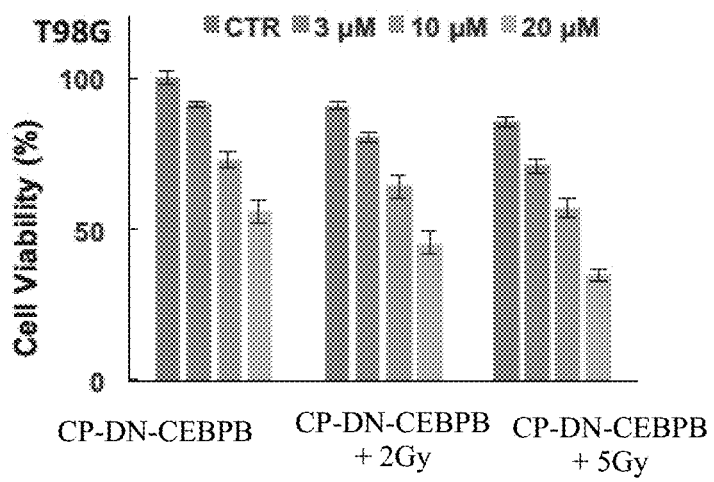

FIG. 24A is a graph reporting exemplary quantification of T98G cells following delayed treatment for 6 days with various concentrations of CP-DN-CEBPB after no irradiation or irradiation of the cells with 2 Gy or 5 Gy of gamma radiation.

Figure 24B:
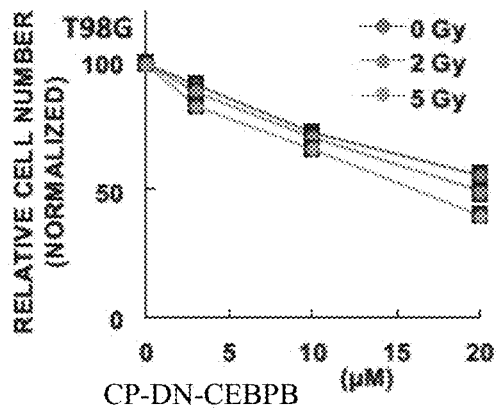

FIG. 24B is a graph reporting exemplary relative cell numbers of T98G cells following delayed treatment for 6 days with various concentrations of CP-DN-CEBPB after no irradiation or irradiation of the cells with 2 Gy or 5 Gy of gamma radiation, as compared to cells that received no CP-DN-CEBPB treatment.

Figure 24C:
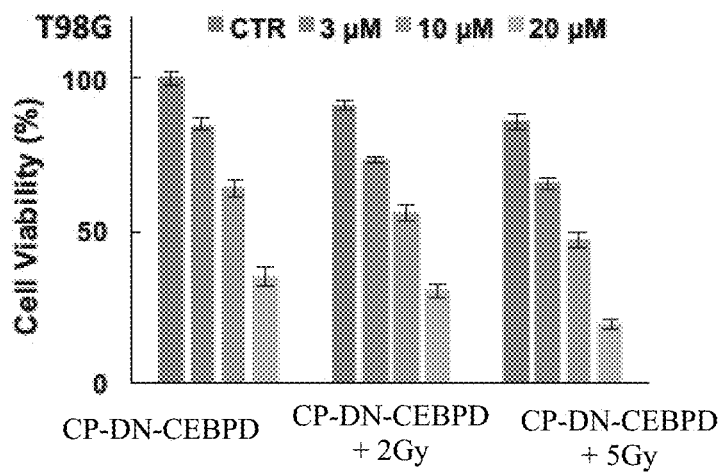

FIG. 24C is a graph reporting exemplary quantification of T98G cells following delayed treatment for 6 days with various concentrations of CP-DN-CEBPD after no irradiation or irradiation of the cells with 2 Gy or 5 Gy of gamma radiation.

Figure 24D:
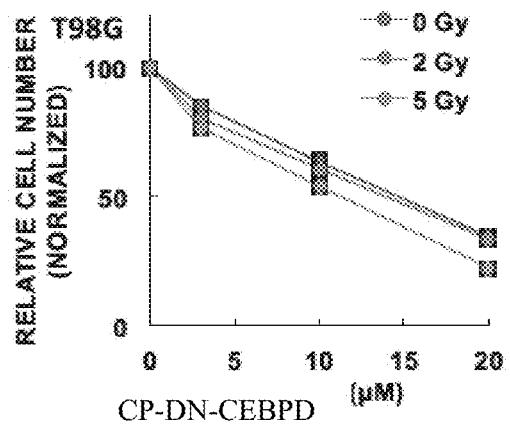

FIG. 24D is a graph reporting exemplary relative cell numbers of T98G cells following delayed treatment for 6 days with various concentrations of CP-DN-CEBPD after no irradiation or irradiation of the cells with 2 Gy or 5 Gy of gamma radiation, as compared to cells that received no CP-DN-CEBPD treatment.

Figure 24E:
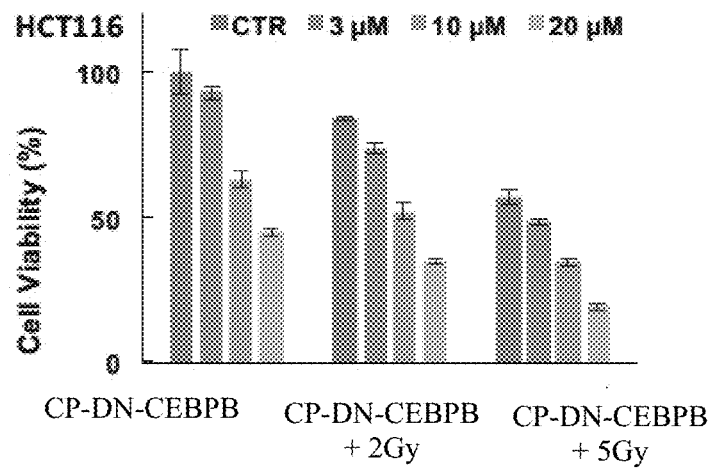

FIG. 24E is a graph reporting exemplary quantification of HCT116 cells following delayed treatment for 6 days with various concentrations of CP-DN-CEBPB after no irradiation or irradiation of the cells with 2 Gy or 5 Gy of gamma radiation.

Figure 24F:
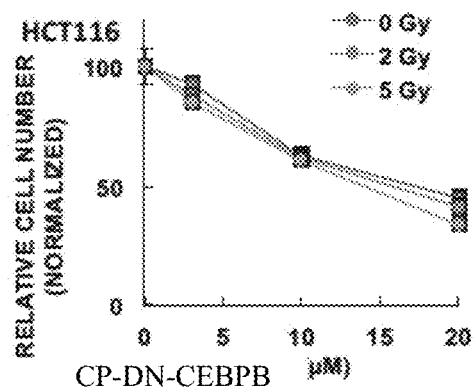

FIG. 24F is a graph reporting exemplary relative cell numbers of HCT116 cells following delayed treatment for 6 days with various concentrations of CP-DN-CEBPB after no irradiation or irradiation of the cells with 2 Gy or 5 Gy of gamma radiation, as compared to cells that received no CP-DN-CEBPB treatment.

Figure 24G:
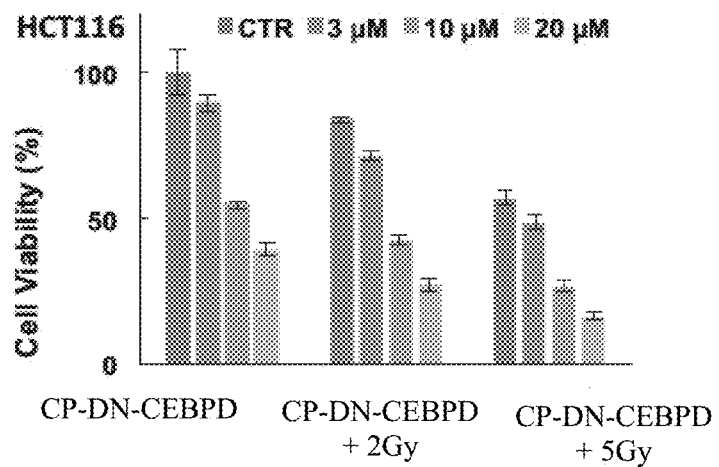

FIG. 24G is a graph reporting exemplary quantification of HCT116 cells following delayed treatment for 6 days with various concentrations of CP-DN-CEBPD after no irradiation or irradiation of the cells with 2 Gy or 5 Gy of gamma radiation.

Figure 24H:
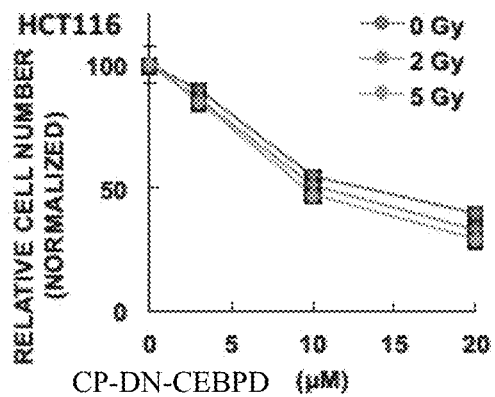

FIG. 24H is a graph reporting exemplary relative cell numbers of HCT116 cells following delayed treatment for 6 days with various concentrations of CP-DN-CEBPD after no irradiation or irradiation of the cells with 2 Gy or 5 Gy of gamma radiation, as compared to cells that received no CP-DN-CEBPD treatment.

Figure 25A:
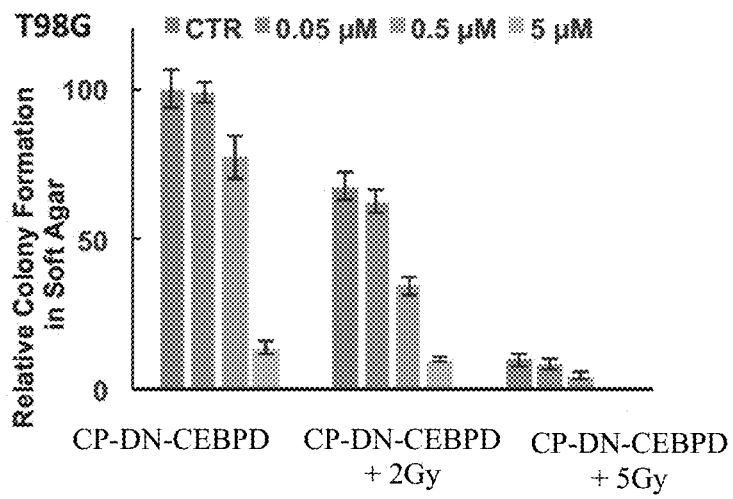

FIG. 25A is a graph reporting exemplary quantification of T98G cells following immediate treatment for 12 days with various concentrations of CP-DN-CEBPD after no irradiation or irradiation of the cells with 2 Gy or 5 Gy of gamma radiation.

Figure 25B:
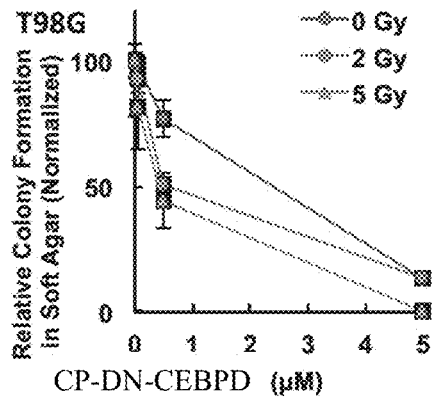

FIG. 25B is a graph reporting exemplary relative cell numbers of T98G cells following immediate treatment for 12 days with various concentrations of CP-DN-CEBPD after no irradiation or irradiation of the cells with 2 Gy or 5 Gy of gamma radiation, as compared to cells that received no CP-DN-CEBPD treatment.

Figure 26A:
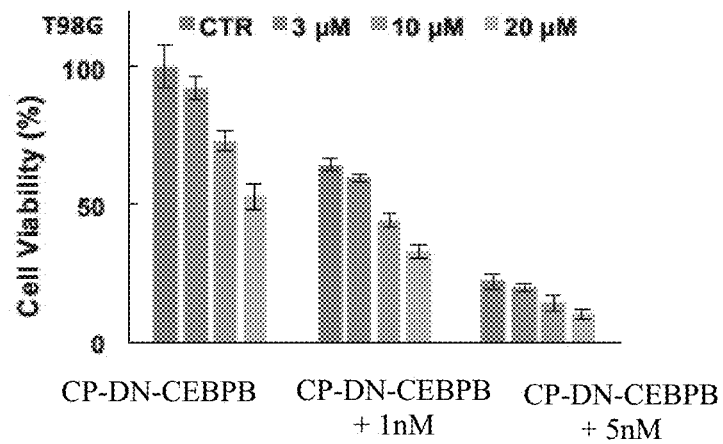

FIG. 26A is a graph reporting exemplary quantification of T98G cells following treatment for 6 days with various concentrations of CP-DN-CEBPB after no treatment or co-treatment of the cells with 1 nM or 5 nm paclitaxel (Taxol).

Figure 26B:
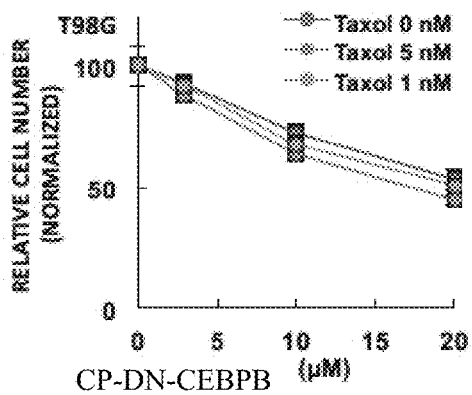

FIG. 26B is a graph reporting exemplary relative cell numbers of T98G cells following treatment for 6 days with various concentrations of CP-DN-CEBPB after no treatment or co-treatment of the cells with 1 nM or 5 nM paclitaxel (Taxol), as compared to cells that received no CP-DN-CEBPB treatment.

Figure 26C:
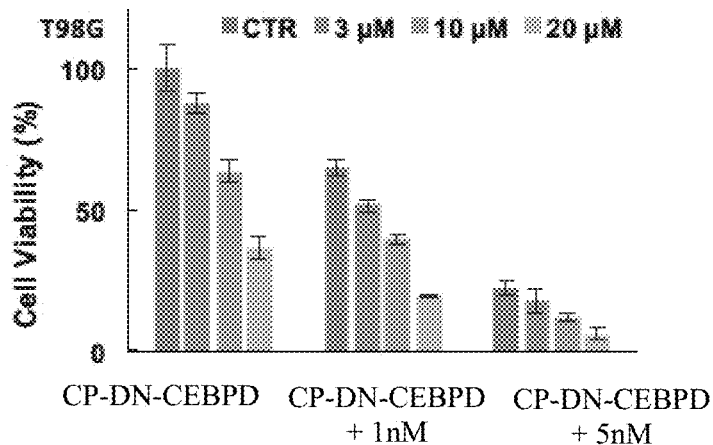

FIG. 26C is a graph reporting exemplary quantification of T98G cells following treatment for 6 days with various concentrations of CP-DN-CEBPD after no treatment or co-treatment of the cells with 1 nM or 5 nM paclitaxel (Taxol).

Figure 26D:
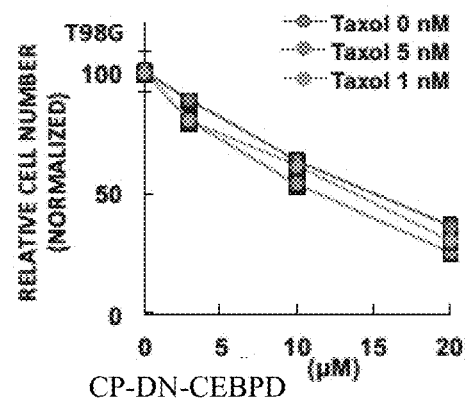

FIG. 26D is a graph reporting exemplary relative cell numbers of T98G cells following treatment for 6 days with various concentrations of CP-DN-CEBPD after no treatment or co-treatment of the cells with 1 nM or 5 nM paclitaxel (Taxol), as compared to cells that received no CP-DN-CEBPD treatment.

Figure 26E:
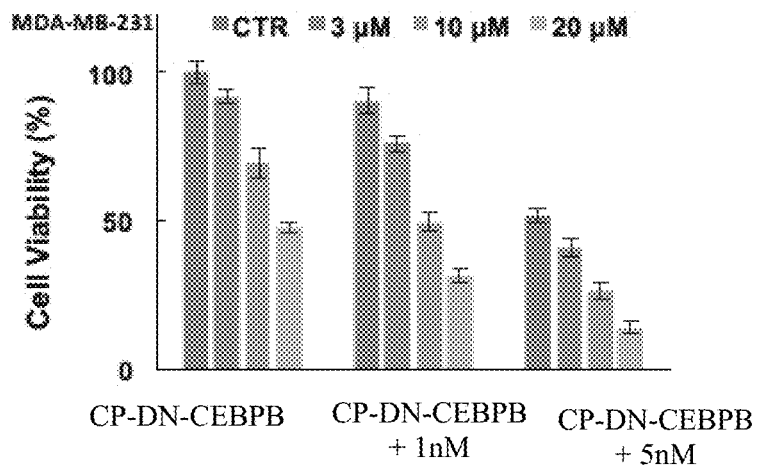

FIG. 26E is a graph reporting exemplary quantification of MDA-MB-231 cells following treatment for 6 days with various concentrations of CP-DN-CEBPB after no treatment or co-treatment of the cells with 1 nM or 5 nM paclitaxel (Taxol).

Figure 26F:
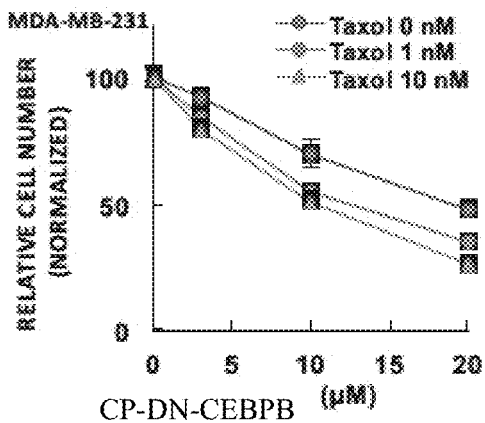

FIG. 26F is a graph reporting relative cell numbers of MDA-MB-231 cells following treatment for 6 days with various concentrations of CP-DN-CEBPB after no treatment or co-treatment of the cells with 1 nM or 5 nM paclitaxel (Taxol), as compared to cells that received no CP-DN-CEBPB treatment.

Figure 26G:
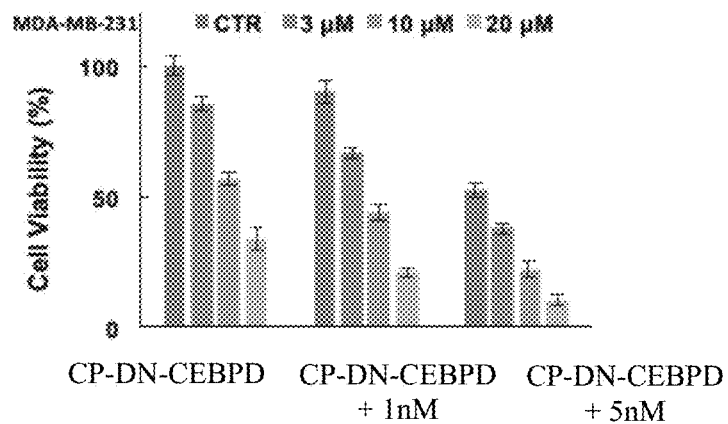

FIG. 26G is a graph reporting exemplary quantification of MDA-MB-231 cells following treatment for 6 days with various concentrations of CP-DN-CEBPD after no treatment or co-treatment of the cells with 1 nM or 5 nM paclitaxel (Taxol).

Figure 26H:
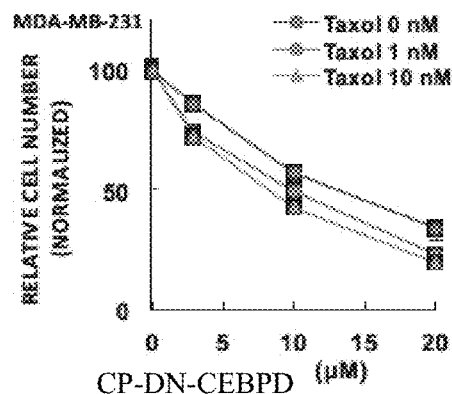

FIG. 26H is a graph reporting exemplary relative cell numbers of MDA-MB-231 cells following treatment for 6 days with various concentrations of CP-DN-CEBPD after no treatment or co-treatment of the cells with 1 nM or 5 nM paclitaxel (Taxol), as compared to cells that received no CP-DN-CEBPD treatment.

Figure 26I:
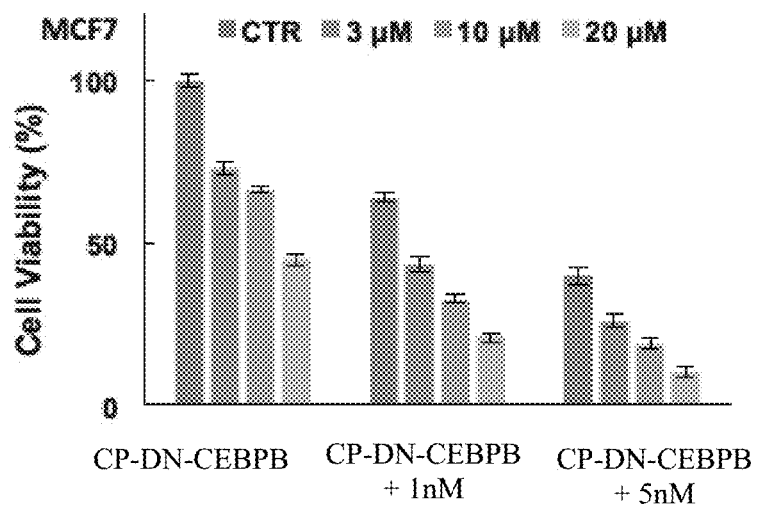

FIG. 26I is a graph reporting exemplary quantification of MCF7 cells following treatment for 6 days with various concentrations of CP-DN-CEBPB after no treatment or co-treatment of the cells with 1 nM or 5 nM paclitaxel (Taxol).

Figure 26J:
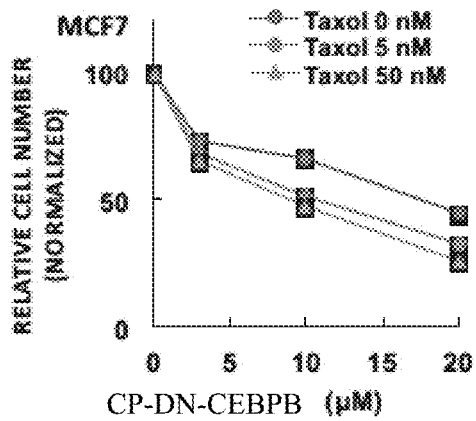

FIG. 26J is a graph reporting exemplary relative cell numbers of MCF7 cells following treatment for 6 days with various concentrations of CP-DN-CEBPB after treatment or co-treatment of the cells with 1 nM or 5 nM paclitaxel (Taxol), as compared to cells that received no CP-DN-CEBPB treatment.

Figure 26K:
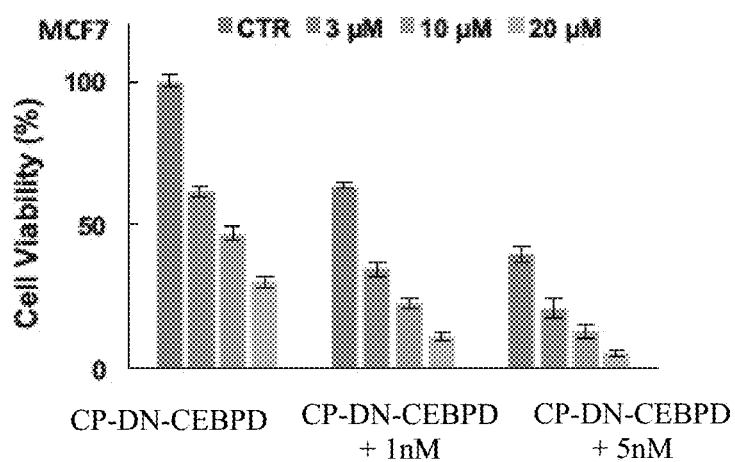

FIG. 26K is a graph reporting exemplary quantification of MCF7 cells following treatment for 6 days with various concentrations of CP-DN-CEBPD after no treatment or co-treatment of the cells with 1 nM or 5 nM paclitaxel (Taxol).

Figure 26L:
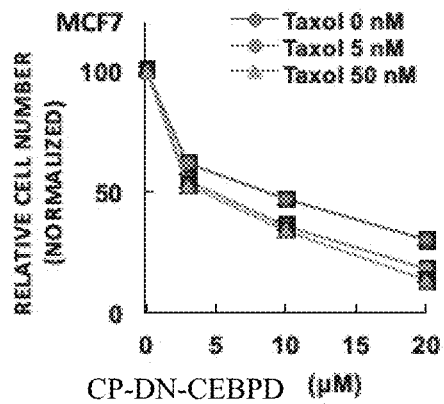

FIG. 26L is a graph reporting exemplary relative cell numbers of MCF7 cells following treatment for 6 days with various concentrations of CP-DN-CEBPD after no treatment or co-treatment of the cells with 1 nM or 5 nM paclitaxel (Taxol), as compared to cells that received no CP-CD-CDBPD treatment.

Figure 27A:
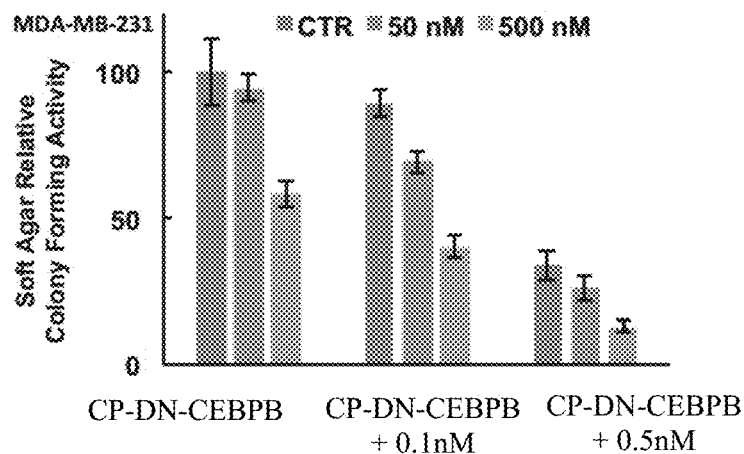

FIG. 27A is a graph reporting exemplary quantification of MDA-MB-231 cells following treatment for 12 days with various concentrations of CP-DN-CEBPB after no treatment or co-treatment of the cells with 1 nM or 5 nM paclitaxel (Taxol).

Figure 27B:
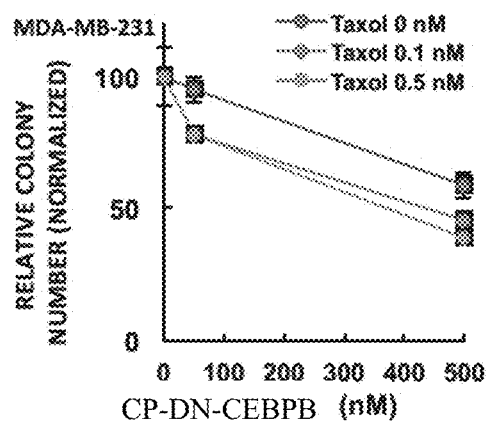

FIG. 27B is a graph reporting exemplary relative cell numbers of MDA-MB-231 cells following treatment for 12 days with various concentrations of CP-DN-CEBPB after no treatment or co-treatment of the cells with 1 nM or 5 nM paclitaxel (Taxol), as compared to cells that received no CP-DN-CEBPB treatment.

Figure 27C:
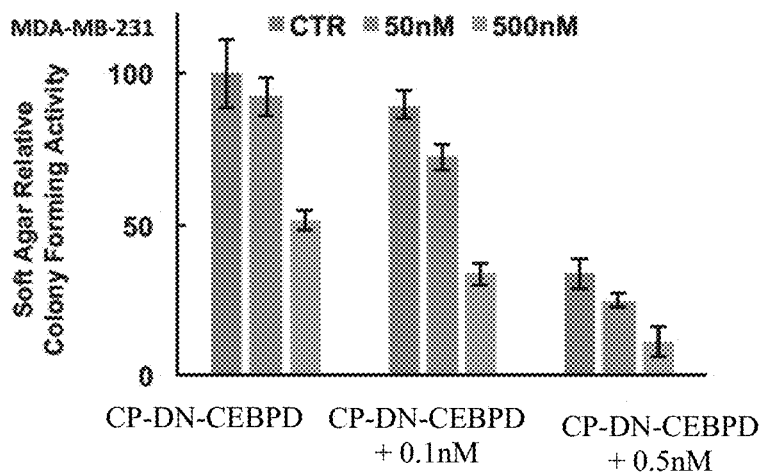

FIG. 27C is a graph reporting exemplary quantification of MDA-MB-231 cells following treatment for 12 days with various concentrations of CP-DN-CEBPD after no treatment or co-treatment of the cells with 1 nM or 5 nM paclitaxel (Taxol).

Figure 27D:
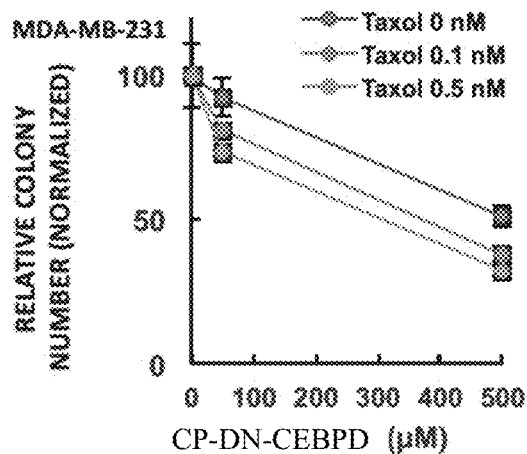

FIG. 27D is a graph reporting exemplary relative cell numbers of MDA-MB-231 cells following treatment for 12 days with various concentrations of CP-DN-CEBPD after no treatment or co-treatment of the cells with 1 nM or 5 nM paclitaxel (Taxol), as compared to cells that received no CP-DN-CEBPD treatment.

Figure 28A:
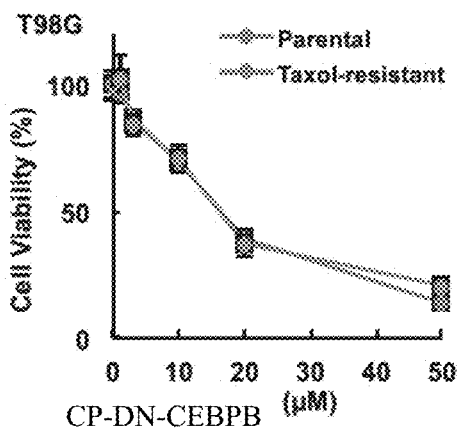

FIG. 28A is a graph reporting exemplary quantification of wild-type (parental) or taxol-resistant T98G cells following co-treatment with various concentrations of CP-DN-CEBPB.

Figure 28B:
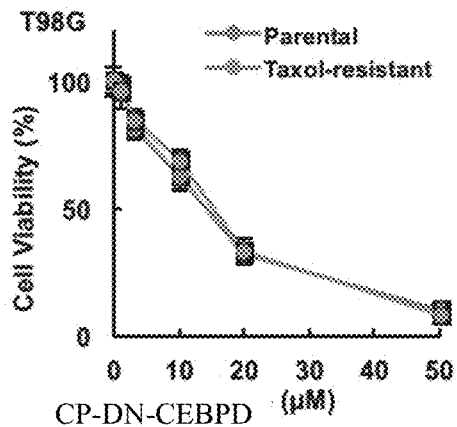

FIG. 28B is a graph reporting exemplary quantification of wild-type (parental) or taxol-resistant T98G cells following co-treatment with various concentrations of CP-CDDN-CEBPD.

Figure 28C:
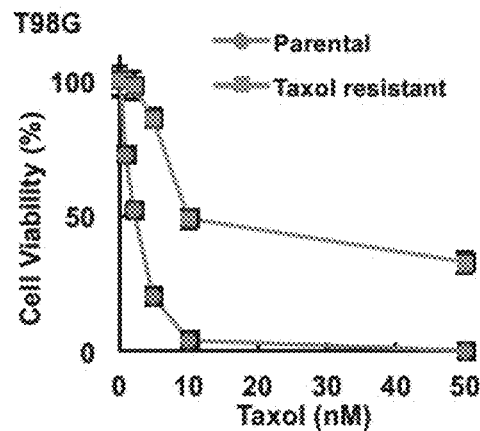

FIG. 28C is a graph reporting exemplary quantification of wild-type (parental) or taxol-resistant T98G cells following co-treatment with taxol only a control for FIGS. 28A and 28B.

Figure 29A:
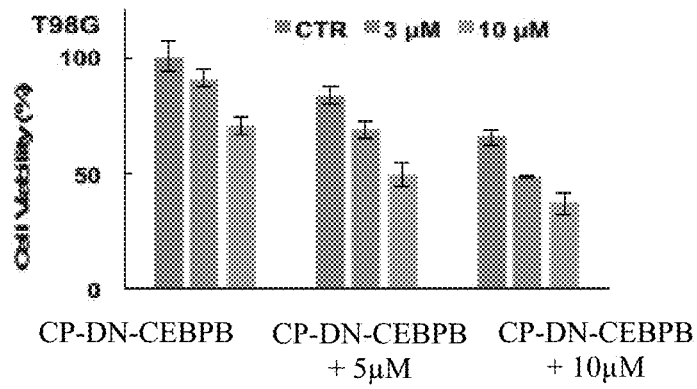

FIG. 29A is a graph reporting exemplary quantification of T98G cells following treatment for 6 days with various concentrations of CP-DN-CEBPB after no treatment or co-treatment of the cells with 1 nM or 5 nM chloroquine.

Figure 29B:
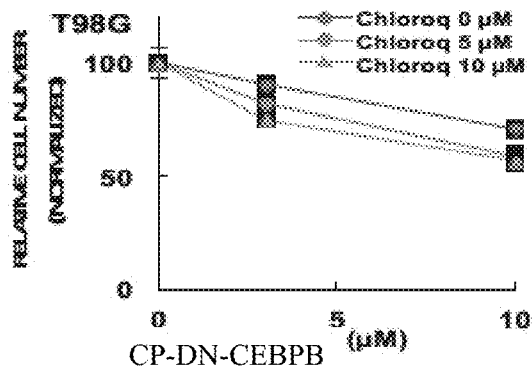

FIG. 29B is a graph reporting exemplary relative cell numbers of T98G cells following treatment for 6 days with various concentrations of CP-DN-CEBPB after no treatment or co-treatment of the cells with 1 nM or 5 nM chloroquine, as compared to cells that received no CP-DN-CEBPB treatment.

Figure 29C:
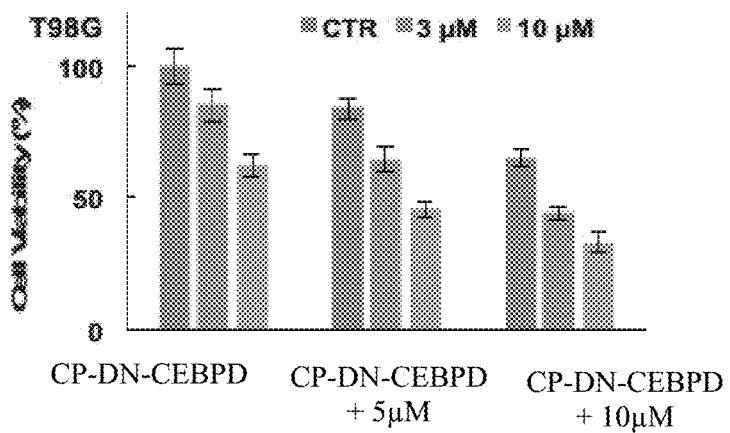

FIG. 29C is a graph reporting exemplary quantification of T98G cells following treatment for 6 days with various concentrations of CP-CD-CDBPD after treatment or co-treatment of the cells with 1 nM or 5 nM chloroquine.

Figure 29D:
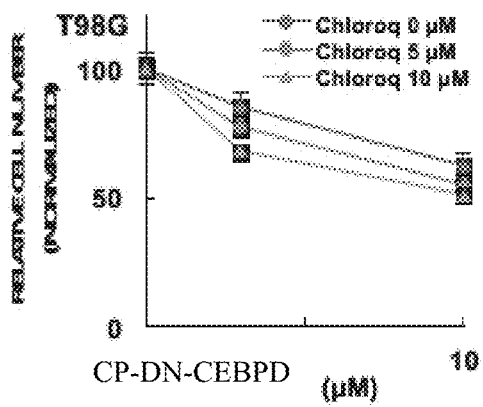

FIG. 29D is a graph reporting exemplary relative cell numbers of T98Gcells following treatment for 6 days with various concentrations of CP-DN-CEBPD after no treatment or co-treatment of the cells with 1 nM or 5 nM chloroquine, as compared to cells that received no CP-DN-CEBPD treatment.

Figure 29E:
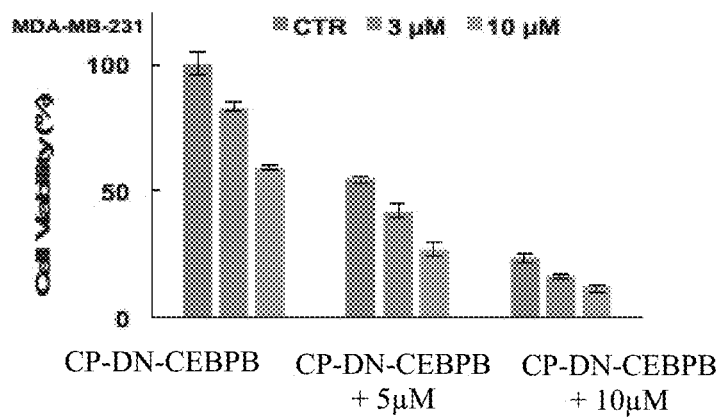

FIG. 29E is a graph reporting exemplary quantification of MD-MBA-231 cells following treatment for 6 days with various concentrations of CP-DN-CEBPB after no treatment or co-treatment of the cells with 1 nM or 5 nM chloroquine.

Figure 29F:
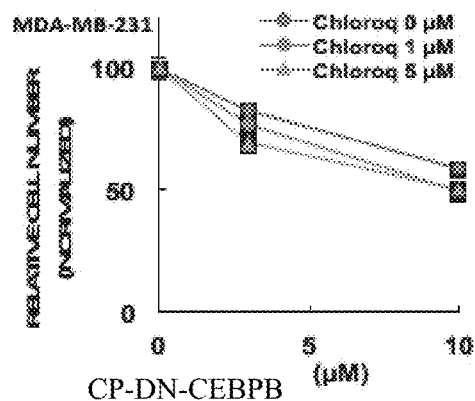

FIG. 29F is a graph reporting exemplary relative cell numbers of MD-MBA-231 cells following treatment for 6 days with various concentrations of CP-DN-CEBPB after no treatment or co-treatment of the cells with 1 nM or 5 nM chloroquine, as compared to cells that received no CP-DN-CEBPB treatment.

Figure 29G:
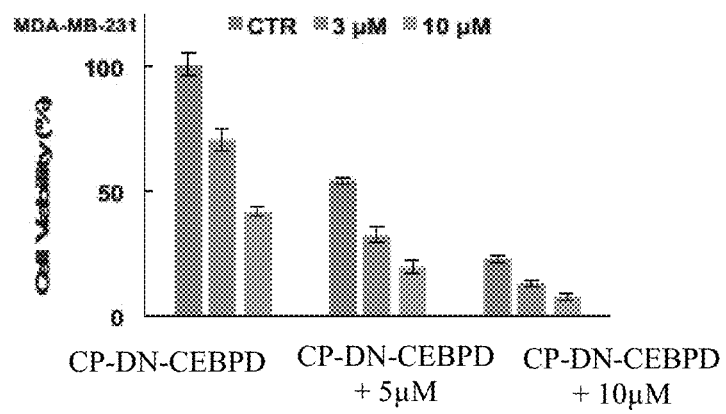

FIG. 29G is a graph reporting exemplary quantification of MD-MBA-231 cells following treatment for 6 days with various concentrations of CP-DN-CEBPD after treatment or co-treatment of the cells with 1 nM or 5 nM chloroquine.

Figure 29H:
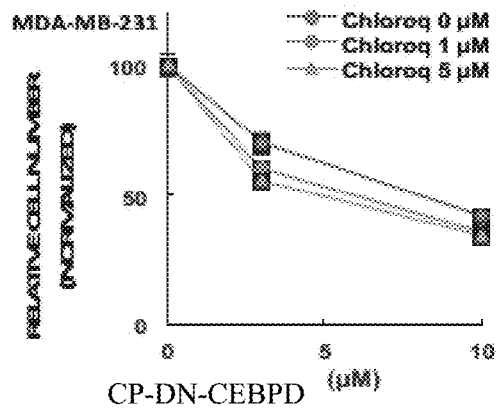

FIG. 29H is a graph reporting exemplary relative cell numbers of MD-MBA-231 cells following treatment for 6 days with various concentrations of CP-DN-CEBPD after no treatment or co-treatment of the cells with 1 nM or 5 nM chloroquine, as compared to cells that received no CP-DN-CEBPD treatment.

Figure 29I:
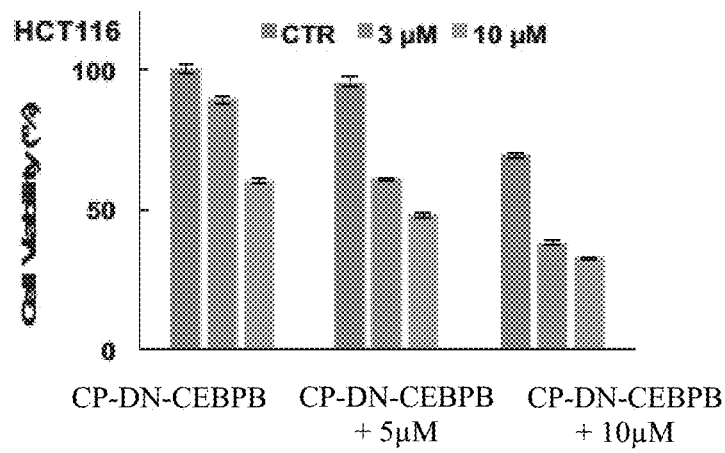

FIG. 29I is a graph reporting exemplary quantification of HCT116 cells following treatment for 6 days with various concentrations of CP-DN-CEBPB after no treatment or co-treatment of the cells with 1 nM or 5 nM chloroquine.

Figure 29J:
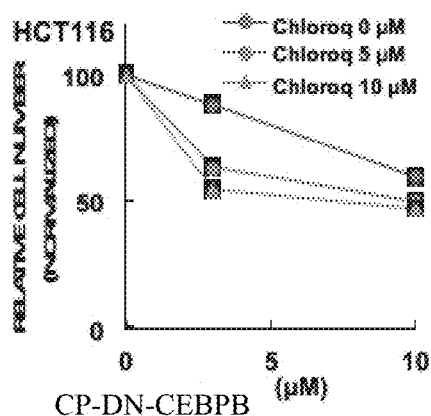

FIG. 29J is a graph reporting exemplary relative cell numbers of HCT116 cells following treatment for 6 days with various concentrations of CP-DN-CEBPB after no treatment or co-treatment of the cells with 1 nM or 5 nM chloroquine, as compared to cells that received no CP-DN-CEBPB treatment.

Figure 29K:
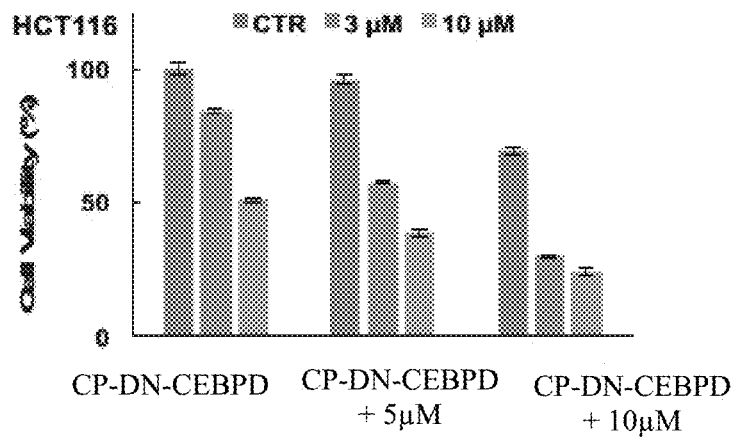

FIG. 29K is a graph reporting exemplary quantification of HCT116 cells following treatment for 6 days with various concentrations of CP-DN-CEBPD after treatment or co-treatment of the cells with 1 nM or 5 nM chloroquine.

Figure 29L:
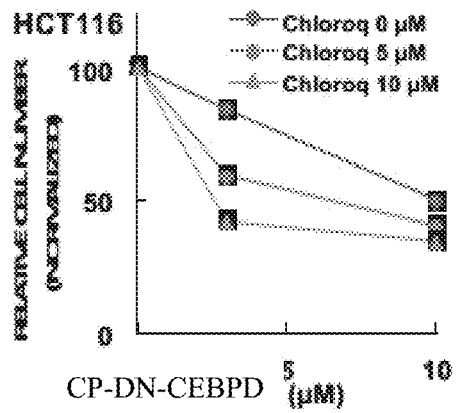

FIG. 29L is a graph reporting exemplary relative cell numbers of HCT116 cells following treatment for 6 days with various concentrations of CP-DN-CEBPD after no treatment or co-treatment of the cells with 1 nM or 5 nM chloroquine, as compared to cells that received no CP-DN-CEDBPD treatment.

Figure 30A:
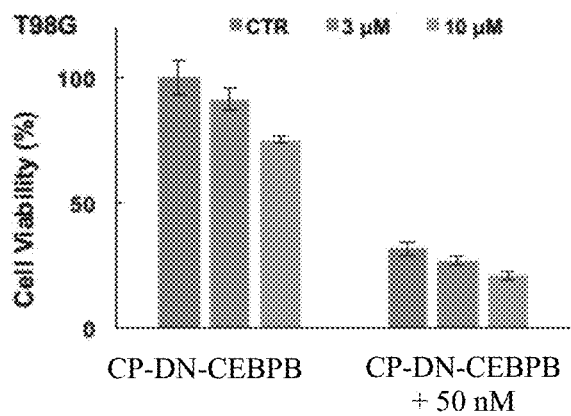

FIG. 30A is a graph reporting exemplary quantification of T98G cells following treatment for 6 days with various concentrations of CP-DN-CEBPB after no treatment or co-treatment of the cells with 50 nM doxorubicin.

Figure 30B:
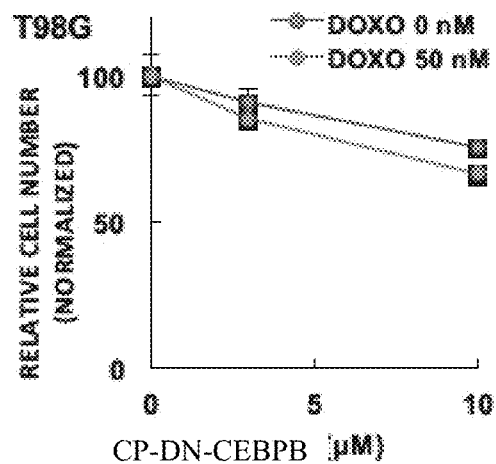

FIG. 30B is a graph reporting exemplary relative cell numbers of T98G cells following treatment for 6 days with various concentrations of CP-DN-CEBPB after no treatment or co-treatment of the cells with 50 nM doxorubicin, as compared to cells that received no CP-DN-CEBPB treatment.

Figure 30C:
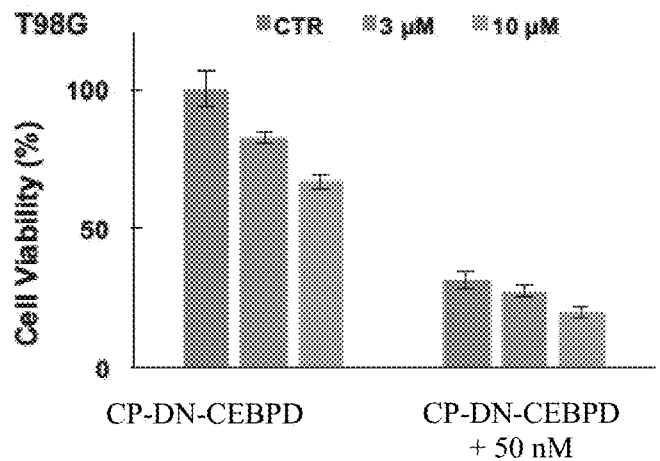

FIG. 30C is a graph reporting exemplary quantification of T98G cells following treatment for 6 days with various concentrations of CP-DN-CEBPD after treatment or co-treatment of the cells with 50 nM doxorubicin.

Figure 30D:
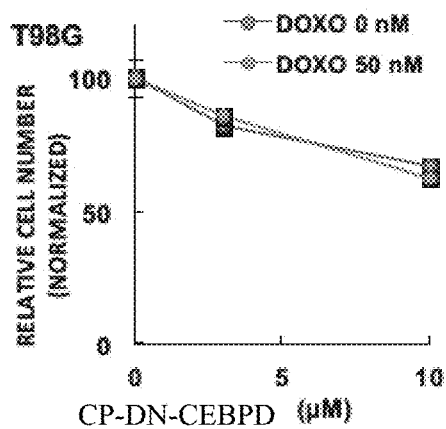

FIG. 30D is a graph reporting exemplary relative cell numbers of T98Gcells following treatment for 6 days with various concentrations of CP-DN-CEBPD after no treatment or co-treatment of the cells with 50 nM doxorubicin, as compared to cells that received no CP-DN-CEBPD treatment.

Figure 30E:
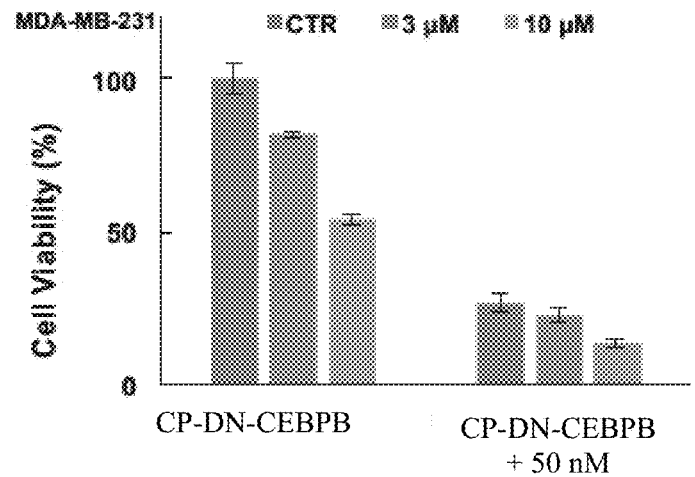

FIG. 30E is a graph reporting exemplary quantification of MD-MBA-231 cells following treatment for 6 days with various concentrations of CP-DN-CEBPB after no treatment or co-treatment of the cells with 50 nM doxorubicin.

Figure 30F:
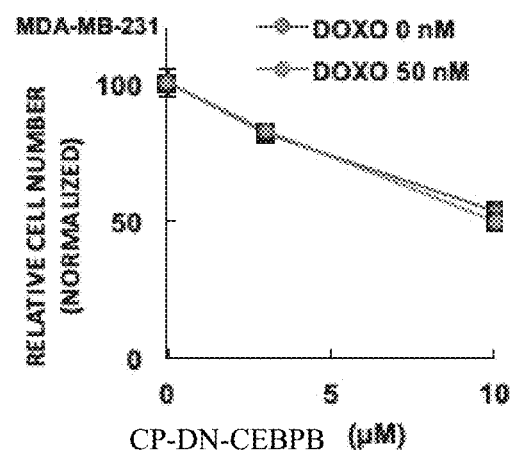

FIG. 30F is a graph reporting exemplary relative cell numbers of MD-MBA-231 cells following treatment for 6 days with various concentrations of CP-DN-CEBPB after no treatment or co-treatment of the cells with 50 nM doxorubicin, as compared to cells that received no CP-DN-CEBPB treatment.

Figure 30G:
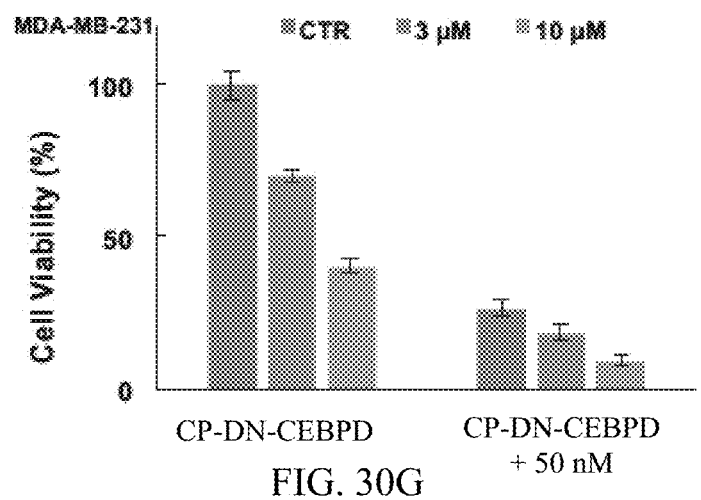

FIG. 30G is a graph reporting exemplary quantification of MD-MBA-231 cells following treatment for 6 days with various concentrations of CP-DN-CEBPD after treatment or co-treatment of the cells with 50 nM doxorubicin.

Figure 30H:
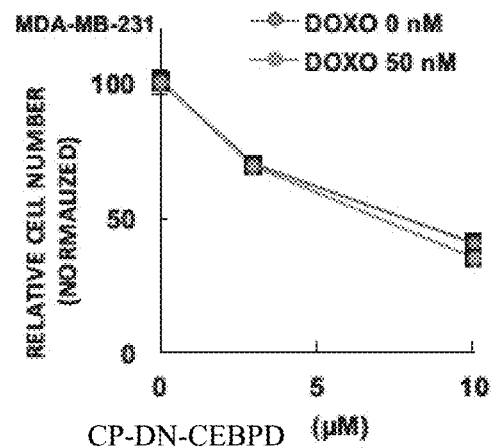

FIG. 30H is a graph reporting exemplary relative cell numbers of MD-MBA-231 cells following treatment for 6 days with various concentrations of CP-DN-CEBPD after no treatment or co-treatment of the cells with 50 nM doxorubicin, as compared to cells that received no CP-DN-CEBPD treatment.

Figure 30I:
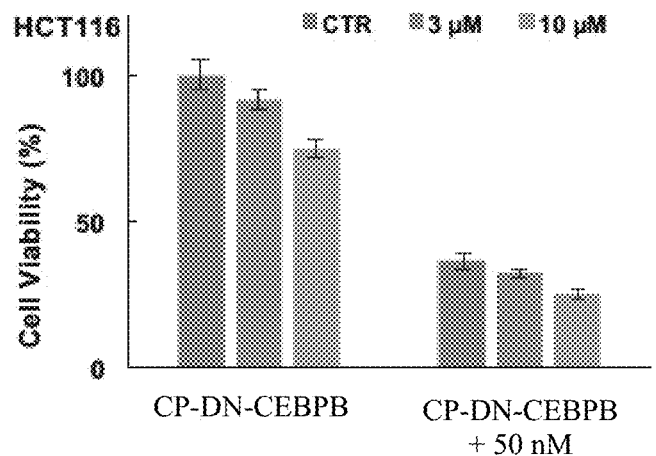

FIG. 30I is a graph reporting exemplary quantification of HCT116 cells following treatment for 6 days with various concentrations of CP-DN-CEBPB after no treatment or co-treatment of the cells with 50 nM doxorubicin.

Figure 30J:
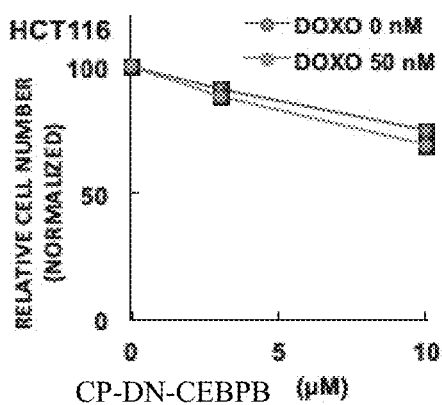

FIG. 30J is a graph reporting exemplary relative cell numbers of HCT116 cells following treatment for 6 days with various concentrations of CP-DN-CEBPB after no treatment or co-treatment of the cells with 50 nM doxorubicin, as compared to cells that received no CP-CD-CDBPB treatment.

Figure 30K:
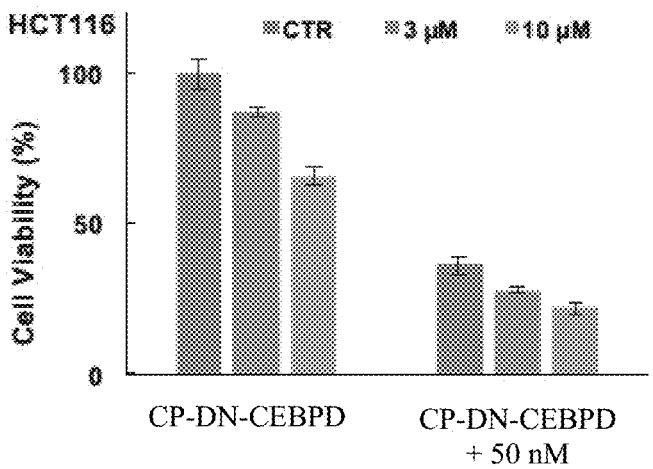

FIG. 30K is a graph reporting exemplary quantification of HCT116 cells following treatment for 6 days with various concentrations of CP-DN-CEBPD after treatment or co-treatment of the cells with 50 nM doxorubicin.

Figure 30L:
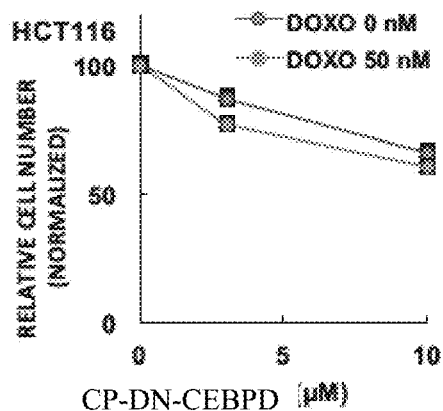

FIG. 30L is a graph reporting exemplary relative cell numbers of HCT116 cells following treatment for 6 days with various concentrations of CP-DN-CEBPD after no treatment or co-treatment of the cells with 50 nM doxorubicin, as compared to cells that received no CP-DN-CEBPD treatment.

Figure 30M:
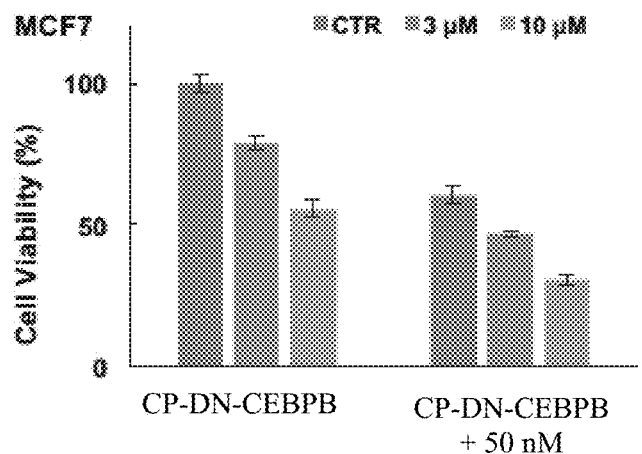

FIG. 30M is a graph reporting exemplary quantification of MCF7 cells following treatment for 6 days with various concentrations of CP-DN-CEBPB after no treatment or co-treatment of the cells with 50 nM doxorubicin.

Figure 30N:
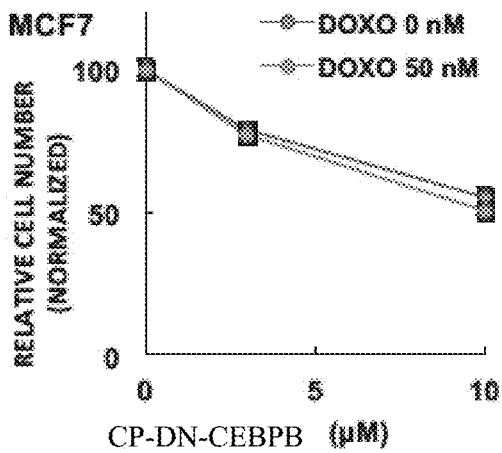

FIG. 30N is a graph reporting exemplary relative cell numbers of MCF7 cells following treatment for 6 days with various concentrations of CP-DN-CEBPB after no treatment or co-treatment of the cells with 50 nM doxorubicin, as compared to cells that received no CP-DN-CEBPB treatment.

Figure 30O:
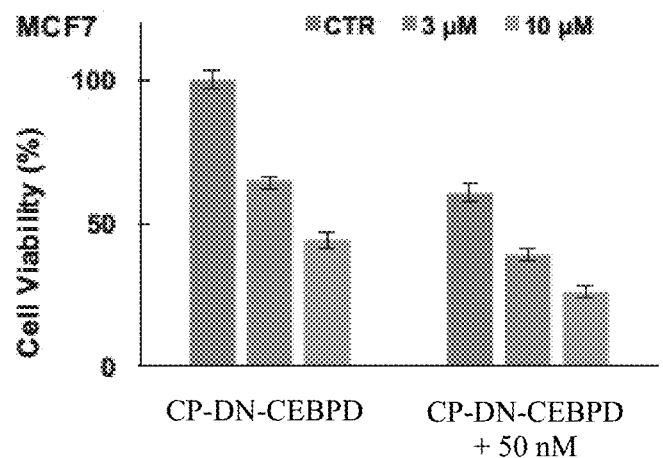

FIG. 30O is a graph reporting exemplary quantification of MCF7 cells following treatment for 6 days with various concentrations of CP-DN-CEBPD after treatment or co-treatment of the cells with 50 nM doxorubicin.

Figure 30P:
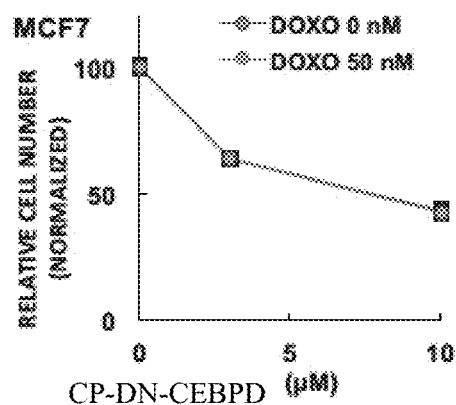

FIG. 30P is a graph reporting exemplary relative cell numbers of MCF7 cells following treatment for 6 days with various concentrations of CP-DN-CEBPD after no treatment or co-treatment of the cells with 50 nM doxorubicin, as compared to cells that received no CP-DN-CEBPD treatment.

Figure 31A:
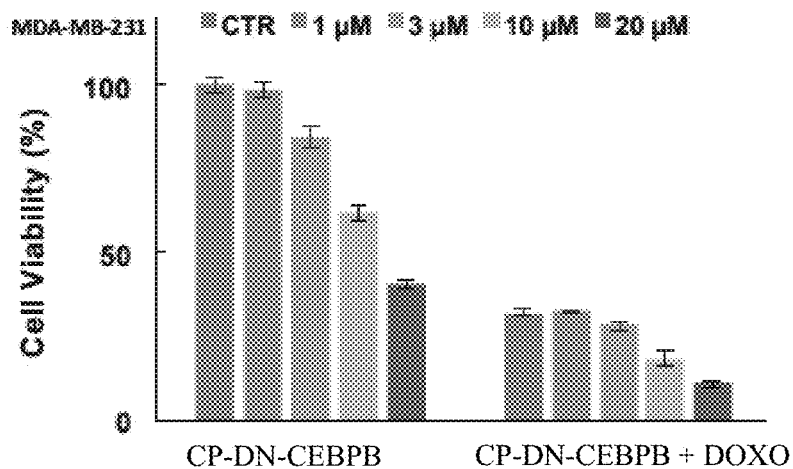

FIG. 31A is a graph reporting exemplary quantification of MD-MBA-231 cells following treatment for 6 days with various concentrations of CP-DN-CEBPB after no treatment or pre-treatment of the cells with 100 nM doxorubicin.

Figure 31B:
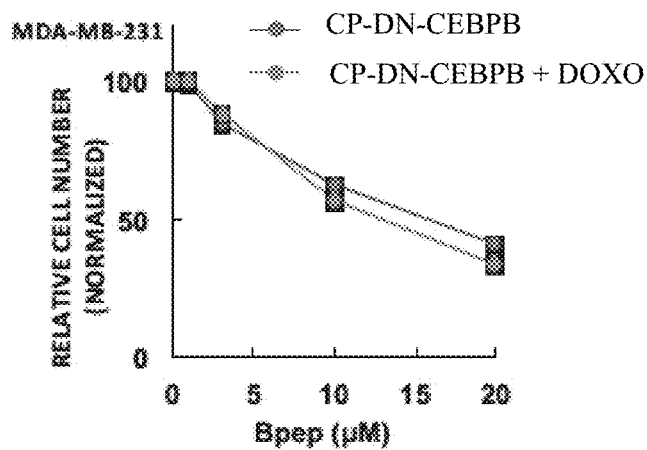

FIG. 31B is a graph reporting exemplary relative cell numbers of MD-MBA-231 cells following treatment for 6 days with various concentrations of CP-DN-CEBPB after no treatment or pre-treatment treatment of the cells with 100 nM doxorubicin, as compared to cells that received no CP-DN-CEBPB treatment.

Figure 31C:
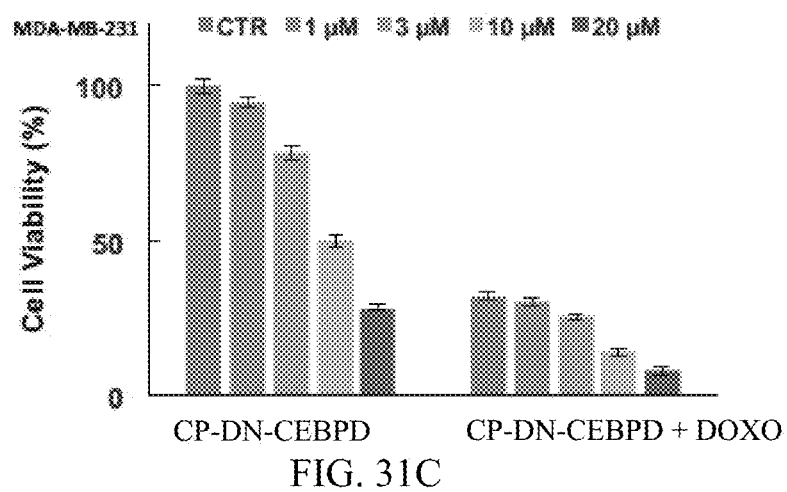

FIG. 31C is a graph reporting exemplary quantification of MD-MBA-231 cells following treatment for 6 days with various concentrations of CP-DN-CEBPD after treatment or pre-treatment of the cells with 100 nM doxorubicin.

Figure 31D:
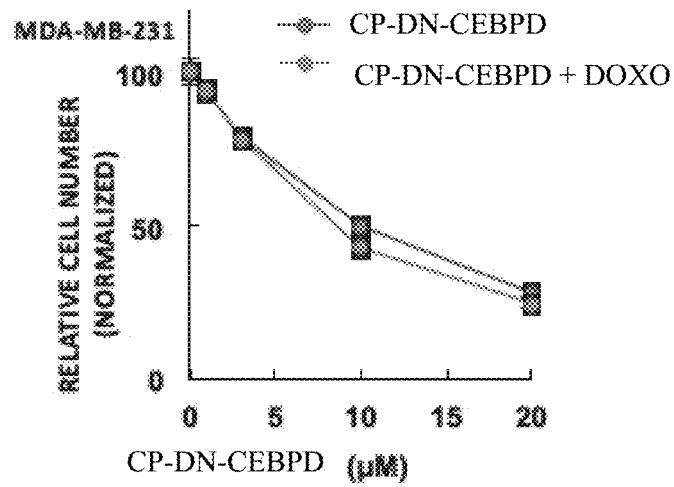

FIG. 31D is a graph reporting exemplary relative cell numbers of MD-MBA-231 cells following treatment for 6 days with various concentrations of CP-DN-CEBPD after no treatment or pre-treatment of the cells with 100 nM doxorubicin, as compared to cells that received no CP-DN-CEBPD treatment.

Figure 31E:
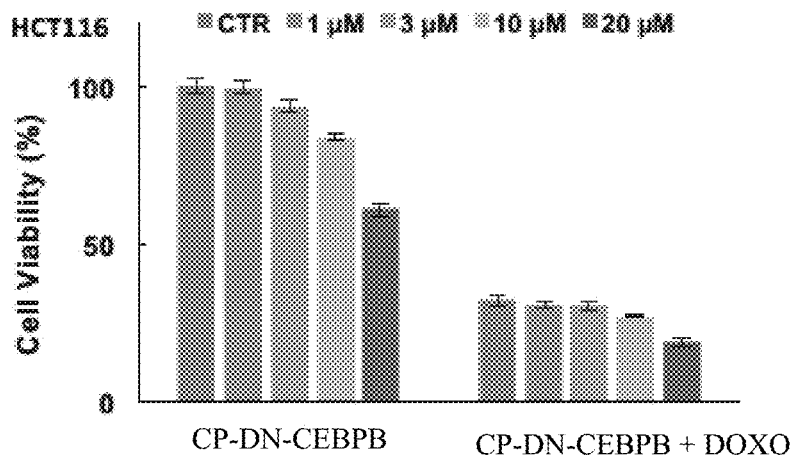

FIG. 31E is a graph reporting exemplary quantification of HCT116 cells following treatment for 6 days with various concentrations of CP-DN-CEBPB after no treatment or pre-treatment of the cells with 100 nM doxorubicin.

Figure 31F:
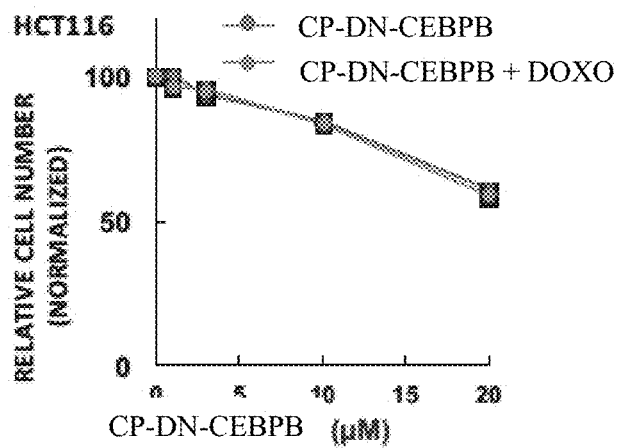

FIG. 31F is a graph reporting exemplary relative cell numbers of HCT116 cells following treatment for 6 days with various concentrations of CP-DN-CEBPB after no treatment or pre-treatment of the cells with 100 nM doxorubicin, as compared to cells that received no CP-DN-CEBPB treatment.

Figure 31G:
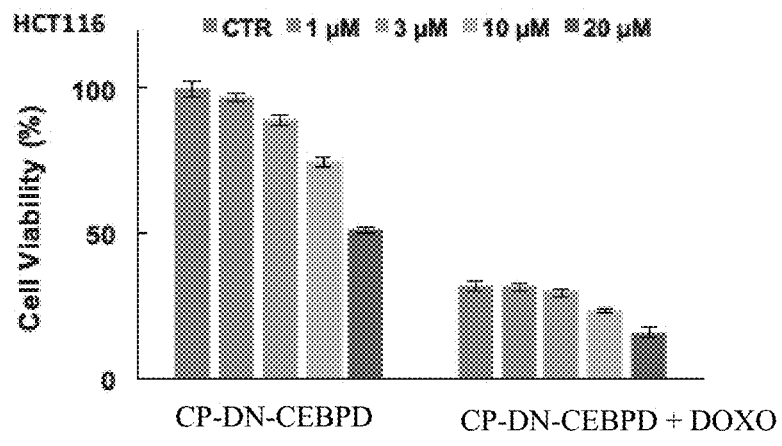

FIG. 31G is a graph reporting exemplary quantification of HCT116 cells following treatment for 6 days with various concentrations of CP-DN-CEBPD after treatment or pre-treatment of the cells with 100 nM doxorubicin.

Figure 31H:
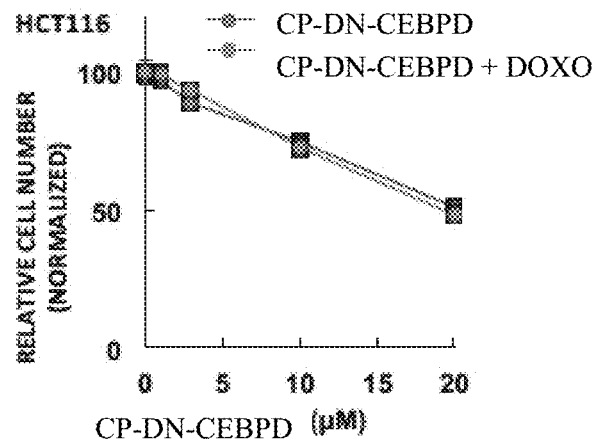

FIG. 31H is a graph reporting exemplary relative cell numbers of HCT116 cells following treatment for 6 days with various concentrations of CP-DN-CEBPD after no treatment or pre-treatment of the cells with 100 nM doxorubicin, as compared to cells that received no CP-DN-CEBPD treatment.

Figure 31I:
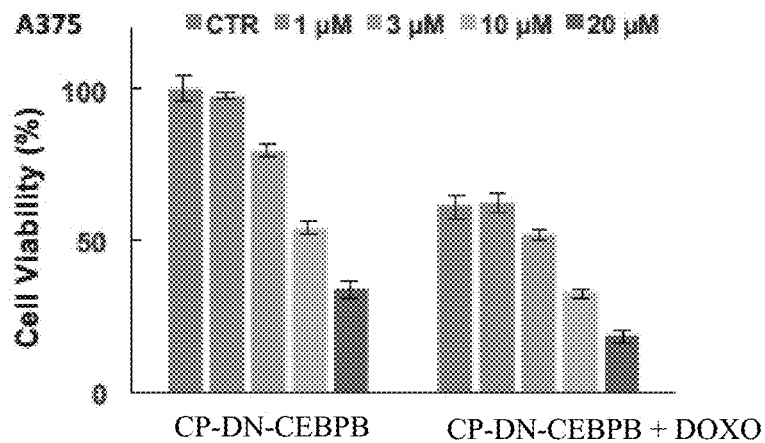

FIG. 31I is a graph reporting exemplary quantification of A375 cells following treatment for 6 days with various concentrations of CP-DN-CEBPB after no treatment or pre-treatment of the cells with 100 nM doxorubicin.

Figure 31J:
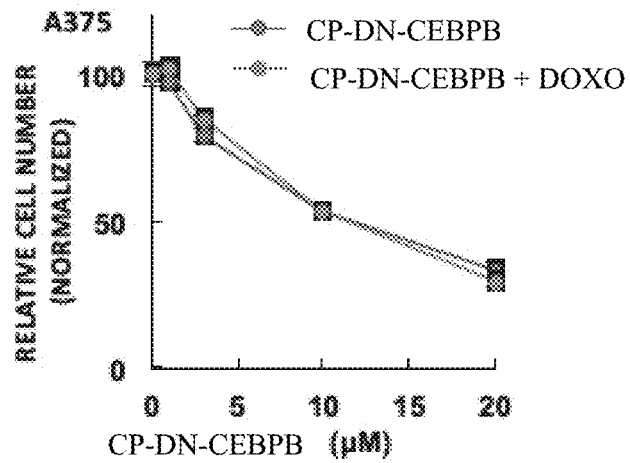

FIG. 31J is a graph reporting exemplary relative cell numbers of A375 cells following treatment for 6 days with various concentrations of CP-DN-CEBPB after no treatment or pre-treatment of the cells with 100 nM doxorubicin, as compared to cells that received no CP-DN-CEBPB treatment.

Figure 31K:
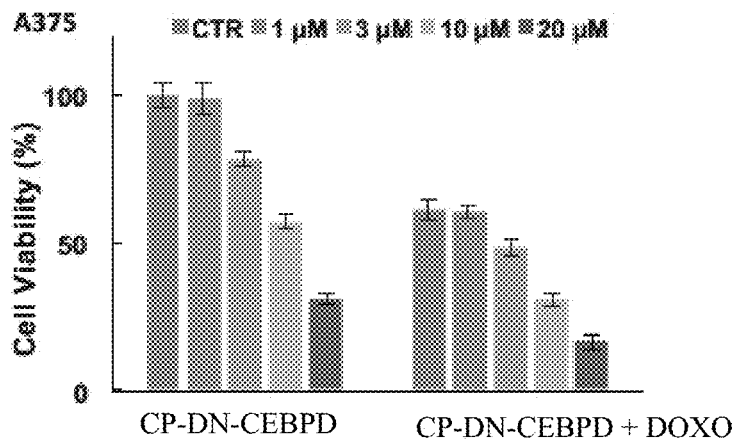

FIG. 31K is a graph reporting exemplary quantification of A375 cells following treatment for 6 days with various concentrations of CP-DN-CEBPD after treatment or pre-treatment of the cells with 100 nM doxorubicin.

Figure 31L:
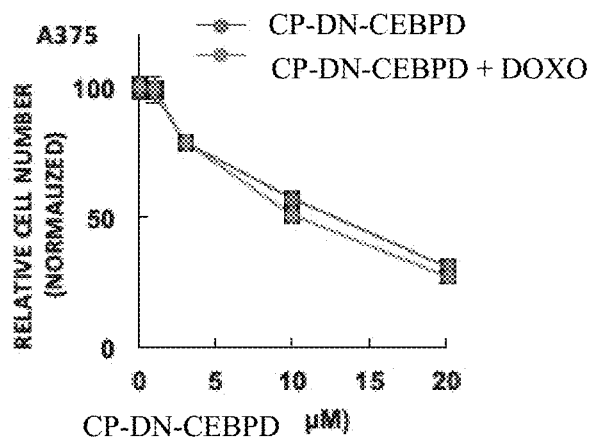

FIG. 31L is a graph reporting exemplary relative cell numbers of A375 cells following treatment for 6 days with various concentrations of CP-DN-CEBPD after no treatment or pre-treatment of the cells with 100 nM doxorubicin, as compared to cells that received no CP-CD-CDBPD treatment.

Figure 31M:
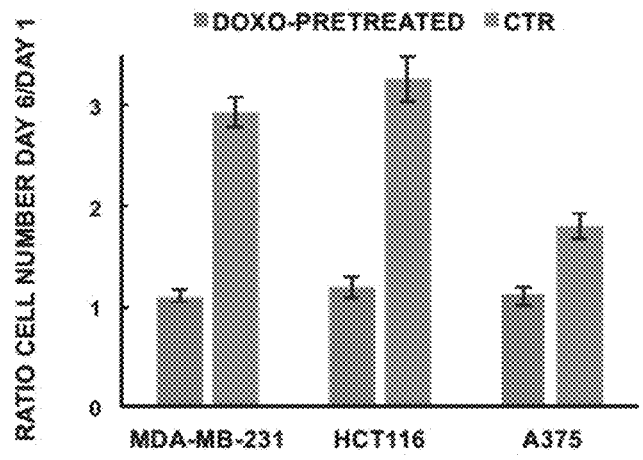

FIG. 31M is a graph reporting exemplary relative cell numbers of the cells of FIGS. 30A-L on day 1 after treatment versus day 6 after treatment.

Figures 32A, 32B, 32C:
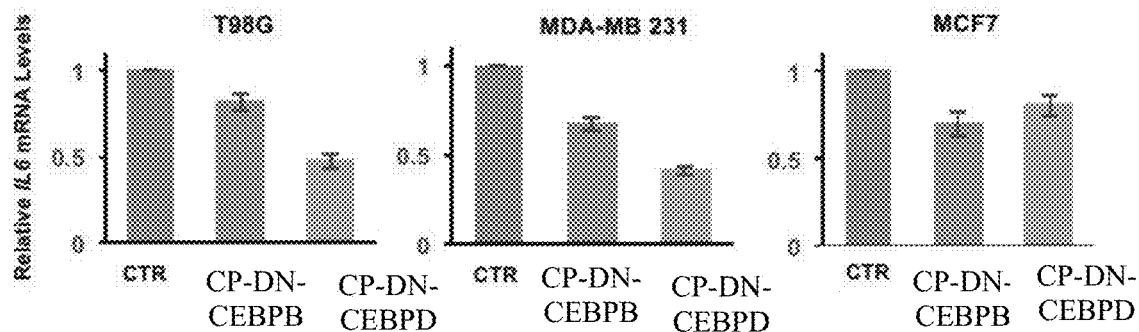

FIG. 32A is a graph reporting the exemplary relative expression levels of interleukin-6 (IL-6) in T98G cells treated with 20 µM CP-DN-CEBPB or 20 µM CP-DN-CEBPD for 3 days as compared to untreated cells.

FIG. 32B is a graph reporting the exemplary relative expression levels of interleukin-6 (IL-6) in MDA-MB-231 cells treated with 20 µM CP-DN-CEBPB or 20 µM CP-DN-CEBPD for 3 days as compared to untreated cells.

FIG. 32C is a graph reporting the exemplary relative expression levels of interleukin-6 (IL-6) in MCF7 cells treated with 20 µM CP-DN-CEBPB or 20 µM CP-DN-CEBPD for 3 days as compared to untreated cells.

Figures 32D, 32E:
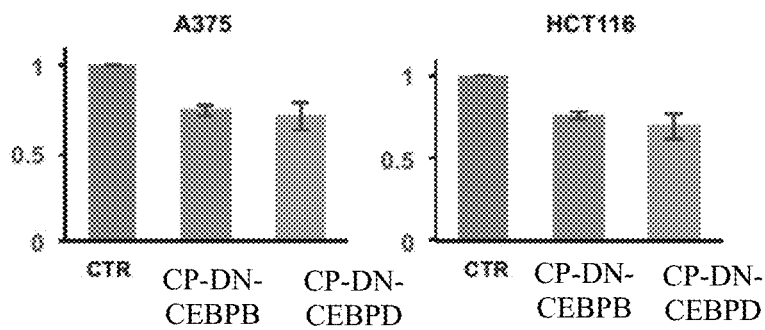

FIG. 32D is a graph reporting the exemplary relative expression levels of interleukin-6 (IL-6) in A375 cells treated with 20 µM CP-DN-CEBPB or 20 µM CP-DN-CEBPD for 3 days as compared to untreated cells.

FIG. 32E is a graph reporting the exemplary relative expression levels of interleukin-6 (IL-6) in HCT116 cells treated with 20 µM CP-CD-CDPRB or 20 µM CP-DN-CEBPD for 3 days as compared to untreated cells.

Figures 32F, 32G, 32H:
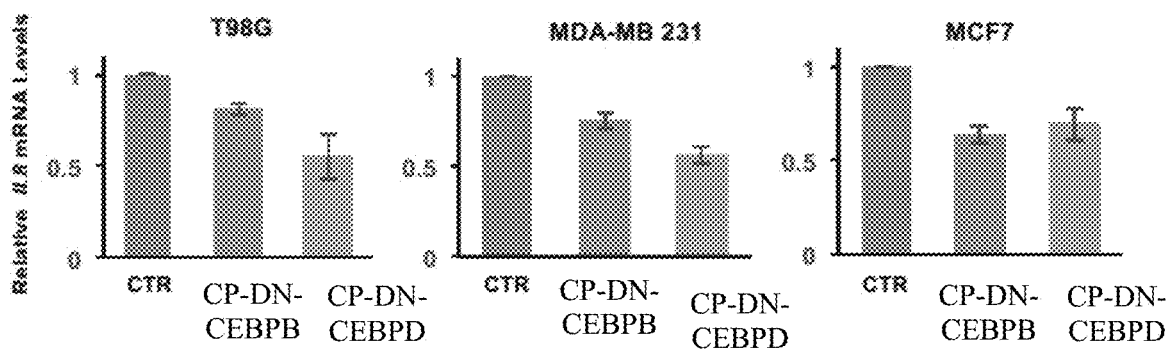

FIG. 32F is a graph reporting the exemplary relative expression levels of interleukin-8 (IL-8) in T98G cells treated with 20 μM CP-DN-CEBPB or 20 μM CP-DN-CEBPD for 3 days as compared to untreated cells.

FIG. 32G is a graph reporting the exemplary relative expression levels of interleukin-8 (IL-8) in MDA-MB-231 cells treated with 20 μM CP-DN-CEBPB or 20 μM CP-DN-CEBPD for 3 days as compared to untreated cells.

FIG. 32H is a graph reporting the exemplary relative expression levels of interleukin-8 (IL-8) in MCF7 cells treated with 20 μM CP-DN-CEBPB or 20 μM CP-DN-CEBPD for 3 days as compared to untreated cells.

Figures 32I, 32J:
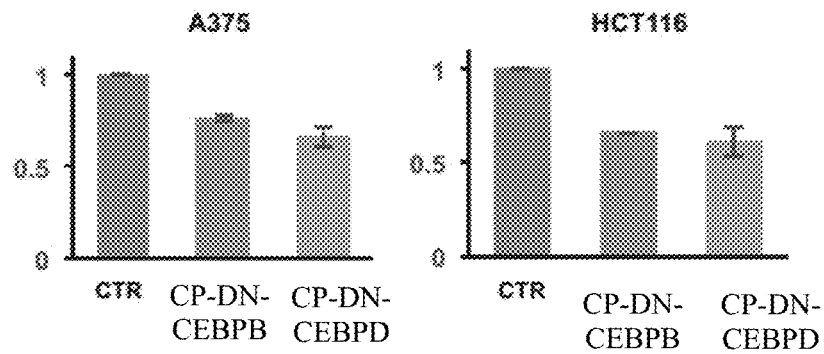

FIG. 32I is a graph reporting the exemplary relative expression levels of interleukin-8 (IL-8) in A375 cells treated with 20 μM CP-DN-CEBPB or 20 μM CP-DN-CEBPD for 3 days as compared to untreated cells.

FIG. 32J is a graph reporting the exemplary relative expression levels of interleukin-8 (IL-8) in HCT116 cells treated with 20 μM CP-DN-CEBPB or 20 μM CP-DN-CEBPD for 3 days as compared to untreated cells.

Figures 33A, 33B, 33C:
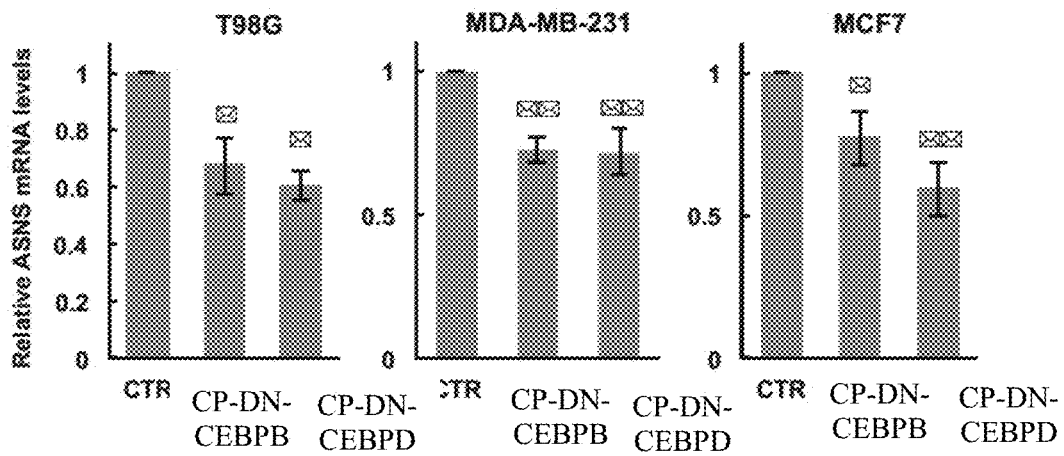

FIG. 33A is a graph reporting the exemplary relative expression levels of Asparagine Synthetase (ASNS) in T98G cells treated with 20 μM CP-DN-CEBPB or 20 μM CP-DN-CEBPD for 3 days as compared to untreated cells.

FIG. 33B is a graph reporting the exemplary relative expression levels of Asparagine Synthetase (ASNS) in MDA-MB-231 cells treated with 20 μM CP-DN-CEBPB or 20 μM CP-DN-CEBPD for 3 days as compared to untreated cells.

FIG. 33C is a graph reporting the exemplary relative expression levels of Asparagine Synthetase (ASNS) in MCF7 cells treated with 20 μM CP-DN-CEBPB or 20 μM CP-DN-CEBPD for 3 days as compared to untreated cells.

Figures 33D, 33E:
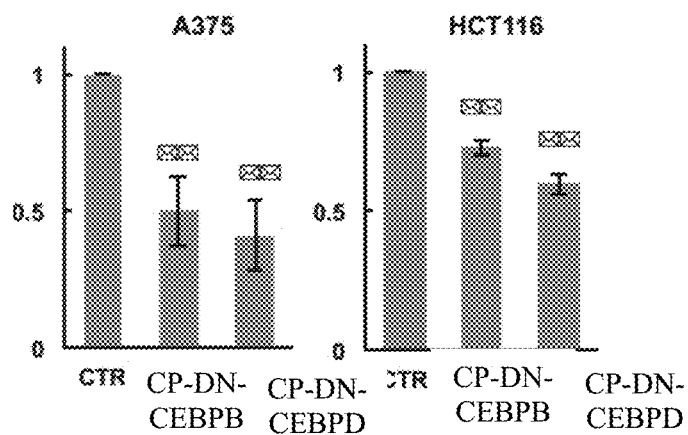

FIG. 33D is a graph reporting the exemplary relative expression levels of Asparagine Synthetase (ASNS) in A375 cells treated with 20 μM CP-DN-CEBPB or 20 μM CP-DN-CEBPD for 3 days as compared to untreated cells.

FIG. 33E is a graph reporting the exemplary relative expression levels of Asparagine Synthetase (ASNS) in HCT116 cells treated with 20 μM CP-DN-CEBPB or 20 μM CP-DN-CEBPD for 3 days as compared to untreated cells.

FIG. 34A is a set of exemplary images of Western immunoblots for BCL2, MCL1 and survivin proteins with actin as loading control of cell lysates from T98G, HCT116, MDA-MB 231, and MCF7 cells treated with 20 μM CP-DN-CEBPB or 20 μM CP-DN-CEBPD for 3 days.

FIG. 34B is a graph reporting the exemplary relative Band Density for survivin as compared to actin in the Western immunoblot of FIG. 34A.

FIG. 34C is a graph reporting the exemplary relative Band Density for BCL2 as compared to actin in the Western immunoblot of FIG. 34A.

FIG. 34D is a graph reporting the exemplary relative Band Density for MCL1 as compared to actin in the Western immunoblot of FIG. 34A.

Figures 35A, 35B, 35C:
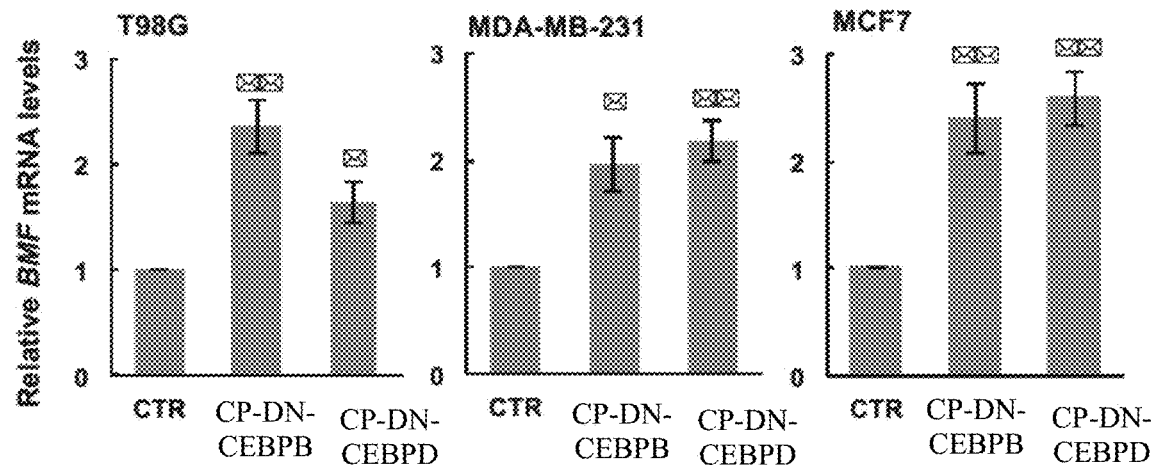

FIG. 35A is a graph reporting the exemplary relative expression levels of pro-apoptotic BMF in T98G cells treated with 20 μM CP-CD-CDPRB or 20 μM CP-DN-CEBPD for 3 days as compared to untreated cells.

FIG. 35B is a graph reporting the exemplary relative expression levels of pro-apoptotic BMF in MDA-MB-231 cells treated with 20 μM CP-DN-CEBPB or 20 μM CP-CD-CEBPD for 3 days as compared to untreated cells.

FIG. 35C is a graph reporting the exemplary relative expression levels of pro-apoptotic BMF in MCF7 cells treated with 20 μM CP-DN-CEBPB or 20 μM CP-DN-CEBPD for 3 days as compared to untreated cells.

Figures 35D, 35E:
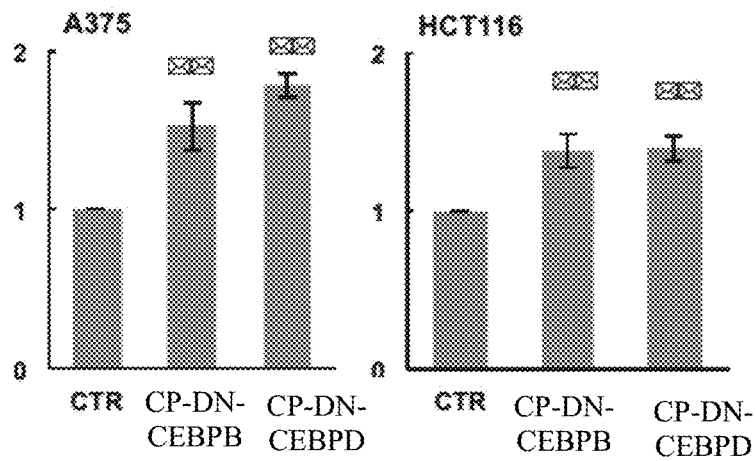

FIG. 35D is a graph reporting the exemplary relative expression levels of pro-apoptotic BMF in A375 cells treated with 20 μM CP-DN-CEBPB or 20 μM CP-DN-CEBPD for 3 days as compared to untreated cells.

FIG. 35E is a graph reporting the exemplary relative expression levels of pro-apoptotic BMF in HCT116 cells treated with 20 μM CP-DN-CEBPB or 20 μM CP-DN-CEBPD for 3 days as compared to untreated cells.

Figure 36B:
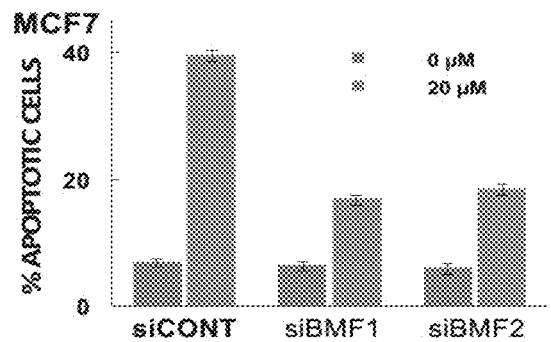
Figure 36C:
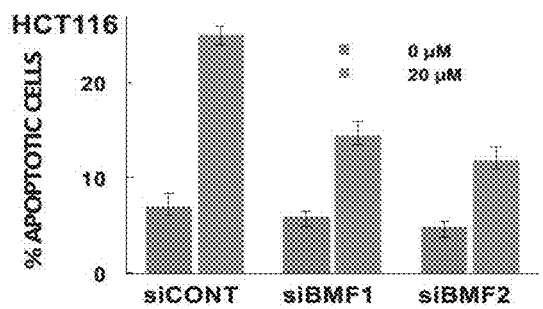
Figure 36D:
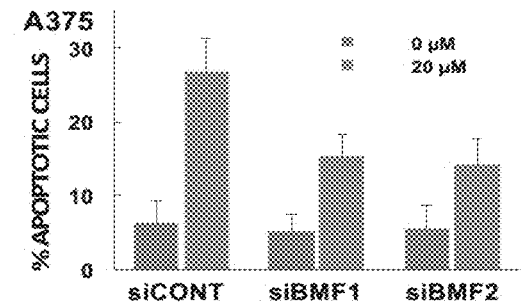
Figure 36A:
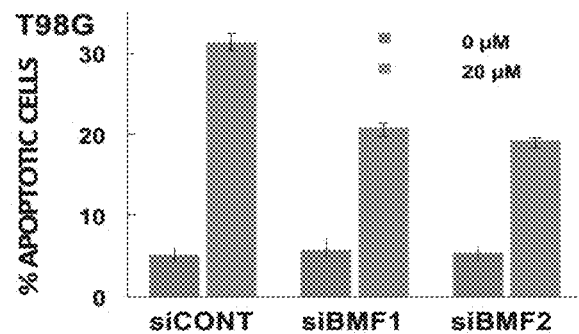

FIG. 36A is a graph reporting the exemplary percent of apoptotic cells when T98G cells in which BMF1 or BMF2 was knocked down with siRNA were treated with 20 μM CP-DN-CEBPD or were untreated.

FIG. 36B is a graph reporting the exemplary percent of apoptotic cells when MCF7 cells in which BMF was knocked down with siRNA control, siRNA-BMF1 or siRNA-BMF2 were treated with 20 μM CP-DN-CEBPD or were untreated.

FIG. 36C is a graph reporting the exemplary percent of apoptotic cells when HCT116 cells in which BMF was knocked down with siRNA control, siRNA-BMF1 or siRNA-BMF2 were treated with 20 μM CP-DN-CEBPD or were untreated.

FIG. 36D is a graph reporting the exemplary percent of apoptotic cells when A375 cells in which BMF was knocked down with siRNA control, siRNA-BMF1 or siRNA-BMF2 were treated with 20 μM CP-DN-CEBPD or were untreated.

Figure 37A:
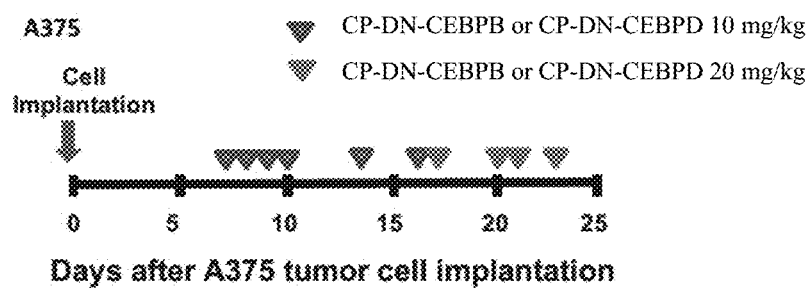

FIG. 37A is a diagram of a treatment scheme for nude mice implanted with A375 cells in which, after tumor formation, the animals were treated intraperitoneally with 10 or 20 mg/kg of CP-DN-CEBPB, CP-DN-CEBPD or vehicle.

Figure 37B:
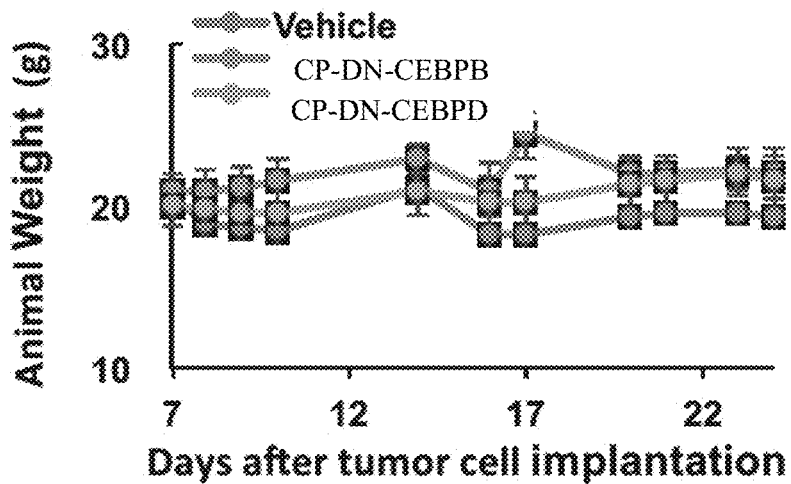

FIG. 37B is a graph of exemplary animal weight after the indicated number of days after tumor implantation in animals treated with the treatment scheme of FIG. 37A.

Figure 37C:
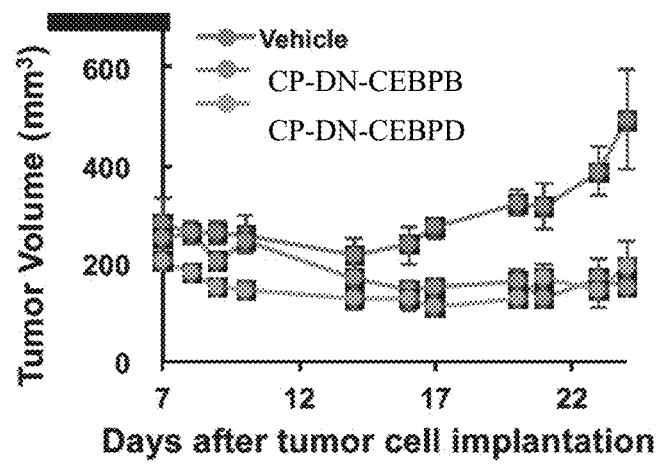

FIG. 37C is a graph of exemplary tumor volume after the indicated number of days after tumor implantation in animals treated with the treatment scheme of FIG. 37A.

Figure 37D:
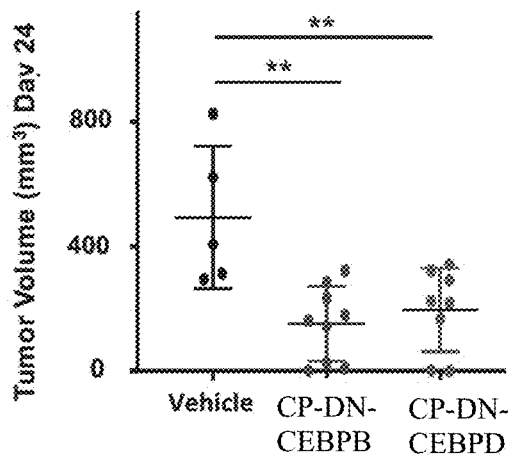

FIG. 37D is a graph of exemplary tumor volume 24 days after tumor implantation in animals treated with the treatment scheme of FIG. 37A.

Figure 38A:
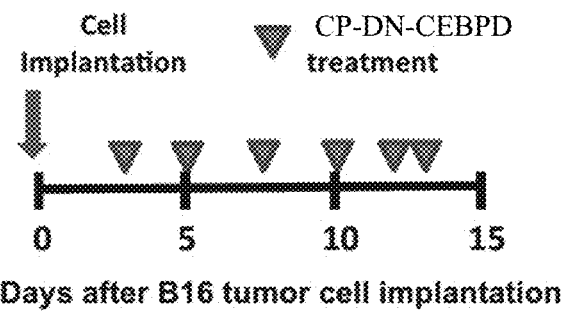

FIG. 38A is a diagram of a treatment scheme for nude mice implanted with B16-F10 melanoma cells in which, after tumor formation, the animals were treated intraperitoneally with 20 or 50 mg/kg of CP-DN-CEBPD or vehicle.

Figure 38B:
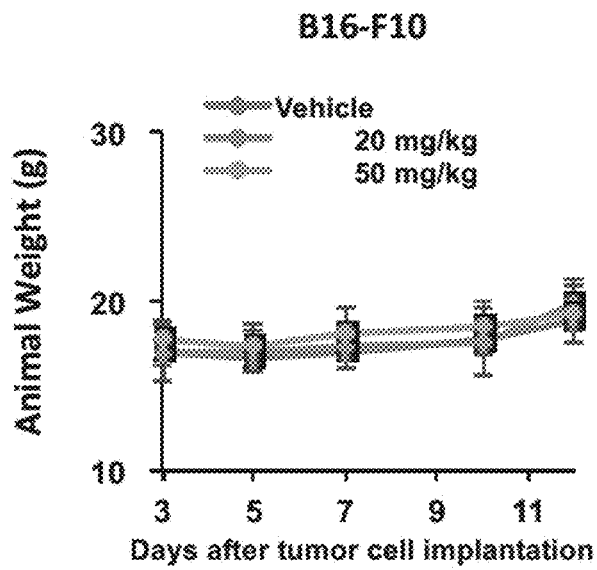

FIG. 38B is a graph of exemplary animal weight after the indicated number of days after tumor implantation in animals treated with the treatment scheme of FIG. 38A.

Figure 38C:
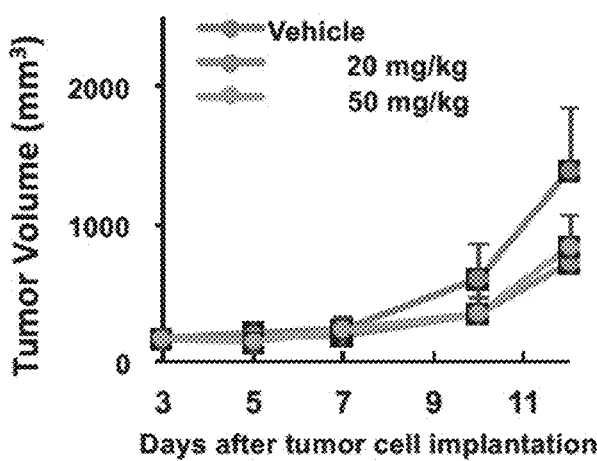

FIG. 38C is a graph of exemplary tumor volume after the indicated number of days after tumor implantation in animals treated with the treatment scheme of FIG. 38A.

Figure 38D:
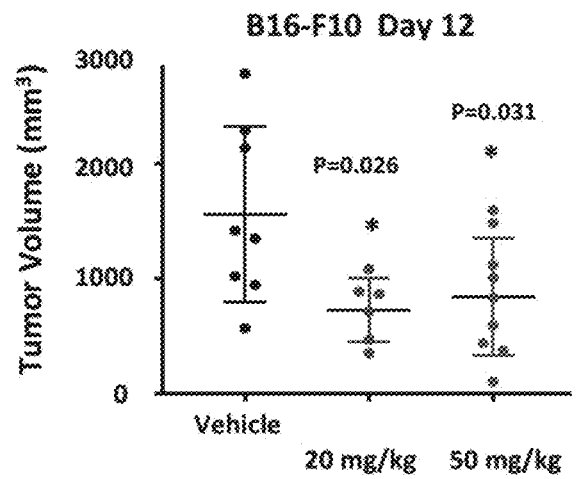

FIG. 38D is a graph of exemplary tumor volume 12 days after tumor implantation in animals treated with the treatment scheme of FIG. 38A.

Figure 39A:
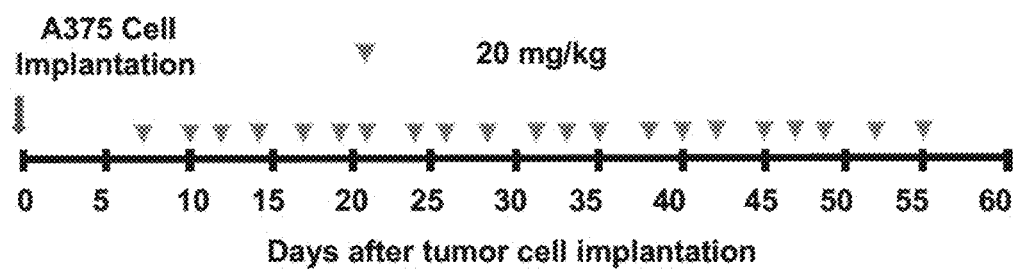

FIG. 39A is a diagram of a treatment scheme for nude mice implanted with A375 cells in which, after tumor formation, the animals were treated intraperitoneally with 20 mg/kg of CP-DN-CEBPD or vehicle.

Figure 39B:
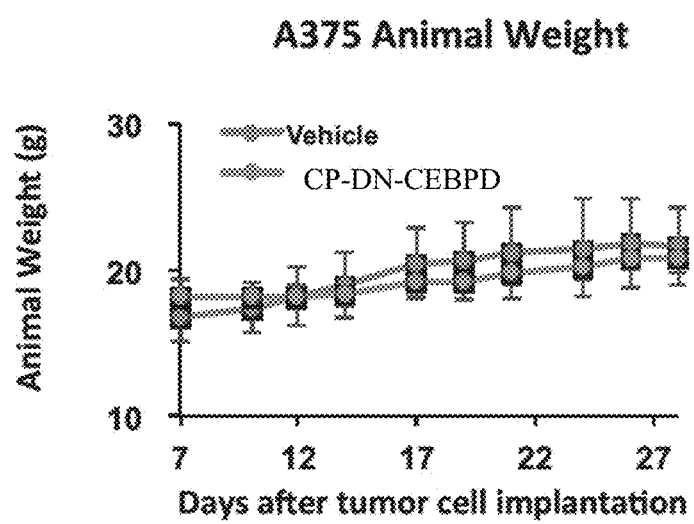

FIG. 39B is a graph of exemplary animal weight after the indicated number of days after tumor implantation in animals treated with the treatment scheme of FIG. 39A.

Figure 39C:
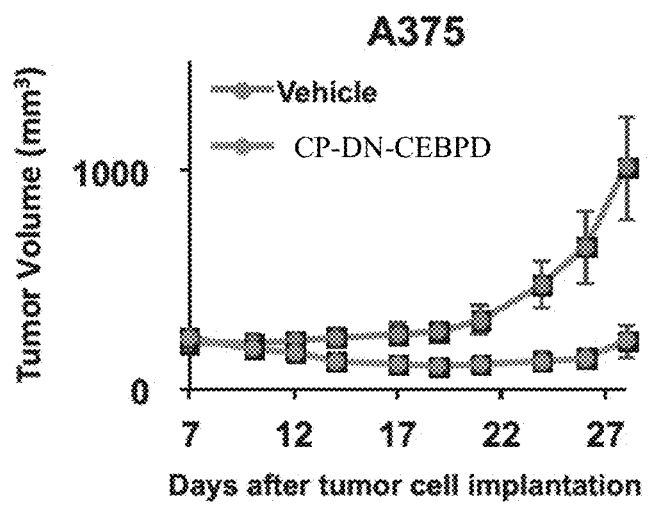

FIG. 39C is a graph of exemplary tumor volume after the indicated number of days after tumor implantation in animals treated with the treatment scheme of FIG. 39A.

Figure 39D:
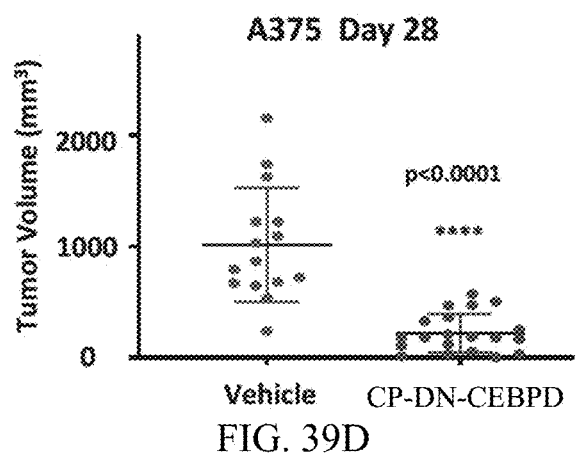

FIG. 39D is a graph of exemplary tumor volume 28 days after tumor implantation in animals treated with the treatment scheme of FIG. 39A.

Figure 39E:
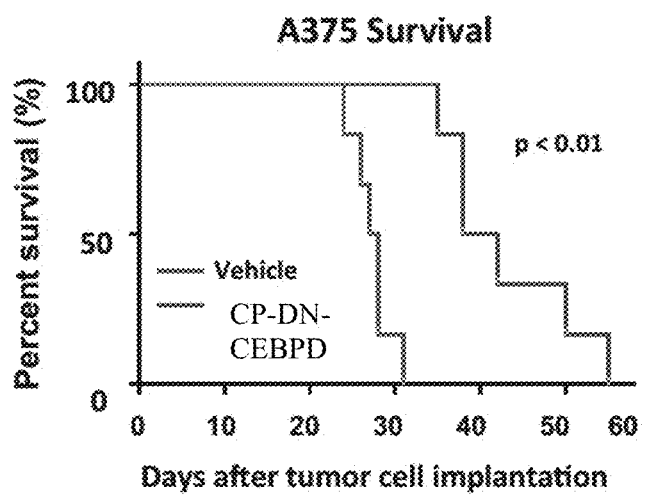

FIG. 39E is a graph of exemplary survival after tumor implantation in animals treated with the treatment scheme of FIG. 39A.

Figure 40A:
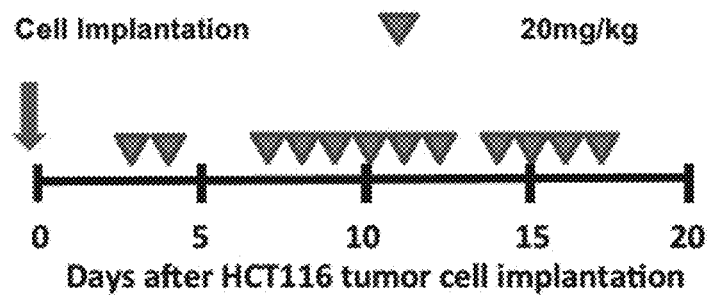

FIG. 40A is a diagram of a treatment scheme for nude mice implanted with HCT116 cells in which, after tumor formation, the animals were treated intraperitoneally with 20 mg/kg of CP-DN-CEBPD or vehicle.

Figure 40B:
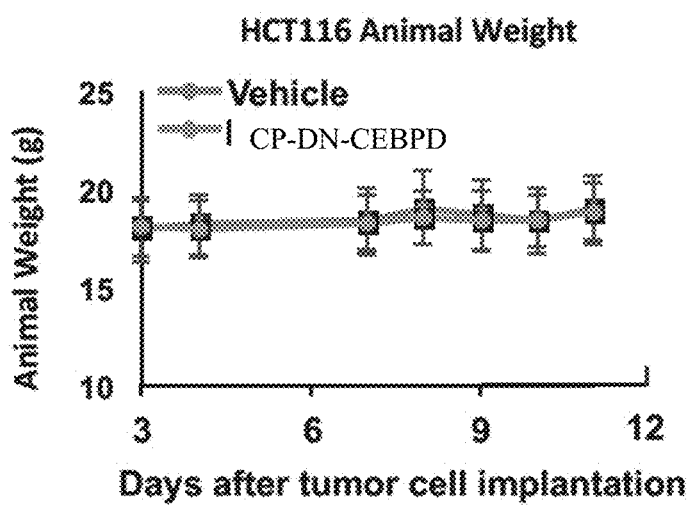

FIG. 40B is a graph of exemplary animal weight after the indicated number of days after tumor implantation in animals treated with the treatment scheme of FIG. 40A.

Figure 40C:
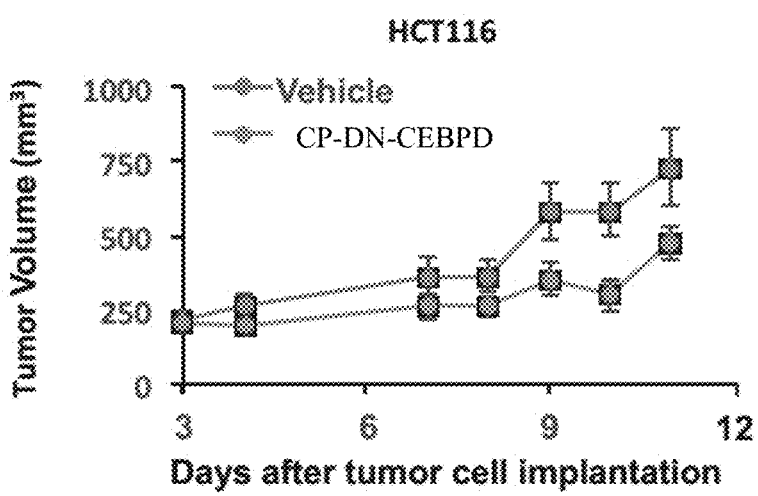

FIG. 40C is a graph of exemplary tumor volume after the indicated number of days after tumor implantation in animals treated with the treatment scheme of FIG. 40A.

Figure 40D:
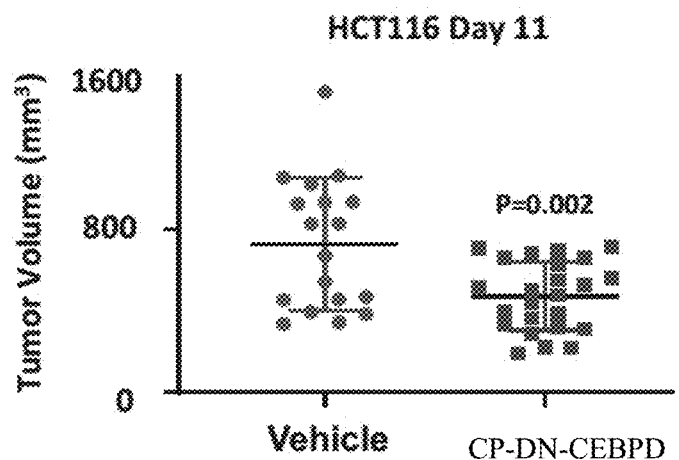

FIG. 40D is a graph of exemplary tumor volume 11 days after tumor implantation in animals treated with the treatment scheme of FIG. 40A.

Figure 40E:
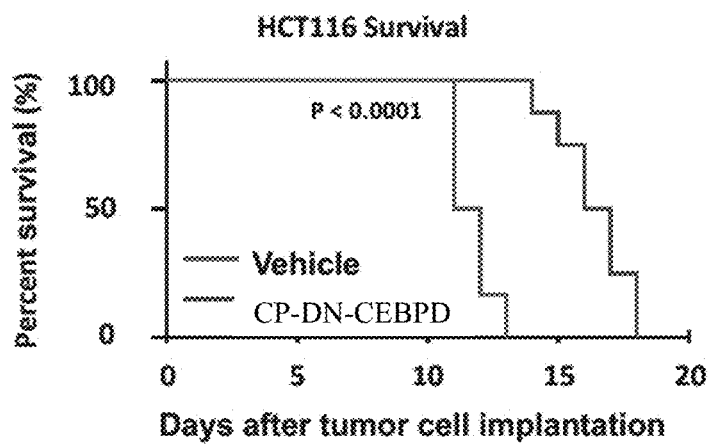

FIG. 40E is a graph of exemplary survival after tumor implantation in animals treated with the treatment scheme of FIG. 40A.

Figure 41:
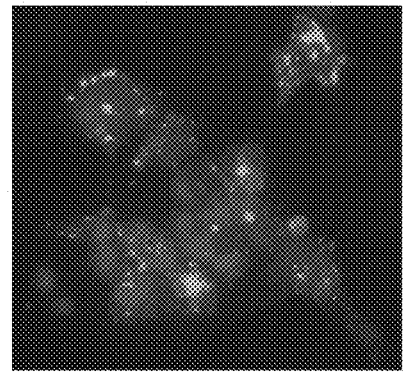

FIG. 41 is an exemplary photomicrograph of cultured GBM12 cells in which N-terminally FAM-labelled CP-DN-CEBPD is green and DAPI is blue.

Figure 42A:
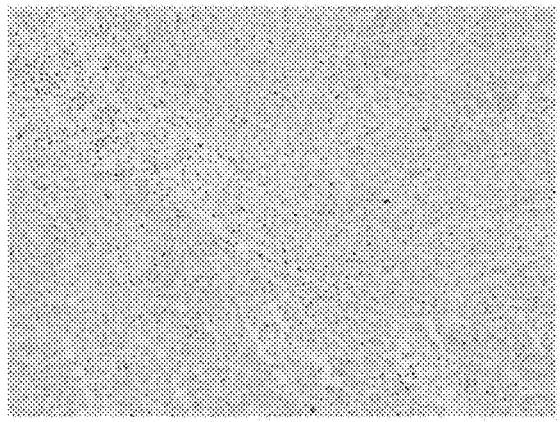

FIG. 42A is an exemplary photomicrograph of a section from a subcutaneous A375 xenograft tumors in a mouse treated with a control vehicle.

Figure 42B:

FIG. 42B is an exemplary photomicrograph of a section from a subcutaneous A375 xenograft tumors in a mouse treated with 20 mg/kg.

DETAILED DESCRIPTION

In the following description, details are set forth by way of example to facilitate discussion of the disclosed subject matter. It should be apparent to a person of ordinary skill in the art, however, that the disclosed implementations are exemplary and not exhaustive of all possible implementations.

The present disclosure relates to dominant negative (DN) proteins and methods for inhibiting activity or viability of neoplastic cells, including tumor cells. In particular, the present disclosure relates to dominant negative forms of CCAAT/enhancer-binding protein beta (CEBPB) and CCAAT/enhancer-binding protein delta (CEBPD), and cell-penetrating forms thereof. The present disclosure also relates to methods for using the dominant negative forms of CEBPB and CEBPD, and cell-penetrating forms thereof, for inhibiting neoplastic cells and for treating cancer in a subject.

Approximately one million people are diagnosed with cancer each year, and many millions of Americans of all ages are currently living with some form of cancer. At some time during the course of their lifetime, one out of every two American men and one out of every three American women will be diagnosed with some form of cancer. Despite intensive research, discovery of new therapeutic targets and development of new drugs for treating cancer remains challenging.

In some implementations, the present disclosure relates to a dominant-negative CEBPB protein.

The term "CEBPB protein" refers to CCAAT/enhancer-binding protein beta protein. CEBPB is a protein that in humans is encoded by the CEBPB gene (Szpirer C, Riviere M, Cortese R, Nakamura T, Islam M Q, Levan G, Szpirer J (July 1992). Genomics. 13 (2): 293-300; Cao Z, Umek R M, McKnight S L (October 1991). Genes Dev. 5 (9): 1538-52). CEBPB is a bZIP transcription factor that can bind as a homodimer to certain DNA regulatory regions. It can also form heterodimers with the related proteins CEBP-alpha, CEBP-delta, and CEBP-gamma and there is evidence that it can form heterodimers with multiple leucine zipper proteins via leucine zipper:leucine zipper interactions (Reinke A W, Baek J, Ashenberg O, Keating A E., Science. 2013 May 10; 340(6133):730-4). Translation of the C/EBP mRNA from different initiation codons leads to the synthesis of two transcriptional activators (LAP-1 and 2) and a transcriptional repressor (LIP). The LIP/LAP ratio is a critical factor in C/EBP-mediated gene transcription (Li et al., 2008, Journal Biological Chemistry, 283:22443). For example, CEBPB is important in the regulation of genes involved in immune and inflammatory responses and has been shown to bind to the IL-1 response element in the IL-6 gene, as well as to regulatory regions of several acute-phase and cytokine genes. In addition, CEBPB can bind the promoter and upstream element and stimulate the expression of the collagen type I gene. CEBPB is capable of increasing the expression of several target genes. Among them, some have specific role in the nervous system such as the preprotachykinin-1 gene, giving rise to substance P and neurokinin A and the choline acetyltransferase responsible for the biosynthesis of the important neurotransmitter acetylcholine. Other targets include genes coding for cytokines such as IL-6, IL-4, IL-5, and TNF-alpha. Genes coding for transporter proteins that confer multidrug resistance to the cells have also been found to be activated by CEBPB. Such genes include ABCC2 and ABCB1.

CEBPB and CEBPD are recognized as oncogenic drivers that are downstream of pathways such as those involving Ras and BRAF. As such, they have been implicated in oncogenic transformation, proliferation, survival, invasiveness, resistance to treatment, and poor clinical outcome for a range of tumor types including blood cell, breast, skin, prostate and brain (Tregnago et al. (2016) Leukemia 30, 1887-1896; Wang et al. (2017) Clin Cancer Res 23, 503-513; Banerjee et al. (2016) Free Radic Biol Med 99, 296-307; Wang, et al. (2015) Oncotarget 6, 31069-31084; Balamurugan and Sterneck (2013) Int J Biol Sci 9, 917-933; Wu et al. (2011) J Biol Chem 286, 28662-28670; Balamurugan et al. (2010) EMBO J 29, 4106-4117; Liu et al. (2018) Nat Commun 9, 1739; Huang et al. (2018) Cancer Lett 421, 63-72; Li et al. (2018) Neoplasma 65, 34-41; Ji et al. (2018) Genet Test Mol Biomarkers 22, 5-10; Yin et al. (2017) Cancer Res 77, 4973-4984; Cao et al. (2017) Exp Ther Med 14, 1554-1560; Gardiner et al. (2017) Oncotarget 8, 26013-26026; Aguilar-Morante et al. (2011) Neuroscience 176, 110-119; Mango et al. (2010) Immunity 32, 790-802; Carro et al. (2010) Nature 463, 318-325; Kim et al. (2009) Prostate 69, 1435-1447; Pal et al. (2009) Blood 114, 3890-3898; Shuman et al. (2004) Mol Cell Biol 24, 7380-7391; Duprez (2004) Cell Cycle 3, 389-390; Grimm and Rosen (2003) J Mammary Gland Biol Neoplasia 8, 191-204; Bundy and Sealy (2003) Oncogene 22, 869-883; Zhu, S., Yoon, K., Sterneck, E., Johnson, P. F., and Smart, R. C. (2002) CCAAT/enhancer binding protein-beta is a mediator of keratinocyte survival and skin tumorigenesis involving oncogenic Ras signaling. Proc Natl Acad Sci USA 99, 207-212). Significantly, many of these characteristics are suppressed by experimental CEBPB/D loss-of-function. Such activities have also been linked to the roles of CEBPB/D as regulators of the "mesenchymal transition". For example, in gliomas, CEBPB and CEBPD have been identified as 2 of the 4 "master regulators" of the mesenchymal transition responsible for many negative properties of these tumors (Carro et al. (2010) Nature 463, 318-325; Califano and Alvarez (2017) Nat Rev Cancer 17, 116-130).

In addition, CEBPB has been described as "a critical regulator of the immunosuppressive environment created by growing cancers" (Mango et al. (2010) Immunity 32, 790-802).

As used herein, "CEBPB" includes both an "CEBPB protein" and an "CEBPB analogue". Unless otherwise indicated, "protein" shall include a protein, protein domain, polypeptide, or peptide, and any fragment thereof. For example, the CEBPB protein can have the amino acid sequence set forth in NCBI Accession No. NP_001272808.1 (human isoform c) or NCBI Accession No. NP_001272807.1 (human isoform b) or NCBI Accession No. NP_005185.2 (human isoform a), including conservative substitutions thereof. As used herein, "conservative substitutions" are those amino acid substitutions which are functionally equivalent to a substituted amino acid residue, either because they have similar polarity or steric arrangement, or because they belong to the same class as the substituted residue (e.g., hydrophobic, acidic, or basic).

A "CEBPB analogue", as used herein, is a functional variant of the CEBPB protein, having CEBPB biological activity, such as ability of the CEBPB analogue's leucine zipper domain to bind to the protein binding partners of CEBPB, that has 60% or greater, 70% or greater or 80% or greater or 90% or greater or 95% or greater amino-acid-sequence homology with the CEBPB protein.

In general, the terms "bind" or "binding" as used herein in connection with inter-molecular interactions such as those between proteins, or domains or motifs thereof, or between proteins and other molecules, such as DNA, refers to the connecting or uniting, at least for a time, of two or more molecules by a bond, link, force or tie in order to keep two or more molecules together, at least for a time. Exemplary bonds include without limitation covalent bond, ionic bond, van der Waals interactions, hydrogen bonds, and other bonds identifiable by a skilled person. In some instances, binding of a first molecule, such as the DN proteins described herein, with a second molecule, such as a binding partner of the DN protein, can result in sequestering, the second molecule, thus providing a type of inhibition of the second molecule.

Persons of ordinary skill in the art will understand that the numbering of amino acid residues in CEBPB may be different than that set forth herein, or may contain certain conservative amino acid substitutions that produce the same CEBPB activity as that described herein. Corresponding amino acids and conservative substitutions in other isoforms or analogues are easily identified by visually inspecting the relevant amino acid sequences, or by using homology software programs identifiable by skilled persons.

The term "leucine zipper" refers to a three-dimensional structural motif found in some proteins, including CEBPB and CEBPD, as described herein.

The term "leucine zipper domain" or "bZIP domain" refers to a dimerization domain, such as found in the bZIP (Basic-region leucine zipper) class of eukaryotic transcription factors. The bZIP domain is typically 60 to 80 amino acids in length with a highly conserved DNA binding basic region and a more diversified leucine zipper dimerization region. The leucine zipper is a common three-dimensional structural motif in proteins. Leucine zipper domains typically contain leucine residues every seven amino acids in the dimerization domain.

The mechanism of transcriptional regulation by bZIP proteins typically occurs through binding affinity for ACGT motifs, which include CACGTG (G box), GACGTC (C box), TACGTA (A box), AACGTT (T box), and a GCN4 motif, namely TGA(G/C)TCA. A small number of bZIP factors such as OsOBF1 can also recognize palindromic sequences. However, the others, including LIP19, OsZIP-2a, and OsZIP-2b, among others, do not bind to DNA sequences. Instead, these bZIP proteins form heterodimers with other bZIPs to regulate transcriptional activities.

For example, the transcription factor ATF5 may be sequestered by interacting with DN-CEBPB and/or DN-CEBPD. As shown in Example 4 and FIG. 3, a dominant negative form of ATF5, having the same ATF5 leucine zipper sequence as wild-type ATF5, interacts with CEBPB, phosphor-CEBPB and CEBPD via it's ATF5 leucine zipper.

In general, the terms "dominant negative" or "DN" as used herein refers to a protein variant capable of blocking the function of the normal, wild-type protein within the same cell. For example, in some instances, dominant negative activity may occur if the protein variant is capable of binding, or otherwise interacting, with the same cellular components (such as protein binding partners) as the wild-type protein, but blocking one or more aspects of the function of the wild type protein. In particular, the terms "dominant negative" or "DN" as used herein refers to a protein that has been modified so that it interacts with the normal binding partners (such as protein binding partners) for that protein, but is lacking the activity that would normally be present when it forms such interactions. In various implementations described herein, the dominant negative activity is due to the modification of or deletion of sequences from the WT protein to provide the DN protein. For example, the DN forms of CEBPB and CEBPD described herein retain the capacity to bind to the binding partners of the WT forms of CEBPB and CEBPD for example through their native leucine zipper domains. However, the homodimers or heterodimers that are formed that include a DN CEBPB or DN CEBPD, are non-functional and have the effect of sequestering their binding partners so that they cannot perform their normal cellular functions. Examples of binding partners that may be sequestered by interacting with DN-CEBPB and/or DN-CEBPD include CEBPB, CEBPD, CEBPA, CEBPE, CEBPG, CEBPZ, JUN, DDIT3, ATF4, ATF5, MAFA, and BATF.

As described herein, the DN CEBPB protein consists essentially of a CEBPB leucine zipper domain capable of binding to binding partners of CEBPB. In some implementations, the CEBPB leucine zipper domain has at least, or at least about, 10%, 20%, 30%, 40%, 50%, 60%, 70%, 80%, or 90% or more of the function of the WT CEBPB leucine zipper domain to bind to the protein binding partners of CEBPB.

For example, in various implementations, the CEBPB leucine zipper domain can have an amino acid sequence (SEQ ID NO: 1)
LETQHKVLELTAENERLQKKVEQLSRELSTLRNLFKQL.

The present disclosure also contemplates and encompasses variants of DN CEBPB proteins, wherein the WT CEBPB leucine zipper domain can have an amino acid sequence that contains one or more insertions, deletions, substitutions or additions to the amino acid sequence of SEQ ID NO: 1 that retains at least, or at least about, 10%, 20%, 30%, 40%, 50%, 60%, 70%, 80%, or 90% or more of the function of the WT CEBPB leucine zipper domain to bind to the protein binding partners of CEBPB. In some implementations, the variant of DN CEBPB protein has a CEBPB leucine zipper domain having at least, or at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% homology to the amino acid sequence of SEQ ID NO: 1.

The generation of variant DN CEBPB proteins having variant sequences of CEBPB leucine zipper domains and screening for function of the variant CEBPB leucine zipper domain to bind to the protein binding partners of CEBPB can be performed by skilled persons using methods known in the art. In some implementations, the DN CEBPB proteins having variant sequences of CEBPB leucine zipper domains can be optimized for efficacy and potency by employing the standard techniques of modeling, amino acid substitution, chemical modifications, use of d-amino acids, and the like, and iterative biological testing for activity and stability. It is contemplated that DN CEBPB proteins having variant CEBPB leucine zipper sequences can be provided by processes of protein engineering, such as those employing rational protein design and/or directed evolution. As would be understood by skilled persons, rational design of proteins refers to an approach of creating new proteins or proteins having sequence variation with a certain functionality, based upon the ability to predict how the molecule's structure will affect its behavior through physical models. This can be done either de novo or by making calculated variations on a known structure. In general, site-directed mutagenesis methods identifiable by skilled persons can be used to introduce one or more insertions, deletions, substitutions or additions to the amino acid sequence. In contrast, in directed evolution approaches, random mutagenesis, e.g. by error-prone PCR or Sequence Saturation Mutagenesis, is applied to a protein, and a selection regime is used to select variants having desired traits. Further rounds of mutation and selection may then be applied. Generally, directed evolution approached follow an iterative two-step process which involves generation of protein mutant libraries, and high throughput screening processes to select for variants with improved traits. This technique does not require prior knowledge of the protein structure and function relationship. Directed evolution utilizes random or focused mutagenesis to generate libraries of mutant proteins. Random mutations can be introduced using either error prone PCR, or site saturation mutagenesis, among other methods identifiable by skilled persons. Screening of variant DN CEBPB proteins produced by rational design or directed evolution processes having a leucine zipper domain sequence containing one or more insertions, deletions, substitutions or additions to the amino acid sequence of SEQ ID NO: 1 can be performed by any method known in the art. For example, phage display methods are one approach for screening proteins. This method involves the fusion of genes encoding the variant polypeptides with phage coat protein genes. Protein variants expressed on phage surfaces are selected by binding with immobilized targets in vitro. Phages with selected protein variants are then amplified in bacteria, followed by the identification of positive clones by enzyme linked immunosorbent assay. These selected phages are then subjected to DNA sequencing. Cell surface display systems can also be utilized to screen mutant polypeptide libraries. The library mutant genes are incorporated into expression vectors which are then transformed into appropriate host cells. These host cells are subjected to further screening methods to identify the cells with desired phenotypes. Other methods may also be used to screen binding activity of variants of DN CEBPB proteins, such as pull-down assays. For example, polynucleotide expression constructs encoding variant DN CEBPB proteins having a leucine zipper domain sequence containing one or more insertions, deletions, substitutions or additions to the amino acid sequence of SEQ ID NO: 1 can be produced having a protein tag, such as a GFP tag or a FLAG tag, among others, fused to the variant DN CEBPB protein. Cultured cells can then be transfected with the expression construct, and protein lysates purified from the cells expressing the construct. The tagged DN CEBPB fusion protein can then be pulled down using antibodies against the tag, and Western blots used to assess the presence of binding partners bound to the variant DN CEBPB protein using antibodies against known binding partners of CEBPB. The present disclosure also contemplates the generation of variant DN CEBPB proteins having variant sequences of CEBPB leucine zipper domains by synthesis of polypeptides in vitro, e.g., by chemical means or in vitro translation of mRNA, and screening thereof for function of the variant CEBPB leucine zipper domain to bind to the protein binding partners of CEBPB. For example, variant DN CEBPB proteins may be synthesized by methods commonly known to one skilled in the art (*Modern Techniques of Peptide and Amino Acid Analysis* (New York: John Wiley & Sons, 1981); Bodansky, M., *Principles of Peptide Synthesis* (New York: Springer-Verlag New York, Inc., 1984). Examples of methods that may be employed in the synthesis of the amino acid sequences, and analogues of these sequences, include, but are not limited to, solid-phase peptide synthesis, solution-method peptide synthesis, and synthesis using any of the commercially-available peptide synthesizers. The amino acid sequences of the present disclosure may contain coupling agents and protecting groups, which are used in the synthesis of protein sequences, and which are well known to one of skill in the art. Similar approaches and methods can be used for producing variants of the DN CEBPD having a leucine zipper domain sequence containing one or more insertions, deletions, substitutions or additions to the amino acid sequence of SEQ ID NO: 2 described herein and screening the activity of the variant proteins.

In addition to the CEBPB leucine zipper domain, the DN CEBPB proteins of the present disclosure may include one or more amino acid residues, provided that the one or more additional amino acid residues do not prevent the function of the CEBPB leucine zipper from binding to the CEBPB binding partners.

In various implementations, a functional DNA binding domain is absent from the dominant negative CEBPB protein. In some implementations, a functional DNA binding domain may have no more than, or no more than about, 10%, 20%, 30%, 40% or 50% of the DNA binding function of the DNA binding domain of wild-type CEBPB, such as that of NCBI Accession No. NP_001272808.1 (human isoform c) or NCBI Accession No. NP_001272807.1 (human isoform b) or NCBI Accession No. NP_005185.2 (human isoform a).

The term "DNA binding domain" refers to a protein domain that contains at least one structural motif configured to recognize and bind double- or single-stranded DNA, wherein the term "motif" refers to a supersecondary structure that appears in multiple proteins, and in particular a three-dimensional protein structure of several adjacent elements of a secondary structure that is typically smaller than a protein domain or a subunit. DNA-binding domains can be part of a larger protein consisting of further protein domains with differing functions including the function of regulating the activity of the DNA-binding domain. The function of DNA binding can be either structural or involve transcription regulation, or both. Many proteins involved in the regulation of gene expression contain DNA-binding domains as will be understood by a skilled person. Such proteins include transcription factors, or transcriptional repressors, among others recognizable by a skilled person.

A DNA-binding domain in the sense of the disclosure can recognize and bind DNA in a DNA sequence-specific or non-sequence-specific manner, which involves molecular complementarity between protein and DNA. The wording "specific" "specifically" or "specificity" as used herein with reference to the binding of a first molecule to second molecule refers to the recognition, contact and formation of a stable complex between the first molecule and the second molecule, together with substantially less to no recognition, contact and formation of a stable complex between each of the first molecule and the second molecule with other molecules that may be present. Exemplary specific bindings are antibody-antigen interaction, cellular receptor-ligand interactions, polynucleotide hybridization, enzyme substrate interactions etc. The term "specific" as used herein with reference to a molecular component of a complex, refers to the unique association of that component to the specific complex which the component is part of. The term "specific" as used herein with reference to a sequence of a polynucleotide refers to the unique association of the sequence with a single polynucleotide which is the complementary sequence. By "stable complex" is meant a complex that is detectable and does not require any arbitrary level of stability, although greater stability is generally preferred.

In some implementations, a DNA-binding domain of a protein can perform DNA recognition and DNA specific binding for example at the major or minor groove of DNA, or at the sugar-phosphate DNA backbone. DNA-binding domains can recognize specific DNA sequences, such as some DNA-binding domains of transcription factors that activate specific genes, or some DNA-binding domains of transcriptional repressors that repress the transcription of specific genes. Another example is that of enzymes that modify DNA at specific sites, such as restriction enzymes. In particular, the DNA binding domain adopts correctly-oriented alignment of its constituent sub-components to effectively interact with DNA.

The specificity of DNA-binding proteins can be detected using many biochemical and biophysical techniques, such as gel electrophoresis, analytical ultracentrifugation, calorimetry, DNA mutation, protein structure mutation or modification, nuclear magnetic resonance, x-ray crystallography, surface plasmon resonance, electron paramagnetic resonance, cross-linking and microscale thermophoresis (MST), among others recognizable by a skilled person. Other assays of DNA binding domain function can include assays of cell viability or function, such as gene expression profiling cell death assays, apoptosis assays, among others, to detect a cell viability or function that is associated with function of a DNA binding domain. Accordingly, for example, the cellular effects of a mutation of a DNA binding domain in a protein may be assessed by using assays of cell viability or function.

In implementations herein described where the DN CEBPB or DN CEBPD lacking a functional DNA binding domain forms a dimer with its binding partner in a cell, the DN CEBPB or DN CEBPD prevents normal dimerization of DNA binding domains and thereby prevents binding with a DNA regulatory sequence upon dimerization of the protein monomers. The term "dimerization" refers to the process of forming a dimer of two monomers, for example two protein monomers. In particular, dimerization dependent DNA binding domains are configured so that dimerization of the monomer components strengthens the interactions of the domain with a corresponding DNA regulatory sequence, rendering the formation or dissociation of the dimers an intrinsic part of the regulatory mechanisms. In particular, dimerization dependent DNA binding domains can bind to DNA sequences that are composed of two very similar "half-sites," typically also arranged symmetrically. This arrangement allows each protein monomer to make a nearly identical set of contacts and enormously increases the binding affinity.

In some implementations, the dimerization dependent DNA binding domains are leucine zipper domains. In other implementations, dimerization dependent DNA binding domains may be selected from helix-loop-helix, helix-turn-helix, zinc finger, winged helix, winged helix turn helix, helix loop helix, HMG-box, Wor3 domain, OB-fold domain, immunoglobulin fold, B3 domain, TAL effector DNA-binding domain, and others recognizable by a skilled person.

In particular, in some implementations, a functional DNA binding domain of a CEBPB protein may have an amino acid sequence KKTVD<u>K</u>HSDEY<u>K</u>IRRER<u>NN</u>IA-VR<u>K</u>SRD<u>KAK</u>MRN (SEQ ID NO: 3). In some implementations, substitution of the bold underlined amino acids of SEQ ID NO: 3 from basic to acidic amino acids can be performed to disrupt binding to DNA. Accordingly, in some implementations, one or more of the bold underlined amino acids of SEQ ID NO: 3 can be mutated to produce a non-functional CEBPB DNA binding domain in a DN CEBPB protein. In some implementations, the specificity of a mutated DNA binding domain of a CEBPB protein can be assessed using biochemical and biophysical techniques, and the cellular effects of a mutated DNA binding domain of a CEBPB protein may be assessed by using assays of cell viability or function, as described herein.

In some implementations of the DN CEBPB protein, the CEBPB leucine zipper domain may have an N-terminal end, wherein an extended leucine zipper domain is linked to the N-terminal end, the extended leucine zipper domain having an amino acid sequence selected from LEQRAEELAR-ENEELEKEAEELEQENAE (SEQ ID NO: 4), LAR-ENEELEKEAEELEQENAE (SEQ ID NO: 5), LEKE-AEELEQENAE (SEQ ID NO: 6), and LEQENAE (SEQ ID NO: 7). The exemplary extended leucine zipper domains of SEQ ID NO: 4, SEQ ID NO: 5, SEQ ID NO: 6, and SEQ ID NO: 7 can be generated by mutating (and thereby inactivating) the DNA binding domain of the WT CEBPB protein. In other words, in some implementations, the DNA binding domain of CEBPB is deleted and replaced with the extended leucine zipper domain.

For example, in some implementations as described in Example 1 and Table 1 therein, the DN CEBPB protein can have an amino acid sequence (SEQ ID NO: 8)
EQKLISEEDLEQKLISEEDLEQKLISEEDLARAGSMASMTGGQQMGRDPD

LEQRAEELARENEELEKEAEELEQENAE*LETQHKVLELTAENE*

*RLQKKVEQLSRELSTLRNLFKQL*PEPLLASX$_1$GHX$_2$, wherein an amino acid residue $X_1$ can be A or S and an amino acid residue $X_2$ can be C or M, or the DN CEBPB protein can have an amino acid sequence (SEQ ID NO: 9)
MEQKLISEEDLEQKLISEEDLEQKLISEEDLARAGSMASMTGGQQMGRDP

DLEQRAEELARENEELEKEAEELEQENAE*LETQHKVLELTAENER*

*LQKKVEQLSRELSTLRNLFKQL*,
or (SEQ ID NO: 10)
MEQKLISEEDLEQKLISEEDLEQKLISEEDLARAGSMASMTGGQQMGRDP

D*LETQHKVLELTAENERLQKKVEQLSRELSTLRNLFKQL*.

In the exemplary DN CEBPB proteins of SEQ ID NO: 8 and SEQ ID NO: 9, an extended leucine zipper domain sequence LEQRAEELARENEELEKEAEELEQENAE (SEQ ID NO: 4) is underlined, and a wild-type (WT) leucine zipper domain sequence LETQHKVLELTAENERLQKKVEQLSRELSTLRNLFKQL (SEQ ID NO: 1) is italicized and bold. In contrast, the exemplary amino acid sequences of SEQ ID NO: 10 does not contain an extended leucine zipper domain sequence. Importantly, all of the exemplary DN CEBPB proteins of SEQ ID NO: 8, SEQ ID NO: 9, and SEQ ID NO: 10 contain a functional CEBPB leucine zipper domain, exemplified by SEQ ID NO: 1, and lack a functional CEBPB DNA binding domain.

In some implementations, the DN CEBPB protein may include a protein tag. For example, in the exemplary DN CEBPB proteins having amino acid sequences of SEQ ID NO: 8, SEQ ID NO: 9 and SEQ ID NO: 10 contain a MYC tag having three consecutive repetitions of the MYC sequence EQKLISEEDL (SEQ ID NO: 11), EQKLISEEDLEQKLISEEDLEQKLISEEDL (SEQ ID NO: 12) following the N-terminal methionine. As would be understood by skilled persons, a tag is not required for the DN function, but allows additional, optional functionality, for example such as allowing immunoprecipitation or isolation on beads coated with MYC antibodies and can function as a reporter for detecting expression of the DN construct in Western blots or in cells by immunostaining.

The term "tag" as used herein means protein tags including peptide sequences typically introduced onto a recombinant protein. Tags can be removable by chemical agents or by enzymatic means, such as proteolysis or splicing. Tags can be attached to proteins for various purposes: Affinity tags are appended to proteins so that they can be purified from their crude biological source using an affinity technique. These include chitin binding protein (CBP), and the poly(His) tag. The poly(His) tag is a widely-used protein tag; it binds to metal matrices. Chromatography tags can be used to alter chromatographic properties of the protein to afford different resolution across a particular separation technique. Often, these consist of polyanionic amino acids, such as FLAG-tag. Epitope tags are short peptide sequences which are chosen because high-affinity antibodies can be reliably produced in many different species. These are usually derived from viral genes, which explain their high immunoreactivity. Epitope tags include V5-tag, Myc-tag, HA-tag and NE-tag. These tags are particularly useful for western blotting, immunofluorescence and immunoprecipitation experiments, although they also find use in antibody purification. Protein tags can allow specific enzymatic modification (such as biotinylation by biotin ligase) or chemical modification (such as reaction with FlAsH-EDT2 for fluorescence imaging). Tags can be combined, in order to connect proteins to multiple other components. However, with the addition of each tag comes the risk that the native function of the protein may be abolished or compromised by interactions with the tag. Therefore, after purification, tags are sometimes removed by specific proteolysis (e.g. by TEV protease, Thrombin, Factor Xa or Enteropeptidase).

Exemplary tags include without limitation the following, among others known to persons skilled in the art: Peptide tags, such as: AviTag, a peptide allowing biotinylation by the enzyme BirA and so the protein can be isolated by streptavidin (GLNDIFEAQKIEWHE (SEQ ID NO: 13)); Calmodulin-tag, a peptide that can be bound by the protein calmodulin (KRRWKKNFIAVSAANRFKKISSSGAL (SEQ ID NO: 14)); polyglutamate tag, a peptide binding efficiently to anion-exchange resin such as Mono-Q (EEEEEE (SEQ ID NO: 15)); E-tag, a peptide recognized by an antibody (GAPVPYPDPLEPR (SEQ ID NO: 16)); FLAG-tag, a peptide recognized by an antibody (DYKDDDDK (SEQ ID NO: 17)); HA-tag, a peptide from hemagglutinin recognized by an antibody (YPYDVPDYA (SEQ ID NO: 18)); His-tag, typically 5-10 histidines that can be bound by a nickel or cobalt chelate (HHHHHH (SEQ ID NO: 19), HHHHHHHHHH (SEQ ID NO: 63); Myc-tag, a peptide derived from c-myc recognized by an antibody (EQKLISEEDL (SEQ ID NO: 20)); NE-tag, a novel 18-amino-acid synthetic peptide (TKENPRSNQEESYDDNES (SEQ ID NO: 21)) recognized by a monoclonal IgG1 antibody, which is useful in a wide spectrum of applications including Western blotting, ELISA, flow cytometry, immunocytochemistry, immunoprecipitation, and affinity purification of recombinant proteins; S-tag, a peptide derived from Ribonuclease A (KETAAAKFERQHMDS (SEQ ID NO: 22)); SBP-tag, a peptide which binds to streptavidin (MDEKTTGWRGGHVVEGLAGELEQLRAR-LEHHPQGQREP (SEQ ID NO: 23)); Softag 1, for mammalian expression (SLAELLNAGLGGS (SEQ ID NO: 24)); Softag 3, for prokaryotic expression (TQDPSRVG (SEQ ID NO: 25)); Strep-tag, a peptide which binds to streptavidin or the modified streptavidin called streptactin (Strep-tag II: WSHPQFEK (SEQ ID NO: 26)); TC tag, a tetracysteine tag that is recognized by FlAsH and ReAsH biarsenical compounds (CCPGCC (SEQ ID NO: 27)); V5 tag, a peptide recognized by an antibody (GKPIPNPLLGLDST (SEQ ID NO: 28)); VSV-tag, a peptide recognized by an antibody (YTDIEMNRLGK (SEQ ID NO: 29)); Xpress tag (DLYDDDDK (SEQ ID NO: 30)); Covalent peptide tags such as: Isopeptag, a peptide which binds covalently to pilin-C protein (TDKDMTITFTNKKDAE (SEQ ID NO: 31));

SpyTag, a peptide which binds covalently to SpyCatcher protein (AHIVMVDAYKPTK (SEQ ID NO: 32)); SnoopTag, a peptide which binds covalently to SnoopCatcher protein (KLGDIEFIKVNK (SEQ ID NO: 33)). In implementations of DN proteins described herein, any of the tags described herein, and other tags known to those skilled in the art, can include one or more amino acid substitutions, insertions, or deletions that do not alter the function of the tag, and can further include one or more additional amino acids, up to a maximum tag length of 100 amino acids.

In some implementations, the dominant negative CEBPB protein may have a cell penetrating peptide linked directly or indirectly to the CEBPB leucine zipper domain.

As used herein, a "cell-penetrating protein", "cell-penetrating peptide" or "CP" is a peptide that has a short amino acid sequence (e.g., in certain implementations, about 12-30 residues) or functional motif that confers the energy-independent or non-endocytotic translocation properties associated with transport of the membrane-permeable complex across the plasma and/or nuclear membranes of a cell. Representative amino acid motifs conferring such properties are listed in U.S. Pat. No. 6,348,185, the contents of which are expressly incorporated herein by reference. The cell-penetrating peptides described herein preferably include, but are not limited to, penetratin 1 (also referred to herein as "penetratin" or "pen"), transportan, pIs1, TAT(48-60), pVEC, MTS, and MAP.

The cell-penetrating peptides described herein may include without limitation those sequences that retain certain structural and functional features of the identified cell-penetrating peptides, yet differ from the identified peptides' amino acid sequences at one or more positions. Such polypeptide variants can be prepared by substituting, deleting, or adding amino acid residues from the original sequences via methods known in the art.

In some implementations, such substantially similar sequences include sequences that incorporate conservative amino acid substitutions, as described above in connection with polypeptide apoptotic target inhibitors. In some implementations, a cell-penetrating peptide of the present disclosure is at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% homologous to the amino acid sequence of the identified peptide and is capable of mediating cell penetration.

In some implementations of the present disclosure, the cell-penetrating peptide is penetratin 1, including the peptide sequence RQIKIWFQNRRMKWKK (SEQ ID NO: 34), or a conservative variant thereof. As used herein, a "conservative variant" is a peptide having one or more amino acid substitutions, wherein the substitutions do not adversely affect the shape—or, therefore, the biological activity, such as transport activity, or membrane toxicity—of the cell-penetrating peptide.

Penetratin 1 is a 16-amino-acid polypeptide derived from the third alpha-helix of the homeodomain of *Drosophila antennapedia*. Its structure and function have been well studied and characterized: Derossi et al., Trends Cell Biol., 8(2):84-87, 1998; Dunican et al., Biopolymers, 60(1):45-60, 2001; Hallbrink et al., Biochim. Biophys. Acta, 1515(2): 101-09, 2001; Bolton et al., Eur. J. Neurosci., 12(8):2847-55, 2000; Kilk et al., Bioconjug. Chem., 12(6):911-16, 2001; Bellet-Amalric et al., Biochim. Biophys. Acta, 1467(1):131-43, 2000; Fischer et al., J. Pept. Res., 55(2): 163-72, 2000; Thoren et al., FEBS Lett., 482(3):265-68, 2000.

It has been shown that penetratin1 efficiently carries avidin, a 63-kDa protein, into human Bowes melanoma cells (Kilk et al., Bioconjug. Chem., 12(6):911-16, 2001). Additionally, it has been shown that the transportation of penetratin1 and its cargo is non-endocytotic and energy-independent, and does not depend upon receptor molecules or transporter molecules. Furthermore, it is known that penetratin1 is able to cross a pure lipid bilayer (Thoren et al., FEBS Lett., 482(3):265-68, 2000). This feature enables penetratin1 to transport its cargo, free from the limitation of cell-surface-receptor-/transporter availability. The delivery vector previously has been shown to enter all cell types (Derossi et al., Trends Cell Biol., 8(2):84-87, 1998), and effectively to deliver peptides (Troy et al., Proc. Natl. Acad. Sci. USA, 93:5635-40, 1996) or antisense oligonucleotides (Troy et al., J. Neurosci., 16:253-61, 1996; Troy et al., J. Neurosci., 17:1911-18, 1997).

Other non-limiting implementations of the present disclosure involve the use of the following exemplary cell permeant molecules: RL16 (RRLRRLLRRLLRRLRR (SEQ ID NO: 35)), a sequence derived from Penetratin1 with slightly different physical properties (Biochim Biophys Acta. 2008 July-August; 1780(7-8):948-59); and RVGRRRRRRRRR (SEQ ID NO: 36), a rabies virus sequence which targets neurons see P. Kumar, H. Wu, J. L. McBride, K. E. Jung, M. H. Kim, B. L. Davidson, S. K. Lee, P. Shankar and N. Manjunath, Transvascular delivery of small interfering RNA to the central nervous system, Nature 448 (2007), pp. 39-43.

In some non-limiting implementations of the present disclosure, the cell-penetrating peptide can be a cell-penetrating peptide selected from the group consisting of: transportan, pIS1, Tat(48-60), pVEC, MAP, and MTS. Transportan is a 27-amino-acid long peptide containing 12 functional amino acids from the amino terminus of the neuropeptide galanin, and the 14-residue sequence of mastoparan in the carboxyl terminus, connected by a lysine (Pooga et al., FASEB J., 12(1):67-77, 1998). It includes the amino acid sequence GWTLNSAGYLLGKINLKA-LAALAKKIL (SEQ ID NO: 37), or a conservative variant thereof.

pIs1 is derived from the third helix of the homeodomain of the rat insulin 1 gene enhancer protein (Magzoub et al., Biochim. Biophys. Acta, 1512(1):77-89, 2001; Kilk et al., Bioconjug. Chem., 12(6):911-16, 2001). pIs1 includes the amino acid sequence PVIRVW FQNKRCKDKK (SEQ ID NO: 38), or a conservative variant thereof.

Tat is a transcription activating factor, of 86-102 amino acids, that allows translocation across the plasma membrane of an HIV-infected cell, to transactivate the viral genome (Hallbrink et al., Biochem. Biophys. Acta, 1515(2):101-09, 2001; Suzuki et al., J. Biol. Chem., 277(4):2437-43, 2002; Futaki et al., J. Biol. Chem., 276(8):5836-40, 2001). A small Tat fragment, extending from residues 48-60, has been determined to be responsible for nuclear import (Vives et al., J. Biol. Chem., 272(25):16010-017, 1997); it includes the amino acid sequence: YGRKKRRQRRR (SEQ ID NO: 39); GRKKRRQRRRPPQ (SEQ ID NO: 40); or a conservative variant thereof.

pVEC is an 18-amino-acid-long peptide derived from the murine sequence of the cell-adhesion molecule, vascular endothelial cadherin, extending from amino acid 615-632 (Elmquist et al., Exp. Cell Res., 269(2):237-44, 2001). pVEC includes the amino acid sequence LLIILRR-RIRKQAHAH (SEQ ID NO: 41), or a conservative variant thereof.

MTSs, or membrane translocating sequences, are those portions of certain peptides which are recognized by the acceptor proteins that are responsible for directing nascent translation products into the appropriate cellular organelles for further processing (Lindgren et al., Trends in Pharmacological Sciences, 21(3):99-103, 2000; Brodsky, J. L., Int. Rev. Cyt., 178:277-328, 1998; Zhao et al., J. Immunol. Methods, 254(1-2):137-45, 2001). An MTS of particular relevance is MPS peptide, a chimera of the hydrophobic terminal domain of the viral gp41 protein and the nuclear localization signal from simian virus 40 large antigen; it represents one combination of a nuclear localization signal and a membrane translocation sequence that is internalized independent of temperature, and functions as a carrier for oligonucleotides (Lindgren et al., Trends in Pharmacological Sciences, 21(3):99-103, 2000; Morris et al., Nucleic Acids Res., 25:2730-36, 1997). MPS includes the amino acid sequence GALFLGWLGAAGSTMGAWSQPKKKRKV (SEQ ID NO: 42), or a conservative variant thereof.

Model amphipathic peptides, or MAPs, form a group of peptides that have, as their essential features, helical amphipathicity and a length of at least four complete helical turns (Scheller et al., J. Peptide Science, 5(4):185-94, 1999; Hallbrink et al., Biochim. Biophys. Acta., 1515(2):101-09, 2001). An exemplary MAP includes the amino acid sequence KLALKLALKALKAALKLA (SEQ ID NO: 43), or a conservative variant thereof.

In some implementations, the cell-penetrating peptides described herein can be covalently bound to another protein, such as the DN-CEBPB or DN-CEBPD proteins described herein, e.g., via a peptide bond. In some implementations, the cell-penetrating peptide is operably linked to another protein, such as the DN-CEBPB or DN-CEBPD proteins described herein via recombinant DNA technology. For example, the DN-CEBPB or DN-CEBPD proteins described herein can be introduced either upstream (for linkage to the amino terminus of the cell-penetrating peptide) or downstream (for linkage to the carboxy terminus of the cell-penetrating peptide), or both, of a nucleic acid sequence encoding the cell-penetrating peptide of interest. Such fusion sequences including both the DN-CEBPB or DN-CEBPD proteins described herein encoding nucleic acid sequence and the cell-penetrating peptide encoding nucleic acid sequence can be expressed using techniques well known in the art.

In some implementations, the DN-CEBPB or DN-CEBPD proteins described herein can be operably linked to the cell-penetrating peptide via a non-covalent linkage. In some implementations, such non-covalent linkage is mediated by ionic interactions, hydrophobic interactions, hydrogen bonds, or van der Waals forces.

In some implementations, the DN-CEBPB or DN-CEBPD proteins described herein is operably linked to the cell penetrating peptide via a chemical linker. Examples of such linkages typically incorporate 1-30 nonhydrogen atoms selected from the group consisting of C, N, O, S and P. Exemplary linkers include, but are not limited to, a substituted alkyl or a substituted cycloalkyl. Alternately, the heterologous moiety may be directly attached (where the linker is a single bond) to the amino or carboxy terminus of the cell-penetrating peptide. When the linker is not a single covalent bond, the linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. In some implementations, the linker incorporates less than 20 nonhydrogen atoms and are composed of any combination of ether, thioether, urea, thiourea, amine, ester, carboxamide, sulfonamide, hydrazide bonds and aromatic or heteroaromatic bonds. In some implementations, the linker is a combination of single carbon-carbon bonds and carboxamide, sulfonamide or thioether bonds.

A general strategy for conjugation involves preparing the cell-penetrating peptide and the DN-CEBPB or DN-CEBPD components separately, wherein each is modified or derivatized with appropriate reactive groups to allow for linkage between the two. The modified DN-CEBPB or DN-CEBPD is then incubated together with a cell-penetrating peptide that is prepared for linkage, for a sufficient time (and under such appropriate conditions of temperature, pH, molar ratio, etc.) as to generate a covalent bond between the cell-penetrating peptide and the DN-CEBPB or DN-CEBPD.

The present disclosure contemplates the use of proteins and protein analogues generated by synthesis of polypeptides in vitro, e.g., by chemical means or in vitro translation of mRNA. For example, DN-CEBPB or DN-CEBPD and inhibitors thereof may be synthesized by methods commonly known to one skilled in the art (Modern Techniques of Peptide and Amino Acid Analysis (New York: John Wiley & Sons, 1981); Bodansky, M., *Principles of Peptide Synthesis* (New York: Springer-Verlag New York, Inc., 1984). Examples of methods that may be employed in the synthesis of the amino acid sequences, and analogues of these sequences, include, but are not limited to, solid-phase peptide synthesis, solution-method peptide synthesis, and synthesis using any of the commercially-available peptide synthesizers. The amino acid sequences of the present disclosure may contain coupling agents and protecting groups, which are used in the synthesis of protein sequences, and which are well known to one of skill in the art.

As used herein, "amino acid residue," "amino acid," or "residue," includes genetically encoded amino acid residues and non-genetically encoded amino acid residues, e.g., non-genetically encoded amino acid residues or non-natural amino acids include, but are not limited to D-enantiomers of naturally occurring chiral amino acids, β-alanine (β-Ala); 2,3-diaminopropionic acid (Dpr); nipecotic acid (Nip); pipecolic acid (Pip); ornithine (Orn); citrulline (Cit); t-butylalanine (t-BuA); 2-t-butylglycine (t-BuG); N-methylisoleucine (MeIle); phenylglycine (PhG); cyclohexylalanine (ChA); norleucine (Nle); naphthylalanine (Nal); 4-chlorophenylalanine (Phe(4-Cl)); 2-fluorophenyl alanine (Phe(2-F)); 3-fluorophenyl alanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,4-diaminobutyric acid (Dbu); 2,3-diaminobutyric acid (Dab); p-aminophenylalanine (Phe (pNH2)); N-methyl valine (MeVal); homocysteine (hCys), homophenylalanine (hPhe); homoserine (hSer); hydroxyproline (Hyp); homoproline (hPro); and the corresponding D-enantiomer of each of the foregoing, e.g., D-O-Ala, D-Dpr, D-Nip, D-Orn, D-Cit, D-t-BuA, D-t-BuG, D-MeIle, D-PhG, D-ChA, D-Nle, D-Nal, D-Phe(4-Cl), D-Phe(2-F), D-Phe(3-F), D-Phe(4-F), D-Pen, D-Tic, D-Thi, D-MSO, D-hArg, D-AcLys, D-Dbu, D-Dab, D-Phe(pNH2), D-MeVal, D-hCys, D-hPhe, D-hSer, D-Hyp, and D-hPro. Additional non-genetically encoded amino acid residues include 3-aminopropionic acid; 4-aminobutyric acid; isonipecotic acid (Inp); aza-pipecolic acid (azPip); aza-proline (azPro); α-aminoisobutyric acid (Aib); ε-aminohexanoic acid (Aha); δ-aminovaleric acid (Ava); N-methylglycine (MeGly).

For example, in some implementations, as described in Example 1 and Table 2 therein, the DN CEBPB protein can have an amino acid sequence (SEQ ID NO: 44)
RQIKIWFQNRRMKWKKEQKLISEEDLMASMTGGQQMGRDPD<u>LEQRAEELA</u>

<u>RENEELEKEAEELEQENAE</u>*LETQHKVLELTAENERLQK*

*KVEQLSRELSTLRNLFKQL*PEPLLASX₁GHX₂, wherein an amino acid residue X₁ can be A or S and an amino acid residue X₂ can be C or M, or the DN CEBPB protein can have an amino acid sequence (SEQ ID NO: 45)
RQIKIWFQNRRMKWKKEQKLISEEDLMASMTGGQQMGRDPD<u>LEQRAEELA</u>

<u>RENEELEKEAEELEQENAE</u>*LETQHKVLELTAENERLQ*

*KKVEQLSRELSTLRNLFKQL*, (SEQ ID NO: 46)
RQIKIWFQNRRMKWKKEQKLISEEDLMASMTGGQQMGRDPD

*LETQHKVLELTAENERLQKKVEQLSRELSTLRNLFKQL*, (SEQ ID NO: 47)
RQIKIWFQNRRMKWKK<u>LEQRAEELARENEELEKEAEELEQENAE</u>

*LETQHKVLELTAENERLQKKVEQLSRELSTLRNLFKQL*,
or (SEQ ID NO: 48)
RQIKIWFQNRRMKWKK*LETQHKVLELTAENERL*

*QKKVEQLSRELSTLRNLFKQL*, wherein the exemplary WT leucine zipper domain of SEQ ID NO:1 is italicized and bold, and the exemplary extended leucine zipper domain sequence of SEQ ID NO: 4 is underlined.

In some implementations of the DN proteins described herein, the penetratin can have an amino acid sequence RQIKIFFQNRRMKFKK (SEQ ID NO: 49) or RQIKIWFRKWKK (SEQ ID NO: 50) (Letoha et al. (2003) Journal of Molecular Recognition 16(5):272-279).

In some implementations, the present disclosure relates to a dominant-negative CEBPD protein.

The term "CEBPD protein" refers to CCAAT/enhancer-binding protein delta protein. CEBPD is a protein that in humans is encoded by the CEBPD gene (Williams S C, Cantwell CA, Johnson P F (September 1991). "A family of C/EBP-related proteins capable of forming covalently linked leucine zipper dimers in vitro". Genes & Development. 5 (9): 1553-67; Cao Z, Umek R M, McKnight S L (October 1991). Genes Dev. 5 (9): 1538-52). CEBPD is a bZIP transcription factor which can bind as a homodimer to certain DNA regulatory regions. It can also form heterodimers with the related protein CEBP-alpha and CEBPB. CEBPD protein is important in the regulation of genes involved in immune and inflammatory responses and may be involved in the regulation of genes associated with activation and/or differentiation of macrophages. CEBPD is involved in regulation of apoptosis and cell proliferation.

As used herein, "CEBPD" includes both an "CEBPD protein" and an "CEBPD analogue". For example, the CEBPD protein can have the amino acid sequence set forth in NCBI Accession No. NP_005186 (human), including conservative substitutions thereof.

A "CEBPD analogue", as used herein, is a functional variant of the CEBPD protein, having CEBPD biological activity, such as ability of the CEBPD analogue's leucine zipper domain to bind to the protein binding partners of CEBPD, that has 60% or greater, 70% or greater or 80% or greater or 90% or greater or 95% or greater amino-acid-sequence homology with the CEBPD protein.

Persons of ordinary skill in the art will understand that the numbering of amino acid residues in CEBPD may be different than that set forth herein, may contain certain conservative amino acid substitutions that produce the same CEBPD activity as that described herein. Corresponding amino acids and conservative substitutions in other isoforms or analogues are easily identified by visually inspecting the relevant amino acid sequences, or by using homology software programs identifiable by skilled persons.

As described herein, the DN CEBPD protein consists essentially of a CEBPD leucine zipper domain capable of binding to binding partners of CEBPD. In some implementations, the CEBPD leucine zipper domain has at least, or at least about, 10%, 20%, 30%, 40%, 50%, 60%, 70%, 80%, or 90% or more of the function of the WT CEBPD leucine zipper domain to bind to the protein binding partners of CEBPB.

For example, in various implementations, the CEBPD leucine zipper domain can have an amino acid sequence KLVELSAENEKLHQRVEQLTRDLAGLRQFFK (SEQ ID NO: 2).

The present disclosure also contemplates and encompasses variants of DN CEBPD proteins, wherein the WT CEBPD leucine zipper domain can have an amino acid sequence that contains one or more insertions, deletions, substitutions or additions to the amino acid sequence of SEQ ID NO: 2 that retains at least, or at least about, 10%, 20%, 30%, 40%, 50%, 60%, 70%, 80%, or 90% or more of the function of the WT CEBPD leucine zipper domain to bind to the protein binding partners of CEBPD. In some implementations, the variant of DN CEBPD protein has a CEBPD leucine zipper domain having at least, or at least about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% homology to the amino acid sequence of SEQ ID NO: 2.

The generation of variant DN CEBPD proteins having variant sequences of CEBPD leucine zipper domains and screening for function of the variant CEBPD leucine zipper domain to bind to the protein binding partners of CEBPD, can be performed by skilled persons using methods known in the art as described herein.

In addition to the CEBPD leucine zipper domain, the DN CEBPD proteins of the present disclosure may include one or more amino acid residues, provided that the one or more additional amino acid residues do not prevent the function of the CEBPD leucine zipper from binding to the CEBPD binding partners.

In various implementations, a functional DNA binding domain is absent from the dominant negative CEBPD protein. In some implementations, a functional DNA binding domain may have no more than 10%, 20%, or 30% of the DNA binding function of the DNA binding domain of wild-type CEBPD, such as that of NCBI Accession No. NP_005186. In particular, in some implementations, a functional DNA binding domain of a CEBPD protein may have an amino acid sequence DRGSPE<u>YRQRRERNNIA-VRKSRDKAKRRNQEMQQK</u> (SEQ ID NO: 51). In some implementations, substitution of the bold underlined amino acids of SEQ ID NO: 51 from basic to acidic amino acids can be performed to disrupt binding to DNA. Accordingly, in some implementations, one or more of the bold underlined amino acids of SEQ ID NO: 51 can be mutated to produce a non-functional CEBPD DNA binding domain in a DN CEBPD protein. In some implementations, the specificity of a mutated DNA binding domain of a CEBPD protein can be assessed using biochemical and biophysical techniques, and the cellular effects of a mutated DNA binding domain of a CEBPD protein may be assessed by using assays of cell viability or function, as described herein.

In some implementations of the DN CEBPD protein, the CEBPD leucine zipper domain may have an N-terminal end, wherein an extended leucine zipper domain is linked to the N-terminal end, the extended leucine zipper domain having an amino acid sequence selected from LEQRAEELARENEELEKEAEELEQENAE (SEQ ID NO: 4), LARENEELEKEAEELEQENAE (SEQ ID NO: 5), LEKEAEELEQENAE (SEQ ID NO: 6), and LEQENAE (SEQ ID NO: 7). The exemplary extended leucine zipper domains of SEQ ID NO: 4, SEQ ID NO: 5, SEQ ID NO: 6, and SEQ ID NO: 7 can be generated by mutating (and thereby inactivating) the DNA binding domain of the WT CEBPD protein. In other words, in some implementations, the DNA binding domain of CEBPD is deleted and replaced with the extended leucine zipper domain.

For example, in some implementations as described in Example 1 and Table 3 therein, the DN CEBPD protein can have an amino acid sequence (SEQ ID NO: 52)
MEQKLISEEDLEQKLISEEDLEQKLISEEDLARAGSMASMTGGQQMGRDP

DLEQRAEELARENEELEKEAEELEQENAEL

*LVELSAENEKLHQRVEQLTRDLAGLRQFFK*QLPSPPFLPAAGTADXR, wherein an amino acid residue X can be C or M, or the DN CEBPD protein can have an amino acid sequence (SEQ ID NO: 53)
MEQKLISEEDLEQKLISEEDLEQKLISEEDLARAGSMASMTGGQQMGRDP

DLEQRAEELARENEELEKEAEELEQENAE

*LVELSAENEKLHQRVEQLTRDLAGLRQFFK*,
or (SEQ ID NO: 54)
MEQKLISEEDLEQKLISEEDLEQKLISEEDLARAGSMASMTGGQQMGRDP

D*LVELSAENEKLHQRVEQLTRDLAGLRQFFK*.

In the exemplary DN CEBPD proteins of SEQ ID NO: 52 and SEQ ID NO: 53, an extended leucine zipper domain sequence LEQRAEELARENEELEKEAEELEQENAE (SEQ ID NO: 4) is underlined, and a wild-type (WT) leucine zipper domain sequence LVELSAENEKLHQRVEQLTRDLAGLRQFFK (SEQ ID NO: 2) is italicized and bold. In contrast, the exemplary amino acid sequences of SEQ ID NO: 54 does not contain an extended leucine zipper domain sequence. Importantly, all of the exemplary DN CEBPD proteins of SEQ ID NO: 52, SEQ ID NO: 53, and SEQ ID NO: 54 contain a functional CEBPD leucine zipper domain, exemplified by SEQ ID NO: 2, and lack a functional CEBPD DNA binding domain.

In some implementations, the DN CEBPD protein may include a protein tag. For example, in the exemplary DN CEBPD proteins having amino acid sequences of SEQ ID NO: 52, SEQ ID NO: 53 and SEQ ID NO: 54 contain a MYC tag having three consecutive repetitions of the MYC sequence EQKLISEEDL (SEQ ID NO: 11), EQKLISEEDLEQKLISEEDLEQKLISEEDL (SEQ ID NO: 12) following the N-terminal methionine.

In some implementations, the dominant negative CEBPD protein may have a cell penetrating peptide, such as penetratin, linked directly or indirectly to the CEBPD leucine zipper domain.

For example, in some implementations, as described in Example 1 and Table 4 therein, the penetratin-linked DN CEBPD protein can have an amino acid sequence (SEQ ID NO: 55)
RQIKIWFQNRRMKWKKEQKLISEEDLMASMTGGQQMGRDPD<u>LEQRAEELA RENEELEKEAEELEQENAE</u>*LVELSAENEKLHQRVEQLTRDLAGLRQFFK*

QLPSPPFLPAAGTADXR, wherein an amino acid residue X can be C or M, or the penetratin-linked DN CFRPD protein can have an amino acid sentience (SEQ ID NO: 56)
RQIKIWFQNRRMKWKKEQKLISEEDLMASMTGGQQMGRDPD<u>LEQRAEELA RENEELEKEAEELEQENAE</u>*LVELSAENEKLHQRVEQLTRDLAGLRQFFK*, (SEQ ID NO: 57)
RQIKIWFQNRRMKWKKEQKLISEEDLMASMTGGQQMGRDPD

*LVELSAENEKLHQRVEQLTRDLAGLRQFFK*, (SEQ ID NO: 58)
RQIKIWFQNRRMKWKK<u>LEQRAEELARENEELEKEAEELEQENAE</u>

*LVELSAENEKLHQRVEQLTRDLAGLRQFFK*,
or (SEQ ID NO: 59)
RQIKIWFQNRRMKWKK*LVELSAENEKLHQRVEQLTRDLAGLRQFFK*, wherein the exemplary WT leucine zipper domain of SEQ ID NO: 2 is italicized and bold, the exemplary extended leucine zipper domain sequence of SEQ ID NO: 4 is underlined, and an exemplary penetratin sequence RQIKIWFQNRRMKWKK (SEQ ID NO: 34) is at position 1-16.

In some implementations, a composition is described. The composition includes a dominant negative CEBPB protein described herein, or a dominant negative CEBPD protein described herein, or a combination thereof, and a pharmaceutically acceptable excipient.

For oral administration, the DN-CEBPB, DN-CEBPD, CP-DN-CEBPB, and/or CP-DN-CEBPD composition can be formulated as capsules, tablets, powders, granules, or as a suspension. The DN-CEBPB, DN-CEBPD, CP-DN-CEBPB, and/or CP-DN-CEBPD composition formulation may have conventional additives, such as lactose, mannitol, corn starch, or potato starch. The DN-CEBPB, DN-CEBPD, CP-DN-CEBPB, and/or CP-DN-CEBPD composition formulation also may be presented with binders, such as crystalline cellulose, cellulose derivatives, acacia, corn starch, or gelatins. Additionally, the DN-CEBPB, DN-CEBPD, CP-DN-CEBPB, and/or CP-DN-CEBPD composition formulation may be presented with disintegrators, such as corn starch, potato starch, or sodium carboxymethylcellulose. The DN-CEBPB, DN-CEBPD, CP-DN-CEBPB, and/or CP-DN-CEBPD composition formulation also may be presented with dibasic calcium phosphate anhydrous or sodium starch glycolate. Finally, the DN-CEBPB, DN-CEBPD, CP-DN-CEBPB, and/or CP-DN-CEBPD composition formulation may be presented with lubricants, such as talc or magnesium stearate.

In some implementations, the composition may include, without limitation, a carrier protein, which may increase activity of the DN-CEBPB, DN-CEBPD, CP-DN-CEBPB, or CP-DN-CEBPD. Without limitation to theory, such a carrier protein may, for example, increase activity by increasing solubility and/or promoting improved protein folding of the DN-CEBPB, DN-CEBPD, CP-DN-CEBPB, or CP-DN-CEBPD in the composition.

For example, and not by way of limitation, the carrier protein may be a serum albumin, such as bovine serum albumin (BSA) or human serum albumin, among others. For example, human serum albumin is often included in some vaccines and is often given at, or at about, 20% weight/volume (w/v) in infusions for some medical conditions. In some implementations, the serum albumin may be added at a concentration (w/v) of, or of about 5%, 10%, 15%, 20%, 25% or 30%.

For example, in some implementations, a composition including, without limitation, a dominant negative CEBPB protein described herein, or a dominant negative CEBPD protein described herein, and a serum albumin, may have increased efficacy and/or potency compared to a composition that does not have a serum albumin. For example, as shown in Example 13, addition of BSA to a cell-penetrating DN CEBPB peptide composition or a cell-penetrating DN CEBPD peptide composition greatly increased the potency of the peptides in suppressing the growth and survival of T98G glioblastoma cells. In some implementations, the serum albumin may have a concentration in the composition of 3 mg/ml.

In some implementations, the composition may include, without limitation, a mixture of glutamate and arginine. Without limitation to theory, glutamine and arginine may, for example, increase activity of the DN-CEBPB, DN-CEBPD, CP-DN-CEBPB, or CP-DN-CEBPD by increasing solubility and/or stability of the DN-CEBPB, DN-CEBPD, CP-DN-CEBPB, or CP-DN-CEBPD in the composition.

For example, addition of a mixture of 20 mM of each of arginine and glutamate to the peptide stock buffer containing DN-CEBPB, DN-CEBPD, CP-DN-CEBPB, or CP-DN-CEBPD maintained solubility after dilution to the concentration used to apply to cultured LN229 cells. In addition, addition of 20 mM of each of arginine and glutamate to the peptide stock buffer containing CP-DN-CEBPB or CP-DN-CEBPD shifted the IC50 of CP-DN-CEBPB from 25 to 1.6 µM when applied to cultured LN229 cells, and for CP-DN-CEBPD from 20 µM to 1.9 µM, of cultured LN229 cells, also a 10-fold shift. In contrast, there was only minimal effect of adding a mixture of arg/glu at 2 mM. In some implementations, the mixture of arg/glu may be added at a molarity of, or of about 5 mM, 10 mM, 15 mM, 20 mM, 25 mM, or 30 mM.

In some implementations, the increased efficacy and/or potency resulting from including the carrier and/or other additive may be additive. In some implementations, the increased efficacy and/or potency may be synergistic.

For parenteral administration, administration by injection through a route other than the alimentary canal, DN-CEBPB, DN-CEBPD, CP-DN-CEBPB, and/or CP-DN-CEBPD composition can be combined with a sterile aqueous solution that is preferably isotonic with the blood of the subject. Such a DN-CEBPB, DN-CEBPD, CP-DN-CEBPB, and/or CP-DN-CEBPD composition formulation can be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The DN-CEBPB, DN-CEBPD, CP-DN-CEBPB, and/or CP-DN-CEBPD composition formulation can be presented in unit or multi-dose containers, such as sealed ampoules or vials. The DN-CEBPB, DN-CEBPD CP-DN-CEBPB, and/or CP-DN-CEBPD, composition formulation can be delivered by any mode of injection, including, without limitation, epifascial, intracapsular, intracranial, intracutaneous, intrathecal, intramuscular, intraorbital, intraperitoneal, intraspinal, intrasternal, intravascular, intravenous, parenchymatous, subcutaneous, or sublingual.

In some implementations, the DN-CEBPB, DN-CEBPD, CP-DN-CEBPB, and/or CP-DN-CEBPD composition formulation is prepared for intranasal delivery. For nasal administration, solutions or suspensions including the DN-CEBPB, DN-CEBPD, CP-DN-CEBPB, and/or CP-DN-CEBPD composition formulation can be prepared for direct application to the nasal cavity by conventional means, for example with a dropper, pipette or spray. Other means for delivering the nasal spray composition, such as inhalation via a metered dose inhaler (MDI), may also be used according to the present disclosure. Several types of MDIs are regularly used for administration by inhalation. These types of devices can include breath-actuated MDI, dry powder inhaler (DPI), spacer/holding chambers in combination with MDI, and nebulizers. The term "MDI" as used herein refers to an inhalation delivery system including, for example, a canister containing an active agent dissolved or suspended in a propellant optionally with one or more excipients, a metered dose valve, an actuator, and a mouthpiece. The canister is usually filled with a solution or suspension of an active agent, such as the nasal spray composition, and a propellant, such as one or more hydrofluoroalkanes. When the actuator is depressed a metered dose of the solution is aerosolized for inhalation. Particles including the active agent are propelled toward the mouthpiece where they may then be inhaled by a subject. The formulations may be provided in single or multidose form. For example, in the case of a dropper or pipette, this may be achieved by the patient administering an appropriate, predetermined volume of the solution or suspension. In the case of a spray, this may be achieved for example by means of a metering atomizing spray pump. To improve nasal delivery and retention the components according to the disclosure may be encapsulated with cyclodextrins, or formulated with agents expected to enhance delivery and retention in the nasal mucosa.

Commercially available administration devices that are used or can be adapted for nasal administration of a composition of the disclosure include the AERONEB™ (Aerogen, San Francisco, Calif.), AERONEB GO™ (Aerogen); PARI LC PLUS™, PARI BOY™ N, PARI™ eflow (a nebulizer disclosed in U.S. Pat. No. 6,962,151), PARI LC SINUS™, PARI SINUSTAR™, PART SINUNEB™, VibrENT™ and PARI DURANEB™ (PART Respiratory Equipment, Inc., Monterey, Calif. or Munich, Germany); MICROAIR™ (Omron Healthcare, Inc, Vernon Hills, Ill.), HALOLITE™ (Profile Therapeutics Inc, Boston, Mass.), RESPIMAT™ (Boehringer Ingelheim, Germany), AERODOSE™ (Aerogen, Inc, Mountain View, Calif.), OMRON ELITE™ (Omron Healthcare, Inc, Vernon Hills, Ill.), OMRON MICROAIR™ (Omron Healthcare, Inc, Vernon Hills, MABISMIST™ II (Mabis Healthcare, Inc, Lake Forest, Ill.), LUMISCOPE™ 6610, (The Lumiscope Company, Inc, East Brunswick, N.J.), AIRSEP MYSTIQUE™, (AirSep Corporation, Buffalo, N.Y.), ACORN-1™ and ACORN-II™ (Vital Signs, Inc, Totowa, N.J.), AQUATOWER™ (Medical Industries America, Adel, Iowa), AVA-NEB™ (Hudson Respiratory Care Incorporated, Temecula, Calif.), AEROCURRENT™ utilizing the AEROCELL™ disposable cartridge (AerovectRx Corporation, Atlanta, Ga.), CIRRUS™ (Intersurgical Incorporated, Liverpool, N.Y.), DART™ (Professional Medical Products, Greenwood, S.C.), DEVILBISS™ PULMO AIDE (DeVilbiss Corp; Somerset, Pa.), DOWNDRAFT™ (Marquest, Englewood, Colo.), FAN JET™ (Marquest, Englewood, Colo.), MB-5™ (Mefar, Bovezzo, Italy), MISTY NEB™ (Baxter, Valencia, Calif.), SALTER8900™ (Salter Labs, Arvin, Calif.), SIDESTREAM™ (Medic-Aid, Sussex, UK), UPDRAFT-II™ (Hudson Respiratory Care; Temecula, Calif.), WHISPER JET™ (Marquest Medical Products, Englewood, Colo.), AIOLOS™ (Aiolos Medicinsk Teknik, Karlstad, Sweden), INSPIRON™ (Intertech Resources, Inc., Bannockburn, Ill.), OPTIMIST™ (Unomedical Inc., McAllen, Tex.), PRODOMO™, SPIRA™ (Respiratory Care Center, Hameenlinna, Finland), AERx™ Essence™ and Ultra™, (Aradigm Corporation, Hayward, Calif.), SONIK™ LDI Nebulizer (Evit Labs, Sacramento, Calif.), ACCUSPRAY™ (BD Medical, Franklin Lake, N.J.), ViaNase ID™ (electronic atomizer; Kurve, Bothell, Wash.), OptiMist™ device or OPTINOSE™ (Oslo, Norway), MAD Nasal™ (Wolfe Tory Medical, Inc., Salt Lake City, Utah), Freepod™ (Valois, Marly le Roi, France), Dolphin™ (Valois), Monopowder™ (Valois), Equadel™ (Valois), VP3™ and VP7™ (Valois), VP6 Pump™ (Valois), Standard Systems Pumps™ (Ing. Erich Pfeiffer, Radolfzell, Germany), AmPump™ (Ing. Erich Pfeiffer), Counting Pump™ (Ing. Erich Pfeiffer), Advanced Preservative Free System™ (Ing. Erich Pfeiffer), Unit Dose System™ (Ing. Erich Pfeiffer), Bidose System™ (Ing. Erich Pfeiffer), Bidose Powder System™ (Ing. Erich Pfeiffer), Sinus Science™ (Aerosol Science Laboratories, Inc., Camarillo, Calif.), ChiSys™ (Archimedes, Reading, UK), Fit-Lizer™ (Bioactis, Ltd, a SNBL subsidiary (Tokyo, J P), Swordfish V™ (Mystic Pharmaceuticals, Austin, Tex.), DirectHaler™ Nasal (DirectHaler, Copenhagen, Denmark) and SWIRLER™ Radioaerosol System (AMICI, Inc., Spring City, Pa.).

For transdermal administration, DN-CEBPB, DN-CEBPD, CP-DN-CEBPB, and/or CP-DN-CEBPD can be combined with skin penetration enhancers, such as propylene glycol, polyethylene glycol, isopropanol, ethanol, oleic acid, N-methylpyrrolidone, and the like, which increase the permeability of the skin to the DN-CEBPB, DN-CEBPD, CP-DN-CEBPB, and/or CP-DN-CEBPD, and permit the DN-CEBPB, DN-CEBPD, CP-DN-CEBPB, and/or CP-DN-CEBPD to penetrate through the skin and into the bloodstream. The DN-CEBPB, DN-CEBPD, CP-DN-CEBPB, and/or CP-DN-CEBPD composition also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch.

The pharmaceutically-acceptable carrier should be "acceptable" in the sense of being compatible with the other ingredients of the composition, and ideally not deleterious to the recipient thereof, or having acceptable tolerability in the subject. The pharmaceutically-acceptable carrier employed herein is selected from various organic or inorganic materials that are used as materials for pharmaceutical formulations, and which may be incorporated as analgesic agents, buffers, binders, disintegrants, diluents, emulsifiers, excipients, extenders, glidants, solubilizers, stabilizers, suspending agents, tonicity agents, vehicles, and viscosity-increasing agents. If necessary, pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc, and water, among others.

The DN-CEBPB, DN-CEBPD, CP-DN-CEBPB, and/or CP-DN-CEBPD composition formulations described herein can be prepared by methods well-known in the pharmaceutical arts. For example, the DN-CEBPB, DN-CEBPD, CP-DN-CEBPB, and/or CP-DN-CEBPD can be brought into association with a carrier or diluent, as a suspension or solution. Optionally, one or more accessory ingredients (e.g., buffers, flavoring agents, surface active agents, and the like) also can be added. The choice of carrier will depend upon the route of administration. The pharmaceutical composition would be useful for administering the DN-CEBPB, DN-CEBPD, CP-DN-CEBPB, and/or CP-DN-CEBPD to a subject to treat a tumor and/or neoplastic cell, as discussed herein. The DN-CEBPB, DN-CEBPD, CP-DN-CEBPB, and/or CP-DN-CEBPD is provided in an amount that is effective to treat the tumor and/or neoplastic cell in a subject to whom the pharmaceutical composition is administered. That amount may be readily determined by the skilled artisan, as described herein.

Compositions of the present disclosure can further include other therapeutic agents. For example, they can include any one or more anti-cancer agents. In some implementations, the one or more anti-cancer agent will be selected from the group consisting of: alkylating agents; anti-metabolites; anti-microtubule agents; topoisomerase inhibitors, antibiotics, and antibodies/antibody-drug conjugates. The amounts of those anti-cancer agents in compositions of the present disclosure can, in some implementations, be reduced as compared to normal doses of such agents administered in a similar fashion.

Compositions of the present disclosure can further be administered in combination with other therapeutic agents such as inhibitors of growth factor receptor signaling, of proteasome activity, of oncogenic kinases and of other oncogenic proteins, STAT3 inhibitors, and/or BH3-mimetics, among others identifiable by skilled persons.

Compositions of the present disclosure can further be administered in combination with other cancer treatments, such as radiation treatment, immunotherapeutics, anti-microtubule agents, alkylating agents, and/or anti-metabolites, among others.

In some implementations, a method of decreasing activity or viability of a neoplastic cell is described. The method includes contacting the neoplastic cell with a dominant negative CEBPB protein described herein, or a dominant negative CEBPD protein described herein, or cell-penetrating forms thereof, or a combination thereof for a time and under conditions sufficient to cause a decrease in activity or viability of the neoplastic cell.

The term "neoplastic cell", "neoplasia", and related terms as used herein, refers to the uncontrolled and progressive multiplication of tumor cells under conditions that would not elicit, or would cause cessation of, multiplication of normal cells. Neoplasia results in the formation of a "neoplasm", which may refer to any new and abnormal growth, particularly a new growth of tissue, in which the growth of cells is uncontrolled and progressive. As used herein, neoplasms include, without limitation, morphological irregularities in cells in tissue of a subject, as well as pathologic proliferation of cells in tissue of a subject, as compared with normal proliferation in the same type of tissue. Additionally, neoplasms include benign tumors and malignant tumors. Malignant neoplasms are distinguished from benign in that the former show a greater degree of anaplasia, or loss of differentiation and orientation of cells, and have the properties of invasion and metastasis. Thus, neoplasia includes "cancer", which refers to a proliferation of tumor cells having the unique trait of loss of normal controls, resulting in unregulated growth, lack of differentiation, local tissue invasion, and metastasis.

In some implementations, the neoplastic cell can be selected from the group consisting of: breast, ovary, endometrium, gastric, colon, liver, pancreas, kidney, bladder, prostate, testis, skin, esophagus, tongue, mouth, parotid, larynx, pharynx, lymph node, lung, and brain. In some implementations, the neoplastic cell can be selected from the group consisting of glioblastoma, astrocytoma, glioma, medulloblastoma and neuroblastoma. The neoplastic cells can include solid tumors or hematological cancers.

Additionally, as used herein, the term "neural tumor" refers to a tumorigenic form of neural cells, and includes astrocytoma cells, including, without limitation, Grades I-IV astrocytomas, anaplastic astrocytoma, astroblastoma, astrocytoma fibrillare, astrocytoma protoplasmaticum, gemistocytic astrocytoma, and glioblastoma multiforme), gliomas, medulloblastomas, neuroblastomas, and other brain tumors. Brain tumors invade and destroy normal tissue, producing such effects as impaired sensorimotor and cognitive function, increased intracranial pressure, cerebral edema, and compression of brain tissue, cranial nerves, and cerebral vessels. Metastases may involve the skull or any intracranial structure. The size, location, rate of growth, and histologic grade of malignancy determine the seriousness of brain tumors. Nonmalignant tumors grow slowly, with few mitoses, no necrosis, and no vascular proliferation. Malignant tumors grow more rapidly, and invade other tissues. However, they rarely spread beyond the CNS, because they cause death by local growth.

Brain tumors may be classified by site (e.g., brain stem, cerebellum, cerebrum, cranial nerves, ependyma, meninges, neuroglia, pineal region, pituitary gland, and skull) or by histologic type (e.g., meningioma, primary CNS lymphoma, or astrocytoma). Common primary childhood tumors are cerebellar astrocytomas and medulloblastomas, ependymomas, gliomas of the brain stem, neuroblastomas, and congenital tumors. In adults, primary tumors include meningiomas, schwannomas, and gliomas of the cerebral hemispheres (particularly the malignant glioblastoma multiforme and anaplastic astrocytoma, and the more benign astrocytoma and oligodendroglioma). Overall incidence of intracranial neoplasms is essentially equal in males and females, but cerebellar medulloblastoma and glioblastoma multiforme are more common in males.

Gliomas are tumors composed of tissue representing neuroglia in any one of its stages of development. They account for 45% of intracranial tumors. Gliomas can encompass all of the primary intrinsic neoplasms of the brain and spinal cord, including astrocytomas, ependymomas, and neurocytomas. Astrocytomas are tumors composed of transformed astrocytes, or astrocytic tumor cells. Such tumors have been classified in order of increasing malignancy: Grade I consists of fibrillary or protoplasmic astrocytes; Grade II is an astroblastoma, consisting of cells with abundant cytoplasm and two or three nuclei; and Grades III and IV are forms of glioblastoma multiforme, a rapidly growing tumor that is usually confined to the cerebral hemispheres and composed of a mixture of astrocytes, spongioblasts, astroblasts, and other astrocytic tumor cells. Astrocytoma, a primary CNS tumor, is frequently found in the brain stem, cerebellum, and cerebrum. Anaplastic astrocytoma and glioblastoma multiforme are commonly located in the cerebrum.

For example, but not by way of limitation, neoplastic cells also include cell lines such as U87 (human glioblastoma); U373 (human glioblastoma); LN229 (human glioblastoma); C6 (rat glioblastoma); Me1501 (human melanoma); H2452 (human mesothelioma); MDA-MB-468 (human breast cancer), Panc-1 (human pancreatic cancer); SH-SY5Y (human neuroblastoma cells); and HCT-116 (colon-carcinoma cancer).

For any of the above tumors, cancers, or neoplastic cells, peptides as disclosed herein, such as DN-CEBPB, DN-CEBPD, CP-DN-CEBPB, and/or CP-DN-CEBPD, may be administered to a subject in order to inhibit metastasis, to inhibit cancer recurrence from dormant cells, particularly dormant cells not inhibited by other therapeutics due to their dormancy, or to inhibit both metastasis and cancer recurrence from dormant cells. Biopsies, cancer type, and other clinical indicia may be used to identify subject likely to experience metastasis or cancer recurrence from dormant cells.

The term "activity" as it relates to cells includes any cellular function or activity of cells such as neoplastic cells, for example including but limited to growth, intracellular signaling, proliferation, and migration, among others identifiable by skilled persons. The term "viability" generally refers to survival; accordingly, a decrease in viability can include an increase in cell death. In some implementations, contacting a neoplastic cell with a DN CEBPB and/or DN CEBPD, or a cell-penetrating forms thereof described herein may increase apoptosis in the neoplastic cell. In some implementations, contacting a neoplastic cell with a DN CEBPB and/or DN CEBPD, or a cell-penetrating forms thereof described herein may decrease growth or proliferation of the neoplastic cell. In some implementations, contacting a neoplastic cell with a DN CEBPB and/or DN CEBPD, or a cell-penetrating forms thereof described herein may increase cell death in the neoplastic cell.

In some implementations, the activity and/or viability of a neoplastic cell may be decreased at least 1%, 5%, 10%, 20%, 30%, 40%, 50%, or greater (inclusive of intermediate ranges between those explicitly recited, e.g., 5-10%, 10-20%, 20-30%, 40-50%, or greater than 50% including 50%-100%).

As described herein, CEBPB and CEBPD contain basic leucine zipper motifs that may be used to create a dominant-negative that may function as a cancer therapeutic.

Example 1 describes exemplary DN constructs including DN-CEBPB, DN-CEBPD, CP-DN-CEBPB, or CP-DN-CEBPD for interference with one or more functions of CEBPB, and/or CEBPD such as signaling including one or more of these proteins, and for treatment of cancers. Example 2 describes exemplary DN-CEBPB and DN-CEPBD constructs that can cause cell loss in Glioblastoma cell T98G cultures. Example 3 provides further evidence that DN-CEBPB and DN-CEPBD such as the exemplary constructs described herein promote apoptotic death of Glioblastoma cell T98G cultures. In addition, Examples 5 and 8 provide further evidence for efficacy of anti-cancer therapy by inhibiting CEBPB or CEBPD, wherein RNAi-mediated depletion of CEBPB or CEBPD causes cell loss in Glioblastoma cell T98G cultures. As shown in Example 6, RNAi-mediated depletion of CEBPB or CEBPD promotes apoptosis in T98G glioblastoma cells, LN229 glioblastoma cells, GBM22 cells, and MDA-MB-468 breast cancer cells. As shown in Example 7, RNAi-mediated knockdown of CEBPB or CEBPD does not affect normal human astrocyte survival. As shown in Example 9, 10, 11, 12, and 13, cell-penetrating DN forms of CEBPB and CEBPD repress growth and survival of T98G glioblastoma cells, MDA-MB-231 breast cancer cells, HCT-116 colon cancer cells, and LN229 glioblastoma cells.

Accordingly, in various implementations of the methods described herein and within the scope of the present disclosure, it is expected that DN-forms of CEBPB and/or CEBPD described herein can function as anti-cancer drugs.

In some implementations, a method of treating cancer in a subject is described. The method includes administering to the subject an effective amount of DN-CEBPB, DN-CEBPD, CP-DN-CEBPB, and/or CP-DN-CEBPD.

The methods of the present disclosure can be performed in vitro as well as in vivo in a subject. The term "subject" as used herein in the context of treatment includes a single animal and in particular higher animals and in particular vertebrates such as mammals and in particular human beings.

The dominant negative proteins and compositions thereof described herein can be administered to a subject by any suitable procedure, including, without limitation, oral administration, parenteral administration, intranasal administration, intraperitoneal administration and transdermal administration. In some implementations, the dominant negative proteins and compositions thereof can be administered parenterally, by intracranial, intraspinal, intrathecal, intraperitoneal or subcutaneous injection.

As used herein, the term "effective amount" refers to an amount of the proteins or compositions thereof necessary to bring about a desired result, such as but not limited to killing or inhibiting activity of a neoplastic cell.

In addition, the term "effective amount" in some implementations means effective to ameliorate or minimize the clinical impairment or symptoms of the neoplastic cell such as a tumor. For example, the clinical impairment or symptoms of the tumor may be ameliorated or minimized by diminishing any pain or discomfort suffered by the subject; by extending the survival of the subject beyond that which would otherwise be expected in the absence of such treatment; by inhibiting or preventing the development or spread of the tumor; or by limiting, suspending, terminating, or otherwise controlling the maturation and proliferation of cells in the tumor. The amount of DN-CEBPB, DN-CEBPD, CP-DN-CEBPB, and/or CP-DN-CEBPD effective to treat a tumor in a subject in need of treatment will vary depending upon the particular factors of each case, including the type of tumor, the stage of the tumor, the subject's weight, the severity of the subject's condition, and the method of administration. This amount can be readily determined by the skilled artisan.

In some implementations, the DN-CEBPB, DN-CEBPD, CP-DN-CEBPB, and/or CP-DN-CEBPD may be provided in a composition at a concentration of, or of about, 0.1-5.0 mM, or about 5 µM-50 µM, or 10 µM-50 µM.

In some implementations, the DN-CEBPB, DN-CEBPD, CP-DN-CEBPB, and/or CP-DN-CEBPD may be administered to a subject, such as a cancer patient, at a dosage of, or of about, 5-50 mg/kg, about 10-50 mg/mg, or about 10-20 mg·kg.

In accordance with methods described herein, CEBPB or CEBPD, or their cellular binding partners can be inhibited in a neoplastic cell by disabling, disrupting, or inactivating the function or activity of CEBPB or CEBPD in the neoplastic cell. The function or activity of CEBPB or CEBPD in the neoplastic cell may be inhibited by contacting the neoplastic cell with a DN-CEBPB, or DN-CEBPD, CP-DN-CEBPB, or CP-DN-CEBPD capable of inhibiting the function or activity of native CEBPB or CEBPD in the cell.

In some implementations, function or activity of the CEBPB or CEBPD, in the cell is inhibited by at least 1%, 5%, 10%, 20%, 30%, 40%, 50%, or greater (inclusive of intermediate ranges between those explicitly recited, e.g., 5-10%, 10-20%, 20-30%, 40-50%, or greater than 50% including 50%-100%).

In some implementations, function or activity of the CEBPB or CEBPD is decreased by inhibiting expression of CEBPB or CEBPD. Such expression can be inhibited by at least 1%, 5%, 10%, 20%, 30%, 40%, 50%, or greater (inclusive of intermediate ranges between those explicitly recited, e.g., 5-10%, 10-20%, 20-30%, 40-50%, or greater than 50% including 50%-100%).

In some implementations, the present disclosure relates to a polynucleotide including a sequence encoding a dominant negative CEBPB protein described herein or a dominant negative CEBPD protein described herein. For example, Examples 2 and 3 describe a polynucleotide vector encoding exemplary DN-CEBPB and DN-CEBPD proteins causing expression of the encoded DN proteins in a glioblastoma cell line, resulting in cell death. Accordingly, in some implementations, the present disclosure contemplates administering a polynucleotide expression vector encoding the DN proteins described herein to a subject as a therapeutic method. Suitable vectors for delivery of polynucleotides encoding the DN proteins described herein include without limitation recombinant adeno-associated virus (AAV) vectors, among others identifiable by skilled persons.

In still other implementations, peptides as disclosed herein, such as DN-CEBPB, DN-CEBPD, CP-DN-CEBPB, and/or CP-DN-CEBPD, may be administered with other cancer therapeutics to achieve a synergistic effect. Administration may involve co-treatment, pre-treatment, or -post treatment with the peptides as disclosed herein as compared to treatment time with the additional therapeutic. Examples additional therapeutics include gamma radiation, paclitaxel, chloroquine, and doxorubicin and chemotherapeutics in the same drug classes or that exert their anti-cancer effects in the same manner as these therapeutics. For example, additional therapeutics may include other taxanes, such as nab-paclitaxel, Abraxane, docetaxel, 10-deacetylbaccatin III, baccatin III, paclitaxel C, and 7-epipaclitaxel. Additional therapeutics may also include other anthracyclines, such as daunorubicin, epirubicin, idarubicin, mitoxantrone, and valrubicin.

Example additional therapeutics further include chemotherapeutics or other therapeutics known to promote apoptosis in cancer cells, such as BH3 mimetics, including ABT263 (Navitoclax).

Peptides of the present disclosure may, in particular, be used as a post-treatment with an additional therapeutic in subjects likely to experience metastasis or cancer recurrence from dormant cells.

EXAMPLES

The DN proteins, methods, compositions, and polynucleotides herein disclosed are further illustrated in the following examples, which are provided by way of illustration and are not intended to be limiting.

Example 1. Exemplary DN Constructs for Interference with One or More Functions of CEBPB, and/or CEBPD This Example describes exemplary amino acid sequences of DN constructs for interference with one or more functions of CEBPB and/or CEBPD, such as signaling including one or more of these proteins, and for treatment of cancers.

The following exemplary sequences were provided in plasmid vectors having 3×MYC pCMV-3Tag-2A, unless stated otherwise.

The amino acid sequences shown in Table 1 are examples of DN constructs including amino acid sequence variants of DN CEBPB protein configured to interfere with one or more functions of CEBPB or CEBPD, among other proteins described herein, such as signaling including one or more of these proteins, and for treatment of cancers. The following exemplary amino acid sequences were encoded in plasmid vectors having 3×MYC pCMV-3Tag-2A.

TABLE 1

Amino acid sequences of DN CEBPB constructs

| Protein construct | Amino acid sequence | SEQ ID NO: |
|---|---|---|
| DN CEBPB 1 | MEQKLISEEDLEQKLISEEDLEQKLISEEDLARAGSMASMTG GQQMGRDPDLEQRAEELARENEELEKEAEELEQENAE*LETQ HKVLELTAENERLQKKVEQLSRELSTLRNLFKQL*PEPLLASX$_1$GHX$_2$ | 8 |
| DN CEBPB 2 | MEQKLISEEDLEQKLISEEDLEQKLISEEDLARAGSMASMTG GQQMGRDPDLEQRAEELARENEELEKEAEELEQENAE*LETQ HKVLELTAENERLQKKVEQLSRELSTLRNLFKQL* | 9 |
| DN CEBPB 3 | MEQKLISEEDLEQKLISEEDLEQKLISEEDLARAGSMASMTG GQQMGRDPD*LETQHKVLELTAENERLQKKVEQLSRELSTLR NLFKQL* | 10 |

SEQ ID NO: 8 is an exemplary amino acid sequence of a construct wherein a MYC tag having three consecutive repetitions of the MYC sequence EQKLISEEDL (SEQ ID NO: 11), EQKLISEEDLEQKLISEEDLEQKLISEEDL (SEQ ID NO: 12) follows the N-terminal methionine, at positions 2-31, an extended leucine zipper domain sequence LEQRAEELARENEELEKEAEELEQENAE (SEQ ID NO: 4), underlined, is at position 52-79, a wild-type (WT) leucine zipper domain sequence LETQHKVLELTAENERLQKKVEQLSRELSTLRNLFKQL (SEQ ID NO: 1), italicized and bold, is at position 80-117, and a C-terminal portion having a sequence PEPLLASXiGHX2, (SEQ ID NO: 60) wherein an amino acid residue X$_1$ can be A or S and an amino acid residue X$_2$ can be C or M, is at position 118-128. The amino acids between the MYC tag and the extended leucine zipper domain are spacer amino acids, which includes a T7 tag having the sequence MASMTGGQQMG (SEQ ID NO: 61), which is an 11 amino acid peptide encoded in the leader sequence of T7 bacteriophage gene10.

SEQ ID NO: 9 is an exemplary sequence of a construct wherein a MYC tag having three consecutive repetitions of the MYC sequence EQKLISEEDL (SEQ ID NO: 11) EQKLISEEDLEQKLISEEDLEQKLISEEDL (SEQ ID NO: 12) follows the N-terminal methionine, at positions 2-31, an extended leucine zipper domain sequence LEQRAEELARENEELEKEAEELEQENAE (SEQ ID NO: 4), underlined, is at position 52-79, and a wild-type (WT) leucine zipper domain sequence LETQHKVLELTAENERLQKKVEQLSRELSTLRNLFKQL (SEQ ID NO: 1), italicized and bold, is at position 80-117. The amino acids between the MYC tag and the extended leucine zipper domain are spacer amino acids, which includes a T7 tag having the sequence MASMTGGQQMG (SEQ ID NO: 61), which is an 11 amino acid peptide encoded in the leader sequence of T7 bacteriophage gene10.

SEQ ID NO: 10 is an exemplary sequence of a construct wherein a MYC tag having three consecutive repetitions of the MYC sequence EQKLISEEDL (SEQ ID NO: 11), EQKLISEEDLEQKLISEEDLEQKLISEEDL (SEQ ID NO: 12) follows the N-terminal methionine, at positions 2-31, and a wild-type (WT) leucine zipper domain sequence LETQHKVLELTAENERLQKKVEQLSRELSTLRNLFKQL (SEQ ID NO: 1), italicized and bold, is at position 52-89. The amino acids between the MYC tag and the WT leucine zipper domain are spacer amino acids, which includes a T7 tag having the sequence MASMTGGQQMG (SEQ ID NO: 61), which is an 11 amino acid peptide encoded in the leader sequence of T7 bacteriophage gene10.

The amino acid sequences shown in Table 2 are examples of DN constructs including amino acid sequence variants of penetratin-linked DN CEBPB protein (Pen-DN-CEBPB) configured to interfere with one or more functions of CEBPB or CEBPD, among other proteins described herein, such as signaling including one or more of these proteins, and for treatment of cancers.

TABLE 2

Amino acid sequences of penetratin-linked DN CEBPB constructs

| Protein construct | Amino acid sequence | SEQ ID NO: |
|---|---|---|
| Pen-DN-CEBPB 1 | RQIKIWFQNRRMKWKKEQKLISEEDLMASMTGGQQMGR DPDLEQRAEELARENEELEKEAEELEQENAE*LETQHKVLE LTAENERLQKKVEQLSRELSTLRNLFKQL*PEPLLASX$_1$GHX$_2$ | 44 |
| Pen-DN-CEBPB 2 | RQIKIWFQNRRMKWKKEQKLISEEDLMASMTGGQQMGR DPDLEQRAEELARENEELEKEAEELEQENAE*LETQHKVLE LTAENERLQKKVEQLSRELSTLRNLFKQL* | 45 |

TABLE 2-continued

Amino acid sequences of penetratin-linked DN CEBPB constructs

| Protein construct | Amino acid sequence | SEQ ID NO: |
|---|---|---|
| Pen-DN-CEBPB 3 | RQIKIWFQNRRMKWKKEQKLISEEDLMASMTGGQQMGR DPD*LETQHKVLELTAENERLQKKVEQLSRELSTLRNLFKQ L* | 46 |
| Pen-DN-CEBPB 4 | RQIKIWFQNRRMKWKKLEQRAEELARENEELEKEAEELE QENAE*LETQHKVLELTAENERLQKKVEQLSRELSTLRNLF KQL* | 47 |
| Pen-DN-CEBPB 5 | RQIKIWFQNRRMKWKK*LETQHKVLELTAENERLQKKVEQ LSRELSTLRNLFKQL* | 48 |

SEQ ID NO: 44 is an exemplary amino acid sequence of a construct wherein a penetratin sequence RQIKIWFQNRRMKWKK (SEQ ID NO: 34) is at position 1-16, a MYC tag having a single MYC sequence EQKLISEEDL (SEQ ID NO: 11), is at positions 17-26, an extended leucine zipper domain sequence LEQRAEELARENEELEKEAEELEQENAE (SEQ ID NO: 4), underlined, is at position 42-69, a wild-type (WT) leucine zipper domain sequence LETQHKVLELTAENERLQKKVEQLSRELSTLRNLFKQL (SEQ ID NO: 1), italicized and bold, is at position 70-107, and a C-terminal portion having a sequence PEPLLASXiGHX2 (SEQ ID NO: 60), wherein an amino acid residue $X_1$ can be A or S and an amino acid residue $X_2$ can be C or M, is at position 108-118. The amino acids between the MYC tag and the extended leucine zipper domain are spacer amino acids, which includes a T7 tag having the sequence MASMTGGQQMG (SEQ ID NO: 61), which is an 11 amino acid peptide encoded in the leader sequence of T7 bacteriophage gene10. In this exemplary construct, a single MYC was used because 3×MYC may interfere with the function of the penetratin.

SEQ ID NO: 45 is an exemplary amino acid sequence of a construct wherein a penetratin sequence RQIKIWFQNRRMKWKK (SEQ ID NO: 34) is at position 1-16, a MYC tag having a single MYC sequence EQKLISEEDL (SEQ ID NO: 11), is at positions 17-26-, an extended leucine zipper domain sequence LEQRAEELARENEELEKEAEELEQENAE (SEQ ID NO: 4), underlined, is at position 42-69, and a wild-type (WT) leucine zipper domain sequence LETQHKVLELTAENERLQKKVEQLSRELSTLRNLFKQL (SEQ ID NO: 1), italicized and bold, is at position 70-107. The amino acids between the MYC tag and the extended leucine zipper domain sequence are spacer amino acids, which includes a T7 tag having the sequence MASMTGGQQMG (SEQ ID NO: 61), which is an 11 amino acid peptide encoded in the leader sequence of T7 bacteriophage gene10. In this exemplary construct, a single MYC was used because 3×MYC may interfere with the function of the penetratin.

SEQ ID NO: 46 is an exemplary amino acid sequence of a construct wherein a penetratin sequence RQIKIWFQNRRMKWKK (SEQ ID NO: 34) is at position 1-16, a MYC tag having a single MYC sequence EQKLISEEDL (SEQ ID NO: 11), is at positions 17-26-, and a wild-type (WT) leucine zipper domain sequence LETQHKVLELTAENERLQKKVEQLSRELSTLRNLFKQL (SEQ ID NO: 1), italicized and bold, is at position 42-79. The amino acids between the MYC tag and the WT leucine zipper domain are spacer amino acids, which includes a T7 tag having the sequence MASMTGGQQMG (SEQ ID NO: 61), which is an 11 amino acid peptide encoded in the leader sequence of T7 bacteriophage gene10. In this exemplary construct, a single MYC was used because 3×MYC may interfere with the function of the penetratin.

SEQ ID NO: 47 is an exemplary amino acid sequence of a construct wherein a penetratin sequence RQIKIWFQNRRMKWKK (SEQ ID NO: 34) is at position 1-16, an extended leucine zipper domain sequence LEQRAEELARENEELEKEAEELEQENAE (SEQ ID NO: 4), underlined, is at position 17-44, and a wild-type (WT) leucine zipper domain sequence LETQHKVLELTAENERLQKKVEQLSRELSTLRNLFKQL (SEQ ID NO: 1), italicized and bold, is at position 45-82.

SEQ ID NO: 48 is an exemplary amino acid sequence of a construct wherein a penetratin sequence RQIKIWFQNRRMKWKK (SEQ ID NO: 34) is at position 1-16, and a wild-type (WT) leucine zipper domain sequence LETQHKVLELTAENERLQKKVEQLSRELSTLRNLFKQL (SEQ ID NO: 1), italicized and bold, is at position 17-54.

The amino acid sequences shown in Table 3 are examples of DN constructs including amino acid sequence variants of DN CEBPD protein configured to interfere with one or more functions of CEBPB or CEBPD, among other proteins described herein, such as signaling including one or more of these proteins, and for treatment of cancers.

TABLE 3

Amino acid sequences of DN CEBPD constructs

| Protein construct | Amino acid sequence | SEQ ID NO: |
|---|---|---|
| DN-CEBPD 1 | MEQKLISEEDLEQKLISEEDLEQKLISEEDLARAGSMASMTG GQQMGRDPD*LEQRAEELARENEELEKEAEELEQENAE*LVEL SAENEKLHQRVEQLTRDLAGLRQFFKQLPSPPFLPAAGTAD XR | 52 |

TABLE 3-continued

Amino acid sequences of DN CEBPD constructs

| Protein construct | Amino acid sequence | SEQ ID NO: |
|---|---|---|
| DN-CEBPD 2 | MEQKLISEEDLEQKLISEEDLEQKLISEEDLARAGSMASMTG GQQMGRDPDLEQRAEELARENEELEKEAEELEQENAE*LVEL SAENEKLHQRVEQLTRDLAGLRQFFK* | 53 |
| DN-CEBPD 3 | MEQKLISEEDLEQKLISEEDLEQKLISEEDLARAGSMASMTG GQQMGRDPD*LVELSAENEKLHQRVEQLTRDLAGLRQFFK* | 54 |

SEQ ID NO: 52 is an exemplary amino acid sequence of a construct wherein a MYC tag having three consecutive repetitions of the MYC sequence EQKLISEEDL (SEQ ID NO: 11), EQKLISEEDLEQKLISEEDLEQKLISEEDL (SEQ ID NO: 12) follows the N-terminal methionine, at positions 2-31, an extended leucine zipper domain sequence LEQRAEELARENEELEKEAEELEQENAE (SEQ ID NO: 4), underlined, is at position 52-79, a wild-type (WT) leucine zipper domain sequence LVELSAENEKLHQRVEQLTRDLAGLRQFFK (SEQ ID NO: 2), italicized and bold, is at position 80-109, and a C-terminal portion having a sequence QLPSPPFLPAAGTADXR (SEQ ID NO: 62), wherein an amino acid residue X can be C or M, is at position 110-126. The amino acids between the MYC tag and the extended leucine zipper domain are spacer amino acids, which includes a T7 tag having the sequence MASMTGGQQMG (SEQ ID NO: 61), which is an 11 amino acid peptide encoded in the leader sequence of T7 bacteriophage gene10.

SEQ ID NO: 53 is an exemplary amino acid sequence of a construct wherein a MYC tag having three consecutive repetitions of the MYC sequence EQKLISEEDL (SEQ ID NO: 11), EQKLISEEDLEQKLISEEDLEQKLISEEDL (SEQ ID NO: 12) follows the N-terminal methionine, at positions 2-31, an extended leucine zipper domain sequence LEQRAEELARENEELEKEAEELEQENAE (SEQ ID NO: 4), underlined, is at position 52-79, and a wild-type (WT) leucine zipper domain sequence LVELSAENEKLHQRVEQLTRDLAGLRQFFK (SEQ ID NO: 2), italicized and bold, is at position 80-109. The amino acids between the MYC tag and the extended leucine zipper domain are spacer amino acids, which includes a T7 tag having the sequence MASMTGGQQMG (SEQ ID NO: 61), which is an 11 amino acid peptide encoded in the leader sequence of T7 bacteriophage gene10.

SEQ ID NO: 54 is an exemplary amino acid sequence of a construct wherein a MYC tag having three consecutive repetitions of the MYC sequence EQKLISEEDL (SEQ ID NO: 11), EQKLISEEDLEQKLISEEDLEQKLISEEDL (SEQ ID NO: 12) follows the N-terminal methionine, at positions 2-31, and a wild-type (WT) leucine zipper domain sequence LVELSAENEKLHQRVEQLTRDLAGLRQFFK (SEQ ID NO: 2), italicized and bold, is at position 52-81. The amino acids between the MYC tag and the WT leucine zipper domain are spacer amino acids, which includes a T7 tag having the sequence MASMTGGQQMG (SEQ ID NO: 61), which is an 11 amino acid peptide encoded in the leader sequence of T7 bacteriophage gene10.

The amino acid sequences shown in Table 4 are examples of DN constructs including amino acid sequence variants of penetratin-linked DN CEBPD protein (Pen-DN-CEBPD) configured to interfere with one or more functions of CEBPB or CEBPD, among other proteins described herein, such as signaling including one or more of these proteins, and for treatment of cancers.

TABLE 4

Amino acid sequences of penetratin-linked DN CEBPD constructs.

| Protein construct | Amino acid sequence | SEQ ID NO: |
|---|---|---|
| Pen-DN-CEBPD 1 | RQIKIWFQNRRMKWKKEQKLISEEDLMASMTGGQQMGRD PDLEQRAEELARENEELEKEAEELEQENAE*LVELSAENEKL HQRVEQLTRDLAGLRQFFK*QLPSPPFLPAAGTADXR | 55 |
| Pen-DN-CEBPD 2 | RQIKIWFQNRRMKWKKEQKLISEEDLMASMTGGQQMGRD PDLEQRAEELARENEELEKEAEELEQENAE*LVELSAENEKL HQRVEQLTRDLAGLRQFFK* | 56 |
| Pen-DN-CEBPD 3 | RQIKIWFQNRRMKWKKEQKLISEEDLMASMTGGQQMGRD PD*LVELSAENEKLHQRVEQLTRDLAGLRQFFK* | 57 |
| Pen-DN-CEBPD 4 | RQIKIWFQNRRMKWKKLEQRAEELARENEELEKEAEELEQE NAE*LVELSAENEKLHQRVEQLTRDLAGLRQFFK* | 58 |
| Pen-DN-CEBPD 5 | RQIKIWFQNRRMKWKK*LVELSAENEKLHQRVEQLTRDLAG LRQFFK* | 59 |

SEQ ID NO: 55 is an exemplary sequence of a construct wherein a penetratin sequence RQIKIWFQNRRMKWKK (SEQ ID NO: 34) is at position 1-16, a MYC tag having a single MYC sequence EQKLISEEDL (SEQ ID NO: 11), is at positions 17-26, an extended leucine zipper domain sequence LEQRAEELARENEELEKEAEELEQENAE (SEQ ID NO: 4), underlined, is at position 42-69, a wild-type (WT) leucine zipper domain sequence LVELSAE-NEKLHQRVEQLTRDLAGLRQFFK (SEQ ID NO: 2), italicized and bold, is at position 70-99, and a C-terminal portion having a sequence QLPSPPFLPAAGTADXR (SEQ ID NO: 62), wherein an amino acid residue X can be C or M, is at position 100-116. The amino acids between the MYC tag and the extended leucine zipper are spacer amino acids, which includes a T7 tag having the sequence MASMTGGQQMG (SEQ ID NO: 61), which is an 11 amino acid peptide encoded in the leader sequence of T7 bacteriophage gene10. In this exemplary construct, a single MYC was used because 3×MYC may interfere with the function of the penetratin.

SEQ ID NO: 56 is an exemplary sequence of a construct wherein a penetratin sequence RQIKIWFQNRRMKWKK (SEQ ID NO: 34) is at position 1-16, a MYC tag having a single MYC sequence EQKLISEEDL (SEQ ID NO: 11), is at positions 17-26, an extended leucine zipper domain sequence LEQRAEELARENEELEKEAEELEQENAE (SEQ ID NO: 4), underlined, is at position 42-69, and a wild-type (WT) leucine zipper domain sequence LVELSAE-NEKLHQRVEQLTRDLAGLRQFFK (SEQ ID NO: 2), italicized and bold, is at position 70-99. The amino acids between the MYC tag and the extended leucine zipper are spacer amino acids, which includes a T7 tag having the sequence MASMTGGQQMG (SEQ ID NO: 61), which is an 11 amino acid peptide encoded in the leader sequence of T7 bacteriophage gene10. In this exemplary construct, a single MYC was used because 3×MYC may interfere with the function of the penetratin.

SEQ ID NO: 57 is an exemplary sequence of a construct wherein a penetratin sequence RQIKIWFQNRRMKWKK (SEQ ID NO: 34) is at position 1-16, a MYC tag having a single MYC sequence EQKLISEEDL (SEQ ID NO: 11), is at positions 17-26, and a wild-type (WT) leucine zipper domain sequence LVELSAENEKLHQRVEQLTRD-LAGLRQFFK (SEQ ID NO: 2), italicized and bold, is at position 42-71. The amino acids between the MYC tag and the WT leucine zipper domain are spacer amino acids, which includes a T7 tag having the sequence MASMTGGQQMG (SEQ ID NO: 61), which is an 11 amino acid peptide encoded in the leader sequence of T7 bacteriophage gene10. In this exemplary construct, a single MYC was used because 3×MYC may interfere with the function of the penetratin.

SEQ ID NO: 58 is an exemplary sequence of a construct wherein a penetratin sequence RQIKIWFQNRRMKWKK (SEQ ID NO: 34) is at position 1-16, an extended leucine zipper domain sequence LEQRAEELARENEELEKE-AEELEQENAE (SEQ ID NO: 4), underlined, is at position 17-44, and a wild-type (WT) leucine zipper domain sequence LVELSAENEKLHQRVEQLTRDLAGLRQFFK (SEQ ID NO: 2), italicized and bold, is at position 45-74.

SEQ ID NO: 59 is an exemplary sequence of a construct wherein a penetratin sequence RQIKIWFQNRRMKWKK (SEQ ID NO: 34) is at position 1-16, and a wild-type (WT) leucine zipper domain sequence LVELSAE-NEKLHQRVEQLTRDLAGLRQFFK (SEQ ID NO: 2), italicized and bold, is at position 17-46.

In the amino acid sequences shown in Tables 1, 2, 3 and 4, The Myc tag is to enable immunoprecipitation or isolation on beads coated with Myc antibodies and serves as a reporter for detecting expression of the DN construct in Western blots or in cells by immunostaining. The WT leucine zipper enables specific coil-coil binding to partners. The spacer amino acids keep the reporter tag (e.g., Myc) from interfering with the leucine zipper and these amino acids are added as a result of cloning into the vector. The C-terminal portion is part of the WT protein that lies between the WT leucine zipper and the C-terminus of the protein. The WT leucine zipper domain is the only portion of the DN CEBPB and DN CEBPD protein constructs that is required for the dominant negative function. Thus, amino acid residues in all other portions of the DN CEBPB and DN CEBPD proteins can be substituted or deleted from the DN CEBPB and DN CEBPD sequences while retaining the DN CEBPB and DN CEBPD function.

Figure 1:
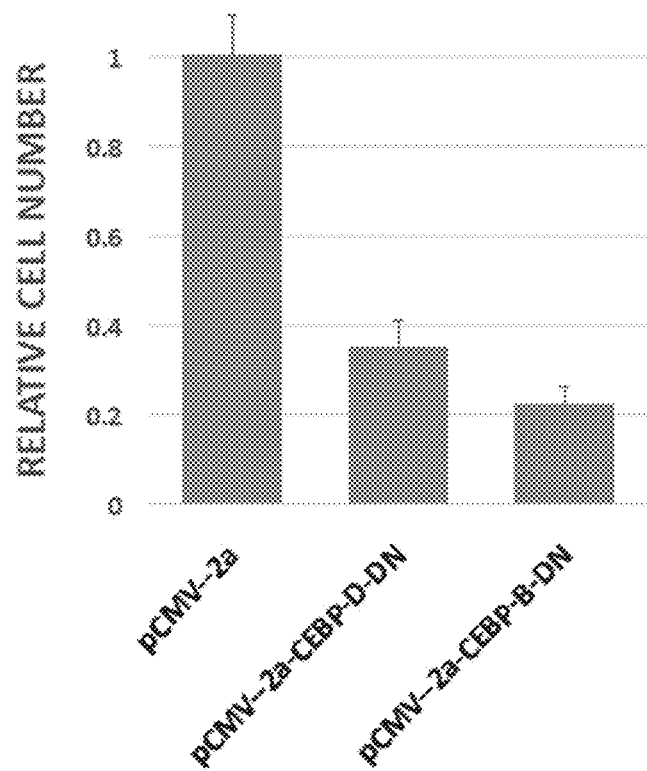
FIG. 1 is a graph reporting exemplary data on survival of cultured Glioblastoma T98G cells following transfection with DNA expressing pCMV-2a, pCMV-2a-DN-CEBPB, or pCMV-2a-DN-CEBPD.
Figure 2:
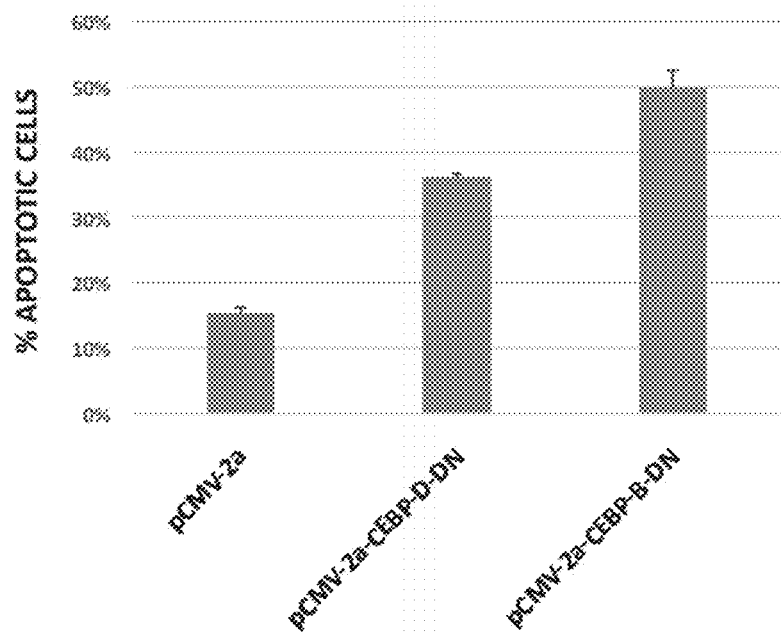
FIG. 2 is a graph reporting exemplary data on percentage of apoptotic cultured Glioblastoma T98G cells following transfection with DNA expressing pCMV-2a, pCMV-2a-DN-CEBPB, or pCMV-2a-DN-CEBPD.

For example, in FIGS. 1 and 2, both DN-CEBPB and DN-CEBPD do not have a C-terminus and are functional. The C-terminus does not contribute to their function. Removing the C-terminus provides a shorter peptide that is easier to synthesize as a fusion protein with a cell-penetrating domain.

Example 2. DN-CEBPB and DN-CEPBD Cause Cell Loss in Glioblastoma Cell T98G Cultures Replicate cultures of T98G glioblastoma cells were transfected with DNA vectors pCMV-2a (empty vector), pCMV-2a-CEBP-D-DN (vector expressing do-CEBPD containing only the WT leucine zipper domain of CEBPD), or pCMV-2a-CEBP-B-DN (vector expressing do-CEBPB containing only the WT leucine zipper domain of CEBPB). To mark transfected cells, vectors were co-transfected with DNA encoding GFP (at a ratio of 3:1). Three days later, cell counts for numbers of GFP+ cells were performed and data were normalized to the values for control empty vector pCMV-2a. Data are from 3 independent experiments each carried out in triplicate. Values represent mean values±SEM.

The results are reported in FIG. 1 and show that DN-CEBPB and DN-CEPBD can cause cell loss in Glioblastoma cell T98G cultures. These results support the development of dominant negative forms of CEBPB and CEBPD proteins as potential cancer therapeutics.

Example 3. DN-CEBPB and DN-CEPBD are Internalized into Cancer Cells and Promote Apoptotic Death of Glioblastoma Cell T98G Cultures and Other Cancer Cells FIG. 41 is a photomicrograph showing a culture of GBM12 cells treated with 10 μM N-terminally FAM-labelled DN-CEPBD (green) for 24 hours. Blue indicates DAPI. The data shows that DN-CEPBD is internalized into the cells.

FIG. 2 is a graph reporting exemplary data showing dominant-negative forms of CEBPB and CEBPD promote apoptotic death of cancer cells. Replicate cultures of T98G glioblastoma cells were transfected with DNA vectors pCMV-2a (empty vector), pCMV-2a-CEBP-D-DN (vector expressing DN-CEBPD containing only the WT leucine zipper domain of CEBPD), or pCMV-2a-CEBP-B-DN (vector expressing DN-CEBPB containing only the WT leucine zipper domain of CEBPB). Two days later, transfected cells were scored for proportion with apoptotic nuclei. Data represent means±SEM (n=3).

The results show that DN-CEBPB and DN-CEPBD can apoptosis in Glioblastoma cell T98G cultures. These results support the development of dominant negative forms of CEBPB and CEBPD proteins as potential cancer therapeutics.

T98G, MDA-MB-231, MCF7, A375, and HCT116 cells were treated with or without 20 μM CP-dn-CEBPB or CP-dn-CEBPD for 3 days and then assessed by qPCR for relative levels of BMF transcripts (FIG. 35A, T98G; FIG. 35B, MDA-MB-231; FIG. 35C, MCF7; FIG. 35D, A375; FIG. 35E, HCT116). The data indicates that CP-dn-CEBPB and CP-dn-CEBPD upregulate pro-apoptotic BMF and suggests a potential mechanism by which CP-dn-CEBPB and CP-dn-CEBPD cause apoptosis of cancer cells.

T98G, MCF7, A375, and HCT116 cells were treated with one of two BMF knockdown siRNAs or control siRNA for 2 days, then treated with or without 20 µM CP-dn-CEBPD for 2 days. Cultures were assessed for % of apoptotic nuclei (n=6 random fields) (FIG. 36A, T98G; FIG. 36B, MCF7; FIG. 38C, A375; FIG. 36D, HCT116). The data further supports the idea that CP-dn-CEBPD kills cancer cells by upregulating pro-apoptotic BMF.

Example 4. The Cancer Target ATF5 Transcription Factor Protein Interacts with CEBPB, Phospho-CEBPB and CEBPD Via its Leucine Zipper LN229 glioblastoma cells were transfected with plasmids expressing a FLAG-tagged intact ATF5 leucine zipper (pCMV-1A-FLAG-DN-ATF5-TRUNC), or a FLAG-tagged intact ATF5 leucine zipper plus a mutated ATF5 DNA binding domain containing an extended leucine zipper (pCMV-1A-FLAG-DN-ATF5), or a variant of pCMV-1A-FLAG-DN-ATF5 also mutated in the leucine zipper to replace the relevant leucine residues with glycine residues (pCMV-1A-FLAG-DN-ATF5-MUT), or a control plasmid lacking an ATF5 construct (pCMV-1A-FLAG).

Two days later cell lysates were subjected to pulldown experiments with FLAG beads to capture the FLAG-tagged constructs and their binding partners and the eluates were probed with antibodies to detect FLAG, CEBPB, p-CEBPB, or CEBPD by Western immunoblotting. FIG. 3 shows that CEBPB, phospho-CEBPB (P-CEBP) and CEBPD interact with the ATF5 leucine zipper, but not with the mutated ATF5 leucine zipper construct.

Example 5. Short-Interfering RNA (siRNA)-Mediated Knockdown of CEBPB or CEBPD Decreases Survival of T98G Cells Replicate T98G cell cultures were transfected with siRNAs targeting CEBPB (si-CEBPB-1), CEBPD (si-CEBPD-1), or a non-targeting siRNA control (si-Cont) and assessed 4 days later for relative cell number. As shown in FIG. 4A and FIG. 4B, siRNA-mediated knockdown of CEBPB and CEBPD reduces cell numbers in cultures of T98G cells. Values are expressed as means±SEM and represent data from 4 independent experiments, each in triplicate (*P<0.001 compared with si-Cont).

Example 6. Short-Interfering RNA (siRNA)-Mediated Knockdown of CEBPB or CEBPD Promotes Apoptosis of T98G Cells, LN229 Cells, GBM22 Cells and MDA-MB-468 Cells Replicate T98G cell cultures were transfected with siRNAs targeting CEBPB (siCEBPB-1 or siCEBPB-2), CEBPD (siCEBPD-1 or siCEBPD-2), or a non-targeting control (siCont) and assessed 4 days later for proportion of cells with apoptotic nuclei. As shown in FIG. 4C, siRNAs targeting CEBPB (siCEBPB-1 or siCEBPB-2), CEBPD (siCEBPD-1 or siCEBPD-2) significantly increased the proportion of T98G cells with apoptotic nuclei. Values are expressed as means±SEM and represent data from 4 independent experiments, each in triplicate. *P<0.001 compared with siCont.

Replicate LN229 cell cultures were transfected with siRNAs targeting CEBPB (siCEBPB-1 or siCEBPB-2), CEBPD (siCEBPD-1 or siCEBPD-2), or a non-targeting control (siCont) and assessed 4 days later for proportion of cells with apoptotic nuclei. As shown in FIG. 4D, siRNAs targeting CEBPB (siCEBPB-1 or siCEBPB-2), CEBPD (siCEBPD-1 or siCEBPD-2) significantly increased the proportion of LN229 cells with apoptotic nuclei. Values are expressed as means±SEM and represent data from 3 independent experiments, each in triplicate. *P<0.001 compared with siCont.

Replicate GBM22 cell cultures were transfected with siRNAs targeting CEBPB (siCEBPB-1), CEBPD (siCEBPD-1), or a non-targeting control (siCont) and assessed 4 days later for proportion of cells with apoptotic nuclei. As shown in FIG. 4E, siRNAs targeting CEBPB (siCEBPB-1), CEBPD (siCEBPD-1) significantly increased the proportion of GBM22 cells with apoptotic nuclei. Values are expressed as means±SEM and represent data from 2 independent experiments, each in triplicate. *P<0.001 compared with siCont.

Replicate MDA-MB-468 cell cultures were transfected with siRNAs targeting CEBPB (siCEBPB-1), CEBPD (siCEBPD-1), or a non-targeting control (siCont) and assessed 4 days later for proportion of cells with apoptotic nuclei. As shown in FIG. 4F, siRNAs targeting CEBPB (siCEBPB-1), CEBPD (siCEBPD-1) significantly increased the proportion of MDA-MB-468 cells with apoptotic nuclei. Values are expressed as means±SEM and represent data from 2 independent experiments, each in triplicate. *P<0.001 compared with siCont.

Example 7. Knockdown of CEBPB and CEBPD does not Affect Astrocyte Survival

Cultures of normal human astrocytes were transfected with siRNAs targeting CEBPB (siCEBPB-1), CEBPD (siCEBPD-1), or a non-targeting control (siCont) and 4 days later assessed for total cell numbers. As shown in FIG. 4G, knockdown of CEBPB and CEBPD does not affect astrocyte survival.

Example 8. Knockdown Efficacy of siRNAs Targeting CEBPB (siCEBPB-1) and CEBPD (siCEBPD-1)

T98G cultures were transfected with siRNAs targeting CEBPB (siCEBPB-1 or siCEBPB-2), CEBPD (siCEBPD-1 or siCEBPD-2), or anon-targeting control (siCont) and assessed 4 days later for expression of CEBPB and CEBPD by Western immunoblotting.

As shown in FIG. 4H, siRNAs targeting CEBPB (siCEBPB-1 or siCEBPD-2) decreased CEBPB protein expression in T98G cells compared to levels of CEBPB protein in T98G cells treated with non-targeting control (siCont). As shown in FIG. 4I, siRNAs targeting CEBPD (siCEBPD-1 or siCEBPD-2) decreased CEBPD protein expression in T98G cells compared to levels of CEBPD protein in T98G cells treated with non-targeting control (siCont). For the CEBPD blots, all samples were analyzed on the same blot and irrelevant intervening lanes have been removed as indicated.

Example 9. Cell Penetrating Forms of CEBPB and CEBPD Affect Morphology, Growth and Survival of T98G Glioblastoma Cells Replicate T98G glioblastoma cell cultures were exposed to dominant negative (DN) synthetic peptides having an N-terminal penetratin sequence followed by a CEBPB or CEBPD native leucine zipper sequence (CP-DN-CEBPB or CP-DN-CEBPD, respectively) for 5 days at final concentrations of 10 µM or 20 µM (CP-DN-CEBPB) or 3 µM, 10 µM, 20 µM or 50 µM (CP-DN-CEBPD). Stock solutions of the peptides were prepared in buffer without added bovine serum albumin (BSA). As shown in FIG. 5, CP-DN-CEBPB or CP-DN-CEBPD dose-responsively affected the morphology, growth and survival of T98G glioblastoma cells.

Example 10. Cell Penetrating Forms of CEBPB and CEBPD Decrease Growth and Survival of T98G Glioblastoma Cells Replicate T98G glioblastoma cell cultures were exposed to CP-DN-CEBPB or CP-DN-CEBPD, for 6-7 days at doses of 0 µM to 50 µM. The number of T98G cells was dose-responsively decreased by CP-DN-CEBPB (FIG. 6A) and CP-DN-CEBPD (FIG. 6B). Stock solutions of the peptides were prepared in buffer without added bovine serum albumin (BSA).

Example 11. Time Course of Repression of T98G Glioblastoma Cell Growth and Survival by CP-DN-CEBPB or CP-DN-CEBPD Replicate T98G cell cultures were exposed to CP-DN-CEBPB or CP-DN-CEBPD peptides (10 µM or 20 µM) for 1, 2, 3, 4, 5, or 6 days. The growth and survival of T98G cells treated with CP-DN-CEBPB (FIG. 7A) or CP-DN-CEBPD (FIG. 7B) was decreased as compared to untreated control cells. Values shown in FIG. 7A and FIG. 7B represent means from 3 replicate cultures. Stock solutions of the peptides were prepared in buffer without added bovine serum albumin (BSA).

Example 12. Bovine Serum Albumin (BSA) Increases the Potency of CP-DN-CEBPB and CP-DN-CEBPD Peptides in Suppressing the Growth and Survival of T98G Glioblastoma Cells Four replicate cultures of T98G cells were treated for 6 days with a cell penetrating dominant negative CEBPB (CP-DN-CEBPB; FIG. 8A) or a cell penetrating dominant negative CEBPD (CP-DN-CEBPD; FIG. 8B) at doses of 0 µM to 50 µM, with or without bovine serum albumin (BSA). As shown in FIG. 8A and FIG. 8B, inclusion of bovine serum albumin (BSA) in buffer used for preparing stock solutions of cell penetrating forms of DN CEBPB and DN CEBPD peptides greatly increased the potency of the peptides in suppressing the growth and survival of T98G glioblastoma cells. Concentration of BSA in the stock solution, when present, was 3 mg/ml. The final concentration of BSA in the cell culture medium was 0.6 mg/ml. Values represent means of determinations made on 4 replicate cultures for each condition.

Example 13. CP-DN-CEBPB or CP-DN-CEBPD Represses Growth and Survival of Cancer Cells Dose-responsive (0 µM to 50 µM) decrease in growth and survival was observed following 6 days treatment of cultures of MDA-MB-231 breast cancer cells with CP-DN-CEBPB (FIG. 9A) or CP-DN-CEBPD (FIG. 9B), as well as in HCT116 colon cancer cells treated for 6 days with CP-DN-CEBPB (FIG. 9C) or CP-DN-CEBPD (FIG. 9D), and in LN229 glioblastoma cells treated for 6 days with CP-DN-CEBPB (FIG. 9E) or CP-DN-CEBPD (FIG. 9F), and also in MCF7 breast cancer cells treated for 6 days with CP-DN-CEBPB (FIG. 9G) or CP-DN-CEBPD (FIG. 9H), and in U251 gliblastoma multiforme cells treated with CP-DN-CEBPB or CP-DN-CEBPD (FIG. 15A), as well as in Mgpp3 murine proneural glioma cells treated with CP-DN-CEBPB or CP-DN-CEBPD (FIG. 15B), and A375 melanoma cells treated with CP-DN-CEBPB or CP-DN-CEBPD (FIG. 15C), and B16 murine melanoma cells (FIG. 15D). Replicate cultures were exposed to the peptides the for 6 days at the indicated concentrations. Stock solutions of the peptides were prepared in buffer without added bovine serum albumin (BSA).

Replicate cultures of MDA-MB-468 breast cancer cells, A549 lung cancer cells and 293T transformed embryonic kidney cells were exposed to CP-DN-CEBPB or CP-DN-CEBPD, for 6 days at doses of 0 µM to 50 µM. CP-DN-CEBPB caused a dose-dependent decrease in the number of MDA-MB-468 cells (FIG. 10A), A549 cells (FIG. 10C) and 293T cells (FIG. 10E). Similarly, CP-DN-CEBPD caused a dose-dependent decrease in the number of MDA-MB-468 cells (FIG. 10B), A549 cells (FIG. 10D) and 293T cells (FIG. 10F). Stock solutions of the peptides were prepared in buffer without added bovine serum albumin (BSA).

Replicate cultures of HCT116, MDA-MB 231, MCF7, and T98G cells were exposed to a 50/50 by concentration mixture of CP-DN-CEBPB and CP-DN-CEBPD for 6 days at doses of 0 µM to 50 µM. Stock solutions of the peptides were prepared in buffer without added bovine serum albumin (BSA). Dose-dependent decreases in the numbers were observed of HCT116 cells (FIG. 16A), MDA-MB 231 cell (FIG. 16B), MCF7 cell (FIG. 16C), and T98G cells (FIG. 16D).

T98G (FIG. 21A), MDA-MB 231 (FIG. 21B), and HCT116 (FIG. 21C) cells were exposed to CP-DN-CEBPB and CP-DN-CEBPD for 6 days at doses of 0.05 µM 0.5 µM, and 5 µM while growing in soft agar. Growth was inhibited by does as low as 0.5 µM. T98G (FIG. 21D), MDA-MB 231 (FIG. 21E), and HCT116 (FIG. 21F) cells were exposed to CP-DN-CEBPB and CP-DN-CEBPD for 6 days at doses of 0.05 µM 0.5 µM, and 5 µM while growing on culture plates. Growth was inhibited by does as low as 0.5 µM. The data from soft agar and culture plates indicates that CP-DN-CEBPB and CP-DN-CEBPD can exert an effect even when cells are growing in low cell number and three-dimensional conditions that are more similar to those found in organism than typical cell culture.

Monolayers of MDA-MB 231 or T98G cells were subjected to formation of a scratch at 0 time and cultured for 20 hours in 20 µM or 40 µM CP-DN-CEBPB and CP-DN-CEBPD. Multiple images taken at 0 time and after 20 hours were analyzed for gap width of the scratches into which cells migrated or not. Example images for T98G are found in FIG. 22A, with compiled data for the T98G samples in FIG. 22B. Example images for MDA-MB 231 are found in FIG. 22C, with compiled data for the MDA-MB 231 samples in FIG. 22D. Both CP-DN-CEBPB and CP-DN-CEBPD were able to inhibit migration of both cell lines, indicating potential anti-metastatic activity.

Example 14. CP-DN-CEBPB and CP-DN-CEBPD Require their Leucine Zipper to Affect Grown of Cancer Cell Lines Replicate cultures of T98G, HCT116, MDA-MB 231, and MCF7 cells were exposed to CP-DN-CEBPB, CP-DN-CEBPD, or a CP-DN-CEBPD in which heptad repeat leucine residues were mutated to glycine residues for 6 days at doses of 0 µM to 50 µM. Stock solutions of the peptides were prepared in buffer without added bovine serum albumin (BSA). Dose-dependent decreases in the numbers of T98G cells (FIG. 17A), HCT116 (FIG. 17B), MDA-MB 231 (FIG. 17C), and MCF7 cells (FIG. 17D) did not occur with exposure to the mutant CP-DN-CEBPD.

Example 15. Cell Penetrating Forms of CEBPB and CEBPD do not Affect the Growth, Survival and Morphology of HIEC-6 Non-Cancer Human Intestinal Epithelial Cells, MCF10A Non-Cancer Human Breast Epithelial Cells, and Normal Human Astrocytes Replicate cultures of HIEC-6 non-cancer human intestinal epithelial cells, MCF10A non-cancer human breast epithelial cells, or normal human astrocytes were exposed to CP-DN-CEBPB or CP-DN-CEBPD, for 6 days at doses of 0 µM to 50 µM. CP-DN-CEBPB did not cause a dose-dependent decrease in the number of HIEC-6 cells (FIG. 11A), MCF10A ells (FIG. 11C). Similarly, CP-DN-CEBPD did not cause a dose-dependent decrease in the number of HIEC-6 cells (FIG. 11B) and MCF10A cells (FIG. 11D). In addition neither CP-DN-CEBPB or CP-DN-CEBPD affected survival of astrocyte. Stock solutions of the peptides were prepared in buffer without added bovine serum albumin (BSA).

Replicate cultures of HIEC-6 non-cancer human intestinal epithelial cells and MCF10A non-cancer human breast epithelial cells were exposed to CP-DN-CEBPB or CP-DN-CEBPD for 5 to 6 days at final concentrations of 20 µM or 50 CP-DN-CEBPB or CP-DC-CEBPD did not affect the morphology of HIEC-6 cells (FIG. 12). CP-DN-CEBPB or CP-DC-CEBPD did not affect the morphology of MCF10A cells (FIG. 13). Stock solutions of the peptides were prepared in buffer without added bovine serum albumin (BSA).

Replicate cultures of human astrocytes were exposed to CP-DN-CEBPB or CP-DN-CEBPD for 6 days at final concentrations of 0 µM or 50 µM. CP-DN-CEBPB or CP-DC-CEBPD did not affect the morphology of human astrocytes (FIG. 18). Stock solutions of the peptides were prepared in buffer without added bovine serum albumin (BSA).

Example 16. CP-Dn-CEBPB and CP-Dn-CEBPD Promote Apoptotic Death in Multiple Cancer Cell Lines MDA-MB-231, MCF7, HCT116 and T98G cancer cell lines were treated for 3 days with 20 µM CP-dn-CEBPB and CP-dn-CEBPD peptides from stock solutions prepared without additives. Cultures were stained with propidium iodide and assessed for proportion of cells with apoptotic nuclei by flow cytometry. Compared to untreated cells (control), CP-dn-CEBPB and CP-dn-CEBPD increased apoptotic cell death in all of the cancer cells (FIG. 14).

MDA-MB-231, MCF7, HCT116 and T98G cancer cell lines and HIEC-6 non-cancer cell lines were treated for 3 days with 20 µM CP-dn-CEBPB and CP-dn-CEBPD peptides from stock solutions prepared without additives, followed by PI-Annexin staining and flow cytometry. Flow cytometry results are presented in FIG. 19. Numbers in upper and lower quadrants indicate % of cells in early (lower) or late (upper) apoptotic phase. CP-dn-CEBPB and CP-dn-CEBPD caused apoptotic death in multiple cancer cell lines, but not in the control non-caner cell line.

subG1 DNA levels, which are indicative of apoptosis, were analyzed for: MCF7 cells treated for 3 days with 20 µM CP-dn-CEBPB (FIG. 20A), CP-dn-CEBPD (FIG. 20B), or a control (FIG. 20C), HCT 116 cells treated for 3 days with 20 µM CP-dn-CEBPB (FIG. 20D), CP-dn-CEBPD (FIG. 20E), or a control (FIG. 20F), MDA-MB 231 cells treated for 3 days with 20 µM CP-dn-CEBPB (FIG. 20G), CP-dn-CEBPD (FIG. 20H), or a control (FIG. 20I), and T98G cells treated for 3 days with 20 µM CP-dn-CEBPB (FIG. 2J), CP-dn-CEBPD (FIG. 20K), or a control (FIG. 20L).

These results indicate that reductions in cancer cell growth observed in other Examples are likely at least partially due to apoptosis of cancer cells and not merely to reduction in growth rate.

Example 17. CP-Dn-CEBPB and CP-Dn-CEBPD with Gamma Radiation

Replicate cultures of T98G and HCT116 cells were exposed to 2 Gy or 5 Gy of gamma radiation. Immediately, the cultures were treated with 3 µM, 10 µM, or 20 µM CP-dn-CEBPB and CP-dn-CEBPD peptides, maintained for 6 days, and then assessed for cell number. The bar graphs of FIGS. 23A (T98G, CP-dn-CEBPB), 23C (T98G, CP-dn-CEBPBD, 23E (HCT116, CP-dn-CEBPB), and 23G (HCT116, CP-dn-CEBPD) show relative cell numbers for each condition as compared to untreated controls. The line graphs of FIGS. 23B (T98G, CP-dn-CEBPB), 23D (T98G, CP-dn-CEBPBD, 23F (HCT116, CP-dn-CEBPB), and 23H (HCT116, CP-dn-CEBPD) show the response as normalized in each case so that 100 represents the relative number of surviving cells that received the indicated level of radiation treatment, but no peptide treatment. Juxtaposition of data points indicate additivity while non-juxtaposition indicates potential synergism or antagonism.

Replicate cultures of T98G and HCT116 cells were exposed to 2 Gy or 5 Gy of gamma radiation. One day later, the cultures were treated with 0.05 µM, 0.5 µM, or 5 µM CP-dn-CEBPB and CP-dn-CEBPD peptides, maintained for 6 days, and then assessed for cell number. The bar graphs of FIGS. 24A (T98G, CP-dn-CEBPB), 24C (T98G, CP-dn-CEBPBD, 24E (HCT116, CP-dn-CEBPD), and 24G (HCT116, CP-dn-CEBPD) show relative cell numbers for each condition as compared to untreated controls. The line graphs of FIGS. 24B (T98G, CP-dn-CEBPB), 24D (T98G, CP-dn-CEBPBD, 24F (HCT116, CP-dn-CEBPB), and 24H (HCT116, CP-dn-CEBPD) show the response as normalized in each case so that 100 represents the relative number of surviving cells that received the indicated level of radiation treatment, but no peptide treatment. Calculated Combination Indexes (CI) are T98G, CI=0.61±0.05 for CP-dn-CEBPB, 0.68±0.07 for CP-dn-CEBPD; HCT116, 0.89±0.04 for CP-dn-CEBPB, 0.86±0.05 for CP-dn-CEBPD. CI=1 indicates additivity; CI<1 indicates synergism; CI>1 indicates antagonism.

Replicate cultures of T98G cells in soft agar were exposed to 2 Gy or 5 Gy of gamma radiation. Immediately, the cultures were treated with 0.05 µM, 0.5 µM, or 5 µM CP-dn-CEBPB and CP-dn-CEBPD peptides, maintained for 12 days, and then assessed for colony number. The bar graph in FIG. 25A shows relative colony number for each condition. The line graph of FIG. 25B shows the response as normalized in each case so that 100 represents the relative number of surviving cells that received the indicated level of radiation treatment, but no peptide treatment.

The data indicates a synergistic effect between treatment with CP-dn-CEBPB and CP-dn-CEBPD peptides and gamma radiation.

Example 18. CP-Dn-CEBPB and CP-Dn-CEBPD with Paclitaxel

Replicate cultures of T98G, MDA-MB 231, and MCF7 cells were treated with 1 nM or 5 nM paclitaxel and 3 μM, 10 μM, or 20 μM CP-dn-CEBPB and CP-dn-CEBPD peptides, maintained for 6 days, and then assessed for cell number. The bar graphs of FIGS. 26A (T98G, CP-dn-CEBPB), 26C (T98G, CP-dn-CEBPBD, 26E (MDA-MB-231, CP-dn-CEBPBD), 26G (MDA-MB-231, CP-dn-CEBPD), 26I (MCF7, CP-dn-CEBPBB), and 26K (MCF7, CP-dn-CEBPBD) show relative cell numbers for each condition as compared to untreated controls. The line graphs of FIGS. 26B (T98G, CP-dn-CEBPB), 26D (T98G, CP-dn-CEBPBD), 26F (MDA-MB-231, CP-dn-CEBPB), 26H (MDA-MB-231, CP-dn-CEBPD), 26J (MCF7, CP-dn-CEBPB), and 26L (MCF7 CP-dn-CEBPBD) show the response as normalized in each case so that 100 represents the relative number of surviving cells that received the indicated level of paclitaxel, but no peptide treatment. Calculated combination indices (CI) were as follows: MCF7: CI=0.41±0.04 for CP-dn-CEBPB; 0.44±0.04 for CP-dn-CEBPD; MDA-MB-231: 0.74±0.03 for CP-dn-CEBPB; 0.74±0.05 for CP-dn-CEBPD; T98G: CI=0.84±0.06 for CP-dn-CEBPB and 0.75±0.07 for CP-dn-CEBPD.

Replicate cultures of MDA-MB-231 cells in soft agar were treated with 0.1 nM or 0.5 nM 50 nM or 500 nM CP-dn-CEBPB and CP-dn-CEBPD peptides, maintained for 12 days, and then assessed for colony number. The bar graphs in FIG. 27A (CP-dn-CEBPB) and 27C (CP-dn-CEBPD) show relative colony number for each condition with. The line graphs of FIG. 27B (CP-dn-CEBPB) and 27D (CP-dn-CEBPD) show the response as normalized in each case so that 100 represents the relative number of surviving cells that received the indicated level paclitaxel, but no peptide treatment.

The data indicates a synergistic effect between treatment with CP-dn-CEBPB and CP-dn-CEBPD peptides and paclitaxel.

Replicate cultures of T98G wild type cells and paclitaxel-resistant T98G cells were treated with 0 nM to 50 nM paclitaxel or 0 μM to 50 μM CP-dn-CEBPB or CP-dn-CEBPD peptides, maintained for 6 days, and then assessed for cell number. Paclitaxel resistant T98G cells were inhibited by both CP-dn-CEBPB (FIG. 28A) and CP-dn-CEBPD (FIG. 28B), but, as expected were not inhibited by paclitaxel (FIG. 28C). This establishes that CP-dn-CEBPB and CP-dn-CEBPD may be effective against chemotherapy-resistant cells.

Example 19. CP-Dn-CEBPB and CP-Dn-CEBPD with Chloroquine

Replicate cultures of T98G, MDA-MB 231, and HCT116 cells were treated with 5 μM or 10 μM chloroquine and 3 μM or 10 μM CP-dn-CEBPB and CP-dn-CEBPD peptides, maintained for 6 days, and then assessed for cell number. The bar graphs of FIGS. 29A (T98G, CP-dn-CEBPB), 29C (T98G, CP-dn-CEBPBD, 29E (MDA-MB-231, CP-dn-CEBPBD), 29G (MDA-MB-231, CP-dn-CEBPD), 29I (HCT116, CP-dn-CEBPBB), and 26K (HCT116, CP-dn-CEBPBD) show relative cell numbers for each condition as compared to untreated controls. The line graphs of FIGS. 26B (T98G, CP-dn-CEBPB), 26D (T98G, CP-dn-CEBPBD), 26F (MDA-MB-231, CP-dn-CEBPB), 26H (MDA-MB-231, CP-dn-CEBPD), 26J (HCT116, CP-dn-CEBPB), and 26L (HCT116 CP-dn-CEBPBD) show the response as normalized in each case so that 100 represents the relative number of surviving cells that received the indicated level of chloroquine, but no peptide treatment. The results ranged from near-additive (HCT116 cells, CI=0.92±0.08 for CP-dn-CEBPB and 0.87±0.07 for CP-dn-CEBPD) to apparent synergy (T98G, CI=0.56±0.06 for CP-dn-CEBPB and 0.75±0.03 for CP-dn-CEBPD; MDA-MB-261, CI=0.59±0.11 for CP-dn-CEBPB and 0.47±0.05 for CP-dn-CEBPD).

Example 20. CP-Dn-CEBPB and CP-Dn-CEBPD with Doxorubicin

Replicate cultures of T98G, MDA-MB 231, HCT116, and MCF7 cells were treated with 0 or 50 nM doxorubicin and 3 μM or 10 μM CP-dn-CEBPB and CP-dn-CEBPD peptides, maintained for 6 days, and then assessed for cell number. The bar graphs of FIGS. 30A (T98G, CP-dn-CEBPB), 30C (T98G, CP-dn-CEBPBD, 30E (MDA-MB-231, CP-dn-CEBPBD), 30G (MDA-MB-231, CP-dn-CEBPD), 30I (HCT116, CP-dn-CEBPBB), 30K (HCT116, CP-dn-CEBPBD), 30M (MCF7, CP-dn-CEBPBB), and 30O (MCF7, CP-dn-CEBPBD) show relative cell numbers for each condition as compared to untreated controls. The line graphs of FIGS. 30B (T98G, CP-dn-CEBPB), 30D (T98G, CP-dn-CEBPBD), 30F. (MDA-MB-231, CP-dn-CEBPB), 30H (MDA-MB-231, CP-dn-CEBPD), 30J (HCT116, CP-dn-CEBPB), 30L (HCT116 CP-dn-CEBPBD), 30N (MCF7, CP-dn-CEBPBB), and 30P (MCF7, CP-dn-CEBPBD) show the response as normalized in each case so that 100 represents the relative number of surviving cells that received the indicated level of doxorubicin, but no peptide treatment.

Replicate cultures of MDA-MB 231, HCT116, and A375 cells were pretreated with 100 nM doxorubicin for 24 hours, and then treated with 1 μM, 3 μM, 10 μM, or 20 μM CP-dn-CEBPB and CP-dn-CEBPD peptides, maintained for 6 days, and then assessed for cell number. The bar graphs of FIGS. 31A (MDA-MB 231, CP-dn-CEBPB), 31C (MDA-MB 231, CP-dn-CEBPBD, 31E (HCT116, CP-dn-CEBPBD), 31G (HCT116, CP-dn-CEBPD), 31I (A375, CP-dn-CEBPBB), and 31K (A375, CP-dn-CEBPBD) show relative cell numbers for each condition as compared to untreated controls. The line graphs of FIGS. 31B (MDA-MB 231, CP-dn-CEBPB), 31D (MDA-MB 231, CP-dn-CEBPBD), 31F (HCT116, CP-dn-CEBPB), 31H (HCT116, CP-dn-CEBPD), 31J (A375, CP-dn-CEBPB), and 31L (A375, CP-dn-CEBPBD) show the response as normalized in each case so that 100 represents the relative number of surviving cells that received the indicated level of doxorubicin, but no peptide treatment. Near-juxtaposition of data points indicates that cells retain similar sensitivity to peptides irrespective of whether or not pre-treated with doxorubicin. FIG. 31M shows ratios of cell numbers at 7 days compared with one day after pre-treatment with or without doxorubicin alone.

Overall, this data indicates that CP-dn-CEBPB and CP-dn-CEBPD are effective to treat reversibly non-growing or slow-growing cancer cells. The pre-treatment with doxorubicin inhibited grown of the cancer cells prior to treatment with CP-dn-CEBPB and CP-dn-CEBPD, but inhibition was still seen. This ability to treat reversibly non-growing or slow-growing cancer cells is significant because such cells, when present in patients, may be a major source of metastatic or recurrent cancer.

Example 21. CP-Dn-CEBPB and CP-Dn-CEBPD Inhibit IL-6 and IL-8

T98G, MDA-MB-231, MCF7, A375, and HCT116 cells were treated with or without 20 µM CP-dn-CEBPB or CP-dn-CEBPD for 3 days and then assessed by qPCR for relative levels of IL6 (FIG. 32A, T98G; FIG. 32B, MDA-MB-231; FIG. 32C, MCF7; FIG. 32D, A375; FIG. 32E, HCT116) and IL8 mRNA (FIG. 32F, T98G; FIG. 32G, MDA-MB-231; FIG. 32H, MCF7; FIG. 32I, A375; FIG. 32J, HCT116). The data indicates that CP-dn-CEBPB and CP-dn-CEBPD suppress expression of IL6 and IL8, two genes that are direct targets of CEBPB and CEBPD. This suggest that CP-dn-CEBPB or CP-dn-CEBPD inhibit the transcriptional activity of the CEBPB and CEBPD transcription factors.

Example 22. CP-Dn-CEBPB and CP-Dn-CEBPD Inhibit ASNS (Asparagine Synthetase

T98G, MDA-MB-231, MCF7, A375, and HCT116 cells were treated with or without 20 µM CP-dn-CEBPB or CP-dn-CEBPD for 3 days and then assessed by qPCR for relative levels of ASNS (Asparagine synthetase) (FIG. 33A, T98G; FIG. 33B, MDA-MB-231; FIG. 33C, MCF7; FIG. 33D, A375; FIG. 33E, HCT116). The data indicates that CP-dn-CEBPB and CP-dn-CEBPD suppress expression of ASNS, a gene that is a direct target of ATF5 and CEBPB. This suggests that CP-dn-CEBPB or CP-dn-CEBPD inhibit the transcriptional activity of the CEBPB and ATF5 transcription factors.

Example 23. CP-Dn-CEBPB and CP-Dn-CEBPD Suppress Expression of Pro-Survival Proteins T98G, HCT116, MDA-MB-231, and MCF7 cell lines were exposed to 0 or 20 µM CP-dn-CEBPB or CP-dn-CEBPD for 3 days and then assessed by Western immunoblotting for levels of BCL2, MCL1 and survivin proteins with actin as loading control (FIG. 34A). Remaining panels show amounts of surviving (FIG. 34B), BCL2 (FIG. 34C) and MCL1 (FIG. 34D) were quantified relative to actin in multiple experiments. The data indicates that CP-dn-CEBPB and CP-dn-CEBPD surpress expression of pro-survival proteins, particularly surviving, in a variety of cancer cells.

Example 24. CP-Dn-CEBPB and CP-Dn-CEBPD Suppress Tumors In Vivo in Numerous Tumor Models A375 cells were subcutaneously implanted in the flanks of NCR nude mice. After tumors had formed, the animals were treated intraperitoneally with 10 or 20 mg/kg of CP-dn-CEBPB, CP-dn-CEBPD or vehicle as indicated in the schema shown in FIG. 37A. Animal weight was monitored (FIG. 37B). Tumor sizes were measured and volumes calculated on each day of injection. FIG. 37C shows calculated mean tumor volumes vs time after tumor cell implantation. The study was ended on day 24 when one of the vehicle-treated animals showed morbid behavior. FIG. 37D compares calculated individual and mean tumor volumes for vehicle, CP-dn-CEBPB and CP-dn-CEBPD treated animals on day 24. CP-dn-CEBPB and CP-dn-CEBPD suppressed tumor growth and had no apparent side effects.

B16-F10 cells were subcutaneously implanted in the flanks of C56BL/6 mice. After the tumors were established, the mice were treated intraperitoneally with 20 or 50 mg/kg of CP-dn-CEBPD or vehicle as indicated in the schema shown in FIG. 38A. Animal weight was monitored (FIG. 38B). FIG. 38C shows calculated mean tumor volumes for each group vs time up to the time (day 13) at which the first vehicle-treated animal reached the experimental endpoint when at least one tumor reached a calculated volume of >1000 mm$^3$. FIG. 38D compares calculated individual and mean tumor volumes for each group of animals on day 12. CP-dn-CEBPD suppressed tumor growth and had no apparent side effects.

A375 cells were subcutaneously implanted in the flanks of NCR nude mice. Once tumors had formed, the animals were treated intraperitoneally with 20 mg/kg of CP-dn-CEBPD or vehicle as indicated in the schema shown in FIG. 39A. Animal weight was monitored (FIG. 39B). Tumor sizes were measured and volumes calculated on each day of injection. FIG. 39C shows calculated mean tumor volumes vs time up to the time (day 28) at which the first vehicle-treated animal reached the experimental endpoint (at least one tumor of calculated volume >1000 mm$^3$). FIG. 39D compares calculated individual and mean tumor volumes for vehicle and CP-dn-CEBPD treated animals on day 28. FIG. 39E shows animal survival vs time for vehicle and CP-dn-CEBPD treated animals. Animals were considered to have reached the survival endpoint either when they showed morbid behavior or when at least one tumor reached a calculated volume of >1000 mm$^3$. CP-dn-CEBPD suppressed tumor growth and increased animal survival with no apparent side effects.

HCT116 cells were subcutaneously implanted in the flanks of NCR nude mice. After tumors formed, the animals were treated intraperitoneally with 20 mg/kg of CP-dn-CEBPD or vehicle as indicated in the schema shown FIG. 40A. Animal weight was monitored (FIG. 40). FIG. 40C shows calculated mean tumor volumes vs time up to the time (day 11) at which the first vehicle-treated animal reached the experimental endpoint (at least one tumor of calculated volume >1000 mm$^3$). FIG. 40D compares calculated individual and mean tumor volumes for vehicle and CP-dn-CEBPD treated animals on day 11. FIG. 40E shows animal survival vs time for vehicle and CP-dn-CEBPD treated animals to day 11. Animals were considered to have reached the survival endpoint either when they showed morbid behavior or when at least one tumor reached a calculated volume of >1000 mm$^3$. CP-dn-CEBPD suppressed tumor growth and increased animal survival with no apparent side effects.

Example 25. CP-Dn-CEBPD Treatment Promotes Apoptosis of Tumor Cells In Vivo

Subcutaneous A375 xenograft tumors were established in mice. When the tumors reached approximately 300 mm$^3$, randomly chosen animals were treated with vehicle or 20 mg/kg of CP-dn-CEBPD. The animals were retreated 2 days later and, after an additional 2 days, the animals were sacrificed, and the tumors harvested for histology and TUNEL staining to detect apoptosis. Results are presented in FIG. 42A (vehicle) and FIG. 42B (CP-dn-CEBPD). The data indicates that CP-dn-CEBPD causes apoptosis of tumor cells in vivo.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The invention claimed is:

1. A composition comprising a dominant negative CEBPD protein construct represented by SEQ ID NOs: 52-54.

2. The composition of claim 1, further comprising a cell penetrating peptide directly linked to the N-terminus of the dominant negative CEBPD protein.

3. The composition of claim 2, wherein the cell penetrating peptide is penetratin 1.

4. The composition of claim 1, which comprises a pharmaceutically acceptable excipient.

5. The composition of claim 4, further comprising a chemotherapeutic agent.

6. A dominant negative CEBPD protein construct represented by SEQ ID NOs: 55-59.

7. A composition comprising the dominant negative CEBPD protein construct of claim 6 and a pharmaceutically acceptable excipient.

8. The composition of claim 6, further comprising a chemotherapeutic agent.

9. The composition of claim 6, wherein the dominant negative CEBPD protein construct is represented by SEQ ID NO: 57.

10. The composition of claim 6, wherein the dominant negative CEBPD protein construct is represented by SEQ ID NO: 59.

11. A method of treating cancer in a subject, comprising:
administering to the subject an effective amount of the dominant negative CEBPD protein construct of claim 6 for a time sufficient to treat a cancer in a subject, wherein the cancer is blood cell, breast, skin, prostate, or brain cancer.

* * * * *

SEQUENCE LISTING

```
<160> NUMBER OF SEQ ID NOS: 63

<210> SEQ ID NO 1
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Leu Glu Thr Gln His Lys Val Leu Glu Leu Thr Ala Glu Asn Glu Arg
1               5                   10                  15

Leu Gln Lys Lys Val Glu Gln Leu Ser Arg Glu Leu Ser Thr Leu Arg
            20                  25                  30

Asn Leu Phe Lys Gln Leu
        35

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Leu Val Glu Leu Ser Ala Glu Asn Glu Lys Leu His Gln Arg Val Glu
1               5                   10                  15

Gln Leu Thr Arg Asp Leu Ala Gly Leu Arg Gln Phe Phe Lys
            20                  25                  30

<210> SEQ ID NO 3
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Lys Lys Thr Val Asp Lys His Ser Asp Glu Tyr Lys Ile Arg Arg Glu
1               5                   10                  15

Arg Asn Asn Ile Ala Val Arg Lys Ser Arg Asp Lys Ala Lys Met Arg
            20                  25                  30

Asn

<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 4

Leu Glu Gln Arg Ala Glu Glu Leu Ala Arg Glu Asn Glu Glu Leu Glu
1               5                   10                  15

Lys Glu Ala Glu Glu Leu Glu Gln Glu Asn Ala Glu
            20                  25

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Ala Arg Glu Asn Glu Glu Leu Glu Lys Glu Ala Glu Glu Leu Glu
1               5                   10                  15

Gln Glu Asn Ala Glu
            20

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Glu Lys Glu Ala Glu Glu Leu Glu Gln Glu Asn Ala Glu
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Glu Gln Glu Asn Ala Glu
1               5

<210> SEQ ID NO 8
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (125)..(125)
<223> OTHER INFORMATION: Ala or Ser
<220> FEATURE:
<221> NAME/KEY: MOD_RES
<222> LOCATION: (128)..(128)
<223> OTHER INFORMATION: Cys or Met

<400> SEQUENCE: 8

Met Glu Gln Lys Leu Ile Ser Glu Glu Asp Leu Glu Gln Lys Leu Ile
1               5                   10                  15

Ser Glu Glu Asp Leu Glu Gln Lys Leu Ile Ser Glu Glu Asp Leu Ala
            20                  25                  30
```

```
Arg Ala Gly Ser Met Ala Ser Met Thr Gly Gly Gln Gln Met Gly Arg
            35                  40                  45

Asp Pro Asp Leu Glu Gln Arg Ala Glu Glu Leu Ala Arg Glu Asn Glu
        50                  55                  60

Glu Leu Glu Lys Glu Ala Glu Glu Leu Glu Gln Glu Asn Ala Glu Leu
65                  70                  75                  80

Glu Thr Gln His Lys Val Leu Glu Leu Thr Ala Glu Asn Glu Arg Leu
                85                  90                  95

Gln Lys Lys Val Glu Gln Leu Ser Arg Glu Leu Ser Thr Leu Arg Asn
            100                 105                 110

Leu Phe Lys Gln Leu Pro Glu Pro Leu Leu Ala Ser Xaa Gly His Xaa
        115                 120                 125

<210> SEQ ID NO 9
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Glu Gln Lys Leu Ile Ser Glu Glu Asp Leu Glu Gln Lys Leu Ile
1               5                   10                  15

Ser Glu Glu Asp Leu Glu Gln Lys Leu Ile Ser Glu Glu Asp Leu Ala
            20                  25                  30

Arg Ala Gly Ser Met Ala Ser Met Thr Gly Gly Gln Gln Met Gly Arg
            35                  40                  45

Asp Pro Asp Leu Glu Gln Arg Ala Glu Glu Leu Ala Arg Glu Asn Glu
        50                  55                  60

Glu Leu Glu Lys Glu Ala Glu Glu Leu Glu Gln Glu Asn Ala Glu Leu
65                  70                  75                  80

Glu Thr Gln His Lys Val Leu Glu Leu Thr Ala Glu Asn Glu Arg Leu
                85                  90                  95

Gln Lys Lys Val Glu Gln Leu Ser Arg Glu Leu Ser Thr Leu Arg Asn
            100                 105                 110

Leu Phe Lys Gln Leu
        115

<210> SEQ ID NO 10
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Glu Gln Lys Leu Ile Ser Glu Glu Asp Leu Glu Gln Lys Leu Ile
1               5                   10                  15

Ser Glu Glu Asp Leu Glu Gln Lys Leu Ile Ser Glu Glu Asp Leu Ala
            20                  25                  30

Arg Ala Gly Ser Met Ala Ser Met Thr Gly Gly Gln Gln Met Gly Arg
            35                  40                  45

Asp Pro Asp Leu Glu Thr Gln His Lys Val Leu Glu Leu Thr Ala Glu
        50                  55                  60

Asn Glu Arg Leu Gln Lys Lys Val Glu Gln Leu Ser Arg Glu Leu Ser
65                  70                  75                  80
```

Thr Leu Arg Asn Leu Phe Lys Gln Leu
            85

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Gln Lys Leu Ile Ser Glu Glu Asp Leu
1               5                   10

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Gln Lys Leu Ile Ser Glu Glu Asp Leu Glu Gln Lys Leu Ile Ser
1               5                   10                  15

Glu Glu Asp Leu Glu Gln Lys Leu Ile Ser Glu Glu Asp Leu
            20                  25                  30

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Leu Asn Asp Ile Phe Glu Ala Gln Lys Ile Glu Trp His Glu
1               5                   10                  15

<210> SEQ ID NO 14
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Glu Glu Glu Glu Glu
1               5

```
<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Ala Pro Val Pro Tyr Pro Asp Pro Leu Glu Pro Arg
1               5                   10

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asp Tyr Lys Asp Asp Asp Asp Lys
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Pro Tyr Asp Val Pro Asp Tyr Ala
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

His His His His His His
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Glu Gln Lys Leu Ile Ser Glu Glu Asp Leu
1               5                   10

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 21

Thr Lys Glu Asn Pro Arg Ser Asn Gln Glu Glu Ser Tyr Asp Asp Asn
1               5                   10                  15

Glu Ser

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Glu Thr Ala Ala Ala Lys Phe Glu Arg Gln His Met Asp Ser
1               5                   10                  15

<210> SEQ ID NO 23
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Leu Ala Glu Leu Leu Asn Ala Gly Leu Gly Gly Ser
1               5                   10

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Gln Asp Pro Ser Arg Val Gly
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26
```

```
Trp Ser His Pro Gln Phe Glu Lys
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Cys Cys Pro Gly Cys Cys
1               5

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Lys Pro Ile Pro Asn Pro Leu Leu Gly Leu Asp Ser Thr
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Thr Asp Ile Glu Met Asn Arg Leu Gly Lys
1               5                   10

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Leu Tyr Asp Asp Asp Asp Lys
1               5

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Thr Asp Lys Asp Met Thr Ile Thr Phe Thr Asn Lys Lys Asp Ala Glu
1               5                   10                  15

<210> SEQ ID NO 32
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 32

Ala His Ile Val Met Val Asp Ala Tyr Lys Pro Thr Lys
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Leu Gly Asp Ile Glu Phe Ile Lys Val Asn Lys
1               5                   10

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Gln Ile Lys Ile Trp Phe Gln Asn Arg Arg Met Lys Trp Lys Lys
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Arg Leu Arg Arg Leu Leu Arg Arg Leu Leu Arg Arg Leu Arg Arg
1               5                   10                  15

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Val Gly Arg Arg Arg Arg Arg Arg Arg Arg Arg
1               5                   10

<210> SEQ ID NO 37
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Trp Thr Leu Asn Ser Ala Gly Tyr Leu Leu Gly Lys Ile Asn Leu
1               5                   10                  15
```

Lys Ala Leu Ala Ala Leu Ala Lys Lys Ile Leu
            20                  25

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Pro Val Ile Arg Val Trp Phe Gln Asn Lys Arg Cys Lys Asp Lys Lys
1               5                   10                  15

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Gly Arg Lys Lys Arg Arg Gln Arg Arg Arg
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Arg Lys Lys Arg Arg Gln Arg Arg Arg Pro Pro Gln
1               5                   10

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Leu Ile Ile Leu Arg Arg Arg Ile Arg Lys Gln Ala His Ala His
1               5                   10                  15

<210> SEQ ID NO 42
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 43
<211> LENGTH: 18

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Leu Ala Leu Lys Leu Ala Leu Lys Ala Leu Lys Ala Ala Leu Lys
1               5                   10                  15

Leu Ala

<210> SEQ ID NO 44
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (115)..(115)
<223> OTHER INFORMATION: Ala or Ser
<220> FEATURE:
<221> NAME/KEY: MOD_RES
<222> LOCATION: (118)..(118)
<223> OTHER INFORMATION: Cys or Met

<400> SEQUENCE: 44

Arg Gln Ile Lys Ile Trp Phe Gln Asn Arg Arg Met Lys Trp Lys Lys
1               5                   10                  15

Glu Gln Lys Leu Ile Ser Glu Glu Asp Leu Met Ala Ser Met Thr Gly
            20                  25                  30

Gly Gln Gln Met Gly Arg Asp Pro Asp Leu Glu Gln Arg Ala Glu Glu
        35                  40                  45

Leu Ala Arg Glu Asn Glu Glu Leu Glu Lys Glu Ala Glu Glu Leu Glu
    50                  55                  60

Gln Glu Asn Ala Glu Leu Glu Thr Gln His Lys Val Leu Glu Leu Thr
65                  70                  75                  80

Ala Glu Asn Glu Arg Leu Gln Lys Lys Val Glu Gln Leu Ser Arg Glu
                85                  90                  95

Leu Ser Thr Leu Arg Asn Leu Phe Lys Gln Leu Pro Glu Pro Leu Leu
            100                 105                 110

Ala Ser Xaa Gly His Xaa
        115

<210> SEQ ID NO 45
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Arg Gln Ile Lys Ile Trp Phe Gln Asn Arg Arg Met Lys Trp Lys Lys
1               5                   10                  15

Glu Gln Lys Leu Ile Ser Glu Glu Asp Leu Met Ala Ser Met Thr Gly
            20                  25                  30

Gly Gln Gln Met Gly Arg Asp Pro Asp Leu Glu Gln Arg Ala Glu Glu
        35                  40                  45

Leu Ala Arg Glu Asn Glu Glu Leu Glu Lys Glu Ala Glu Glu Leu Glu
    50                  55                  60
```

```
Gln Glu Asn Ala Glu Leu Glu Thr Gln His Lys Val Leu Glu Leu Thr
 65                  70                  75                  80

Ala Glu Asn Glu Arg Leu Gln Lys Lys Val Glu Gln Leu Ser Arg Glu
                 85                  90                  95

Leu Ser Thr Leu Arg Asn Leu Phe Lys Gln Leu
                100                 105

<210> SEQ ID NO 46
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Arg Gln Ile Lys Ile Trp Phe Gln Asn Arg Arg Met Lys Trp Lys Lys
  1               5                  10                  15

Glu Gln Lys Leu Ile Ser Glu Glu Asp Leu Met Ala Ser Met Thr Gly
                 20                  25                  30

Gly Gln Gln Met Gly Arg Asp Pro Asp Leu Glu Thr Gln His Lys Val
                 35                  40                  45

Leu Glu Leu Thr Ala Glu Asn Glu Arg Leu Gln Lys Lys Val Glu Gln
 50                  55                  60

Leu Ser Arg Glu Leu Ser Thr Leu Arg Asn Leu Phe Lys Gln Leu
 65                  70                  75

<210> SEQ ID NO 47
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Arg Gln Ile Lys Ile Trp Phe Gln Asn Arg Arg Met Lys Trp Lys Lys
  1               5                  10                  15

Leu Glu Gln Arg Ala Glu Glu Leu Ala Arg Glu Asn Glu Glu Leu Glu
                 20                  25                  30

Lys Glu Ala Glu Glu Leu Glu Gln Glu Asn Ala Glu Leu Glu Thr Gln
                 35                  40                  45

His Lys Val Leu Glu Leu Thr Ala Glu Asn Glu Arg Leu Gln Lys Lys
                 50                  55                  60

Val Glu Gln Leu Ser Arg Glu Leu Ser Thr Leu Arg Asn Leu Phe Lys
 65                  70                  75                  80

Gln Leu

<210> SEQ ID NO 48
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Arg Gln Ile Lys Ile Trp Phe Gln Asn Arg Arg Met Lys Trp Lys Lys
  1               5                  10                  15

Leu Glu Thr Gln His Lys Val Leu Glu Leu Thr Ala Glu Asn Glu Arg
                 20                  25                  30
```

```
Leu Gln Lys Lys Val Glu Gln Leu Ser Arg Glu Leu Ser Thr Leu Arg
        35                  40                  45

Asn Leu Phe Lys Gln Leu
    50
```

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

```
Arg Gln Ile Lys Ile Phe Phe Gln Asn Arg Arg Met Lys Phe Lys Lys
1               5                   10                  15
```

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

```
Arg Gln Ile Lys Ile Trp Phe Arg Lys Trp Lys Lys
1               5                   10
```

<210> SEQ ID NO 51
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Asp Arg Gly Ser Pro Glu Tyr Arg Gln Arg Arg Glu Arg Asn Asn Ile
1               5                   10                  15

Ala Val Arg Lys Ser Arg Asp Lys Ala Lys Arg Arg Asn Gln Glu Met
            20                  25                  30

Gln Gln Lys
        35
```

<210> SEQ ID NO 52
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (125)..(125)
<223> OTHER INFORMATION: Cys or Met

<400> SEQUENCE: 52

```
Met Glu Gln Lys Leu Ile Ser Glu Glu Asp Leu Glu Gln Lys Leu Ile
1               5                   10                  15

Ser Glu Glu Asp Leu Glu Gln Lys Leu Ile Ser Glu Glu Asp Leu Ala
            20                  25                  30

Arg Ala Gly Ser Met Ala Ser Met Thr Gly Gly Gln Gln Met Gly Arg
        35                  40                  45
```

```
Asp Pro Asp Leu Glu Gln Arg Ala Glu Leu Ala Arg Glu Asn Glu
    50                  55                  60

Glu Leu Glu Lys Glu Ala Glu Leu Glu Gln Glu Asn Ala Glu Leu
65                  70                  75                  80

Val Glu Leu Ser Ala Glu Asn Glu Lys Leu His Gln Arg Val Glu Gln
                85                  90                  95

Leu Thr Arg Asp Leu Ala Gly Leu Arg Gln Phe Phe Lys Gln Leu Pro
            100                 105                 110

Ser Pro Pro Phe Leu Pro Ala Ala Gly Thr Ala Asp Xaa Arg
            115                 120                 125

<210> SEQ ID NO 53
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Glu Gln Lys Leu Ile Ser Glu Glu Asp Leu Glu Gln Lys Leu Ile
1               5                   10                  15

Ser Glu Glu Asp Leu Glu Gln Lys Leu Ile Ser Glu Glu Asp Leu Ala
                20                  25                  30

Arg Ala Gly Ser Met Ala Ser Met Thr Gly Gly Gln Gln Met Gly Arg
            35                  40                  45

Asp Pro Asp Leu Glu Gln Arg Ala Glu Leu Ala Arg Glu Asn Glu
    50                  55                  60

Glu Leu Glu Lys Glu Ala Glu Leu Glu Gln Glu Asn Ala Glu Leu
65                  70                  75                  80

Val Glu Leu Ser Ala Glu Asn Glu Lys Leu His Gln Arg Val Glu Gln
                85                  90                  95

Leu Thr Arg Asp Leu Ala Gly Leu Arg Gln Phe Phe Lys
            100                 105

<210> SEQ ID NO 54
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Met Glu Gln Lys Leu Ile Ser Glu Glu Asp Leu Glu Gln Lys Leu Ile
1               5                   10                  15

Ser Glu Glu Asp Leu Glu Gln Lys Leu Ile Ser Glu Glu Asp Leu Ala
                20                  25                  30

Arg Ala Gly Ser Met Ala Ser Met Thr Gly Gly Gln Gln Met Gly Arg
            35                  40                  45

Asp Pro Asp Leu Val Glu Leu Ser Ala Glu Asn Glu Lys Leu His Gln
    50                  55                  60

Arg Val Glu Gln Leu Thr Arg Asp Leu Ala Gly Leu Arg Gln Phe Phe
65                  70                  75                  80

Lys

<210> SEQ ID NO 55
<211> LENGTH: 116
<212> TYPE: PRT
```

<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (115)..(115)
<223> OTHER INFORMATION: Cys or Met

<400> SEQUENCE: 55

Arg Gln Ile Lys Ile Trp Phe Gln Asn Arg Arg Met Lys Trp Lys Lys
1               5                   10                  15

Glu Gln Lys Leu Ile Ser Glu Glu Asp Leu Met Ala Ser Met Thr Gly
            20                  25                  30

Gly Gln Gln Met Gly Arg Asp Pro Asp Leu Glu Gln Arg Ala Glu Glu
        35                  40                  45

Leu Ala Arg Glu Asn Glu Glu Leu Glu Lys Glu Ala Glu Glu Leu Glu
    50                  55                  60

Gln Glu Asn Ala Glu Leu Val Glu Leu Ser Ala Glu Asn Glu Lys Leu
65                  70                  75                  80

His Gln Arg Val Glu Gln Leu Thr Arg Asp Leu Ala Gly Leu Arg Gln
                85                  90                  95

Phe Phe Lys Gln Leu Pro Ser Pro Pro Phe Leu Pro Ala Ala Gly Thr
            100                 105                 110

Ala Asp Xaa Arg
        115

<210> SEQ ID NO 56
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Arg Gln Ile Lys Ile Trp Phe Gln Asn Arg Arg Met Lys Trp Lys Lys
1               5                   10                  15

Glu Gln Lys Leu Ile Ser Glu Glu Asp Leu Met Ala Ser Met Thr Gly
            20                  25                  30

Gly Gln Gln Met Gly Arg Asp Pro Asp Leu Glu Gln Arg Ala Glu Glu
        35                  40                  45

Leu Ala Arg Glu Asn Glu Glu Leu Glu Lys Glu Ala Glu Glu Leu Glu
    50                  55                  60

Gln Glu Asn Ala Glu Leu Val Glu Leu Ser Ala Glu Asn Glu Lys Leu
65                  70                  75                  80

His Gln Arg Val Glu Gln Leu Thr Arg Asp Leu Ala Gly Leu Arg Gln
                85                  90                  95

Phe Phe Lys

<210> SEQ ID NO 57
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Arg Gln Ile Lys Ile Trp Phe Gln Asn Arg Arg Met Lys Trp Lys Lys
1               5                   10                  15

```
Glu Gln Lys Leu Ile Ser Glu Asp Leu Met Ala Ser Met Thr Gly
            20                  25                  30

Gly Gln Gln Met Gly Arg Asp Pro Asp Leu Val Glu Leu Ser Ala Glu
        35                  40                  45

Asn Glu Lys Leu His Gln Arg Val Glu Gln Leu Thr Arg Asp Leu Ala
    50                  55                  60

Gly Leu Arg Gln Phe Phe Lys
65                  70

<210> SEQ ID NO 58
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Arg Gln Ile Lys Ile Trp Phe Gln Asn Arg Arg Met Lys Trp Lys Lys
1               5                   10                  15

Leu Glu Gln Arg Ala Glu Glu Leu Ala Arg Glu Asn Glu Glu Leu Glu
            20                  25                  30

Lys Glu Ala Glu Glu Leu Glu Gln Glu Asn Ala Glu Leu Val Glu Leu
        35                  40                  45

Ser Ala Glu Asn Glu Lys Leu His Gln Arg Val Glu Gln Leu Thr Arg
    50                  55                  60

Asp Leu Ala Gly Leu Arg Gln Phe Phe Lys
65                  70

<210> SEQ ID NO 59
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Arg Gln Ile Lys Ile Trp Phe Gln Asn Arg Arg Met Lys Trp Lys Lys
1               5                   10                  15

Leu Val Glu Leu Ser Ala Glu Asn Glu Lys Leu His Gln Arg Val Glu
            20                  25                  30

Gln Leu Thr Arg Asp Leu Ala Gly Leu Arg Gln Phe Phe Lys
        35                  40                  45

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ala or Ser
<220> FEATURE:
<221> NAME/KEY: MOD_RES
<222> LOCATION: (11)..(11)
<223> OTHER INFORMATION: Cys or Met

<400> SEQUENCE: 60

Pro Glu Pro Leu Leu Ala Ser Xaa Gly His Xaa
```

```
<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Met Ala Ser Met Thr Gly Gly Gln Gln Met Gly
1               5                   10

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Cys or Met

<400> SEQUENCE: 62

Gln Leu Pro Ser Pro Pro Phe Leu Pro Ala Ala Gly Thr Ala Asp Xaa
1               5                   10                  15

Arg

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 5-10 residues

<400> SEQUENCE: 63

His His His His His His His His His His
1               5                   10
```